(12) United States Patent
Kodama et al.

(10) Patent No.: US 10,668,075 B2
(45) Date of Patent: Jun. 2, 2020

(54) RET INHIBITOR

(71) Applicant: CHUGAI SEIYAKU KABUSHIKI KAISHA, Kita-ku, Tokyo (JP)

(72) Inventors: Tatsushi Kodama, Kanagawa (JP); Hiroshi Sakamoto, Kanagawa (JP); Toshiyuki Tsukaguchi, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/429,834

(22) PCT Filed: Sep. 24, 2013

(86) PCT No.: PCT/JP2013/075621
§ 371 (c)(1),
(2) Date: Mar. 20, 2015

(87) PCT Pub. No.: WO2014/050781
PCT Pub. Date: Apr. 3, 2014

(65) Prior Publication Data
US 2015/0272958 A1 Oct. 1, 2015

(30) Foreign Application Priority Data
Sep. 25, 2012 (JP) .................. 2012-211040

(51) Int. Cl.
*A61K 31/5377* (2006.01)
*C07D 401/04* (2006.01)
*C12Q 1/6886* (2018.01)
*G01N 33/574* (2006.01)
*C12Q 1/6883* (2018.01)
*G01N 33/573* (2006.01)

(52) U.S. Cl.
CPC ........ *A61K 31/5377* (2013.01); *C07D 401/04* (2013.01); *C12Q 1/6883* (2013.01); *C12Q 1/6886* (2013.01); *G01N 33/573* (2013.01); *G01N 33/57407* (2013.01); *G01N 33/57423* (2013.01); *C12Q 2600/106* (2013.01); *C12Q 2600/156* (2013.01); *G01N 2333/912* (2013.01); *G01N 2800/52* (2013.01)

(58) Field of Classification Search
CPC ................................. A61K 31/5377
See application file for complete search history.

(56) References Cited

U.S. PATENT DOCUMENTS

| | | | |
|---|---|---|---|
| 5,721,267 A | 2/1998 | Broka | |
| 5,936,084 A | 8/1999 | Jirousek et al. | |
| 9,126,931 B2 | 9/2015 | Kinoshita et al. | |
| 9,365,514 B2 | 6/2016 | Furumoto et al. | |
| 9,440,922 B2 | 9/2016 | Kinoshita et al. | |
| 9,714,229 B2 | 7/2017 | Tanaka et al. | |
| 10,344,014 B2 | 7/2019 | Shiraki et al. | |
| 10,350,214 B2 | 7/2019 | Tomimatsu et al. | |
| 2004/0191254 A1 | 9/2004 | Fagin | |
| 2005/0107364 A1 | 5/2005 | Hutchinson et al. | |
| 2007/0031907 A1 | 2/2007 | Pinna et al. | |
| 2007/0099893 A1 | 5/2007 | Boyd et al. | |
| 2007/0249653 A1 | 10/2007 | Jagtap et al. | |
| 2008/0058320 A1 | 3/2008 | Herold et al. | |
| 2008/0262021 A1 | 10/2008 | Capraro et al. | |
| 2009/0209580 A1 | 8/2009 | Matsui | |
| 2009/0221555 A1 | 9/2009 | Ahmed et al. | |
| 2010/0099658 A1 | 4/2010 | Kondoh et al. | |
| 2012/0083488 A1 | 4/2012 | Kinoshita et al. | |
| 2012/0322050 A1 | 12/2012 | Abassi et al. | |
| 2013/0116280 A1 | 5/2013 | Ju et al. | |
| 2013/0143877 A1 | 6/2013 | Furumoto et al. | |
| 2014/0221404 A1 | 8/2014 | Kohno et al. | |
| 2015/0150845 A1 | 6/2015 | Kinoshita et al. | |

(Continued)

FOREIGN PATENT DOCUMENTS

CN 1902200 A 1/2007
CN 103305598 B 4/2015
(Continued)

OTHER PUBLICATIONS

Ju et al. Genome Research, Online Dec. 2011, vol. 22, p. 436-445.*
Eng et al. Hum. Mol. Genetics, 1992, vol. 3, No. 2, see abstract.*
Li et al. Cell Research, Feb. 2012, 928-931.*
Takeuchi et al., "RET, ROS1 and ALK fusions in lung cancer," Nature Medicine, Mar. 2012, 18(3):378-381.
(Continued)

Primary Examiner — Samira J Jean-Louis
(74) Attorney, Agent, or Firm — Foley & Lardner LLP

(57) ABSTRACT

A compound represented by the following general formula (I) [the symbol in the formula are as defined in the description], a salt thereof, or the like is a RET inhibitor or RET tyrosine kinase inhibitor that can be used as an agent for the prevention or treatment of disorders including cancers and cancer metastasis having mutations in RET.

(I)

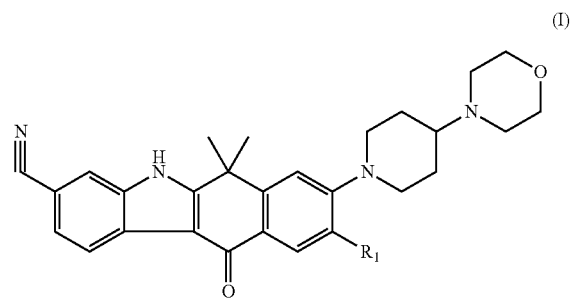

10 Claims, 1 Drawing Sheet
Specification includes a Sequence Listing.

(56) References Cited

U.S. PATENT DOCUMENTS

| | | | |
|---|---|---|---|
| 2015/0177246 | A1 | 6/2015 | Shibata et al. |
| 2015/0272958 | A1 | 10/2015 | Kodama et al. |
| 2016/0317494 | A1 | 11/2016 | Furumoto et al. |
| 2016/0340308 | A1 | 11/2016 | Kinoshita et al. |
| 2017/0035773 | A1 | 2/2017 | Tomimatsu et al. |
| 2017/0081306 | A1 | 3/2017 | Tanaka et al. |
| 2017/0119781 | A1 | 5/2017 | Meier et al. |
| 2017/0217927 | A1 | 8/2017 | Shiraki et al. |
| 2019/0284163 | A1 | 9/2019 | Shiraki et al. |

FOREIGN PATENT DOCUMENTS

| | | | |
|---|---|---|---|
| EA | 001450 | B1 | 4/2001 |
| JP | 08-092090 | A | 4/1996 |
| JP | 2012-126711 | A | 7/2012 |
| RU | 2162089 | C2 | 1/2001 |
| RU | 2448708 | C2 | 6/2010 |
| WO | WO 00/69856 | A1 | 11/2000 |
| WO | WO 2004/080980 | A1 | 9/2004 |
| WO | WO 2005/009389 | A2 | 2/2005 |
| WO | WO 2005/097765 | A1 | 10/2005 |
| WO | WO 2006/021884 | A2 | 3/2006 |
| WO | WO 2007/023310 | A2 | 3/2007 |
| WO | WO 2007/056497 | A1 | 5/2007 |
| WO | WO 2007/130468 | A2 | 11/2007 |
| WO | WO 2008/021369 | A2 | 2/2008 |
| WO | WO 2008/051547 | A1 | 5/2008 |
| WO | WO 2008/130951 | A1 | 10/2008 |
| WO | WO 2009/008371 | A1 | 1/2009 |
| WO | WO 2009/013126 | A1 | 1/2009 |
| WO | WO 2009/073620 | A2 | 6/2009 |
| WO | WO 2010/128324 | A1 | 11/2010 |
| WO | WO 2010/142423 | A2 | 12/2010 |
| WO | WO 2010/142685 | A1 | 12/2010 |
| WO | WO 2010/143664 | A1 | 12/2010 |
| WO | WO 2011/146945 | A2 | 11/2011 |
| WO | WO 2012/023597 | A1 | 2/2012 |
| WO | WO 2012/138783 | A2 | 10/2012 |
| WO | WO 2012/138789 | A2 | 10/2012 |
| WO | WO 2013/006864 | A2 | 1/2013 |
| WO | WO 2013/018882 | A1 | 2/2013 |
| WO | WO 2013/028817 | A1 | 2/2013 |
| WO | WO 2013/059740 | A1 | 4/2013 |
| WO | WO 2013/066047 | A1 | 5/2013 |
| WO | WO 2013/111668 | A1 | 8/2013 |
| WO | WO 2013/134693 | A1 | 9/2013 |
| WO | WO 2013/141266 | A1 | 9/2013 |
| WO | WO 2013/158859 | A1 | 10/2013 |
| WO | WO 2013/163428 | A1 | 10/2013 |
| WO | WO 2013/169339 | A1 | 11/2013 |
| WO | WO 2014/017491 | A1 | 1/2014 |
| WO | WO 2014/071419 | A2 | 5/2014 |
| WO | WO 2014/130975 | A1 | 8/2014 |
| WO | WO 2014/150300 | A2 | 9/2014 |
| WO | WO 2014/165710 | A2 | 10/2014 |
| WO | WO 2014/172046 | A2 | 10/2014 |

OTHER PUBLICATIONS

Sakamoto et al., "Cancer Cell-D-10-00840R3, Supplemental Information, CH5424802, a Selective ALK Inhibitor Capable of Blocking the Resistant Gatekeeper Mutant," Cancer Cell, May 17, 2011, 19:1-11, XP55248839.

Capalletti et al., "Discovery of recurrent KIF5B-RET fusions and other targetable alterations from clinical NSCLC specimens," J. Clin. Oncol., 2012, 30(suppl.;abstr. No. 7510), 2 pages.

Drilon et al., "Response to Bacozantinib in Patients with RET Fusion-Positive Lung Adenocarcinomas," Cancer Discovery, Jun. 2013, 3(6):630-635.

Gummadi et al., "Discovery of 7-azaindole based anaplastic lymphoma kinase (ALK) inhibitors: Wild type and mutant (L1196M) active compounds with unique binding mode," Biorganic & Medicinal Chemistry Letters, 2013, 23:4911-4918.

Ju et al., "Fusion of KIF5B and RET transforming gene in lung adenocarcinoma revealed from whole-genome and transcriptome sequencing," Genome Research, published online Dec. 22, 2011, 35 pages.

Katayama et al., Mechanisms of Acquired Crizotibin Resistance in ALK-Rearranged Lung Cancers,: Sci. Transl. Med., Feb. 8, 2012, 4(120):120ra17, 13 pages.

Kinoshita et al., Design and synthesis of a highly selective, orally active and potent anaplastic lymphoma kinase inhibitor (CH5424802), Bioorganic & Medicinal Chemistry, 2012, 20(3):1271-1280.

Kohno et al., "KIF5B-RET fusions in lung adenocarcinoma," Nature Medicine, published online Feb. 2, 2012, 18(3):375-377.

Latif et al., "Journey of the ALK-inhibitor CH5424802 to phase II clinical trial," Arch. Pharm. Res., 2013, 36(9):1051-1054.

Li et al., "Identification of RET gene fusion by exon array analyses in 'pan-negative' lung cancer from never smokers," Cell Research, 2012, 22:928-931.

Mologni, L, "Development of RET Kinase Inhibitors for Targeted Cancer Therapy," Current Medicinal Chemistry, 2011, 18(2):162-175.

Sakamoto et al., "CH5424802, a Selective ALK Inhibitor Capable of Blocking the Reistant Gatekeeper Mutant," Cancer Cell, May 17, 2011, 19(5):679-690.

Sakamoto et al., "ALK inhibitor CH5424802," Cell, 2013, 45(6):292-296, with English abstract.

Sakamoto et al., "ALK inhibitor CH5424802," BIO Clinica, 2013, 28(9):866-871, with English abstract.

Sang et al., "Targeted Inhibition of the Molecular Chaperone Hsp90 Overcomes ALK Inhibitor Resistance in Non-Small Cell Lung Cancer," Cancer Discovery, Mar. 26, 2013, 3(4):430-443.

Seto et al., "CH5424802 (RO5424802) for patients with ALK-rearranged advanced non-small-cell lung cancer (AF-001JP study): a single-arm, open-label, phase 1-2 study," Lancet Oncology, 2013, 14(7):590-598.

Solomon et al., "Current Status of Targeted Therapy for Anaplastic Lymphoma Kinase-Rearranged Non-Small Cell Lung Cancer," Clinical Pharmacology & Therapeutics, Jan. 2014, 95(1):15-23.

Suzuki et al., "Discovery of novel fusion gene and the drug development study," The Medical Frontline, Dec. 2012, 67(12):2724-2730, with English abstract.

Stephens et al., "The landscape of cancer genes and mutational processes in breast cancer," Natura, Jun. 21, 2012, 486:400-406.

Utsumi et al., "Novel Anticancer Agent Expected in Lung Cancer Region," Aspiration, 2013, 32(8):717-722, with English abstract.

Yun et al., "Novel 2,4-dianilino-5-fluoropyrimidine derivatives possessing ALK inhibitory activities," Arch. Pharm. Res., 2014, 37(7):873-881.

Zdzalik et al., "Activating mutations in ALK kinase domain confer resistance to structurally unrelated ALK inhibitors in NPM-ALK-positive anaplastic large-cell lymphoma," J. Cancer Res. Clin. Oncol., 2014, 140(4):589-598.

Office Action dated Sep. 27, 2016, in JP 2015-040242, with English translation.

Bilsland et al., "Behavioral and Neurochemical Alterations in Mice Deficient in Anaplastic Lymphoma Kinase Suggest Therapeutic Potential for Psychiatric Indications," Neuropsychopharmacolgy, 2008, 33:685-700.

Bunz, F., "Chapter 1, The Genetic Basis of Cancer," Principles of Cancer Genetics, 2008, 1-47.

CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.
CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.

Chen et al., "Oncogenic mutations of ALK kinase in neuroblastoma," Nature, Oct. 16, 2008, 455:971-974, and Methods page.

(56) References Cited

OTHER PUBLICATIONS

Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.
Druker et al., "Section 1: Chronic Myelogenous Leukemia," Cancer: Principles & Practice of Oncology, $7^{th}$ Edition (DeVita et al., Eds.), 2121.
Faderl et al., "Section 3: Myelodysplastic Syndromes," Cancer: Principles & Practice of Oncology, $7^{th}$ Edition (DeVita et al., Eds.), 2144.
Fine et al., "Section 2: Neoplasms of the Central Nervous System," Cancer: Principles & Practice of Oncology, $7^{th}$ Edition (DeVita et al., Eds.), 1834-1887.
Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
George et al., "Activating mutations in ALK provide a therapeutic target in neuroblastoma," Nature, 2008, 455:975-978.
Girouard et al., "Neurovascular coupling in the normal brain and in hypertension, stroke, and Alzheimer disease," Journal of Applied Physiology, 2006, 100:328-335.
Glick et al., "Treatment with atypical antipsychotics: new indications and new populations," Journal of Psychiatric Research, 2001, 35:187-191.
Goel et al., "Mice transgenic for BRAF V600E demonstrate phenotype affecting melanocyte and neural lineages," Proceedings of the American Association for Cancer Research, Apr. 2006, 47:#273.
Goodman & Gilman's, Chemotherapy of Neoplastic Diseases, The Pharmacological Basis of Therapeutics, Brunton et al., Eds., 2008, $11^{th}$ Ed., 853-908.
Griffin et al., "Recurrent Involvement of 2p23 in Inflammatory Myofibroblastic Tumors," Cancer Research, Jun. 15, 1999, 59:2776-2780.
Herbst et al., "ALK Gene Products in Anaplastic Large Cell Lymphomas and Hodgkin's Disease," Blood, Sep. 1, 1995, 86(5):1694-1700.
Huang et al., "An in vivo model to study human GSTP1 polymorphisms in osteosarcoma," Proceedings of the American Association for Cancer Research, Apr. 2006, 47:#271.
Hübinger et al., "CD30-mediated cell cycle arrest associated with induced expression of p21$^{CIP/WAF1}$ in the anaplastic large cell lymphoma cell line Karpas 299," Oncogene, 2001, 20:590-598.
Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Kirsch, Gilbert H., "Heterocyclic Analogues of Carbazole Alkaloids," Current Organic Chemistry, 2001, 5:507-518.
Kuppen et al., "Tumor structure and extracellular matrix as a possible barrier for therapeutic approaches using immune cells or adenoviruses in colorectal cancer," Histochem. Cell, Biol., 2001, 115:67-72.
Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors."
Kwak et al., "Anaplastic Lymphoma Kinase Inhibition in Non-Small-Cell Lung Cancer," The New England Journal of Medicine, Oct. 28, 2010, 363(18):1693-1703.
Lamant et al., "Establishment of a novel anaplastic large-cell lymphoma-cell line (COST) from a 'small-cell variant' of ALCL," Leukemia, 2004, 18:1693-1698.
Lissoni et al., "Biotherapy with the pineal hormone melatonin plus aloe and myrrh tincture in untreatable metastatic cancer patients as an essence therapy of cancer," Cancer Therapy, 2009, 7:397-401.
Luo et al., "Principles of Cancer Therapy: Oncogene and Non-oncogene Addiction," Cell, Mar. 6, 2009, 136:823-837.
Mosse et al., "Identification of ALK as a major familial neuroblastoma predisposition gene," Nature, Oct. 16, 2008, 455:930-935, and Methods page.
National Cancer Institute, http://www.cancer.gov/, "A to Z List of Cancers," downloaded May 29, 2014, 22 pages.
O'Brien et al., "Section 2: Chronic Lymphoid Leukemias," Cancer: Principles & Practice of Oncology, $7^{th}$ Edition (DeVita et al., Eds.), 2133.
O'Brien et al., "Vascular cognitive impairment," The Lancet Neurology, Feb. 2003, 2:89-98.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Piva et al., "Ablation of oncogenic ALK is a viable therapeutic approach for anaplastic large-cell lymphomas," Blood, Jan. 2006, 107(2):689-697.
Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.
Scheinberg et al., "Section 2: Management of Acute Leukemias," Cancer: Principles & Practice of Oncology, $7^{th}$ Edition (DeVita et al., Eds.), 2005, 2088, 2092.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soda et al., "Identification of the transforming EML4-ALK fusion gene in non-small-cell lung cancer," Nature, Aug. 2, 2007, 448:561-566, and Methods page.
Soussi, Thierry, "p53 Antibodies in the Sera of Patients with Various Types of Cancer: A Review," Cancer Res., 2000, 60:1777-1788.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Wanner et al., "A convenient synthesis of 6-methylellipticine and 6-methylolivacine," Heterocycles, 1982, 19(12):2295-2300.
Wood et al., "Lack of the t(2;5) or Other Mutations Resulting in Expression of Anaplastic Lymphoma Kinase Catalytic Domain in CD30⁺Primary Cutaneous Lymphoproliferative Disorders and Hodgkin's Disease," Blood, Sep. 1, 1996, 88(5):1765-1770.
Zhao et al., "The progress of the research on anaplastic lymphoma kinase genetic abnormality of anaplastic large cell lymphoma," Foreign Medical Sciences (Section of Blood Transfusion and Heanatology), Oct. 15, 2004, 27(5):403-406.
Jhiang, Sissy M., "The RET proto-oncogene in human cancers," Oncogene, Nov. 20, 2000, 19(49):5590-5597.
Kiura et al., "A first-in-human phase I/II study of ALK inhibitor CN5424802 in patients with ALK-positive positive NSCLC," Journal of Clinical Oncology, May 2012, 30(15Suppl):7602, Abstract.
Kodama et al., "Alectinib shows potent antitumor activity against RET-rearranged non-small cell lung cancer," Molecular Cancer Therapeutics, Oct. 27, 2014, 13(12):2910-2918.
Hallberg et al., "ALK and NSCLC: Targeted therapy with ALK inhibitors," F1000 Reports Medicine, Nov. 1, 2011, 3:21:1-9.

(56) References Cited

OTHER PUBLICATIONS

Lipson et al., "Identification of new ALK and RET gene fusions from colorectal and lung cancer biopsies," Nature Medicine, 2012, vol. 18, pp. 382-384.
Communication of a Notice of Opposition for corresponding European Application No. 13842266.2 dated May 15, 2019.
U.S. Appl. No. 16/239,839, filed Jan. 4, 2019, Kinoshita et al.
U.S. Appl. No. 16/508,760, filed Jul. 11, 2019, Tomimatsu et al.

\* cited by examiner

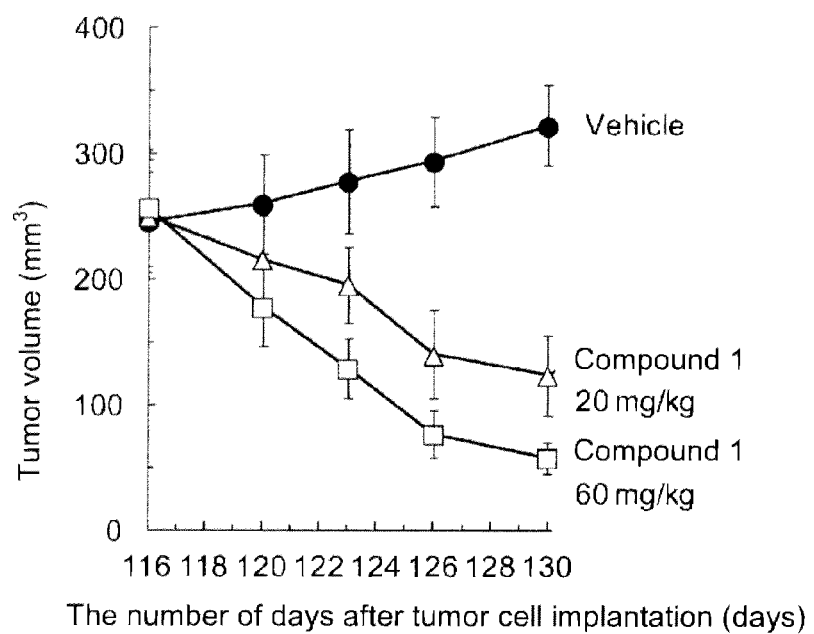

SEQUENCE LISTING

<160> NUMBER OF SEQ ID NOS: 46

<210> SEQ ID NO 1
<211> LENGTH: 4174
<212> TYPE: DNA
<213> ORGANISM: Homo sapiens
<220> FEATURE:
<221> NAME/KEY: misc_feature
<223> OTHER INFORMATION: RET transcript variant 4 (NM_020630.4 )

<400> SEQUENCE: 1

```
agtcccgcga ccgaagcagg gcgcgcagca gcgctgagtg ccccggaacg tgcgtcgcgc      60
ccccagtgtc cgtcgcgtcc gccgcgcccc gggcggggat ggggcggcca gactgagcgc     120
cgcacccgcc atccagaccc gccggcccta gccgcagtcc ctccagccgt ggccccagcg     180
cgcacgggcg atgcgaagg cgacgtccgg tgccgcgggg ctgcgtctgc tgttgctgct     240
gctgctgccg ctgctaggca aagtggcatt gggcctctac ttctcgaggg atgcttactg     300
ggagaagctg tatgtggacc aggcggccgg cacgcccttg ctgtacgtcc atgccctgcg     360
ggacgcccct gaggaggtgc ccagcttccg cctgggccag catctctacg gcacgtaccg     420
cacacggctg catgagaaca actggatctg catccaggag gacaccggcc tcctctacct     480
taaccggagc ctggaccata gctcctggga aagctcagt gtccgcaacc gcggctttcc     540
cctgctcacc gtctacctca aggtcttcct gtcacccaca tcccttcgtg agggcgagtg     600
ccagtggcca ggctgtgccc gcgtatactt ctccttcttc aacacctcct ttccagcctg     660
cagctccctc aagccccggg agctctgctt cccagagaca aggccctcct tccgcattcg     720
ggagaaccga cccccaggca ccttccacca gttccgcctg ctgcctgtgc agttcttgtg     780
ccccaacatc agcgtggcct acaggctcct ggagggtgag ggtctgccct tccgctgcgc     840
cccggacagc ctggaggtga gcacgcgctg ggccctggac cgcgagcagc gggagaagta     900
cgagctggtg gccgtgtgca ccgtgcacgc cggcgcgcgc gaggaggtgg tgatggtgcc     960 cttccggtg accgtgtacg acgaggacga ctcggcgccc accttccccg cgggcgtcga    1020
caccgccagc gccgtggtgg agttcaagcg gaaggaggac accgtggtgg ccacgctgcg    1080
tgtcttcgat gcagacgtgg tacctgcatc aggggagctg gtgaggcggt acacaagcac    1140
gctgctcccc ggggacacct gggccagca gaccttccgg gtggaacact ggccaacga    1200 gacctcggtc caggccaacg gcagcttcgt gcgggcgacc gtacatgact ataggctggt    1260
tctcaaccgg aacctctcca tctcggagaa ccgcaccatg cagctggcgg tgctggtcaa    1320
tgactcagac ttcagggcc caggagcggg cgtcctcttg ctccacttca acgtgtcggt    1380
gctgccggtc agcctgcacc tgcccagtac ctactccctc tccgtgagca ggagggctcg    1440
```

```
ccgatttgcc cagatcggga aagtctgtgt ggaaaactgc caggcattca gtggcatcaa    1500
cgtccagtac aagctgcatt cctctggtgc caactgcagc acgctagggg tggtcacctc    1560
agccgaggac acctcgggga tcctgtttgt gaatgacacc aaggccctgc ggcggcccaa    1620
gtgtgccgaa cttcactaca tggtggtggc caccgaccag cagacctcta ggcaggccca    1680
ggcccagctg cttgtaacag tggaggggtc atatgtggcc gaggaggcgg gctgcccct     1740 gtcctgtgca gtcagcaaga gacggctgga gtgtgaggag tgtggcggcc tgggctcccc    1800
aacaggcagg tgtgagtgga ggcaaggaga tggcaaaggg atcaccagga acttctccac    1860
ctgctctccc agcaccaaga cctgccccga cggccactgc gatgttgtgg agacccaaga    1920
catcaacatt tgccctcagg actgcctccg gggcagcatt gttggggac acgagcctgg     1980 ggagccccgg gggattaaag ctggctatgg cacctgcaac tgcttccctg aggaggagaa    2040
gtgcttctgc gagcccgaag acatccagga tccactgtgc gacgagctgt gccgcacggt    2100
gatcgcagcc gctgtcctct tctccttcat cgtctcggtg ctgctgtctg ccttctgcat    2160
ccactgctac cacaagtttg cccacaagcc acccatctcc tcagctgaga tgaccttccg    2220 gagggcccgcc caggccttcc cggtcagcta ctcctcttcc ggtgcccgcc ggccctcgct    2280
ggactccatg gagaaccagg tctccgtgga tgccttcaag atcctggagg atccaaagtg    2340
ggaattccct cggaagaact tggttcttgg aaaaactcta ggagaaggcg aatttggaaa    2400
agtggtcaag gcaacggcct ccatctgaa aggcagagca gggtacacca cggtggccgt     2460
gaagatgctg aaagagaacg cctccccgag tgagcttcga acctgctgt cagagttcaa      2520 cgtcctgaag caggtcaacc acccacatgt catcaaattg tatggggcct gcagccagga    2580 tggccccgctc ctcctcatcg tggagtacgc caaatacggc tccctgcggg gcttcctccg    2640
cgagagccgc aaagtggggc ctggctacct gggcagtgga ggcagccgca actccagctc    2700
cctggaccac ccggatgagc gggccctcac catgggcgac ctcatctcat ttgcctggca    2760
gatctcacag gggatgcagt atctggccga gatgaagctc gttcatcggg acttggcagc    2820
cagaaacatc ctggtagctg aggggcgaa gatgaagatt tcggatttcg gcttgtcccg      2880
agatgtttat gaagaggatt cctacgtgaa gaggagccag ggtcggattc cagttaaatg    2940
gatggcaatt gaatccctt tttgatcatat ctacaccacg caaagtgatg tatggtcttt      3000
tggtgtcctg ctgtgggaga tcgtgaccct aggggggaaac ccctatcctg ggattcctcc    3060
tgagcggctc ttcaaccttc tgaagaccgg ccaccggatg gagaggccag acaactgcag    3120
cgaggagatg taccgcctga tgctgcaatg ctggaagcag gagccggaca aaaggccggt    3180
gtttgcggac atcagcaaag acctggagaa gatgatggtt aagaggagag actacttgga    3240
ccttgcggcg tccactccat ctgactccct gatttatgac gacggcctct cagaggagga    3300
gacaccgctg gtggactgta ataatgcccc cctccctcga gccctccctt ccacatggat    3360
tgaaaacaaa ctctatggta gaatttccca tgcatttact agattctagc accgctgtcc    3420
cctctgcact atccttcctc tctgtgatgc ttttaaaa tgtttctggt ctgaacaaaa       3480
ccaaagtctg ctctgaacct ttttatttgt aaatgtctga ctttgcatcc agtttacatt    3540
taggcattat tgcaactatg tttttctaaa aggaagtgaa aataagtgta attaccacat    3600
tgcccagcaa cttaggatgg tagaggaaaa aacagatcag ggcggaactc tcagggaga     3660 ccaagaacag gttgaataag gcgcttctgg ggtgggaatc aagtcatagt acttctactt    3720
taactaagtg gataaatata caaatctggg gaggtattca gttgagaaag gagccaccag    3780
```

| | |
|---|---|
| caccactcag cctgcactgg gagcacagcc aggttccccc agacccctcc tgggcaggca | 3840 |
| ggtgcctctc agaggccacc cggcactggc gagcagccac tggccaagcc tcagcccag | 3900 |
| tcccagccac atgtcctcca tcaggggtag cgaggttgca ggagctggct ggccctggga | 3960 |
| ggacgcaccc ccactgctgt tttcacatcc tttcccttac ccaccttcag gacggttgtc | 4020 |
| acttatgaag tcagtgctaa agctggagca gttgcttttt gaaagaacat ggtctgtggt | 4080 |
| gctgtggtct tacaatggac agtaaatatg gttcttgcca aaactccttc ttttgtcttt | 4140 |
| gattaaatac tagaaattta aaaaaaaaaa aaaa | 4174 |

<210> SEQ ID NO 2
<211> LENGTH: 5629
<212> TYPE: DNA
<213> ORGANISM: Homo sapiens
<220> FEATURE:
<221> NAME/KEY: misc_feature
<223> OTHER INFORMATION: RET transcript variant 2 (NM_020975.4)

<400> SEQUENCE: 2

| | |
|---|---|
| agtcccgcga ccgaagcagg gcgcgcagca gcgctgagtg ccccggaacg tgcgtcgcgc | 60 |
| ccccagtgtc cgtcgcgtcc gccgcgcccc gggcggggat ggggcggcca gactgagcgc | 120 |
| cgcacccgcc atccagaccc gccggcccta gccgcagtcc ctccagccgt ggccccagcg | 180 |
| cgcacgggcg atggcgaagg cgacgtccgg tgccgcgggg ctgcgtctgc tgttgctgct | 240 |
| gctgctgccg ctgctaggca aagtggcatt gggcctctac ttctcgaggg atgcttactg | 300 |
| ggagaagctc tatgtggacc aggcggccgg cacgcccttg ctgtacgtcc atgccctgcg | 360 |
| ggacgcccct gaggaggtgc ccagcttccg cctgggccag catctctacg gcacgtaccg | 420 |
| cacacgctg catgagaaca actggatctg catccaggag gacaccggcc tcctctacct | 480 |
| taaccggagc ctggaccata gctcctggga aagctcagt gtccgcaacc gcggctttcc | 540 |
| cctgctcacc gtctacctca aggtcttcct gtcacccaca tcccttcgtg agggcgagtg | 600 |
| ccagtggcca ggctgtgccc gcgtatactt ctccttcttc aacacctcct ttccagcctg | 660 |
| cagctcctc aagccccggg agctctgctt cccagagaca aggccctcct tccgcattcg | 720 |
| ggagaaccga ccccaggca ccttccacca gttccgcctg ctgcctgtgc agttcttgtg | 780 |
| ccccaacatc agcgtggcct acaggctcct ggagggtgag ggtctgccct tccgctgcgc | 840 |
| cccgacagc ctggaggtga gcacgcgctg ggcctggac cgcgagcagc gggagaagta | 900 |
| cgagctggtg gccgtgtgca ccgtgcacgc cggcgcgcgc gaggaggtgg tgatggtgcc | 960 |
| cttcccggtg accgtgtacg acgaggacga ctcggcgccc accttccccg cgggcgtcga | 1020 |
| caccgccagc gccgtggtgg agttcaagcg gaaggaggac accgtggtgg ccacgctgcg | 1080 |
| tgtcttcgat gcagacgtgg tacctgcatc aggggagctg gtgaggcggt acacaagcac | 1140 |
| gctgctcccc ggggacacct gggcccagca gaccttccgg gtgaacact ggcccaacga | 1200 |
| gacctcggtc caggccaacg gcagcttcgt gcgggcgacc gtacatgact ataggctggt | 1260 |
| tctcaaccgg aacctctcca tctcggagaa ccgcaccatg cagctggcgg tgctggtcaa | 1320 |
| tgactcagac ttccagggcc caggagcggg cgtcctcttg ctccacttca acgtgtcggt | 1380 |
| gctgccggta gcctgcacc tgcccagtac ctactccctc tccgtgagca ggagggctcg | 1440 |
| ccgatttgcc cagatcggga aagtctgtgt ggaaaactgc caggcattca gtggcatcaa | 1500 |
| cgtccagtac aagctgcatt cctctggtgc caactgcagc acgctagggg tggtcacctc | 1560 |
| agccgaggac acctcgggga tcctgtttgt gaatgacacc aaggcctgc ggcggcccaa | 1620 |

-continued

```
gtgtgccgaa cttcactaca tggtggtggc caccgaccag cagacctcta ggcaggccca    1680
ggcccagctg cttgtaacag tggaggggtc atatgtggcc gaggaggcgg ctgccccct     1740 gtcctgtgca gtcagcaaga cggctggaa gtgtgaggag tgtggcggcc tgggctcccc    1800
aacaggcagg tgtgagtgga ggcaaggaga tggcaaaggg atcaccagga acttctccac    1860
ctgctctccc agcaccaaga cctgccccga cggccactgc gatgttgtgg agacccaaga    1920
catcaacatt tgccctcagg actgcctccg gggcagcatt gttggggac acgagcctgg     1980 ggagccccgg gggattaaag ctggctatgg cacctgcaac tgcttccctg aggaggagaa    2040
gtgcttctgc gagcccgaag acatccagga tccactgtgc gacgagctgt gccgcacggt    2100
gatcgcagcc gctgtcctct tctccttcat cgtctcggtg ctgctgtctg ccttctgcat    2160
ccactgctac cacaagtttg cccacaagcc acccatctcc tcagctgaga tgaccttccg    2220
gaggcccgcc caggccttcc cggtcagcta ctcctcttcc ggtgcccgcc ggccctcgct    2280
ggactccatg gagaaccagg tctccgtgga tgccttcaag atcctggagg atccaaagtg    2340
ggaattccct cggaagaact tggttcttgg aaaaactcta ggagaaggcg aatttggaaa    2400
agtggtcaag gcaacggcct tccatctgaa aggcagagca gggtacacca cggtggccgt    2460
gaagatgctg aaagagaacg cctccccgag tgagcttcga gacctgctgt cagagttcaa    2520
cgtcctgaag caggtcaacc acccacatgt catcaaattg tatgggcct gcagccagga    2580 tggcccgctc ctcctcatcg tggagtacgc caaatacggc tccctgcggg gcttcctccg    2640
cgagagccgc aaagtggggc ctggctacct gggcagtgga ggcagccgca actccagctc    2700
cctggaccac ccggatgagc gggccctcac catgggcgac ctcatctcat ttgcctggca    2760
gatctcacag gggatgcagt atctggccga gatgaagctc gttcatcggg acttggcagc    2820
cagaaacatc ctggtagctg aggggcgaa gatgaagatt tcggatttcg gcttgtcccg    2880
agatgtttat gaagaggatt cctacgtgaa gaggagccag ggtcggattc cagttaaatg    2940
gatggcaatt gaatcccttt ttgatcatat ctacaccacg caaagtgatg tatggtcttt    3000
tggtgtcctg ctgtgggaga tcgtgaccct agggggaaac ccctatcctg ggattcctcc    3060
tgagcggctc ttcaaccttc tgaagaccgg ccaccggatg gagaggccag acaactgcag    3120
cgaggagatg taccgcctga tgctgcaatg ctggaagcag gagccggaca aaaggccggt    3180
gtttgcggac atcagcaaag acctggaaa gatgatggtt aagaggagag actacttgga     3240
ccttgcggcg tccactccat ctgactccct gatttatgac gacggcctct cagaggagga    3300
gacaccgctg gtggactgta ataatgcccc cctccctcga gccctccctt ccacatggat    3360
tgaaaacaaa ctctatggca tgtcagaccc gaactggcct ggagagagtc ctgtaccact    3420
cacgagagct gatggcacta acactgggtt tccaagatat ccaaatgata gtgtatatgc    3480
taactggatg ctttcacccct cagcggcaaa attaatggac acgtttgata gttaacattt    3540
ctttgtgaaa ggtaatggac tcacaagggg aagaaacatg ctgagaatgg aaagtctacc    3600 ggcccttct ttgtgaacgt cacattggcc gagccgtgtt cagttcccag gtggcagact     3660 cgttttggt agtttgtttt aacttccaag gtggttttac ttctgatagc cggtgatttt    3720
ccctcctagc agacatgcca caccgggtaa gagctctgag tcttagtggt taagcattcc    3780
tttctcttca gtgcccagca gcacccagtg ttggtctgtg tccatcagtg accaccaaca    3840
ttctgtgttc acatgtgtgg gtccaacact tactacctgg tgtatgaaat tggacctgaa    3900
ctgttggatt tttctagttg ccgccaaaca aggcaaaaaa atttaaacat gaagcacaca    3960
cacaaaaaag gcagtaggaa aaatgctggc cctgatgacc tgtccttatt cagaatgaga    4020
```

-continued

```
gactgcgggg ggggcctggg ggtagtgtca atgcccctcc agggctggag gggaagaggg    4080
gccccgagga tgggcctggg ctcagcattc gagatcttga gaatgatttt tttttaatca    4140 tgcaacctttt ccttaggaag acatttggtt ttcatcatga ttaagatgat cctagatttt   4200
agcacaatgg agagattcca tgccatcttt actatgtgga tggtggtatc agggaagagg    4260
gctcacaaga cacatttgtc ccccgggccc accacatcat cctcacgtgt tcggtactga    4320
gcagccacta cccctgatga aacagtatg aagaagggg gctgttggag tcccagaatt      4380
gctgacagca gaggctttgc tgctgtgaat cccacctgcc accagcctgc agcacacccc    4440
acagccaagt agaggcgaaa gcagtggctc atcctacctg ttaggagcag gtagggcttg    4500
tactcacttt aatttgaatc ttatcaactt actcataaag ggacaggcta gctagctgtg    4560
ttagaagtag caatgacaat gaccaaggac tgctacacct ctgattacaa ttctgatgtg    4620
aaaaagatgg tgtttggctc ttatagagcc tgtgtgaaag gcccatggat cagctcttcc    4680
tgtgtttgta atttaatgct gctacaagat gtttctgttt cttagattct gaccatgact    4740
cataagcttc ttgtcattct tcattgcttg tttgtggtca cagatgcaca acactcctcc    4800
agtcttgtgg gggcagcttt tgggaagtct cagcagctct tctggctgtg ttgtcagcac    4860
tgtaacttcg cagaaaagag tcggattacc aaaacactgc ctgctcttca gacttaaagc    4920
actgatagga cttaaaatag tctcattcaa atactgtatt ttatataggc atttcacaaa    4980
aacagcaaaa ttgtggcatt tgtgaggcc aaggcttgga tgcgtgtgta atagagcctt     5040
gtggtgtgtg cgcacacacc cagagggaga gtttgaaaaa tgcttattgg acacgtaacc    5100
tggctctaat ttgggctgtt tttcagatac actgtgataa gttctttttac aaatatctat   5160 agacatggta aactttttggt tttcagatat gcttaatgat agtcttacta aatgcagaaa   5220
taagaataaa ctttctcaaa ttattaaaaa tgcctacaca gtaagtgtga attgctgcaa    5280
caggtttgtt ctcaggaggg taagaactcc aggtctaaac agctgaccca gtgatgggga    5340
atttatcctt gaccaattta tccttgacca ataacctaat tgtctattcc tgagttataa    5400
aagtccccat ccttattagc tctactggaa ttttcataca cgtaaatgca gaagttacta    5460
agtattaagt attactgagt attaagtagt aatctgtcag ttattaaaat ttgtaaaatc    5520
tatttatgaa aggtcattaa accagatcat gttccttttt ttgtaatcaa ggtgactaag    5580
aaaatcagtt gtgtaaataa aatcatgtat cataaaaaaa aaaaaaaa                 5629
```

<210> SEQ ID NO 3
<211> LENGTH: 1072
<212> TYPE: PRT
<213> ORGANISM: Homo sapiens
<220> FEATURE:
<221> NAME/KEY: MISC_FEATURE
<223> OTHER INFORMATION: RET isoform c precursor (NP_065681.1)

<400> SEQUENCE: 3

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
```

-continued

```
             65                  70                  75                  80
His Glu Asn Asn Trp Ile Cys Ile Gln Glu Asp Thr Gly Leu Leu Tyr
                    85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
                115                 120                 125

Pro Thr Ser Leu Arg Glu Gly Glu Cys Gln Trp Pro Gly Cys Ala Arg
130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
                180                 185                 190

Val Gln Phe Leu Cys Pro Asn Ile Ser Val Ala Tyr Arg Leu Leu Glu
                195                 200                 205

Gly Glu Gly Leu Pro Phe Arg Cys Ala Pro Asp Ser Leu Glu Val Ser
                210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
                260                 265                 270

Pro Ala Gly Val Asp Thr Ala Ser Ala Val Val Glu Phe Lys Arg Lys
                275                 280                 285

Glu Asp Thr Val Val Ala Thr Leu Arg Val Phe Asp Ala Asp Val Val
290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
                355                 360                 365

Thr Met Gln Leu Ala Val Leu Val Asn Asp Ser Asp Phe Gln Gly Pro
370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
                435                 440                 445

Cys Ser Thr Leu Gly Val Val Thr Ser Ala Glu Asp Thr Ser Gly Ile
450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495
```

```
Gln Ala Gln Leu Leu Val Thr Val Glu Gly Ser Tyr Val Ala Glu
            500                 505                 510
Ala Gly Cys Pro Leu Ser Cys Ala Val Ser Lys Arg Leu Glu Cys
            515                 520                 525
Glu Glu Cys Gly Gly Leu Gly Ser Pro Thr Gly Arg Cys Glu Trp Arg
    530                 535                 540
Gln Gly Asp Gly Lys Gly Ile Thr Arg Asn Phe Ser Thr Cys Ser Pro
545                 550                 555                 560
Ser Thr Lys Thr Cys Pro Asp Gly His Cys Asp Val Val Glu Thr Gln
                565                 570                 575
Asp Ile Asn Ile Cys Pro Gln Asp Cys Leu Arg Gly Ser Ile Val Gly
            580                 585                 590
Gly His Glu Pro Gly Glu Pro Arg Gly Ile Lys Ala Gly Tyr Gly Thr
        595                 600                 605
Cys Asn Cys Phe Pro Glu Glu Lys Cys Phe Cys Glu Pro Glu Asp
    610                 615                 620
Ile Gln Asp Pro Leu Cys Asp Glu Leu Cys Arg Thr Val Ile Ala Ala
625                 630                 635                 640
Ala Val Leu Phe Ser Phe Ile Val Ser Val Leu Leu Ser Ala Phe Cys
            645                 650                 655
Ile His Cys Tyr His Lys Phe Ala His Lys Pro Pro Ile Ser Ser Ala
            660                 665                 670
Glu Met Thr Phe Arg Arg Pro Ala Gln Ala Phe Pro Val Ser Tyr Ser
        675                 680                 685
Ser Ser Gly Ala Arg Arg Pro Ser Leu Asp Ser Met Glu Asn Gln Val
    690                 695                 700
Ser Val Asp Ala Phe Lys Ile Leu Glu Asp Pro Lys Trp Glu Phe Pro
705                 710                 715                 720
Arg Lys Asn Leu Val Leu Gly Lys Thr Leu Gly Glu Gly Glu Phe Gly
            725                 730                 735
Lys Val Val Lys Ala Thr Ala Phe His Leu Lys Gly Arg Ala Gly Tyr
            740                 745                 750
Thr Thr Val Ala Val Lys Met Leu Lys Glu Asn Ala Ser Pro Ser Glu
        755                 760                 765
Leu Arg Asp Leu Leu Ser Glu Phe Asn Val Leu Lys Gln Val Asn His
    770                 775                 780
Pro His Val Ile Lys Leu Tyr Gly Ala Cys Ser Gln Asp Gly Pro Leu
785                 790                 795                 800
Leu Leu Ile Val Glu Tyr Ala Lys Tyr Gly Ser Leu Arg Gly Phe Leu
            805                 810                 815
Arg Glu Ser Arg Lys Val Gly Pro Gly Tyr Leu Gly Ser Gly Gly Ser
            820                 825                 830
Arg Asn Ser Ser Ser Leu Asp His Pro Asp Glu Arg Ala Leu Thr Met
        835                 840                 845
Gly Asp Leu Ile Ser Phe Ala Trp Gln Ile Ser Gln Gly Met Gln Tyr
    850                 855                 860
Leu Ala Glu Met Lys Leu Val His Arg Asp Leu Ala Ala Arg Asn Ile
865                 870                 875                 880
Leu Val Ala Glu Gly Arg Lys Met Lys Ile Ser Asp Phe Gly Leu Ser
            885                 890                 895
Arg Asp Val Tyr Glu Glu Asp Ser Tyr Val Lys Arg Ser Gln Gly Arg
            900                 905                 910
```

```
Ile Pro Val Lys Trp Met Ala Ile Glu Ser Leu Phe Asp His Ile Tyr
            915                 920                 925

Thr Thr Gln Ser Asp Val Trp Ser Phe Gly Val Leu Leu Trp Glu Ile
        930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Arg Ile Ser His Ala
    1055                1060                1065

Phe Thr Arg Phe
    1070

<210> SEQ ID NO 4
<211> LENGTH: 1114
<212> TYPE: PRT
<213> ORGANISM: Homo sapiens
<220> FEATURE:
<221> NAME/KEY: MISC_FEATURE
<223> OTHER INFORMATION: RET isoform a precursor (NP_066124.1)

<400> SEQUENCE: 4

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190
```

```
Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
                275                 280                 285

Glu Asp Thr Val Val Ala Thr Leu Arg Val Phe Asp Ala Asp Val Val
        290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
            355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
        500                 505                 510

Ala Gly Cys Pro Leu Ser Cys Ala Val Ser Lys Arg Arg Leu Glu Cys
            515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605
```

```
Cys Asn Cys Phe Pro Glu Glu Glu Lys Cys Phe Cys Glu Pro Glu Asp
        610                 615                 620

Ile Gln Asp Pro Leu Cys Asp Glu Leu Cys Arg Thr Val Ile Ala Ala
625                 630                 635                 640

Ala Val Leu Phe Ser Phe Ile Ser Val Leu Leu Ser Ala Phe Cys
                645                 650                 655

Ile His Cys Tyr His Lys Phe Ala His Lys Pro Pro Ile Ser Ser Ala
        660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
                740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
                820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
                900                 905                 910

Ile Pro Val Lys Trp Met Ala Ile Glu Ser Leu Phe Asp His Ile Tyr
                915                 920                 925

Thr Thr Gln Ser Asp Val Trp Ser Phe Gly Val Leu Leu Trp Glu Ile
930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
                980                 985                 990

Asp Lys Arg Pro Val Phe Ala Asp Ile Ser Lys Asp Leu Glu Lys Met
                995                 1000                1005

Met Val Lys Arg Arg Asp Tyr Leu Asp Leu Ala Ala Ser Thr Pro
        1010                1015                1020

Ser Asp Ser Leu Ile Tyr Asp Asp Gly Leu Ser Glu Glu Glu Thr
```

```
               1025                1030                1035

Pro Leu Val Asp Cys Asn Asn Ala Pro Leu Pro Arg Ala Leu Pro
         1040                1045                1050

Ser Thr Trp Ile Glu Asn Lys Leu Tyr Gly Met Ser Asp Pro Asn
         1055                1060                1065

Trp Pro Gly Glu Ser Pro Val Pro Leu Thr Arg Ala Asp Gly Thr
         1070                1075                1080

Asn Thr Gly Phe Pro Arg Tyr Pro Asn Asp Ser Val Tyr Ala Asn
         1085                1090                1095

Trp Met Leu Ser Pro Ser Ala Ala Lys Leu Met Asp Thr Phe Asp
         1100                1105                1110

Ser

<210> SEQ ID NO 5
<211> LENGTH: 2808
<212> TYPE: DNA
<213> ORGANISM: Homo sapiens
<220> FEATURE:
<221> NAME/KEY: misc_feature
<223> OTHER INFORMATION: KIF5B-RET (K15;R12 variant 4)

<400> SEQUENCE: 5
atggcggacc tggccgagtg caacatcaaa gtgatgtgtc gcttcagacc tctcaacgag     60
tctgaagtga accgcggcga caagtacatc gccaagtttc agggagaaga cacggtcgtg    120
atcgcgtcca agccttatgc atttgatcgg gtgttccagt caagcacatc tcaagagcaa    180
gtgtataatg actgtgcaaa agagattgtt aaagatgtac ttgaaggata taatggaaca    240
atatttgcat atggacaaac atcctctggg aagacacaca atggaggg taaacttcat    300 gatccagaag gcatgggaat tattccaaga atagtgcaag atattttaa ttatatttac    360 tccatggatg aaaatttgga atttcatatt aaggtttcat attttgaaat atatttggat    420
aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg gtagtgaaaa ggttagtaaa    720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaagaaaaa aataagatcc tgcggaacac tattcagtgg   1080
cttgaaaatg agctcaacag atggcgtaat ggggagacgg tgcctattga tgaacagttt   1140
gacaaagaga agccaacctt ggaagctttc acagtggata agatattac tcttaccaat   1200 gataaaccag caaccgcaat tggagttata ggaaatttta ctgatgctga agaagaaag   1260 tgtgaagaag aaattgctaa attatacaaa cagcttgatg acaaggatga agaaattaac   1320
cagcaaagtc aactggtaga gaaactgaag acgcaaatgt tggatcagga ggagctttg   1380 gcatctacca aagggatca agacaatatg caagctgagc tgaatcgcct tcaagcagaa   1440
aatgatgcct ctaaagaaga agtgaaagaa gttttacagg ccctagaaga acttgctgtc   1500
```

```
aattatgatc agaagtctca ggaagttgaa gacaaaacta aggaatatga attgcttagt    1560
gatgaattga atcagaaatc ggcaacttta gcgagtatag atgctgagct tcagaaactt    1620
aaggaaatga ccaaccacca gaaaaaacga gcagctgaga tgatggcatc tttactaaaa    1680
gaccttgcag aaataggaat tgctgtggga ataatgatg taaaggagga tccaaagtgg    1740
gaattccctc ggaagaactt ggttcttgga aaaactctag gagaaggcga atttggaaaa    1800
gtggtcaagg caacggcctt ccatctgaaa ggcagagcag gtacaccac ggtggccgtg     1860 aagatgctga agagaacgc ctccccgagt gagctgcgag acctgctgtc agagttcaac     1920
gtcctgaagc aggtcaacca cccacatgtc atcaaattgt atggggcctg cagccaggat    1980
ggcccgctcc tcctcatcgt ggagtacgcc aaatacggct ccctgcgggg cttcctccgc    2040
gagagccgca agtggggcc tggctacctg ggcagtggag gcagccgcaa ctccagctcc     2100
ctggaccacc cggatgagcg ggccctcacc atgggcgacc tcatctcatt tgcctggcag    2160
atctcacagg ggatgcagta tctggccgag atgaagctcg ttcatcggga cttggcagcc    2220
agaaacatcc tggtagctga ggggcggaag atgaagattt cggatttcgg cttgtcccga    2280
gatgtttatg aagaggattc ctacgtgaag aggagccagg gtcggattcc agttaaatgg    2340
atggcaattg aatcccttt tgatcatatc tacaccacgc aaagtgatgt atggtctttt     2400
ggtgtcctgc tgtgggagat cgtgacccta ggggaaaacc cctatcctgg gattcctcct    2460
gagcggctct tcaaccttct gaagaccggc caccggatgg agaggccaga caactgcagc    2520
gaggagatgt accgcctgat gctgcaatgc tggaagcagg agccggacaa aaggccggtg    2580
tttgcggaca tcagcaaaga cctggagaag atgatggtta agaggagaga ctacttggac    2640
cttgcggcgt ccactccatc tgactccctg atttatgacg acggcctctc agaggaggag    2700
acaccgctgg tggactgtaa taatgcccccc ctccctcgag ccctcccttc cacatggatt    2760
gaaaacaaac tctatggtag aatttcccat gcatttacta gattctag                2808
```

<210> SEQ ID NO 6
<211> LENGTH: 2997
<212> TYPE: DNA
<213> ORGANISM: Homo sapiens
<220> FEATURE:
<221> NAME/KEY: misc_feature
<223> OTHER INFORMATION: KIF5B-RET (K16;R12 variant4)

<400> SEQUENCE: 6

```
atggcggacc tggccgagtg caacatcaaa gtgatgtgtc gcttcagacc tctcaacgag      60
tctgaagtga accgcggcga caagtacatc gccaagtttc agggagaaga cacggtcgtg     120
atcgcgtcca agcctattgc atttgatcgg gtgttccagt caagcacatc tcaagagcaa     180
gtgtataatg actgtgcaaa gaagattgtt aaagatgtac ttgaaggata taatggaaca     240
atatttgcat atggacaaac atcctctggg aagacacaca atgtgaggg taaacttcat     300 gatccagaag gcatgggaat tattccaaga atagtgcaag atatttttaa ttatatttac     360
tccatggatg aaaatttgga atttcatatt aaggtttcat atttttgaaat atatttggat    420 aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atcaacagaa catgtagcag ttacaaatat gaatgaacat    600
agctctagga gtcacagtat atttctta atgtcaaac aagagaacac acaaacggaa      660
caaaagctga gtggaaaact ttatctggtt gatttagctg gtagtgaaaa ggttagtaaa    720
```

```
actggagctg aaggtgctgt gctggatgaa gctaaaaaca tcaacaagtc actttctgct      780
cttgaaaatg ttatttctgc tttggctgag ggtagtacat atgttccata tcgagatagt      840
aaaatgacaa gaatccttca agattcatta ggtggcaact gtagaaccac tattgtaatt      900
tgctgctctc catcatcata caatgagtct gaaacaaaat ctacactctt atttggccaa      960
agggccaaaa caattaagaa cacagtttgt gtcaatgtgg agttaactgc agaacagtgg     1020
aaaaagaagt atgaaaaaga aaagaaaaa aataagatcc tgcggaacac tattcagtgg      1080
cttgaaaatg agctcaacag atggcgtaat ggggagacgg tgcctattga tgaacagttt     1140
gacaaagaga aagccaactt ggaagctttc acagtggata agatattac tcttaccaat      1200
gataaaccag caaccgcaat tggagttata ggaaatttta ctgatgctga agaagaaag      1260
tgtgaagaag aaattgctaa attatacaaa cagcttgatg acaaggatga agaaattaac     1320
cagcaaagtc aactggtaga gaaactgaag acgcaaatgt tggatcagga ggagcttttg     1380
gcatctacca aagggatca agacaatatg caagctgagc tgaatcgcct tcaagcagaa      1440
aatgatgcct ctaaagaaga agtgaaagaa gttttacagg ccctagaaga acttgctgtc     1500
aattatgatc agaagtctca ggaagttgaa gacaaaacta aggaatatga attgcttagt     1560
gatgaattga atcagaaatc ggcaacttta gcgagtatag atgctgagct tcagaaactt     1620
aaggaaatga ccaaccacca gaaaaaacga gcagctgaga tgatggcatc tttactaaaa     1680
gaccttgcag aaataggaat tgctgtggga aataatgatg taaagcagcc tgagggaact     1740
ggcatgatag atgaagagtt cactgttgca agactctaca ttagcaaaat gaagtcagaa     1800
gtaaaaacca tggtgaaacg ttgcaagcag ttagaaagca cacaaactga gagcaacaaa     1860
aaaatggaag aaaatgaaaa ggagttagca gcatgtcagc ttcgtatctc tcaagaggat     1920
ccaaagtggg aattccctcg gaagaacttg gttcttggaa aaactctagg agaaggcgaa     1980
tttggaaaag tggtcaaggc aacggccttc catctgaaag gcagagcagg gtacaccacg     2040
gtggccgtga agatgctgaa agagaacgcc tccccgagtg agcttcgaga cctgctgtca     2100
gagttcaacg tcctgaagca ggtcaaccac ccacatgtca tcaaattgta tggggcctgc     2160
agccaggatg gcccgctcct cctcatcgtg gagtacgcca aatacggctc cctgcggggc     2220
ttcctccgcg agagccgcaa agtggggcct ggctacctgg gcagtggagg cagccgcaac     2280
tccagctccc tggaccaccc ggatgagcgg gccctcacca tgggcgacct catctcattt     2340
gcctggcaga tctcacaggg gatgcagtat ctggccgaga tgaagctcgt tcatcgggac     2400
ttggcagcca gaaacatcct ggtagctgag gggcggaaga tgaagatttc ggatttcggc     2460
ttgtcccgag atgtttatga agaggattcg tacgtgaaga ggagccaggg tcggattcca     2520
gttaaatgga tggcaattga atccttttt gatcatatct acaccacgca aagtgatgta     2580
tggtcttttg gtgtcctgct gtgggagatc gtgaccctag ggggaaaccc ctatcctggg     2640
attcctcctg agcggctctt caaccttctg aagaccggcc accggatgga gaggccagac     2700
aactgcagcg aggagatgta ccgcctgatg ctgcaatgct ggaagcagga gccggacaaa     2760
aggccggtgt ttcgcgacat cagcaaagac ctggagaaga tgatggttaa gaggagagac     2820
tacttggacc ttgcggcgtc cactccatct gactccctga tttatgacga cggcctctca     2880
gaggaggaga caccgctggt ggactgtaat aatgccccc tccctcgagc cctcccttcc     2940
acatggattg aaaacaaact ctatggtaga atttcccatg catttactag attctag      2997
```

<210> SEQ ID NO 7

<211> LENGTH: 3522
<212> TYPE: DNA
<213> ORGANISM: Homo sapiens
<220> FEATURE:
<221> NAME/KEY: misc_feature
<223> OTHER INFORMATION: KIF5B-RET (K22;R12 variant4)

<400> SEQUENCE: 7

```
atggcggacc tggccgagtg caacatcaaa gtgatgtgtc gcttcagacc tctcaacgag      60
tctgaagtga accgcggcga caagtacatc gccaagtttc agggagaaga cacggtcgtg     120
atcgcgtcca agccttatgc atttgatcgg gtgttccagt caagcacatc tcaagagcaa     180
gtgtataatg actgtgcaaa gaagattgtt aaagatgtac ttgaaggata taatggaaca     240
atatttgcat atggacaaac atcctctggg aagacacaca atggagggg taaacttcat     300
gatccagaag gcatgggaat tattccaaga atagtgcaag atatttttaa ttatatttac     360
tccatggatg aaaatttgga atttcatatt aaggtttcat attttgaaat atatttggat     420
aagataaggg acctgttaga tgtttcaaag accaaccttt cagttcatga agacaaaaac     480
cgagttccct atgtaaaggg gtgcacagag cgttttgtat gtagtccaga tgaagttatg     540
gataccatag atgaaggaaa atccaacaga catgtagcag ttacaaatat gaatgaacat     600
agctctagga gtcacagtat atttcttatt aatgtcaaac aagagaacac acaaacggaa     660
caaaagctga gtggaaaact ttatctggtt gatttagctg gtagtgaaaa ggttagtaaa     720
actggagctg aaggtgctgt gctggatgaa gctaaaaaca tcaacaagtc actttctgct     780
cttggaaatg ttatttctgc tttggctgag ggtagtacat atgttccata tcgagatagt     840
aaaatgacaa gaatccttca agattcatta ggtggcaact gtagaaccac tattgtaatt     900
tgctgctctc catcatcata caatgagtct gaaacaaaat ctacactctt atttggccaa     960
agggccaaaa caattaagaa cacagtttgt gtcaatgtgg agttaactgc agaacagtgg    1020
aaaaagaagt atgaaaaaga aaagaaaaa aataagatcc tgcggaacac tattcagtgg    1080
cttgaaaatg agctcaacag atggcgtaat ggggagacgg tgcctattga tgaacagttt    1140
gacaaagaga agccaacctt ggaagctttc acagtggata agatattac tcttaccaat    1200
gataaaccag caaccgcaat tggagttata ggaaatttta ctgatgctga agaagaaag    1260
tgtgaagaag aaattgctaa attatacaaa cagcttgatg acaaggatga agaaattaac    1320
cagcaaagtc aactggtaga aaactgaag acgcaaatgt tggatcagga ggagctttg    1380
gcatctacca gaagggatca agacaatatg caagctgagc tgaatcgcct tcaagcagaa    1440
aatgatgcct ctaaagaaga agtgaaagaa gttttacagg ccctagaaga acttgctgtc    1500
aattatgatc agaagtctca ggaagttgaa gacaaaacta aggaatatga attgcttagt    1560
gatgaattga atcagaaatc ggcaacttta gcgagtatag atgctgagct tcagaaactt    1620
aaggaaatga ccaaccacca gaaaaaacga gcagctgaga tgatggcatc tttactaaaa    1680
gaccttgcag aaataggaat tgctgtggga ataatgatg taaagcagcc tgagggaact    1740
ggcatgatag atgaagagtt cactgttgca agactctaca ttagcaaaat gaagtcagaa    1800
gtaaaaacca tggtgaaacg ttgcaagcag ttagaaagca cacaaactga gcaacaaaa    1860
aaaatggaag aaaatgaaaa ggagttagca gcatgtcagc ttcgtatctc tcaacatgaa    1920
gccaaaatca gtcattgac tgaatacctt caaaatgtgg aacaaaagaa aagacagttg    1980
gaggaatctg tcgatgccct cagtgaagaa ctagtccagc ttcgagcaca agagaaagtc    2040
catgaaatgg aaaaggagca cttaaataag gttcagactg caaatgaagt taagcaagct    2100
```

| | |
|---|---:|
| gttgaacagc agatccagag ccatagagaa actcatcaaa aacagatcag tagtttgaga | 2160 |
| gatgaagtag aagcaaaagc aaaacttatt actgatcttc aagaccaaaa ccagaaaatg | 2220 |
| atgttagagc aggaacgtct aagagtagaa catgagaagt tgaaagccac agatcaggaa | 2280 |
| aagagcagaa aactacatga acttacggtt atgcaagata dacgaaaca agcaagacaa | 2340 |
| gacttgaagg gtttggaaga dacagtggca aaagaacttc agactttaca aacctgcgc | 2400 |
| aaactctttg ttcaggacct ggctacaaga gttaaaaagg aggatccaaa gtgggaattc | 2460 |
| cctcggaaga acttggttct tggaaaaact ctaggagaag gcgaatttgg aaaagtggtc | 2520 |
| aaggcaacgg ccttccatct gaaaggcaga gcagggtaca ccacggtggc cgtgaagatg | 2580 |
| ctgaaagaga acgcctcccc gagtgagctg cgagacctgc tgtcagagtt caacgtcctg | 2640 |
| aagcaggtca accacccaca tgtcatcaaa ttgtatgggg cctgcagcca ggatggcccg | 2700 |
| ctcctcctca tcgtggagta cgccaaatac ggctccctgc ggggcttcct ccgcgagagc | 2760 |
| cgcaaagtgg ggcctggcta cctgggcagt ggaggcagcc gcaactccag ctccctggac | 2820 |
| cacccgatg agcgggccct caccatgggc gacctcatct catttgcctg gcagatctca | 2880 |
| caggggatgc agtatctggc cgagatgaag ctcgttcatc gggacttggc agccagaaac | 2940 |
| atcctggtag ctgaggggcg gaagatgaag atttcggatt tcggcttgtc ccgagatgtt | 3000 |
| tatgaagagg attcctacgt gaagaggagc cagggtcgga ttccagttaa atggatggca | 3060 |
| attgaatccc tttttgatca tatctacacc acgcaaagtg atgtatggtc ttttggtgtc | 3120 |
| ctgctgtggg agatcgtgac cctaggggga accccctatc ctgggattcc tctgagcgg | 3180 |
| ctcttcaacc ttctgaagac cggccaccgg atggagaggc cagacaactg cagcgaggag | 3240 |
| atgtaccgcc tgatgctgca atgctggaag caggagccgg acaaaaggcc ggtgtttgcg | 3300 |
| gacatcagca agaccctgga gaagatgatg gttaagagga gagactactt ggaccttgcg | 3360 |
| gcgtccactc catctgactc cctgatttat gacgacggcc tctcagagga ggagacaccg | 3420 |
| ctggtggact gtaataatgc cccctccct cgagccctcc cttccacatg gattgaaaac | 3480 |
| aaactctatg gtagaatttc ccatgcattt actagattct ag | 3522 |

<210> SEQ ID NO 8
<211> LENGTH: 3627
<212> TYPE: DNA
<213> ORGANISM: Homo sapiens
<220> FEATURE:
<221> NAME/KEY: misc_feature
<223> OTHER INFORMATION: KIF5B-RET (K23;R12 variant4)

<400> SEQUENCE: 8

| | |
|---|---:|
| atggcggacc tggccgagtg caacatcaaa gtgatgtgtc gcttcagacc tctcaacgag | 60 |
| tctgaagtga accgcggcga caagtacatc gccaagtttc aggagaaga cacggtcgtg | 120 |
| atcgcgtcca agcctttgc atttgatcgg gtgttccagt caagcacatc tcaagagcaa | 180 |
| gtgtataatg actgtgcaaa gaagattgtt aaagatgtac ttgaaggata taatggaaca | 240 |
| atatttgcat atggacaaac atcctctggg aagacacaca caatggaggg taaacttcat | 300 |
| gatccagaag gcatgggaat tattccaaga atagtgcaag atattttta ttatatttac | 360 |
| tccatggatg aaaatttgga atttcatatt aaggtttcat attttgaaat atatttggat | 420 |
| aagataaggg acctgttaga tgtttcaaag accaacctttt cagttcatga agacaaaaac | 480 |
| cgagttccct atgtaaaggg gtgcacagag cgttttgtat gtagtccaga tgaagttatg | 540 |
| gataccatag atgaaggaaa atccaacaga catgtagcag ttacaaatat gaatgaacat | 600 |

```
agctctagga gtcacagtat atttcttatt aatgtcaaac aagagaacac acaaacggaa      660
caaaagctga gtggaaaact ttatctggtt gatttagctg gtagtgaaaa ggttagtaaa      720
actggagctg aaggtgctgt gctggatgaa gctaaaaaca tcaacaagtc actttctgct      780
cttggaaatg ttatttctgc tttggctgag ggtagtacat atgttccata tcgagatagt      840
aaaatgacaa gaatccttca agattcatta ggtggcaact gtagaaccac tattgtaatt      900
tgctgctctc catcatcata caatgagtct gaaacaaaat ctacactctt atttggccaa      960
agggccaaaa caattaagaa cacagtttgt gtcaatgtgg agttaactgc agaacagtgg     1020
aaaaagaagt atgaaaaaga aaagaaaaa aataagatcc tgcggaacac tattcagtgg      1080
cttgaaaatg agctcaacag atggcgtaat ggggagacgg tgcctattga tgaacagttt     1140
gacaaagaga aagccaactt ggaagctttc acagtggata agatattac tcttaccaat       1200 gataaaccag caaccgcaat tggagttata ggaaatttta ctgatgctga agaagaaag       1260 tgtgaagaag aaattgctaa attatacaaa cagcttgatg acaaggatga agaaattaac      1320
cagcaaagtc aactggtaga gaaactgaag acgcaaatgt tggatcagga ggagcttttg     1380
gcatctacca gaaggggatca agacaatatg caagctgagc tgaatcgcct tcaagcagaa    1440
aatgatgcct ctaaagaaga agtgaaagaa gttttacagg ccctagaaga acttgctgtc     1500
aattatgatc agaagtctca ggaagttgaa gacaaaacta aggaatatga attgcttagt    1560
gatgaattga atcagaaatc ggcaacttta gcgagtatag atgctgagct tcagaaactt    1620
aaggaaatga ccaaccacca gaaaaaacga gcagctgaga tgatggcatc tttactaaaa    1680
gaccttgcag aaataggaat tgctgtggga aataatgatg taaagcagcc tgagggaact    1740
ggcatgatag atgaagagtt cactgttgca agactctaca ttagcaaaat gaagtcagaa    1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaacatgaa   1920
gccaaaatca agtcattgac tgaataccct caaaatgtgg aacaaaagaa aagacagttg   1980
gaggaatctg tcgatgccct cagtgaagaa ctagtccagc ttcgagcaca agagaaagtc   2040
catgaaatgg aaaaggagca cttaaataag gttcagactg caaatgaagt taagcaagct   2100
gttgaacagc agatccagag ccatagagaa actcatcaaa aacagatcag tagtttgaga   2160
gatgaagtag aagcaaaagc aaaacttatt actgatcttc aagaccaaaa ccagaaaatg   2220
atgttagagc aggaacgtct aagagtagaa catgagaagt tgaaagccac agatcaggaa   2280
aagagcagaa aactacatga acttacggtt atgcaagata gacgagaaca agcaagacaa   2340
gacttgaagg gtttggaaga gacagtggca aaagaacttc agactttaca caacctgcgc   2400
aaactctttg ttcaggacct ggctacaaga gttaaaaaga gtgctgagat tgattctgat   2460
gacaccggag gcagcgctgc tcagaagcaa aaaatctcct ttcttgaaaa taatcttgaa   2520
cagctcacta aagtgcacaa acaggaggat ccaaagtggg aattccctcg gaagaacttg   2580
gttcttggaa aaactctagg agaaggcgaa tttggaaaag tggtcaaggc aacggccttc   2640
catctgaaag gcagagcagg gtacaccacg gtggccgtga agatgctgaa agagaacgcc   2700
tccccgagtg agcttcgaga cctgctgtca gagttcaacg tcctgaagca ggtcaaccac   2760
ccacatgtca tcaaattgta tggggcctgc agccaggatg gcccgctcct cctcatcgtg   2820
gagtacgcca aatacggctc cctgcggggc ttcctccgcg agagccgcaa agtggggcct   2880
ggctacctgg gcagtggagg cagccgcaac tccagctccc tggaccaccc ggatgagcgg   2940
gccctcacca tgggcgacct catctcattt gcctggcaga tctcacaggg gatgcagtat   3000
```

```
ctggccgaga tgaagctcgt tcatcgggac ttggcagcca gaaacatcct ggtagctgag    3060
gggcggaaga tgaagatttc ggatttcggc ttgtcccgag atgtttatga agaggattcc    3120
tacgtgaaga ggagccaggg tcggattcca gttaaatgga tggcaattga atccctttt    3180 gatcatatct acaccacgca aagtgatgta tggtcttttg gtgtcctgct gtgggagatc    3240
gtgaccctag ggggaaaccc ctatcctggg attcctcctg agcggctctt caaccttctg    3300
aagaccggcc accggatgga gaggccagac aactgcagcg aggagatgta ccgcctgatg    3360
ctgcaatgct ggaagcagga gccggacaaa aggccggtgt ttgcggacat cagcaaagac    3420
ctggagaaga tgatggttaa gaggagagac tacttggacc ttgcggcgtc cactccatct    3480
gactccctga tttatgacga cggcctctca gaggaggaga caccgctggt ggactgtaat    3540 aatgccccc tccctcgagc cctcccttcc acatggattg aaaacaaact ctatggtaga    3600
atttcccatg catttactag attctag                                        3627
```

<210> SEQ ID NO 9
<211> LENGTH: 4101
<212> TYPE: DNA
<213> ORGANISM: Homo sapiens
<220> FEATURE:
<221> NAME/KEY: misc_feature
<223> OTHER INFORMATION: KIF5B-RET (K24;R11 variant4)

<400> SEQUENCE: 9

```
atggcggacc tggccgagtg caacatcaaa gtgatgtgtc gcttcagacc tctcaacgag     60
tctgaagtga accgcggcga caagtacatc gccaagtttc agggagaaga cacggtcgtg    120
atcgcgtcca agccttatgc atttgatcgg gtgttccagt caagcacatc tcaagagcaa    180
gtgtataatg actgtgcaaa gaagattgtt aaagatgtac ttgaaggata taatggaaca    240
atatttgcat atggacaaac atcctctggg aagacacaca atgtgagggg taaacttcat    300
gatccagaag gcatgggaat tattccaaga atagtgcaag atatttttaa ttatatttac    360
tccatggatg aaaatttgga atttcatatt aaggtttcat attttgaaat atatttggat    420
aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg gtagtgaaaa ggttagtaaa    720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg    1020
aaaaagaagt atgaaaaaga aaagaaaaa aataagatcc tgcggaacac tattcagtgg    1080
cttgaaaatg agctcaacag atggcgtaat ggggagacgg tgcctattga tgaacagttt    1140
gacaaagaga agccaactt ggaagctttc acagtggata agatattac tcttaccaat    1200 gataaaccag caaccgcaat tggagttata ggaaattta ctgatgctga agaagaaag    1260 tgtgaagaag aaattgctaa attatacaaa cagcttgatg acaaggatga agaaattaac    1320
cagcaaagtc aactggtaga gaaactgaag acgcaaatgt tggatcagga ggagcttttg    1380
```

```
gcatctacca gaagggatca agacaatatg caagctgagc tgaatcgcct tcaagcagaa    1440
aatgatgcct ctaaagaaga agtgaaagaa gttttacagg ccctagaaga acttgctgtc    1500
aattatgatc agaagtctca ggaagttgaa gacaaaacta aggaatatga attgcttagt    1560
gatgaattga atcagaaatc ggcaacttta gcgagtatag atgctgagct tcagaaactt    1620
aaggaaatga ccaaccacca gaaaaaacga gcagctgaga tgatggcatc tttactaaaa    1680
gaccttgcag aaataggaat tgctgtggga aataatgatg taaagcagcc tgagggaact    1740
ggcatgatag atgaagagtt cactgttgca agactctaca ttagcaaaat gaagtcagaa    1800
gtaaaaacca tggtgaaacg ttgcaagcag ttagaaagca cacaaactga gagcaacaaa    1860
aaaatggaag aaaatgaaaa ggagttagca gcatgtcagc ttcgtatctc tcaacatgaa    1920
gccaaaatca agtcattgac tgaataccct caaaatgtgg aacaaaagaa aagacagttg    1980
gaggaatctg tcgatgccct cagtgaagaa ctagtccagc ttcgagcaca agagaaagtc    2040
catgaaatgg aaaaggagca cttaaataag gttcagactg caaatgaagt taagcaagct    2100
gttgaacagc agatccagag ccatagagaa actcatcaaa aacagatcag tagtttgaga    2160
gatgaagtag aagcaaaagc aaaacttatt actgatcttc aagaccaaaa ccagaaaatg    2220
atgttagagc aggaacgtct aagagtagaa catgagaagt tgaaagccac agatcaggaa    2280
aagagcagaa aactacatga acttacggtt atgcaagata gacgaaaca agcaagacaa    2340
gacttgaagg gtttggaaga gacagtggca aaagaacttc agactttaca caacctgcgc    2400
aaactctttg ttcaggacct ggctacaaga gttaaaaaga gtgctgagat tgattctgat    2460
gacaccggag gcagcgctgc tcagaagcaa aaaatctcct ttcttgaaaa taatcttgaa    2520
cagctcacta aagtgcacaa acagttggta cgtgataatg cagatctccg ctgtgaactt    2580
cctaagttgg aaaagcgact tcgagctaca gctgagagag tgaaagcttt ggaatcagca    2640
ctgaaagaag ctaaagaaaa tgcatctcgt gatcgcaaac gctatcagca agaagtagat    2700
cgcataaagg aagcagtcag gtcaaagaat atggccagaa gagggcattc tgcacagatt    2760
gatccactgt gcgacgagct gtgccgcacg gtgatcgcag ccgctgtcct cttctccttc    2820
atcgtctcgg tgctgctgtc tgccttctgc atccactgct accacaagtt tgcccacaag    2880
ccacccatct cctcagctga gatgaccttc cggaggcccg cccaggcctt cccggtcagc    2940
tactcctctt ccggtgcccg ccggccctcg ctggactcca tggagaacca ggtctccgtg    3000
gatgccttca agatcctgga ggatccaaag tgggaattcc ctcggaagaa cttggttctt    3060
ggaaaaactc taggagaagg cgaatttgga aaagtggtca aggcaacggc cttccatctg    3120
aaaggcagag cagggtacac cacggtggcc gtgaagatgc tgaaagagaa cgcctccccg    3180
agtgagcttc gagacctgct gtcagagttc aacgtcctga gcaggtcaa ccacccacat    3240
gtcatcaaat tgtatgggc ctgcagccag gatggcccgc tcctcctcat cgtggagtac    3300
gccaaatacg gctccctgcg gggcttcctc cgcgagagcc gcaaagtggg gcctggctac    3360
ctgggcagtg gaggcagccg caactccagc tccctggacc accggatga gcgggccctc    3420
accatgggcg acctcatctc atttgcctgg cagatctcac aggggatgca gtatctggcc    3480
gagatgaagc tcgttcatcg ggacttggca gccagaaaca tcctggtagc tgaggggcgg    3540
aagatgaaga tttcggattt cggcttgtcc cgagatgttt atgaagagga ttcctacgtg    3600
aagaggagcc agggtcggat tccagttaaa tggatggcaa ttgaatccct ttttgatcat    3660
atctacacca cgcaaagtga tgtatggtct tttggtgtcc tgctgtggga gatcgtgacc    3720
```

```
ctaggggga  accoctatcc  tgggattcct  cctgagcggc  tcttcaacct  tctgaagacc    3780
ggccaccgga  tggagaggcc  agacaactgc  agcgaggaga  tgtaccgcct  gatgctgcaa    3840
tgctggaagc  aggagccgga  caaaaggccg  gtgtttgcgg  acatcagcaa  agacctggag    3900
aagatgatgg  ttaagaggag  agactacttg  gaccttgcgg  cgtccactcc  atctgactcc    3960
ctgatttatg  acgacggcct  ctcagaggag  gagacaccgc  tggtggactg  taataatgcc    4020
cccctccctc  gagccctccc  ttccacatgg  attgaaaaca  aactctatgg  tagaattccc    4080
catgcattta  ctagattcta  g                                                 4101
```

<210> SEQ ID NO 10
<211> LENGTH: 2934
<212> TYPE: DNA
<213> ORGANISM: Homo sapiens
<220> FEATURE:
<221> NAME/KEY: misc_feature
<223> OTHER INFORMATION: KIF5B-RET (K15;R12 variant2)

<400> SEQUENCE: 10

```
atggcggacc  tggccgagtg  caacatcaaa  gtgatgtgtc  gcttcagacc  tctcaacgag     60
tctgaagtga  accgcggcga  caagtacatc  gccaagtttc  agggagaaga  cacggtcgtg    120
atcgcgtcca  agccttatgc  atttgatcgg  gtgttccagt  caagcacatc  tcaagagcaa    180
gtgtataatg  actgtgcaaa  ggagattgtt  aaagatgtac  ttgaaggata  taatggaaca    240
atatttgcat  atggacaaac  atcctctggg  aagacacaca  caatggaggg  taaacttcat    300
gatccagaag  gcatgggaat  tattccaaga  atagtgcaag  atattttaa   ttatatttac    360 tccatggatg  aaaatttgga  atttcatatt  aaggtttcat  attttgaaat  atatttggat    420
aagataaggg  acctgttaga  tgtttcaaag  accaaccttt  cagttcatga  agacaaaaac    480
cgagttccct  atgtaaaggg  gtgcacagag  cgttttgtat  gtagtccaga  tgaagttatg    540
gataccatag  atgaaggaaa  atccaacaga  catgtagcag  ttacaaatat  gaatgaacat    600
agctctagga  gtcacagtat  atttcttatt  aatgtcaaac  aagagaacac  acaaacggaa    660
caaaagctga  gtggaaaact  ttatctggtt  gatttagctg  gtagtgaaaa  ggttagtaaa    720
actggagctg  aaggtgctgt  gctggatgaa  gctaaaaaca  tcaacaagtc  actttctgct    780
cttggaaatg  ttatttctgc  tttggctgag  ggtagtacat  atgttccata  tcgagatagt    840
aaaatgacaa  gaatccttca  agattcatta  ggtggcaact  gtagaaccac  tattgtaatt    900
tgctgctctc  catcatcata  caatgagtct  gaaacaaaat  ctacactctt  atttggccaa    960
agggccaaaa  caattaagaa  cacagtttgt  gtcaatgtgg  agttaactgc  agaacagtgg   1020
aaaaagaagt  atgaaaaaga  aaaagaaaaa  aataagatcc  tgcggaacac  tattcagtgg   1080
cttgaaaatg  agctcaacag  atggcgtaat  ggggagacgt  gcctattga   tgaacagttt   1140 gacaaagaga  agccaacctt  ggaagctttc  acagtggata  agatattac   tcttaccaat   1200 gataaaccag  caaccgcaat  tggagttata  ggaaatttta  ctgatgctga  agaagaaag    1260 tgtgaagaag  aaattgctaa  attatacaaa  cagcttgatg  acaaggatga  agaaattaac   1320
cagcaaagtc  aactggtaga  gaaactgaag  acgcaaatgt  tggatcagga  ggagcttttg   1380
gcatctacca  gaagggatca  agacaatatg  caagctgagc  tgaatcgcct  tcaagcagaa   1440
aatgatgcct  ctaaagaaga  agtgaaagaa  gttttacagg  ccctagaaga  acttgctgtc   1500
aattatgatc  agaagtctca  ggaagttgaa  gacaaaacta  aggaatatga  attgcttagt   1560
gatgaattga  atcagaaatc  ggcaacttta  gcgagtatag  atgctgagct  tcagaaactt   1620
```

| | |
|---|---|
| aaggaaatga ccaaccacca gaaaaaacga gcagctgaga tgatggcatc tttactaaaa | 1680 |
| gaccttgcag aaataggaat tgctgtggga ataatgatg taaaggagga tccaaagtgg | 1740 |
| gaattccctc ggaagaactt ggttcttgga aaaactctag gagaaggcga atttggaaaa | 1800 |
| gtggtcaagg caacggcctt ccatctgaaa ggcagagcag ggtacaccac ggtggccgtg | 1860 |
| aagatgctga aagagaacgc ctccccgagt gagctgcgag acctgctgtc agagttcaac | 1920 |
| gtcctgaagc aggtcaacca cccacatgtc atcaaattgt atgggggcctg cagccaggat | 1980 |
| ggcccgctcc tcctcatcgt ggagtacgcc aaatacggct ccctgcgggg cttcctccgc | 2040 |
| gagagccgca aagtggggcc tggctacctg ggcagtggag gcagccgcaa ctccagctcc | 2100 |
| ctggaccacc cggatgagcg ggccctcacc atgggcgacc tcatctcatt tgcctggcag | 2160 |
| atctcacagg ggatgcagta tctggccgag atgaagctcg ttcatcggga cttggcagcc | 2220 |
| agaaacatcc tggtagctga ggggcggaag atgaagattt cggatttcgg cttgtcccga | 2280 |
| gatgtttatg aagaggattc ctacgtgaag gagagccagg gtcggattcc agttaaatgg | 2340 |
| atggcaattg aatccctttt tgatcatatc tacaccacgc aaagtgatgt atggtctttt | 2400 |
| ggtgtcctgc tgtgggagat cgtgacccta gggggaaacc cctatcctgg gattcctcct | 2460 |
| gagcggctct tcaaccttct gaagaccggc caccggatgg agaggccaga caactgcagc | 2520 |
| gaggagatgt accgcctgat gctgcaatgc tggaagcagg agccggacaa aaggccggtg | 2580 |
| tttgcggaca tcagcaaaga cctggagaag atgatggtta agaggagaga ctacttggac | 2640 |
| cttgcggcgt ccactccatc tgactccctg atttatgacg acggcctctc agaggaggag | 2700 |
| acaccgctgg tggactgtaa taatgccccc ctccctcgag ccctcccttc acatggatt | 2760 |
| gaaaacaaac tctatggcat gtcagacccg aactggcctg agagagtcc tgtaccactc | 2820 |
| acgagagctg atggcactaa cactgggttt ccaagatatc caaatgatag tgtatatgct | 2880 |
| aactggatgc tttcacccctc agcggcaaaa ttaatggaca cgtttgatag ttaa | 2934 |

<210> SEQ ID NO 11
<211> LENGTH: 3123
<212> TYPE: DNA
<213> ORGANISM: Homo sapiens
<220> FEATURE:
<221> NAME/KEY: misc_feature
<223> OTHER INFORMATION: KIF5B-RET (K16;R12 variant2)

<400> SEQUENCE: 11

| | |
|---|---|
| atggcggacc tggccgagtg caacatcaaa gtgatgtgtc gcttcagacc tctcaacgag | 60 |
| tctgaagtga accgcggcga caagtacatc gccaagtttc aggagaaga cacggtcgtg | 120 |
| atcgcgtcca gccttatgc atttgatcgg gtgttccagt caagcacatc tcaagagcaa | 180 |
| gtgtataatg actgtgcaaa gaagattgtt aaagatgtac ttgaaggata taatggaaca | 240 |
| atatttgcat atggacaaac atcctctggg aagacacaca caatggaggg taaacttcat | 300 |
| gatccagaag gcatgggaat tattccaaga atagtgcaag atatttttaa ttatatttac | 360 |
| tccatggatg aaaatttgga atttcatatt aaggtttcat attttgaaat atatttggat | 420 |
| aagataaggg acctgttaga tgtttcaaag accaacctt cagttcatga agacaaaaac | 480 |
| cgagttcccct atgtaaaggg gtgcacagag cgttttgtat gtagtccaga tgaagttatg | 540 |
| gataccatag atgaaggaaa atccaacaga catgtagcag ttacaaatat gaatgaacat | 600 |
| agctctagga gtcacagtat atttcttatt aatgtcaaac aagagaacac acaaacggaa | 660 |
| caaaagctga gtggaaaact ttatctggtt gatttagctg gtagtgaaaa ggttagtaaa | 720 |

```
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata agatattac tcttaccaat    1200 gataaaccag caaccgcaat tggagttata ggaaatttta ctgatgctga agaagaaag   1260 tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta ggaatatgaa attgcttagt   1560
gatgaattga atcagaaatc ggcaaccttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860 aaatggaag aaaatgaaaa ggagttagca gcatgtcagc ttcgtatctc tcaagaggat   1920
ccaaagtggg aattccctcg gaagaacttg gttcttggaa aaactctagg agaaggcgaa   1980
tttggaaaag tggtcaaggc aacggccttc catctgaaag gcagagcagg gtacaccacg   2040
gtggccgtga agatgctgaa agagaacgcc tccccgagtg agcttcgaga cctgctgtca   2100
gagttcaacg tcctgaagca ggtcaaccac ccacatgtca tcaaattgta tgggcctgc   2160 agccaggatg gcccgctcct cctcatcgtg gagtacgcca aatacggctc cctgcggggc   2220
ttcctccgcg agagccgcaa agtggggcct ggctacctgg gcagtggagg cagccgcaac   2280
tccagctccc tggaccaccc ggatgagcgg gccctcacca tgggcgacct catctcattt   2340
gcctggcaga tctcacaggg gatgcagtat ctggccgaga tgaagctcgt tcatcgggac   2400
ttggcagcca gaaacatcct ggtagctgag gggcggaaga tgaagatttc ggatttcggc   2460
ttgtcccgag atgtttatga agaggattcg tacgtgaaga ggagccaggg tcggattcca   2520
gttaaatgga tggcaattga atcccttttt gatcatatct acaccacgca agtgatgta   2580 tggtcttttg gtgtcctgct gtgggagatc gtgaccctag ggggaaaccc ctatcctggg   2640
attcctcctg agcggctctt caaccttctg aagaccggcc accggatgga gaggccagac   2700
aactgcagcg aggagatgta ccgcctgatg ctgcaatgct ggaagcagga gccgacaaa   2760 aggccggtgt ttgcggacat cagcaaagac ctggagaaga tgatggttaa gaggagagac   2820
tacttggacc ttgcgcgtc cactccatct gactccctga tttatgacga cggcctctca   2880
gaggaggaga caccgctggt ggactgtaat aatgcccccc tccctcgagc cctcccttcc   2940
acatggattg aaaacaaact ctatggcatg tcagacccga actggcctgg agagagtcct   3000
gtaccactca cgagagctga tggcactaac actgggtttc caagatatcc aaatgatagt   3060
gtatatgcta actggatgct ttcaccctca gcggcaaaat taatggacac gtttgatagt   3120
``` taa                                                          3123

<210> SEQ ID NO 12
<211> LENGTH: 3648
<212> TYPE: DNA
<213> ORGANISM: Homo sapiens
<220> FEATURE:
<221> NAME/KEY: misc_feature
<223> OTHER INFORMATION: KIF5B-RET (K22;R12 variant2)

<400> SEQUENCE: 12

```
atggcggacc tggccgagtg caacatcaaa gtgatgtgtc gcttcagacc tctcaacgag    60
tctgaagtga accgcggcga caagtacatc gccaagtttc agggagaaga cacggtcgtg   120
atcgcgtcca agccttatgc atttgatcgg gtgttccagt caagcacatc tcaagagcaa   180
gtgtataatg actgtgcaaa gaagattgtt aaagatgtac ttgaaggata taatggaaca   240
atatttgcat atggacaaac atcctctggg aagacacaca caatggaggg taaacttcat   300
gatccagaag gcatgggaat tattccaaga atagtgcaag atatttttaa ttatatttac   360
tccatggatg aaaatttgga atttcatatt aaggtttcat attttgaaat atatttggat   420
aagataaggg acctgttaga tgtttcaaag accaaccttt cagttcatga agacaaaaac   480
cgagttccct atgtaaaggg gtgcacagag cgttttgtat gtagtccaga tgaagttatg   540
gataccatag atgaaggaaa atccaacaga catgtagcag ttacaaatat gaatgaacat   600
agctctagga gtcacagtat atttcttatt aatgtcaaac aagagaacac acaaacggaa   660
caaaagctga gtggaaaact ttatctggtt gatttagctg gtagtgaaaa ggttagtaaa   720
actggagctg aaggtgctgt gctggatgaa gctaaaaaca tcaacaagtc actttctgct   780
cttggaaatg ttatttctgc tttggctgag ggtagtacat atgttccata tcgagatagt   840
aaaatgacaa gaatccttca agattcatta ggtggcaact gtagaaccac tattgtaatt   900
tgctgctctc catcatcata caatgagtct gaaacaaaat ctacactctt atttggccaa   960
agggccaaaa caattaagaa cacagttttgt gtcaatgtgg agttaactgc agaacagtgg  1020
aaaaagaagt atgaaaaaga aaagaaaaaa aataagatcc tgcggaacac tattcagtgg  1080
cttgaaaatg agctcaacag atggcgtaat ggggagacgg tgcctattga tgaacagttt  1140
gacaaagaga agccaacttt ggaagctttc acagtggata agatattac tcttaccaat  1200 gataaaccag caaccgcaat tggagttata ggaaatttta ctgatgctga agaagaaag   1260 tgtgaagaag aaattgctaa attatacaaa cagcttgatg acaaggatga agaaattaac  1320
cagcaaagtc aactggtaga gaaactgaag acgcaaatgt tggatcagga ggagcttttg  1380
gcatctacca gaagggatca agacaatatg caagctgagc tgaatcgcct tcaagcagaa  1440
aatgatgcct ctaaagaaga agtgaaagaa gttttacagg ccctagaaga acttgctgtc  1500
aattatgatc agaagtctca ggaagttgaa gacaaaacta aggaatatga attgcttagt  1560
gatgaattga atcagaaatc ggcaacttta gcgagtatag atgctgagct tcagaaactt  1620
aaggaaatga ccaaccacca gaaaaaacga gcagctgaga tgatggcatc tttactaaaa  1680
gaccttgcag aaataggaat tgctgtggga aataatgatg taaagcagcc tgagggaact  1740
ggcatgatag atgaagagtt cactgttgca agactctaca ttagcaaaat gaagtcagaa  1800
gtaaaaacca tggtgaaacg ttgcaagcag ttagaaagca cacaaactga gcaacaaaa   1860 aaaatggaag aaaatgaaaa ggagttagca gcatgtcagc ttcgtatctc tcaacatgaa  1920
gccaaaatca agtcattgac tgaataccct tcaaaatgtg gaacaaaagaa aagacagttg  1980
```

| | |
|---|---|
| gaggaatctg tcgatgccct cagtgaagaa ctagtccagc ttcgagcaca agagaaagtc | 2040 |
| catgaaatgg aaaaggagca cttaaataag gttcagactg caaatgaagt taagcaagct | 2100 |
| gttgaacagc agatccagag ccatagaaga actcatcaaa aacagatcag tagtttgaga | 2160 |
| gatgaagtag aagcaaaagc aaaacttatt actgatcttc aagaccaaaa ccagaaaatg | 2220 |
| atgttagagc aggaacgtct aagagtagaa catgagaagt tgaaagccac agatcaggaa | 2280 |
| aagagcagaa aactacatga acttacggtt atgcaagata gacgagaaca agcaagacaa | 2340 |
| gacttgaagg gtttggaaga gacagtggca aaagaacttc agactttaca caacctgcgc | 2400 |
| aaactctttg ttcaggacct ggctacaaga gttaaaaagg aggatccaaa gtgggaattc | 2460 |
| cctcggaaga acttggttct tggaaaaact ctaggagaag gcgaatttgg aaaagtggtc | 2520 |
| aaggcaacgg ccttccatct gaaaggcaga gcagggtaca ccacggtggc cgtgaagatg | 2580 |
| ctgaaagaga acgcctcccc gagtgagctg cgagacctgc tgtcagagtt caacgtcctg | 2640 |
| aagcaggtca accacccaca tgtcatcaaa ttgtatgggg cctgcagcca ggatggcccg | 2700 |
| ctcctcctca tcgtggagta cgccaaatac ggctccctgc ggggcttcct ccgcgagagc | 2760 |
| cgcaaagtgg ggcctggcta cctgggcagt ggaggcagcc gcaactccag ctccctggac | 2820 |
| cacccggatg agcgggccct caccatgggc gacctcatct catttgcctg gcagatctca | 2880 |
| caggggatgc agtatctggc cgagatgaag ctcgttcatc gggacttggc agccagaaac | 2940 |
| atcctggtag ctgaggggcg gaagatgaag atttcggatt tcggcttgtc ccgagatgtt | 3000 |
| tatgaagagg attcctacgt gaagaggagc cagggtcgga ttccagttaa atggatggca | 3060 |
| attgaatccc tttttgatca tatctacacc acgcaaagtg atgtatggtc ttttggtgtc | 3120 |
| ctgctgtggg agatcgtgac cctaggggga accccctatc ctgggattcc tcctgagcgg | 3180 |
| ctcttcaacc ttctgaagac cggccaccgg atggagaggc cagacaactg cagcgaggag | 3240 |
| atgtaccgcc tgatgctgca atgctggaag caggagccgg acaaaaggcc ggtgtttgcg | 3300 |
| gacatcagca aagacctgga gaagatgatg gttaagagga gagactactt ggaccttgcg | 3360 |
| gcgtccactc catctgactc cctgatttat gacgacggcc tctcagagga ggagacaccg | 3420 |
| ctggtggact gtaataatgc cccccctccct cgagccctcc cttccacatg gattgaaaac | 3480 |
| aaactctatg gcatgtcaga cccgaactgg cctggagaga gtcctgtacc actcacgaga | 3540 |
| gctgatggca ctaacactgg gtttccaaga tatccaaatg atagtgtata tgctaactgg | 3600 |
| atgctttcac cctcagcggc aaaattaatg gacacgtttg atagttaa | 3648 |

<210> SEQ ID NO 13
<211> LENGTH: 3753
<212> TYPE: DNA
<213> ORGANISM: Homo sapiens
<220> FEATURE:
<221> NAME/KEY: misc_feature
<223> OTHER INFORMATION: KIF5B-RET (K23;R12 variant2)

<400> SEQUENCE: 13

| | |
|---|---|
| atggcggacc tggccgagtg caacatcaaa gtgatgtgtc gcttcagacc tctcaacgag | 60 |
| tctgaagtga accgcggcga caagtacatc gccaagtttc agggagaaga cacggtcgtg | 120 |
| atcgcgtcca agccttatgc atttgatcgg gtgttccagt caagcacatc tcaagagcaa | 180 |
| gtgtataatg actgtgcaaa gaagattgtt aaagatgtac ttgaaggata taatggaaca | 240 |
| atatttgcat atggacaaac atcctctggg aagacacaca caatggaggg taaacttcat | 300 |
| gatccagaag gcatgggaat tattccaaga atagtgcaag atatttttaa ttatatttac | 360 |

```
tccatggatg aaaatttgga atttcatatt aaggtttcat attttgaaat atatttggat    420
aagataaggg acctgttaga tgtttcaaag accaacecttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg tagtgaaaa ggttagtaaa     720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata agatattac tcttaccaat    1200
gataaaccag caaccgcaat tggagttata ggaaatttta ctgatgctga agaagaaag    1260
tgtgaagaag aaattgctaa attatacaaa cagcttgatg acaaggatga agaaattaac   1320
cagcaaagtc aactggtaga gaaactgaag acgcaaatgt tggatcagga ggagctttg     1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaacatgaa   1920
gccaaaatca agtcattgac tgaataccet caaaatgtgg aacaaaagaa aagacagttg   1980
gaggaatctg tcgatgccct cagtgaagaa ctagtccagc ttcgagcaca agagaaagtc   2040
catgaaatgg aaaaggagca cttaaataag gttcagactg caaatgaagt taagcaagct   2100
gttgaacagc agatccagag ccatagagaa actcatcaaa aacagatcag tagtttgaga   2160
gatgaagtag aagcaaaagc aaaacttatt actgatcttc aagaccaaaa ccagaaaatg   2220
atgttagagc aggaacgtct aagagtagaa catgagaagt tgaaagccac agatcaggaa   2280
aagagcagaa aactacatga acttacggtt atgcaagata gacgagaaca agcaagacaa   2340
gacttgaagg gtttggaaga gacagtggca aaagaacttc agactttaca caacctgcgc   2400
aaactctttg ttcaggacct ggctacaaga gttaaaaaga gtgctgagat tgattctgat   2460
gacaccggag gcagcgctgc tcagaagcaa aaaatctcct ttcttgaaaa taatcttgaa   2520
cagctcacta aagtgcacaa acaggaggat ccaaagtggg aattccctcg gaagaacttg   2580
gttcttggaa aaactctagg agaaggcgaa tttggaaaag tggtcaaggc aacggccttc   2640
catctgaaag gcagagcagg gtacaccacg gtggccgtga agatgctgaa agagaacgcc   2700
```

```
tccccgagtg agcttcgaga cctgctgtca gagttcaacg tcctgaagca ggtcaaccac    2760
ccacatgtca tcaaattgta tggggcctgc agccaggatg gcccgctcct cctcatcgtg    2820
gagtacgcca atacggctcc cctgcggggc ttcctccgcg agagccgcaa agtggggcct    2880
ggctacctgg gcagtggagg cagccgcaac tccagctccc tggaccaccc ggatgagcgg    2940
gccctcacca tgggcgacct catctcattt gcctggcaga tctcacaggg gatgcagtat    3000
ctggccgaga tgaagctcgt tcatcggggac ttggcagcca gaaacatcct ggtagctgag    3060
gggcggaaga tgaagatttc ggatttcggc ttgtcccgag atgtttatga agaggattcc    3120
tacgtgaaga ggagccaggg tcggattcca gttaaatgga tggcaattga atcccttttt    3180
gatcatatct acaccacgca aagtgatgta tggtcttttg gtgtcctgct gtgggagatc    3240
gtgaccctag ggggaaaccc ctatcctggg attcctcctg agcggctctt caaccttctg    3300
aagaccggcc accggatgga gaggccagac aactgcagcg aggagatgta ccgcctgatg    3360
ctgcaatgct ggaagcagga gccggacaaa aggccggtgt tgcggacat cagcaaagac    3420 ctggagaaga tgatggttaa gaggagagac tacttggacc ttgcggcgtc cactccatct    3480
gactccctga tttatgacga cggcctctca gaggaggaga caccgctggt ggactgtaat    3540
aatgcccccc tccctcgagc cctcccttcc acatggattg aaaacaaact ctatggcatg    3600
tcagacccga actggcctgg agagagtcct gtaccactca cgagagctga tggcactaac    3660
actgggtttc caagatatcc aaatgatagt gtatatgcta actggatgct ttcaccctca    3720
gcggcaaaat taatggacac gtttgatagt taa                                 3753

<210> SEQ ID NO 14
<211> LENGTH: 2958
<212> TYPE: DNA
<213> ORGANISM: Homo sapiens
<220> FEATURE:
<221> NAME/KEY: misc_feature
<223> OTHER INFORMATION: KIF5B-RET (K15;R11 variant4)

<400> SEQUENCE: 14
atggcggacc tggccgagtg caacatcaaa gtgatgtgtc gcttcagacc tctcaacgag      60
tctgaagtga accgcggcga caagtacatc gccaagtttc agggagaaga cacggtcgtg     120
atcgcgtcca agccttatgc atttgatcgg gtgttccagt caagcacatc tcaagagcaa     180
gtgtataatg actgtgcaaa agagattgtt aaagatgtac ttgaaggata taatggaaca     240
atatttgcat atggacaaac atcctctggg aagacacaca atggagggg taaacttcat     300 gatccagaag gcatgggaat tattccaaga atagtgcaag atatttttaa ttatatttac     360
tccatggatg aaaatttgga atttcatatt aaggtttcat attttgaaat atatttggat     420
aagataaggg acctgttaga tgtttcaaag accaaccttt cagttcatga agacaaaaac     480 cgagttcct atgtaaaggg gtgcacagag cgttttgtat gtagtccaga tgaagttatg     540
gataccatag atgaaggaaa atccaacaga catgtagcag ttacaaatat gaatgaacat     600
agctctagga gtcacagtat atttcttatt aatgtcaaac aagagaacac acaaacggaa     660
caaaagctga gtggaaaact ttatctggtt gatttagctg gtagtgaaaa ggttagtaaa     720
actggagctg aaggtgctgt gctggatgaa gctaaaaaca tcaacaagtc actttctgct     780
cttggaaatg ttatttctgc tttggctgag ggtagtacat atgttccata tcgagatagt     840
aaaatgacaa gatccttcag attcattta ggtggcaact gtagaaccac tattgtaatt     900
tgctgctctc tccatcatca taatgagtct gaaacaaaat ctacactctt atttggccaa     960
```

```
agggccaaaa caattaagaa cacagtttgt gtcaatgtgg agttaactgc agaacagtgg    1020
aaaaagaagt atgaaaaaga aaagaaaaa aataagatcc tgcggaacac tattcagtgg     1080
cttgaaaatg agctcaacag atggcgtaat ggggagacgg tgcctattga tgaacagttt    1140
gacaaagaga agccaacttt ggaagctttc acagtggata agatattac tcttaccaat     1200 gataaaccag caaccgcaat tggagttata ggaaatttta ctgatgctga agaagaaag     1260 tgtgaagaag aaattgctaa attatacaaa cagcttgatg acaaggatga agaaattaac    1320
cagcaaagtc aactggtaga gaaactgaag acgcaaatgt tggatcagga ggagcttttg    1380
gcatctacca gagggatca agacaatatg caagctgagc tgaatcgcct tcaagcagaa     1440
aatgatgcct ctaagaaga agtgaaagaa gttttacagg ccctagaaga acttgctgtc     1500
aattatgatc agaagtctca ggaagttgaa gacaaaacta aggaatatga attgcttagt    1560
gatgaattga atcagaaatc ggcaacttta gcgagtatag atgctgagct tcagaaactt    1620
aaggaaatga ccaaccacca gaaaaaacga gcagctgaga tgatggcatc tttactaaaa    1680
gaccttgcag aaataggaat tgctgtggga aataatgatg taaagtttgc ccacaagcca    1740
cccatctcct cagctgagat gaccttccgg aggcccgccc aggccttccc ggtcagctac    1800
tcctcttccg gtgcccgccg gccctcgctg gactccatgg agaaccaggt ctccgtggat    1860
gccttcaaga tcctggagga tccaaagtgg gaattccctc ggaagaactt ggttcttgga    1920
aaaactctag gagaaggcga atttggaaaa gtggtcaagg caacggcctt ccatctgaaa    1980
ggcagagcag ggtacaccac ggtggccgtg aagatgctga agagaacgc ctcccccgagt    2040 gagctgcgag acctgctgtc agagttcaac gtcctgaagc aggtcaacca cccacatgtc    2100
atcaaattgt atggggcctg cagccaggat ggcccgctcc tcctcatcgt ggagtacgcc    2160
aaatacggct ccctgcgggg cttcctccgc gagagccgca agtgggggcc tggctacctg    2220
ggcagtggag gcagccgcaa ctccagctcc ctggaccacc cggatgagcg ggccctcacc    2280
atgggcgacc tcatctcatt tgcctggcag atctcacagg ggatgcagta tctggccgag    2340
atgaagctcg ttcatcggga cttggcagcc agaaacatcc tggtagctga ggggcggaag    2400
atgaagattt cggatttcgg cttgtcccga gatgtttatg aagaggattc ctacgtgaag    2460
aggagccagg gtcggattcc agttaaatgg atggcaattg aatccctttt tgatcatatc    2520
tacaccacgc aaagtgatgt atggtctttt ggtgtcctgc tgtgggagat cgtgacccta    2580
gggggaaacc cctatcctgg gattcctcct gagcggctct caaccttct gaagaccggc    2640 caccggatgg agaggccaga caactgcagc gaggagatgt accgcctgat gctgcaatgc    2700
tggaagcagg agccggacaa aaggccggtg tttcgcggaca tcagcaaaga cctggagaag    2760
atgatggtta agaggagaga ctacttggac cttgcggcgt ccactccatc tgactccctg    2820
atttatgacg acggcctctc agaggaggag acaccgctgg tggactgtaa taatgccccc    2880
ctccctcgag ccctcccttc cacatggatt gaaaacaaac tctatggtag aatttcccat    2940
gcatttacta gattctag                                                  2958
```

<210> SEQ ID NO 15
<211> LENGTH: 935
<212> TYPE: PRT
<213> ORGANISM: Homo sapiens
<220> FEATURE:
<221> NAME/KEY: misc_feature
<223> OTHER INFORMATION: KIF5B-RET (K15;R12 variant 4)

<400> SEQUENCE: 15

-continued

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
```

```
            420                 425                 430
Asp Asp Lys Asp Glu Glu Ile Asn Gln Gln Ser Gln Leu Val Glu Lys
            435                 440                 445
Leu Lys Thr Gln Met Leu Asp Gln Glu Glu Leu Leu Ala Ser Thr Arg
            450                 455                 460
Arg Asp Gln Asp Asn Met Gln Ala Glu Leu Asn Arg Leu Gln Ala Glu
465                 470                 475                 480
Asn Asp Ala Ser Lys Glu Glu Val Lys Glu Val Leu Gln Ala Leu Glu
                    485                 490                 495
Glu Leu Ala Val Asn Tyr Asp Gln Lys Ser Gln Glu Val Glu Asp Lys
                500                 505                 510
Thr Lys Glu Tyr Glu Leu Leu Ser Asp Glu Leu Asn Gln Lys Ser Ala
                515                 520                 525
Thr Leu Ala Ser Ile Asp Ala Glu Leu Gln Lys Leu Lys Glu Met Thr
                530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Glu
                    565                 570                 575
Asp Pro Lys Trp Glu Phe Pro Arg Lys Asn Leu Val Leu Gly Lys Thr
                580                 585                 590
Leu Gly Glu Gly Glu Phe Gly Lys Val Val Lys Ala Thr Ala Phe His
                595                 600                 605
Leu Lys Gly Arg Ala Gly Tyr Thr Thr Val Ala Val Lys Met Leu Lys
            610                 615                 620
Glu Asn Ala Ser Pro Ser Glu Leu Arg Asp Leu Leu Ser Glu Phe Asn
625                 630                 635                 640
Val Leu Lys Gln Val Asn His Pro His Val Ile Lys Leu Tyr Gly Ala
                    645                 650                 655
Cys Ser Gln Asp Gly Pro Leu Leu Leu Ile Val Glu Tyr Ala Lys Tyr
                660                 665                 670
Gly Ser Leu Arg Gly Phe Leu Arg Glu Ser Arg Lys Val Gly Pro Gly
                675                 680                 685
Tyr Leu Gly Ser Gly Gly Ser Arg Asn Ser Ser Ser Leu Asp His Pro
            690                 695                 700
Asp Glu Arg Ala Leu Thr Met Gly Asp Leu Ile Ser Phe Ala Trp Gln
705                 710                 715                 720
Ile Ser Gln Gly Met Gln Tyr Leu Ala Glu Met Lys Leu Val His Arg
                    725                 730                 735
Asp Leu Ala Ala Arg Asn Ile Leu Val Ala Glu Gly Arg Lys Met Lys
                740                 745                 750
Ile Ser Asp Phe Gly Leu Ser Arg Asp Val Tyr Glu Glu Asp Ser Tyr
                755                 760                 765
Val Lys Arg Ser Gln Gly Arg Ile Pro Val Lys Trp Met Ala Ile Glu
                770                 775                 780
Ser Leu Phe Asp His Ile Tyr Thr Thr Gln Ser Asp Val Trp Ser Phe
785                 790                 795                 800
Gly Val Leu Leu Trp Glu Ile Val Thr Leu Gly Gly Asn Pro Tyr Pro
                    805                 810                 815
Gly Ile Pro Pro Glu Arg Leu Phe Asn Leu Leu Lys Thr Gly His Arg
                820                 825                 830
Met Glu Arg Pro Asp Asn Cys Ser Glu Glu Met Tyr Arg Leu Met Leu
                835                 840                 845
```

```
Gln Cys Trp Lys Gln Glu Pro Asp Lys Arg Pro Val Phe Ala Asp Ile
    850                 855                 860

Ser Lys Asp Leu Glu Lys Met Met Val Lys Arg Arg Asp Tyr Leu Asp
865                 870                 875                 880

Leu Ala Ala Ser Thr Pro Ser Asp Ser Leu Ile Tyr Asp Asp Gly Leu
                885                 890                 895

Ser Glu Glu Glu Thr Pro Leu Val Asp Cys Asn Asn Ala Pro Leu Pro
            900                 905                 910

Arg Ala Leu Pro Ser Thr Trp Ile Glu Asn Lys Leu Tyr Gly Arg Ile
            915                 920                 925

Ser His Ala Phe Thr Arg Phe
    930                 935

<210> SEQ ID NO 16
<211> LENGTH: 998
<212> TYPE: PRT
<213> ORGANISM: Homo sapiens
<220> FEATURE:
<221> NAME/KEY: misc_feature
<223> OTHER INFORMATION: KIF5B-RET (K16;R12 variant4)

<400> SEQUENCE: 16

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
```

```
            260                 265                 270
Thr Tyr Val Pro Tyr Arg Asp Ser Lys Met Thr Arg Ile Leu Gln Asp
            275                 280                 285
Ser Leu Gly Gly Asn Cys Arg Thr Thr Ile Val Ile Cys Cys Ser Pro
            290                 295                 300
Ser Ser Tyr Asn Glu Ser Glu Thr Lys Ser Thr Leu Leu Phe Gly Gln
305                 310                 315                 320
Arg Ala Lys Thr Ile Lys Asn Thr Val Cys Val Asn Val Glu Leu Thr
            325                 330                 335
Ala Glu Gln Trp Lys Lys Tyr Glu Lys Glu Lys Asn Lys
            340                 345                 350
Ile Leu Arg Asn Thr Ile Gln Trp Leu Glu Asn Glu Leu Asn Arg Trp
            355                 360                 365
Arg Asn Gly Glu Thr Val Pro Ile Asp Glu Gln Phe Asp Lys Glu Lys
            370                 375                 380
Ala Asn Leu Glu Ala Phe Thr Val Asp Lys Asp Ile Thr Leu Thr Asn
385                 390                 395                 400
Asp Lys Pro Ala Thr Ala Ile Gly Val Ile Gly Asn Phe Thr Asp Ala
                405                 410                 415
Glu Arg Arg Lys Cys Glu Glu Ile Ala Lys Leu Tyr Lys Gln Leu
                420                 425                 430
Asp Asp Lys Asp Glu Glu Ile Asn Gln Gln Ser Gln Leu Val Glu Lys
            435                 440                 445
Leu Lys Thr Gln Met Leu Asp Gln Glu Glu Leu Leu Ala Ser Thr Arg
    450                 455                 460
Arg Asp Gln Asp Asn Met Gln Ala Glu Leu Asn Arg Leu Gln Ala Glu
465                 470                 475                 480
Asn Asp Ala Ser Lys Glu Glu Val Lys Glu Val Leu Gln Ala Leu Glu
                485                 490                 495
Glu Leu Ala Val Asn Tyr Asp Gln Lys Ser Gln Glu Val Glu Asp Lys
                500                 505                 510
Thr Lys Glu Tyr Glu Leu Leu Ser Asp Glu Leu Asn Gln Lys Ser Ala
            515                 520                 525
Thr Leu Ala Ser Ile Asp Ala Glu Leu Gln Lys Leu Lys Glu Met Thr
        530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
            580                 585                 590
Tyr Ile Ser Lys Met Lys Ser Glu Val Lys Thr Met Val Lys Arg Cys
            595                 600                 605
Lys Gln Leu Glu Ser Thr Gln Thr Glu Ser Asn Lys Lys Met Glu Glu
        610                 615                 620
Asn Glu Lys Glu Leu Ala Ala Cys Gln Leu Arg Ile Ser Gln Glu Asp
625                 630                 635                 640
Pro Lys Trp Glu Phe Pro Arg Lys Asn Leu Val Leu Gly Lys Thr Leu
                645                 650                 655
Gly Glu Gly Glu Phe Gly Lys Val Val Lys Ala Thr Ala Phe His Leu
            660                 665                 670
Lys Gly Arg Ala Gly Tyr Thr Thr Val Ala Val Lys Met Leu Lys Glu
        675                 680                 685
```

```
Asn Ala Ser Pro Ser Glu Leu Arg Asp Leu Leu Ser Glu Phe Asn Val
            690                 695                 700

Leu Lys Gln Val Asn His Pro His Val Ile Lys Leu Tyr Gly Ala Cys
705                 710                 715                 720

Ser Gln Asp Gly Pro Leu Leu Leu Ile Val Glu Tyr Ala Lys Tyr Gly
                    725                 730                 735

Ser Leu Arg Gly Phe Leu Arg Glu Ser Arg Lys Val Gly Pro Gly Tyr
            740                 745                 750

Leu Gly Ser Gly Gly Ser Arg Asn Ser Ser Ser Leu Asp His Pro Asp
            755                 760                 765

Glu Arg Ala Leu Thr Met Gly Asp Leu Ile Ser Phe Ala Trp Gln Ile
770                 775                 780

Ser Gln Gly Met Gln Tyr Leu Ala Glu Met Lys Leu Val His Arg Asp
785                 790                 795                 800

Leu Ala Ala Arg Asn Ile Leu Val Ala Glu Gly Arg Lys Met Lys Ile
                805                 810                 815

Ser Asp Phe Gly Leu Ser Arg Asp Val Tyr Glu Glu Asp Ser Tyr Val
            820                 825                 830

Lys Arg Ser Gln Gly Arg Ile Pro Val Lys Trp Met Ala Ile Glu Ser
            835                 840                 845

Leu Phe Asp His Ile Tyr Thr Thr Gln Ser Asp Val Trp Ser Phe Gly
850                 855                 860

Val Leu Leu Trp Glu Ile Val Thr Leu Gly Gly Asn Pro Tyr Pro Gly
865                 870                 875                 880

Ile Pro Pro Glu Arg Leu Phe Asn Leu Leu Lys Thr Gly His Arg Met
                885                 890                 895

Glu Arg Pro Asp Asn Cys Ser Glu Glu Met Tyr Arg Leu Met Leu Gln
            900                 905                 910

Cys Trp Lys Gln Glu Pro Asp Lys Arg Pro Val Phe Ala Asp Ile Ser
            915                 920                 925

Lys Asp Leu Glu Lys Met Met Val Lys Arg Arg Asp Tyr Leu Asp Leu
930                 935                 940

Ala Ala Ser Thr Pro Ser Asp Ser Leu Ile Tyr Asp Asp Gly Leu Ser
945                 950                 955                 960

Glu Glu Glu Thr Pro Leu Val Asp Cys Asn Asn Ala Pro Leu Pro Arg
                965                 970                 975

Ala Leu Pro Ser Thr Trp Ile Glu Asn Lys Leu Tyr Gly Arg Ile Ser
            980                 985                 990

His Ala Phe Thr Arg Phe
            995

<210> SEQ ID NO 17
<211> LENGTH: 1173
<212> TYPE: PRT
<213> ORGANISM: Homo sapiens
<220> FEATURE:
<221> NAME/KEY: misc_feature
<223> OTHER INFORMATION: KIF5B-RET (K22;R12 variant4)

<400> SEQUENCE: 17

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
```

```
              35                  40                  45
Asp Arg Val Phe Gln Ser Ser Thr Ser Gln Glu Gln Val Tyr Asn Asp
        50                  55                  60

Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                    85                  90                  95

Gly Lys Leu His Asp Pro Glu Gly Met Gly Ile Ile Pro Arg Ile Val
                100                 105                 110

Gln Asp Ile Phe Asn Tyr Ile Tyr Ser Met Asp Glu Asn Leu Glu Phe
                115                 120                 125

His Ile Lys Val Ser Tyr Phe Glu Ile Tyr Leu Asp Lys Ile Arg Asp
                130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
                180                 185                 190

Ala Val Thr Asn Met Asn Glu His Ser Ser Arg Ser His Ser Ile Phe
                195                 200                 205

Leu Ile Asn Val Lys Gln Glu Asn Thr Gln Thr Glu Gln Lys Leu Ser
                210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
                260                 265                 270

Thr Tyr Val Pro Tyr Arg Asp Ser Lys Met Thr Arg Ile Leu Gln Asp
                275                 280                 285

Ser Leu Gly Gly Asn Cys Arg Thr Thr Ile Val Ile Cys Cys Ser Pro
                290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
                340                 345                 350

Ile Leu Arg Asn Thr Ile Gln Trp Leu Glu Asn Glu Leu Asn Arg Trp
                355                 360                 365

Arg Asn Gly Glu Thr Val Pro Ile Asp Glu Gln Phe Asp Lys Glu Lys
                370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                    405                 410                 415

Glu Arg Arg Lys Cys Glu Glu Glu Ile Ala Lys Leu Tyr Lys Gln Leu
                420                 425                 430

Asp Asp Lys Asp Glu Glu Ile Asn Gln Gln Ser Gln Leu Val Glu Lys
                435                 440                 445

Leu Lys Thr Gln Met Leu Asp Gln Glu Glu Leu Leu Ala Ser Thr Arg
450                 455                 460
```

```
Arg Asp Gln Asp Asn Met Gln Ala Glu Leu Asn Arg Leu Gln Ala Glu
465                 470                 475                 480

Asn Asp Ala Ser Lys Glu Val Lys Glu Val Leu Gln Ala Leu Glu
            485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
            515                 520                 525

Thr Leu Ala Ser Ile Asp Ala Glu Leu Gln Lys Leu Lys Glu Met Thr
            530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
            565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
            595                 600                 605

Lys Gln Leu Glu Ser Thr Gln Thr Glu Ser Asn Lys Lys Met Glu Glu
            610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
            645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
            675                 680                 685

Asn Lys Val Gln Thr Ala Asn Glu Val Lys Gln Ala Val Glu Gln Gln
            690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
            725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
            755                 760                 765

Thr Val Met Gln Asp Arg Arg Glu Gln Ala Arg Gln Asp Leu Lys Gly
            770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Glu Asp Pro
            805                 810                 815

Lys Trp Glu Phe Pro Arg Lys Asn Leu Val Leu Gly Lys Thr Leu Gly
            820                 825                 830

Glu Gly Glu Phe Gly Lys Val Val Lys Ala Thr Ala Phe His Leu Lys
            835                 840                 845

Gly Arg Ala Gly Tyr Thr Thr Val Ala Val Lys Met Leu Lys Glu Asn
            850                 855                 860

Ala Ser Pro Ser Glu Leu Arg Asp Leu Leu Ser Glu Phe Asn Val Leu
865                 870                 875                 880
```

Lys Gln Val Asn His Pro His Val Ile Lys Leu Tyr Gly Ala Cys Ser
                885                 890                 895

Gln Asp Gly Pro Leu Leu Leu Ile Val Glu Tyr Ala Lys Tyr Gly Ser
            900                 905                 910

Leu Arg Gly Phe Leu Arg Glu Ser Arg Lys Val Gly Pro Gly Tyr Leu
        915                 920                 925

Gly Ser Gly Gly Ser Arg Asn Ser Ser Ser Leu Asp His Pro Asp Glu
    930                 935                 940

Arg Ala Leu Thr Met Gly Asp Leu Ile Ser Phe Ala Trp Gln Ile Ser
945                 950                 955                 960

Gln Gly Met Gln Tyr Leu Ala Glu Met Lys Leu Val His Arg Asp Leu
                965                 970                 975

Ala Ala Arg Asn Ile Leu Val Ala Glu Gly Arg Lys Met Lys Ile Ser
            980                 985                 990

Asp Phe Gly Leu Ser Arg Asp Val Tyr Glu Glu Asp Ser Tyr Val Lys
        995                 1000                1005

Arg Ser Gln Gly Arg Ile Pro Val Lys Trp Met Ala Ile Glu Ser
    1010                1015                1020

Leu Phe Asp His Ile Tyr Thr Thr Gln Ser Asp Val Trp Ser Phe
    1025                1030                1035

Gly Val Leu Leu Trp Glu Ile Val Thr Leu Gly Gly Asn Pro Tyr
    1040                1045                1050

Pro Gly Ile Pro Pro Glu Arg Leu Phe Asn Leu Leu Lys Thr Gly
    1055                1060                1065

His Arg Met Glu Arg Pro Asp Asn Cys Ser Glu Glu Met Tyr Arg
    1070                1075                1080

Leu Met Leu Gln Cys Trp Lys Gln Glu Pro Asp Lys Arg Pro Val
    1085                1090                1095

Phe Ala Asp Ile Ser Lys Asp Leu Glu Lys Met Met Val Lys Arg
    1100                1105                1110

Arg Asp Tyr Leu Asp Leu Ala Ala Ser Thr Pro Ser Asp Ser Leu
    1115                1120                1125

Ile Tyr Asp Asp Gly Leu Ser Glu Glu Glu Thr Pro Leu Val Asp
    1130                1135                1140

Cys Asn Asn Ala Pro Leu Pro Arg Ala Leu Pro Ser Thr Trp Ile
    1145                1150                1155

Glu Asn Lys Leu Tyr Gly Arg Ile Ser His Ala Phe Thr Arg Phe
    1160                1165                1170

<210> SEQ ID NO 18
<211> LENGTH: 1208
<212> TYPE: PRT
<213> ORGANISM: Homo sapiens
<220> FEATURE:
<221> NAME/KEY: misc_feature
<223> OTHER INFORMATION: KIF5B-RET (K23;R12 variant4)

<400> SEQUENCE: 18

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

```
Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                 85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
            115                 120                 125

His Ile Lys Val Ser Tyr Phe Glu Ile Tyr Leu Asp Lys Ile Arg Asp
            130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
            195                 200                 205

Leu Ile Asn Val Lys Gln Glu Asn Thr Gln Thr Glu Gln Lys Leu Ser
210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
            275                 280                 285

Ser Leu Gly Gly Asn Cys Arg Thr Thr Ile Val Ile Cys Cys Ser Pro
290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
            355                 360                 365

Arg Asn Gly Glu Thr Val Pro Ile Asp Glu Gln Phe Asp Lys Glu Lys
            370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
            405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
            435                 440                 445

Leu Lys Thr Gln Met Leu Asp Gln Glu Glu Leu Leu Ala Ser Thr Arg
            450                 455                 460

Arg Asp Gln Asp Asn Met Gln Ala Glu Leu Asn Arg Leu Gln Ala Glu
465                 470                 475                 480
```

```
Asn Asp Ala Ser Lys Glu Glu Val Lys Glu Val Leu Gln Ala Leu Glu
            485                 490                 495
Glu Leu Ala Val Asn Tyr Asp Gln Lys Ser Gln Glu Val Glu Asp Lys
        500                 505                 510
Thr Lys Glu Tyr Glu Leu Leu Ser Asp Glu Leu Asn Gln Lys Ser Ala
    515                 520                 525
Thr Leu Ala Ser Ile Asp Ala Glu Leu Gln Lys Leu Lys Glu Met Thr
530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
            565                 570                 575
Pro Glu Gly Thr Gly Met Ile Asp Glu Glu Phe Thr Val Ala Arg Leu
        580                 585                 590
Tyr Ile Ser Lys Met Lys Ser Glu Val Lys Thr Met Val Lys Arg Cys
    595                 600                 605
Lys Gln Leu Glu Ser Thr Gln Thr Glu Ser Asn Lys Lys Met Glu Glu
    610                 615                 620
Asn Glu Lys Glu Leu Ala Ala Cys Gln Leu Arg Ile Ser Gln His Glu
625                 630                 635                 640
Ala Lys Ile Lys Ser Leu Thr Glu Tyr Leu Gln Asn Val Glu Gln Lys
            645                 650                 655
Lys Arg Gln Leu Glu Glu Ser Val Asp Ala Leu Ser Glu Glu Leu Val
        660                 665                 670
Gln Leu Arg Ala Gln Glu Lys Val His Glu Met Glu Lys Glu His Leu
    675                 680                 685
Asn Lys Val Gln Thr Ala Asn Glu Val Lys Gln Ala Val Glu Gln Gln
    690                 695                 700
Ile Gln Ser His Arg Glu Thr His Gln Lys Gln Ile Ser Ser Leu Arg
705                 710                 715                 720
Asp Glu Val Glu Ala Lys Ala Lys Leu Ile Thr Asp Leu Gln Asp Gln
            725                 730                 735
Asn Gln Lys Met Met Leu Glu Gln Glu Arg Leu Arg Val Glu His Glu
        740                 745                 750
Lys Leu Lys Ala Thr Asp Gln Glu Lys Ser Arg Lys Leu His Glu Leu
    755                 760                 765
Thr Val Met Gln Asp Arg Arg Glu Gln Ala Arg Gln Asp Leu Lys Gly
770                 775                 780
Leu Glu Glu Thr Val Ala Lys Glu Leu Gln Thr Leu His Asn Leu Arg
785                 790                 795                 800
Lys Leu Phe Val Gln Asp Leu Ala Thr Arg Val Lys Lys Ser Ala Glu
            805                 810                 815
Ile Asp Ser Asp Asp Thr Gly Gly Ser Ala Ala Gln Lys Gln Lys Ile
        820                 825                 830
Ser Phe Leu Glu Asn Asn Leu Glu Gln Leu Thr Lys Val His Lys Gln
    835                 840                 845
Glu Asp Pro Lys Trp Glu Phe Pro Arg Lys Asn Leu Val Leu Gly Lys
    850                 855                 860
Thr Leu Gly Glu Gly Glu Phe Gly Lys Val Val Lys Ala Thr Ala Phe
865                 870                 875                 880
His Leu Lys Gly Arg Ala Gly Tyr Thr Thr Val Ala Val Lys Met Leu
            885                 890                 895
Lys Glu Asn Ala Ser Pro Ser Glu Leu Arg Asp Leu Leu Ser Glu Phe
```

```
                    900             905             910
Asn Val Leu Lys Gln Val Asn His Pro His Val Ile Lys Leu Tyr Gly
            915                 920                 925
Ala Cys Ser Gln Asp Gly Pro Leu Leu Leu Ile Val Glu Tyr Ala Lys
        930                 935                 940
Tyr Gly Ser Leu Arg Gly Phe Leu Arg Glu Ser Arg Lys Val Gly Pro
945                 950                 955                 960
Gly Tyr Leu Gly Ser Gly Gly Ser Arg Asn Ser Ser Ser Leu Asp His
                965                 970                 975
Pro Asp Glu Arg Ala Leu Thr Met Gly Asp Leu Ile Ser Phe Ala Trp
            980                 985                 990
Gln Ile Ser Gln Gly Met Gln Tyr Leu Ala Glu Met Lys Leu Val His
        995                 1000                1005
Arg Asp Leu Ala Ala Arg Asn Ile Leu Val Ala Glu Gly Arg Lys
    1010                1015                1020
Met Lys Ile Ser Asp Phe Gly Leu Ser Arg Asp Val Tyr Glu Glu
    1025                1030                1035
Asp Ser Tyr Val Lys Arg Ser Gln Gly Arg Ile Pro Val Lys Trp
    1040                1045                1050
Met Ala Ile Glu Ser Leu Phe Asp His Ile Tyr Thr Thr Gln Ser
    1055                1060                1065
Asp Val Trp Ser Phe Gly Val Leu Leu Trp Glu Ile Val Thr Leu
    1070                1075                1080
Gly Gly Asn Pro Tyr Pro Gly Ile Pro Pro Glu Arg Leu Phe Asn
    1085                1090                1095
Leu Leu Lys Thr Gly His Arg Met Glu Arg Pro Asp Asn Cys Ser
    1100                1105                1110
Glu Glu Met Tyr Arg Leu Met Leu Gln Cys Trp Lys Gln Glu Pro
    1115                1120                1125
Asp Lys Arg Pro Val Phe Ala Asp Ile Ser Lys Asp Leu Glu Lys
    1130                1135                1140
Met Met Val Lys Arg Arg Asp Tyr Leu Asp Leu Ala Ala Ser Thr
    1145                1150                1155
Pro Ser Asp Ser Leu Ile Tyr Asp Asp Gly Leu Ser Glu Glu Glu
    1160                1165                1170
Thr Pro Leu Val Asp Cys Asn Asn Ala Pro Leu Pro Arg Ala Leu
    1175                1180                1185
Pro Ser Thr Trp Ile Glu Asn Lys Leu Tyr Gly Arg Ile Ser His
    1190                1195                1200
Ala Phe Thr Arg Phe
    1205

<210> SEQ ID NO 19
<211> LENGTH: 1366
<212> TYPE: PRT
<213> ORGANISM: Homo sapiens
<220> FEATURE:
<221> NAME/KEY: misc_feature
<223> OTHER INFORMATION: KIF5B-RET (K24;R11 variant4)

<400> SEQUENCE: 19

Met Ala Asp Leu Ala Glu Cys Asn Ile Lys Val Met Cys Arg Phe Arg
1               5                   10                  15
Pro Leu Asn Glu Ser Glu Val Asn Arg Gly Asp Lys Tyr Ile Ala Lys
            20                  25                  30
```

-continued

```
Phe Gln Gly Glu Asp Thr Val Val Ile Ala Ser Lys Pro Tyr Ala Phe
         35                  40                  45

Asp Arg Val Phe Gln Ser Ser Thr Ser Gln Glu Gln Val Tyr Asn Asp
 50                  55                  60

Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                 85                  90                  95

Gly Lys Leu His Asp Pro Glu Gly Met Gly Ile Ile Pro Arg Ile Val
                100                 105                 110

Gln Asp Ile Phe Asn Tyr Ile Tyr Ser Met Asp Glu Asn Leu Glu Phe
            115                 120                 125

His Ile Lys Val Ser Tyr Phe Glu Ile Tyr Leu Asp Lys Ile Arg Asp
        130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
                180                 185                 190

Ala Val Thr Asn Met Asn Glu His Ser Ser Arg Ser His Ser Ile Phe
            195                 200                 205

Leu Ile Asn Val Lys Gln Glu Asn Thr Gln Thr Glu Gln Lys Leu Ser
        210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
                260                 265                 270

Thr Tyr Val Pro Tyr Arg Asp Ser Lys Met Thr Arg Ile Leu Gln Asp
            275                 280                 285

Ser Leu Gly Gly Asn Cys Arg Thr Thr Ile Val Ile Cys Cys Ser Pro
        290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Tyr Glu Lys Glu Lys Glu Lys Asn Lys
                340                 345                 350

Ile Leu Arg Asn Thr Ile Gln Trp Leu Glu Asn Glu Leu Asn Arg Trp
            355                 360                 365

Arg Asn Gly Glu Thr Val Pro Ile Asp Glu Gln Phe Asp Lys Glu Lys
        370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Ile Ala Lys Leu Tyr Lys Gln Leu
                420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
```

```
                450              455              460
Arg Asp Gln Asp Asn Met Gln Ala Glu Leu Asn Arg Leu Gln Ala Glu
465              470              475              480

Asn Asp Ala Ser Lys Glu Val Lys Glu Val Leu Gln Ala Leu Glu
                485              490              495

Glu Leu Ala Val Asn Tyr Asp Gln Lys Ser Gln Glu Val Glu Asp Lys
                500              505              510

Thr Lys Glu Tyr Glu Leu Leu Ser Asp Glu Leu Asn Gln Lys Ser Ala
                515              520              525

Thr Leu Ala Ser Ile Asp Ala Glu Leu Gln Lys Leu Lys Glu Met Thr
                530              535              540

Asn His Gln Lys Lys Arg Ala Ala Glu Met Met Ala Ser Leu Leu Lys
545              550              555              560

Asp Leu Ala Glu Ile Gly Ile Ala Val Gly Asn Asn Asp Val Lys Gln
                565              570              575

Pro Glu Gly Thr Gly Met Ile Asp Glu Glu Phe Thr Val Ala Arg Leu
                580              585              590

Tyr Ile Ser Lys Met Lys Ser Glu Val Lys Thr Met Val Lys Arg Cys
                595              600              605

Lys Gln Leu Glu Ser Thr Gln Thr Glu Ser Asn Lys Lys Met Glu Glu
                610              615              620

Asn Glu Lys Glu Leu Ala Ala Cys Gln Leu Arg Ile Ser Gln His Glu
625              630              635              640

Ala Lys Ile Lys Ser Leu Thr Glu Tyr Leu Gln Asn Val Glu Gln Lys
                645              650              655

Lys Arg Gln Leu Glu Glu Ser Val Asp Ala Leu Ser Glu Glu Leu Val
                660              665              670

Gln Leu Arg Ala Gln Glu Lys Val His Glu Met Glu Lys Glu His Leu
                675              680              685

Asn Lys Val Gln Thr Ala Asn Glu Val Lys Gln Ala Val Glu Gln Gln
                690              695              700

Ile Gln Ser His Arg Glu Thr His Gln Lys Gln Ile Ser Ser Leu Arg
705              710              715              720

Asp Glu Val Glu Ala Lys Ala Lys Leu Ile Thr Asp Leu Gln Asp Gln
                725              730              735

Asn Gln Lys Met Met Leu Glu Gln Glu Arg Leu Arg Val Glu His Glu
                740              745              750

Lys Leu Lys Ala Thr Asp Gln Glu Lys Ser Arg Lys Leu His Glu Leu
                755              760              765

Thr Val Met Gln Asp Arg Arg Glu Gln Ala Arg Gln Asp Leu Lys Gly
                770              775              780

Leu Glu Glu Thr Val Ala Lys Glu Leu Gln Thr Leu His Asn Leu Arg
785              790              795              800

Lys Leu Phe Val Gln Asp Leu Ala Thr Arg Val Lys Lys Ser Ala Glu
                805              810              815

Ile Asp Ser Asp Asp Thr Gly Gly Ser Ala Ala Gln Lys Gln Lys Ile
                820              825              830

Ser Phe Leu Glu Asn Asn Leu Glu Gln Leu Thr Lys Val His Lys Gln
                835              840              845

Leu Val Arg Asp Asn Ala Asp Leu Arg Cys Glu Leu Pro Lys Leu Glu
                850              855              860

Lys Arg Leu Arg Ala Thr Ala Glu Arg Val Lys Ala Leu Glu Ser Ala
865              870              875              880
```

```
Leu Lys Glu Ala Lys Glu Asn Ala Ser Arg Asp Arg Lys Tyr Gln
            885                 890                 895

Gln Glu Val Asp Arg Ile Lys Glu Ala Val Arg Ser Lys Asn Met Ala
                900                 905                 910

Arg Arg Gly His Ser Ala Gln Ile Asp Pro Leu Cys Asp Glu Leu Cys
            915                 920                 925

Arg Thr Val Ile Ala Ala Val Leu Phe Ser Phe Ile Val Ser Val
            930                 935                 940

Leu Leu Ser Ala Phe Cys Ile His Cys Tyr His Lys Phe Ala His Lys
945                 950                 955                 960

Pro Pro Ile Ser Ser Ala Glu Met Thr Phe Arg Arg Pro Ala Gln Ala
            965                 970                 975

Phe Pro Val Ser Tyr Ser Ser Ser Gly Ala Arg Arg Pro Ser Leu Asp
            980                 985                 990

Ser Met Glu Asn Gln Val Ser Val Asp Ala Phe Lys Ile Leu Glu Asp
            995                 1000                1005

Pro Lys Trp Glu Phe Pro Arg Lys Asn Leu Val Leu Gly Lys Thr
    1010                1015                1020

Leu Gly Glu Gly Glu Phe Gly Lys Val Val Lys Ala Thr Ala Phe
    1025                1030                1035

His Leu Lys Gly Arg Ala Gly Tyr Thr Thr Val Ala Val Lys Met
    1040                1045                1050

Leu Lys Glu Asn Ala Ser Pro Ser Glu Leu Arg Asp Leu Leu Ser
    1055                1060                1065

Glu Phe Asn Val Leu Lys Gln Val Asn His Pro His Val Ile Lys
    1070                1075                1080

Leu Tyr Gly Ala Cys Ser Gln Asp Gly Pro Leu Leu Leu Ile Val
    1085                1090                1095

Glu Tyr Ala Lys Tyr Gly Ser Leu Arg Gly Phe Leu Arg Glu Ser
    1100                1105                1110

Arg Lys Val Gly Pro Gly Tyr Leu Gly Ser Gly Gly Ser Arg Asn
    1115                1120                1125

Ser Ser Ser Leu Asp His Pro Asp Glu Arg Ala Leu Thr Met Gly
    1130                1135                1140

Asp Leu Ile Ser Phe Ala Trp Gln Ile Ser Gln Gly Met Gln Tyr
    1145                1150                1155

Leu Ala Glu Met Lys Leu Val His Arg Asp Leu Ala Ala Arg Asn
    1160                1165                1170

Ile Leu Val Ala Glu Gly Arg Lys Met Lys Ile Ser Asp Phe Gly
    1175                1180                1185

Leu Ser Arg Asp Val Tyr Glu Glu Asp Ser Tyr Val Lys Arg Ser
    1190                1195                1200

Gln Gly Arg Ile Pro Val Lys Trp Met Ala Ile Glu Ser Leu Phe
    1205                1210                1215

Asp His Ile Tyr Thr Thr Gln Ser Asp Val Trp Ser Phe Gly Val
    1220                1225                1230

Leu Leu Trp Glu Ile Val Thr Leu Gly Gly Asn Pro Tyr Pro Gly
    1235                1240                1245

Ile Pro Pro Glu Arg Leu Phe Asn Leu Leu Lys Thr Gly His Arg
    1250                1255                1260

Met Glu Arg Pro Asp Asn Cys Ser Glu Glu Met Tyr Arg Leu Met
    1265                1270                1275
```

```
Leu Gln Cys Trp Lys Gln Glu Pro Asp Lys Arg Pro Val Phe Ala
    1280                1285                1290

Asp Ile Ser Lys Asp Leu Glu Lys Met Met Val Lys Arg Arg Asp
    1295                1300                1305

Tyr Leu Asp Leu Ala Ala Ser Thr Pro Ser Asp Ser Leu Ile Tyr
    1310                1315                1320

Asp Asp Gly Leu Ser Glu Glu Thr Pro Leu Val Asp Cys Asn
    1325                1330                1335

Asn Ala Pro Leu Pro Arg Ala Leu Pro Ser Thr Trp Ile Glu Asn
    1340                1345                1350

Lys Leu Tyr Gly Arg Ile Ser His Ala Phe Thr Arg Phe
    1355                1360                1365

<210> SEQ ID NO 20
<211> LENGTH: 977
<212> TYPE: PRT
<213> ORGANISM: Homo sapiens
<220> FEATURE:
<221> NAME/KEY: misc_feature
<223> OTHER INFORMATION: KIF5B-RET (K15;R12 variant2)

<400> SEQUENCE: 20

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270
```

```
Thr Tyr Val Pro Tyr Arg Asp Ser Lys Met Thr Arg Ile Leu Gln Asp
            275                 280                 285

Ser Leu Gly Gly Asn Cys Arg Thr Thr Ile Val Ile Cys Cys Ser Pro
        290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Glu
                565                 570                 575

Asp Pro Lys Trp Glu Phe Pro Arg Lys Asn Leu Val Leu Gly Lys Thr
            580                 585                 590

Leu Gly Glu Gly Glu Phe Gly Lys Val Val Lys Ala Thr Ala Phe His
        595                 600                 605

Leu Lys Gly Arg Ala Gly Tyr Thr Thr Val Ala Val Lys Met Leu Lys
    610                 615                 620

Glu Asn Ala Ser Pro Ser Glu Leu Arg Asp Leu Leu Ser Glu Phe Asn
625                 630                 635                 640

Val Leu Lys Gln Val Asn His Pro His Val Ile Lys Leu Tyr Gly Ala
                645                 650                 655

Cys Ser Gln Asp Gly Pro Leu Leu Leu Ile Val Glu Tyr Ala Lys Tyr
            660                 665                 670

Gly Ser Leu Arg Gly Phe Leu Arg Glu Ser Arg Lys Val Gly Pro Gly
        675                 680                 685
```

```
Tyr Leu Gly Ser Gly Gly Ser Arg Asn Ser Ser Ser Leu Asp His Pro
    690                 695                 700

Asp Glu Arg Ala Leu Thr Met Gly Asp Leu Ile Ser Phe Ala Trp Gln
705                 710                 715                 720

Ile Ser Gln Gly Met Gln Tyr Leu Ala Glu Met Lys Leu Val His Arg
                725                 730                 735

Asp Leu Ala Ala Arg Asn Ile Leu Val Ala Glu Gly Arg Lys Met Lys
            740                 745                 750

Ile Ser Asp Phe Gly Leu Ser Arg Asp Val Tyr Glu Glu Asp Ser Tyr
        755                 760                 765

Val Lys Arg Ser Gln Gly Arg Ile Pro Val Lys Trp Met Ala Ile Glu
770                 775                 780

Ser Leu Phe Asp His Ile Tyr Thr Thr Gln Ser Asp Val Trp Ser Phe
785                 790                 795                 800

Gly Val Leu Leu Trp Glu Ile Val Thr Leu Gly Gly Asn Pro Tyr Pro
                805                 810                 815

Gly Ile Pro Pro Glu Arg Leu Phe Asn Leu Leu Lys Thr Gly His Arg
            820                 825                 830

Met Glu Arg Pro Asp Asn Cys Ser Glu Glu Met Tyr Arg Leu Met Leu
        835                 840                 845

Gln Cys Trp Lys Gln Glu Pro Asp Lys Arg Pro Val Phe Ala Asp Ile
850                 855                 860

Ser Lys Asp Leu Glu Lys Met Met Val Lys Arg Arg Asp Tyr Leu Asp
865                 870                 875                 880

Leu Ala Ala Ser Thr Pro Ser Asp Ser Leu Ile Tyr Asp Asp Gly Leu
                885                 890                 895

Ser Glu Glu Glu Thr Pro Leu Val Asp Cys Asn Asn Ala Pro Leu Pro
            900                 905                 910

Arg Ala Leu Pro Ser Thr Trp Ile Glu Asn Lys Leu Tyr Gly Met Ser
        915                 920                 925

Asp Pro Asn Trp Pro Gly Glu Ser Pro Val Pro Leu Thr Arg Ala Asp
930                 935                 940

Gly Thr Asn Thr Gly Phe Pro Arg Tyr Pro Asn Asp Ser Val Tyr Ala
945                 950                 955                 960

Asn Trp Met Leu Ser Pro Ser Ala Ala Lys Leu Met Asp Thr Phe Asp
                965                 970                 975

Ser

<210> SEQ ID NO 21
<211> LENGTH: 1040
<212> TYPE: PRT
<213> ORGANISM: Homo sapiens
<220> FEATURE:
<221> NAME/KEY: misc_feature
<223> OTHER INFORMATION: KIF5B-RET (K16;R12 variant2)

<400> SEQUENCE: 21

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
                20                  25                  30

Phe Gln Gly Glu Asp Thr Val Val Ile Ala Ser Lys Pro Tyr Ala Phe
            35                  40                  45

Asp Arg Val Phe Gln Ser Ser Thr Ser Gln Glu Gln Val Tyr Asn Asp
        50                  55                  60
```

```
Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                 85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
```

```
            485                 490                 495
Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
            515                 520                 525

Thr Leu Ala Ser Ile Asp Ala Glu Leu Gln Lys Leu Lys Glu Met Thr
            530                 535             540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
            595                 600                 605

Lys Gln Leu Glu Ser Thr Gln Thr Glu Ser Asn Lys Lys Met Glu Glu
            610                 615                 620

Asn Glu Lys Glu Leu Ala Ala Cys Gln Leu Arg Ile Ser Gln Glu Asp
625                 630                 635                 640

Pro Lys Trp Glu Phe Pro Arg Lys Asn Leu Val Leu Gly Lys Thr Leu
                645                 650                 655

Gly Glu Gly Glu Phe Gly Lys Val Val Lys Ala Thr Ala Phe His Leu
            660                 665                 670

Lys Gly Arg Ala Gly Tyr Thr Thr Val Ala Val Lys Met Leu Lys Glu
            675                 680                 685

Asn Ala Ser Pro Ser Glu Leu Arg Asp Leu Leu Ser Glu Phe Asn Val
            690                 695                 700

Leu Lys Gln Val Asn His Pro His Val Ile Lys Leu Tyr Gly Ala Cys
705                 710                 715                 720

Ser Gln Asp Gly Pro Leu Leu Leu Ile Val Glu Tyr Ala Lys Tyr Gly
                725                 730                 735

Ser Leu Arg Gly Phe Leu Arg Glu Ser Arg Lys Val Gly Pro Gly Tyr
            740                 745                 750

Leu Gly Ser Gly Gly Ser Arg Asn Ser Ser Ser Leu Asp His Pro Asp
            755                 760                 765

Glu Arg Ala Leu Thr Met Gly Asp Leu Ile Ser Phe Ala Trp Gln Ile
            770                 775                 780

Ser Gln Gly Met Gln Tyr Leu Ala Glu Met Lys Leu Val His Arg Asp
785                 790                 795                 800

Leu Ala Ala Arg Asn Ile Leu Val Ala Glu Gly Arg Lys Met Lys Ile
                805                 810                 815

Ser Asp Phe Gly Leu Ser Arg Asp Val Tyr Glu Asp Ser Tyr Val
                820                 825                 830

Lys Arg Ser Gln Gly Arg Ile Pro Val Lys Trp Met Ala Ile Glu Ser
            835                 840                 845

Leu Phe Asp His Ile Tyr Thr Thr Gln Ser Asp Val Trp Ser Phe Gly
            850                 855                 860

Val Leu Leu Trp Glu Ile Val Thr Leu Gly Gly Asn Pro Tyr Pro Gly
865                 870                 875                 880

Ile Pro Pro Glu Arg Leu Phe Asn Leu Leu Lys Thr Gly His Arg Met
                885                 890                 895

Glu Arg Pro Asp Asn Cys Ser Glu Glu Met Tyr Arg Leu Met Leu Gln
            900                 905                 910
```

```
Cys Trp Lys Gln Glu Pro Asp Lys Arg Pro Val Phe Ala Asp Ile Ser
        915                 920                 925

Lys Asp Leu Glu Lys Met Met Val Lys Arg Arg Asp Tyr Leu Asp Leu
930                 935                 940

Ala Ala Ser Thr Pro Ser Asp Ser Leu Ile Tyr Asp Asp Gly Leu Ser
945                 950                 955                 960

Glu Glu Glu Thr Pro Leu Val Asp Cys Asn Asn Ala Pro Leu Pro Arg
                965                 970                 975

Ala Leu Pro Ser Thr Trp Ile Glu Asn Lys Leu Tyr Gly Met Ser Asp
            980                 985                 990

Pro Asn Trp Pro Gly Glu Ser Pro  Val Pro Leu Thr Arg Ala Asp Gly
        995                 1000                1005

Thr Asn Thr Gly Phe Pro Arg  Tyr Pro Asn Asp Ser  Val Tyr Ala
    1010                1015                1020

Asn Trp  Met Leu Ser Pro Ser  Ala Ala Lys Leu Met  Asp Thr Phe
    1025                1030                1035

Asp Ser
    1040

<210> SEQ ID NO 22
<211> LENGTH: 1215
<212> TYPE: PRT
<213> ORGANISM: Homo sapiens
<220> FEATURE:
<221> NAME/KEY: misc_feature
<223> OTHER INFORMATION: KIF5B-RET (K22;R12 variant2)

<400> SEQUENCE: 22

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
```

```
            210                 215                 220
Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
                260                 265                 270

Thr Tyr Val Pro Tyr Arg Asp Ser Lys Met Thr Arg Ile Leu Gln Asp
            275                 280                 285

Ser Leu Gly Gly Asn Cys Arg Thr Thr Ile Val Ile Cys Cys Ser Pro
290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
                340                 345                 350

Ile Leu Arg Asn Thr Ile Gln Trp Leu Glu Asn Glu Leu Asn Arg Trp
                355                 360                 365

Arg Asn Gly Glu Thr Val Pro Ile Asp Glu Gln Phe Asp Lys Glu Lys
370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Ile Ala Lys Leu Tyr Lys Gln Leu
                420                 425                 430

Asp Asp Lys Asp Glu Glu Ile Asn Gln Gln Ser Gln Leu Val Glu Lys
                435                 440                 445

Leu Lys Thr Gln Met Leu Asp Gln Glu Glu Leu Leu Ala Ser Thr Arg
                450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
                500                 505                 510

Thr Lys Glu Tyr Glu Leu Leu Ser Asp Glu Leu Asn Gln Lys Ser Ala
                515                 520                 525

Thr Leu Ala Ser Ile Asp Ala Glu Leu Gln Lys Leu Lys Glu Met Thr
                530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
                580                 585                 590

Tyr Ile Ser Lys Met Lys Ser Glu Val Lys Thr Met Val Lys Arg Cys
                595                 600                 605

Lys Gln Leu Glu Ser Thr Gln Thr Glu Ser Asn Lys Lys Met Glu Glu
                610                 615                 620

Asn Glu Lys Glu Leu Ala Ala Cys Gln Leu Arg Ile Ser Gln His Glu
625                 630                 635                 640
```

```
Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
    770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Glu Asp Pro
                805                 810                 815

Lys Trp Glu Phe Pro Arg Lys Asn Leu Val Leu Gly Lys Thr Leu Gly
            820                 825                 830

Glu Gly Glu Phe Gly Lys Val Val Lys Ala Thr Ala Phe His Leu Lys
        835                 840                 845

Gly Arg Ala Gly Tyr Thr Thr Val Ala Val Lys Met Leu Lys Glu Asn
    850                 855                 860

Ala Ser Pro Ser Glu Leu Arg Asp Leu Leu Ser Glu Phe Asn Val Leu
865                 870                 875                 880

Lys Gln Val Asn His Pro His Val Ile Lys Leu Tyr Gly Ala Cys Ser
                885                 890                 895

Gln Asp Gly Pro Leu Leu Leu Ile Val Glu Tyr Ala Lys Tyr Gly Ser
            900                 905                 910

Leu Arg Gly Phe Leu Arg Glu Ser Arg Lys Val Gly Pro Gly Tyr Leu
        915                 920                 925

Gly Ser Gly Gly Ser Arg Asn Ser Ser Ser Leu Asp His Pro Asp Glu
    930                 935                 940

Arg Ala Leu Thr Met Gly Asp Leu Ile Ser Phe Ala Trp Gln Ile Ser
945                 950                 955                 960

Gln Gly Met Gln Tyr Leu Ala Glu Met Lys Leu Val His Arg Asp Leu
                965                 970                 975

Ala Ala Arg Asn Ile Leu Val Ala Glu Gly Arg Lys Met Lys Ile Ser
            980                 985                 990

Asp Phe Gly Leu Ser Arg Asp Val Tyr Glu Glu Asp Ser Tyr Val Lys
        995                 1000                1005

Arg Ser Gln Gly Arg Ile Pro Val Lys Trp Met Ala Ile Glu Ser
    1010                1015                1020

Leu Phe Asp His Ile Tyr Thr Thr Gln Ser Asp Val Trp Ser Phe
    1025                1030                1035

Gly Val Leu Leu Trp Glu Ile Val Thr Leu Gly Gly Asn Pro Tyr
    1040                1045                1050
```

```
Pro Gly Ile Pro Pro Glu Arg Leu Phe Asn Leu Leu Lys Thr Gly
    1055                1060                1065

His Arg Met Glu Arg Pro Asp Asn Cys Ser Glu Met Tyr Arg
    1070                1075                1080

Leu Met Leu Gln Cys Trp Lys Gln Glu Pro Asp Lys Arg Pro Val
    1085                1090                1095

Phe Ala Asp Ile Ser Lys Asp Leu Glu Lys Met Met Val Lys Arg
    1100                1105                1110

Arg Asp Tyr Leu Asp Leu Ala Ala Ser Thr Pro Ser Asp Ser Leu
    1115                1120                1125

Ile Tyr Asp Asp Gly Leu Ser Glu Glu Glu Thr Pro Leu Val Asp
    1130                1135                1140

Cys Asn Asn Ala Pro Leu Pro Arg Ala Leu Pro Ser Thr Trp Ile
    1145                1150                1155

Glu Asn Lys Leu Tyr Gly Met Ser Asp Pro Asn Trp Pro Gly Glu
    1160                1165                1170

Ser Pro Val Pro Leu Thr Arg Ala Asp Gly Thr Asn Thr Gly Phe
    1175                1180                1185

Pro Arg Tyr Pro Asn Asp Ser Val Tyr Ala Asn Trp Met Leu Ser
    1190                1195                1200

Pro Ser Ala Ala Lys Leu Met Asp Thr Phe Asp Ser
    1205                1210                1215

<210> SEQ ID NO 23
<211> LENGTH: 1250
<212> TYPE: PRT
<213> ORGANISM: Homo sapiens
<220> FEATURE:
<221> NAME/KEY: misc_feature
<223> OTHER INFORMATION: KIF5B-RET (K23;R12 variant2)

<400> SEQUENCE: 23

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
                20                  25                  30

Phe Gln Gly Glu Asp Thr Val Val Ile Ala Ser Lys Pro Tyr Ala Phe
            35                  40                  45

Asp Arg Val Phe Gln Ser Ser Thr Ser Gln Glu Gln Val Tyr Asn Asp
        50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
                100                 105                 110

Gln Asp Ile Phe Asn Tyr Ile Tyr Ser Met Asp Glu Asn Leu Glu Phe
            115                 120                 125

His Ile Lys Val Ser Tyr Phe Glu Ile Tyr Leu Asp Lys Ile Arg Asp
        130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
                180                 185                 190
```

-continued

```
Ala Val Thr Asn Met Asn Glu His Ser Ser Arg Ser His Ser Ile Phe
            195                 200                 205
Leu Ile Asn Val Lys Gln Glu Asn Thr Gln Thr Glu Gln Lys Leu Ser
210                 215                 220
Gly Lys Leu Tyr Leu Val Asp Leu Ala Gly Ser Glu Lys Val Ser Lys
225                 230                 235                 240
Thr Gly Ala Glu Gly Ala Val Leu Asp Glu Ala Lys Asn Ile Asn Lys
                245                 250                 255
Ser Leu Ser Ala Leu Gly Asn Val Ile Ser Ala Leu Ala Glu Gly Ser
                260                 265                 270
Thr Tyr Val Pro Tyr Arg Asp Ser Lys Met Thr Arg Ile Leu Gln Asp
            275                 280                 285
Ser Leu Gly Gly Asn Cys Arg Thr Thr Ile Val Ile Cys Cys Ser Pro
290                 295                 300
Ser Ser Tyr Asn Glu Ser Glu Thr Lys Ser Thr Leu Leu Phe Gly Gln
305                 310                 315                 320
Arg Ala Lys Thr Ile Lys Asn Thr Val Cys Val Asn Val Glu Leu Thr
                325                 330                 335
Ala Glu Gln Trp Lys Lys Lys Tyr Glu Lys Glu Lys Glu Lys Asn Lys
            340                 345                 350
Ile Leu Arg Asn Thr Ile Gln Trp Leu Glu Asn Glu Leu Asn Arg Trp
            355                 360                 365
Arg Asn Gly Glu Thr Val Pro Ile Asp Glu Gln Phe Asp Lys Glu Lys
            370                 375                 380
Ala Asn Leu Glu Ala Phe Thr Val Asp Lys Asp Ile Thr Leu Thr Asn
385                 390                 395                 400
Asp Lys Pro Ala Thr Ala Ile Gly Val Ile Gly Asn Phe Thr Asp Ala
                405                 410                 415
Glu Arg Arg Lys Cys Glu Glu Ile Ala Lys Leu Tyr Lys Gln Leu
                420                 425                 430
Asp Asp Lys Asp Glu Glu Ile Asn Gln Gln Ser Gln Leu Val Glu Lys
            435                 440                 445
Leu Lys Thr Gln Met Leu Asp Gln Glu Glu Leu Leu Ala Ser Thr Arg
            450                 455                 460
Arg Asp Gln Asp Asn Met Gln Ala Glu Leu Asn Arg Leu Gln Ala Glu
465                 470                 475                 480
Asn Asp Ala Ser Lys Glu Glu Val Lys Glu Val Leu Gln Ala Leu Glu
                485                 490                 495
Glu Leu Ala Val Asn Tyr Asp Gln Lys Ser Gln Glu Val Glu Asp Lys
            500                 505                 510
Thr Lys Glu Tyr Glu Leu Leu Ser Asp Glu Leu Asn Gln Lys Ser Ala
            515                 520                 525
Thr Leu Ala Ser Ile Asp Ala Glu Leu Gln Lys Leu Lys Glu Met Thr
530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
            580                 585                 590
Tyr Ile Ser Lys Met Lys Ser Glu Val Lys Thr Met Val Lys Arg Cys
            595                 600                 605
```

-continued

```
Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
            645                 650                 655

Lys Arg Gln Leu Glu Glu Ser Val Asp Ala Leu Ser Glu Glu Leu Val
                660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
                805                 810                 815

Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
        835                 840                 845

Glu Asp Pro Lys Trp Glu Phe Pro Arg Lys Asn Leu Val Leu Gly Lys
850                 855                 860

Thr Leu Gly Glu Gly Glu Phe Gly Lys Val Val Lys Ala Thr Ala Phe
865                 870                 875                 880

His Leu Lys Gly Arg Ala Gly Tyr Thr Thr Val Ala Val Lys Met Leu
                885                 890                 895

Lys Glu Asn Ala Ser Pro Ser Glu Leu Arg Asp Leu Leu Ser Glu Phe
            900                 905                 910

Asn Val Leu Lys Gln Val Asn His Pro His Val Ile Lys Leu Tyr Gly
        915                 920                 925

Ala Cys Ser Gln Asp Gly Pro Leu Leu Leu Ile Val Glu Tyr Ala Lys
930                 935                 940

Tyr Gly Ser Leu Arg Gly Phe Leu Arg Glu Ser Arg Lys Val Gly Pro
945                 950                 955                 960

Gly Tyr Leu Gly Ser Gly Gly Ser Arg Asn Ser Ser Ser Leu Asp His
                965                 970                 975

Pro Asp Glu Arg Ala Leu Thr Met Gly Asp Leu Ile Ser Phe Ala Trp
            980                 985                 990

Gln Ile Ser Gln Gly Met Gln Tyr Leu Ala Glu Met Lys Leu Val His
        995                 1000                1005

Arg Asp Leu Ala Ala Arg Asn Ile Leu Val Ala Glu Gly Arg Lys
    1010                1015                1020

Met Lys Ile Ser Asp Phe Gly Leu Ser Arg Asp Val Tyr Glu Glu
```

```
                1025                1030                1035

Asp Ser Tyr Val Lys Arg Ser Gln Gly Arg Ile Pro Val Lys Trp
        1040                1045                1050

Met Ala Ile Glu Ser Leu Phe Asp His Ile Tyr Thr Thr Gln Ser
    1055                1060                1065

Asp Val Trp Ser Phe Gly Val Leu Leu Trp Glu Ile Val Thr Leu
    1070                1075                1080

Gly Gly Asn Pro Tyr Pro Gly Ile Pro Pro Glu Arg Leu Phe Asn
    1085                1090                1095

Leu Leu Lys Thr Gly His Arg Met Glu Arg Pro Asp Asn Cys Ser
    1100                1105                1110

Glu Glu Met Tyr Arg Leu Met Leu Gln Cys Trp Lys Gln Glu Pro
    1115                1120                1125

Asp Lys Arg Pro Val Phe Ala Asp Ile Ser Lys Asp Leu Glu Lys
    1130                1135                1140

Met Met Val Lys Arg Arg Asp Tyr Leu Asp Leu Ala Ala Ser Thr
    1145                1150                1155

Pro Ser Asp Ser Leu Ile Tyr Asp Asp Gly Leu Ser Glu Glu Glu
    1160                1165                1170

Thr Pro Leu Val Asp Cys Asn Asn Ala Pro Leu Pro Arg Ala Leu
    1175                1180                1185

Pro Ser Thr Trp Ile Glu Asn Lys Leu Tyr Gly Met Ser Asp Pro
    1190                1195                1200

Asn Trp Pro Gly Glu Ser Pro Val Pro Leu Thr Arg Ala Asp Gly
    1205                1210                1215

Thr Asn Thr Gly Phe Pro Arg Tyr Pro Asn Asp Ser Val Tyr Ala
    1220                1225                1230

Asn Trp Met Leu Ser Pro Ser Ala Ala Lys Leu Met Asp Thr Phe
    1235                1240                1245

Asp Ser
    1250

<210> SEQ ID NO 24
<211> LENGTH: 985
<212> TYPE: PRT
<213> ORGANISM: Homo sapiens
<220> FEATURE:
<221> NAME/KEY: misc_feature
<223> OTHER INFORMATION: KIF5B-RET (K15;R11 variant4)

<400> SEQUENCE: 24

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110
```

```
Gln Asp Ile Phe Asn Tyr Ile Tyr Ser Met Asp Glu Asn Leu Glu Phe
            115                 120                 125
His Ile Lys Val Ser Tyr Phe Glu Ile Tyr Leu Asp Lys Ile Arg Asp
        130                 135                 140
Leu Leu Asp Val Ser Lys Thr Asn Leu Ser Val His Glu Asp Lys Asn
145                 150                 155                 160
Arg Val Pro Tyr Val Lys Gly Cys Thr Glu Arg Phe Val Cys Ser Pro
                165                 170                 175
Asp Glu Val Met Asp Thr Ile Asp Gly Lys Ser Asn Arg His Val
            180                 185                 190
Ala Val Thr Asn Met Asn Glu His Ser Ser Arg Ser His Ser Ile Phe
        195                 200                 205
Leu Ile Asn Val Lys Gln Glu Asn Thr Gln Thr Glu Gln Lys Leu Ser
    210                 215                 220
Gly Lys Leu Tyr Leu Val Asp Leu Ala Gly Ser Glu Lys Val Ser Lys
225                 230                 235                 240
Thr Gly Ala Glu Gly Ala Val Leu Asp Glu Ala Lys Asn Ile Asn Lys
                245                 250                 255
Ser Leu Ser Ala Leu Gly Asn Val Ile Ser Ala Leu Ala Glu Gly Ser
            260                 265                 270
Thr Tyr Val Pro Tyr Arg Asp Ser Lys Met Thr Arg Ile Leu Gln Asp
        275                 280                 285
Ser Leu Gly Gly Asn Cys Arg Thr Thr Ile Val Ile Cys Cys Ser Pro
    290                 295                 300
Ser Ser Tyr Asn Glu Ser Glu Thr Lys Ser Thr Leu Leu Phe Gly Gln
305                 310                 315                 320
Arg Ala Lys Thr Ile Lys Asn Thr Val Cys Val Asn Val Glu Leu Thr
                325                 330                 335
Ala Glu Gln Trp Lys Lys Lys Tyr Glu Lys Glu Lys Glu Lys Asn Lys
            340                 345                 350
Ile Leu Arg Asn Thr Ile Gln Trp Leu Glu Asn Glu Leu Asn Arg Trp
        355                 360                 365
Arg Asn Gly Glu Thr Val Pro Ile Asp Glu Gln Phe Asp Lys Glu Lys
    370                 375                 380
Ala Asn Leu Glu Ala Phe Thr Val Asp Lys Asp Ile Thr Leu Thr Asn
385                 390                 395                 400
Asp Lys Pro Ala Thr Ala Ile Gly Val Ile Gly Asn Phe Thr Asp Ala
                405                 410                 415
Glu Arg Arg Lys Cys Glu Glu Ile Ala Lys Leu Tyr Lys Gln Leu
            420                 425                 430
Asp Asp Lys Asp Glu Glu Ile Asn Gln Gln Ser Gln Leu Val Glu Lys
        435                 440                 445
Leu Lys Thr Gln Met Leu Asp Gln Glu Glu Leu Leu Ala Ser Thr Arg
    450                 455                 460
Arg Asp Gln Asp Asn Met Gln Ala Glu Leu Asn Arg Leu Gln Ala Glu
465                 470                 475                 480
Asn Asp Ala Ser Lys Glu Glu Val Lys Glu Val Leu Gln Ala Leu Glu
                485                 490                 495
Glu Leu Ala Val Asn Tyr Asp Gln Lys Ser Gln Glu Val Glu Asp Lys
            500                 505                 510
Thr Lys Glu Tyr Glu Leu Leu Ser Asp Glu Leu Asn Gln Lys Ser Ala
        515                 520                 525
Thr Leu Ala Ser Ile Asp Ala Glu Leu Gln Lys Leu Lys Glu Met Thr
```

-continued

```
                530                 535                 540
Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Phe
                565                 570                 575

Ala His Lys Pro Pro Ile Ser Ser Ala Glu Met Thr Phe Arg Arg Pro
                580                 585                 590

Ala Gln Ala Phe Pro Val Ser Tyr Ser Ser Gly Ala Arg Arg Pro
                595                 600                 605

Ser Leu Asp Ser Met Glu Asn Gln Val Ser Val Asp Ala Phe Lys Ile
                610                 615                 620

Leu Glu Asp Pro Lys Trp Glu Phe Pro Arg Lys Asn Leu Val Leu Gly
625                 630                 635                 640

Lys Thr Leu Gly Glu Gly Glu Phe Gly Lys Val Val Lys Ala Thr Ala
                645                 650                 655

Phe His Leu Lys Gly Arg Ala Gly Tyr Thr Thr Val Ala Val Lys Met
                660                 665                 670

Leu Lys Glu Asn Ala Ser Pro Ser Glu Leu Arg Asp Leu Leu Ser Glu
                675                 680                 685

Phe Asn Val Leu Lys Gln Val Asn His Pro His Val Ile Lys Leu Tyr
                690                 695                 700

Gly Ala Cys Ser Gln Asp Gly Pro Leu Leu Leu Ile Val Glu Tyr Ala
705                 710                 715                 720

Lys Tyr Gly Ser Leu Arg Gly Phe Leu Arg Glu Ser Arg Lys Val Gly
                725                 730                 735

Pro Gly Tyr Leu Gly Ser Gly Gly Ser Arg Asn Ser Ser Ser Leu Asp
                740                 745                 750

His Pro Asp Glu Arg Ala Leu Thr Met Gly Asp Leu Ile Ser Phe Ala
                755                 760                 765

Trp Gln Ile Ser Gln Gly Met Gln Tyr Leu Ala Glu Met Lys Leu Val
                770                 775                 780

His Arg Asp Leu Ala Ala Arg Asn Ile Leu Val Ala Glu Gly Arg Lys
785                 790                 795                 800

Met Lys Ile Ser Asp Phe Gly Leu Ser Arg Asp Val Tyr Glu Glu Asp
                805                 810                 815

Ser Tyr Val Lys Arg Ser Gln Gly Arg Ile Pro Val Lys Trp Met Ala
                820                 825                 830

Ile Glu Ser Leu Phe Asp His Ile Tyr Thr Thr Gln Ser Asp Val Trp
                835                 840                 845

Ser Phe Gly Val Leu Leu Trp Glu Ile Val Thr Leu Gly Gly Asn Pro
850                 855                 860

Tyr Pro Gly Ile Pro Pro Glu Arg Leu Phe Asn Leu Leu Lys Thr Gly
865                 870                 875                 880

His Arg Met Glu Arg Pro Asp Asn Cys Ser Glu Glu Met Tyr Arg Leu
                885                 890                 895

Met Leu Gln Cys Trp Lys Gln Glu Pro Asp Lys Arg Pro Val Phe Ala
                900                 905                 910

Asp Ile Ser Lys Asp Leu Glu Lys Met Met Val Lys Arg Arg Asp Tyr
                915                 920                 925

Leu Asp Leu Ala Ala Ser Thr Pro Ser Asp Ser Leu Ile Tyr Asp Asp
                930                 935                 940

Gly Leu Ser Glu Glu Glu Thr Pro Leu Val Asp Cys Asn Asn Ala Pro
945                 950                 955                 960
```

Leu Pro Arg Ala Leu Pro Ser Thr Trp Ile Glu Asn Lys Leu Tyr Gly
            965                 970                 975

Arg Ile Ser His Ala Phe Thr Arg Phe
            980                 985

<210> SEQ ID NO 25
<211> LENGTH: 1512
<212> TYPE: DNA
<213> ORGANISM: Homo sapiens
<220> FEATURE:
<221> NAME/KEY: misc_feature
<223> OTHER INFORMATION: CCDC6-RET variant a (AB698668.1)

<400> SEQUENCE: 25

| | | | | | |
|---|---|---|---|---|---|
| atggcggaca | gcgccagcga | gagcgacacg | gacggggcgg | ggggcaacag | cagcagctcg | 60 |
| gccgccatgc | agtcgtcctg | ctcgtcgacc | tcgggcggcg | gcggtggcgg | cggggaggc | 120 |
| ggcggcggtg | ggaagtcggg | gggcattgtc | atctcgccgt | tccgcctgga | ggagctcacc | 180 |
| aaccgcctgg | cctcgctgca | gcaagagaac | aaggtgctga | gatagagct | ggagacctac | 240 |
| aaactgaagt | gcaaggcact | gcaggaggag | aaccgcgacc | tgcgcaaagc | cagcgttacc | 300 |
| atcgaggatc | caaagtggga | attccctcgg | aagaacttgg | ttcttggaaa | aactctagga | 360 |
| gaaggcgaat | ttggaaaagt | ggtcaaggca | acggccttcc | atctgaaagg | cagagcaggg | 420 |
| tacaccacgg | tggccgtgaa | gatgctgaaa | gagaacgcct | ccccgagtga | gctgcgagac | 480 |
| ctgctgtcag | agttcaacgt | cctgaagcag | gtcaaccacc | cacatgtcat | caaattgtat | 540 |
| ggggcctgca | gccaggatgg | cccgctcctc | ctcatcgtgg | agtacgccaa | atacggctcc | 600 |
| ctgcggggct | tcctccgcga | gagccgcaaa | gtggggcctg | gctacctggg | cagtggaggc | 660 |
| agccgcaact | ccagctccct | ggaccacccg | gatgagcggg | ccctcaccat | gggcgacctc | 720 |
| atctcatttg | cctggcagat | ctcacagggg | atgcagtatc | tggccgagat | gaagctcgtt | 780 |
| catcgggact | tggcagccag | aaacatcctg | gtagctgagg | ggcggaagat | gaagatttcg | 840 |
| gatttcggct | tgtcccgaga | tgtttatgaa | gaggattcct | acgtgaagag | gagccagggt | 900 |
| cggattccag | ttaaatggat | ggcaattgaa | tccctttttg | atcatatcta | caccacgcaa | 960 |
| agtgatgtat | ggtcttttgg | tgtcctgctg | tgggagatcg | tgaccctagg | ggaaaccccc | 1020 |
| tatcctggga | ttcctcctga | gcggctcttc | aaccttctga | agaccggcca | ccggatggag | 1080 |
| aggccagaca | actgcagcga | ggagatgtac | cgcctgatgc | tgcaatgctg | gaagcaggag | 1140 |
| ccggacaaaa | ggccggtgtt | tcggacatc | agcaaagacc | tggagaagat | gatggttaag | 1200 |
| aggagagact | acttggacct | tgcggcgtcc | actccatctg | actccctgat | ttatgacgac | 1260 |
| ggcctctcag | aggaggagac | accgctggtg | gactgtaata | atgcccccct | ccctcgagcc | 1320 |
| ctcccttcca | catggattga | aaacaaactc | tatggcatgt | cagacccgaa | ctggcctgga | 1380 |
| gagagtcctg | taccactcac | gagagctgat | ggcactaaca | ctgggtttcc | aagatatcca | 1440 |
| aatgatagtg | tatatgctaa | ctggatgctt | tcaccctcag | cggcaaaatt | aatggacacg | 1500 |
| tttgatagtt | aa | | | | | 1512 |

<210> SEQ ID NO 26
<211> LENGTH: 1386
<212> TYPE: DNA
<213> ORGANISM: Homo sapiens
<220> FEATURE:
<221> NAME/KEY: misc_feature
<223> OTHER INFORMATION: CCDC6-RET variant c (AB698669.1)

<400> SEQUENCE: 26

```
atggcggaca gcgccagcga gagcgacacg gacggggcgg ggggcaacag cagcagctcg      60
gccgccatgc agtcgtcctg ctcgtcgacc tcgggcggcg gcggtggcgg cggggggaggc    120
ggcggcggtg ggaagtcggg gggcattgtc atctcgccgt tccgcctgga ggagctcacc    180
aaccgcctgg cctcgctgca gcaagagaac aaggtgctga agatagagct ggagacctac    240
aaactgaagt gcaaggcact gcaggaggag aaccgcgacc tgcgcaaagc cagcgttacc    300
atcgaggatc caaagtggga attccctcgg aagaacttgg ttcttggaaa aactctagga    360
gaaggcgaat ttggaaaagt ggtcaaggca acggccttcc atctgaaagg cagagcaggg    420
tacaccacgg tggccgtgaa gatgctgaaa gagaacgcct ccccgagtga gctgcgagac    480
ctgctgtcag agttcaacgt cctgaagcag gtcaaccacc acatgtcat caaattgtat    540
ggggcctgca gccaggatgg cccgctcctc ctcatcgtgg agtacgccaa atacggctcc    600
ctgcggggct tcctccgcga gagccgcaaa gtggggcctg gctacctggg cagtggaggc    660
agccgcaact ccagctccct ggaccacccg gatgagcggg ccctcaccat gggcgacctc    720
atctcatttg cctggcagat ctcacagggg atgcagtatc tggccgagat gaagctcgtt    780
catcgggact tggcagccag aaacatcctg gtagctgagg gcggaagat gaagatttcg    840
gatttcggct tgtcccgaga tgtttatgaa gaggattcct acgtgaagag gagccagggt    900
cggattccag ttaaatggat ggcaattgaa tcccttttg atcatatcta caccacgcaa    960
agtgatgtat ggtcttttgg tgtcctgctg tgggagatcg tgaccctagg gggaaacccc   1020
tatcctggga ttcctcctga gcggctcttc aaccttctga agaccggcca ccggatggag   1080
aggccagaca actgcagcga ggagatgtac cgcctgatgc tgcaatgctg gaagcaggag   1140
ccggacaaaa ggccggtgtt tgcggacatc agcaaagacc tggagaagat gatggttaag   1200
aggagagact acttggacct tgcggcgtcc actccatctg actccctgat ttatgacgac   1260
ggcctctcag aggaggagac accgctggtg gactgtaata atgcccccct ccctcgagcc   1320
ctcccttcca catggattga aaacaaactc tatggtagaa tttcccatgc atttactaga   1380
ttctag                                                              1386
```

<210> SEQ ID NO 27
<211> LENGTH: 503
<212> TYPE: PRT
<213> ORGANISM: Homo sapiens
<220> FEATURE:
<221> NAME/KEY: misc_feature
<223> OTHER INFORMATION: CCDC6-RET variant a (BAM36435.1)

<400> SEQUENCE: 27

```
Met Ala Asp Ser Ala Ser Glu Ser Asp Thr Asp Gly Ala Gly Gly Asn
 1               5                  10                  15

Ser Ser Ser Ser Ala Ala Met Gln Ser Ser Cys Ser Ser Thr Ser Gly
            20                  25                  30

Gly Gly Gly Gly Gly Gly Gly Gly Gly Gly Lys Ser Gly Gly
            35                  40                  45

Ile Val Ile Ser Pro Phe Arg Leu Glu Glu Leu Thr Asn Arg Leu Ala
        50                  55                  60

Ser Leu Gln Gln Glu Asn Lys Val Leu Lys Ile Glu Leu Glu Thr Tyr
65                  70                  75                  80

Lys Leu Lys Cys Lys Ala Leu Gln Glu Glu Asn Arg Asp Leu Arg Lys
                85                  90                  95
```

-continued

```
Ala Ser Val Thr Ile Glu Asp Pro Lys Trp Glu Phe Pro Arg Lys Asn
            100                 105                 110

Leu Val Leu Gly Lys Thr Leu Gly Glu Gly Phe Gly Lys Val Val
        115                 120                 125

Lys Ala Thr Ala Phe His Leu Lys Gly Arg Ala Gly Tyr Thr Thr Val
    130                 135                 140

Ala Val Lys Met Leu Lys Glu Asn Ala Ser Pro Ser Glu Leu Arg Asp
145                 150                 155                 160

Leu Leu Ser Glu Phe Asn Val Leu Lys Gln Val Asn His Pro His Val
                165                 170                 175

Ile Lys Leu Tyr Gly Ala Cys Ser Gln Asp Gly Pro Leu Leu Leu Ile
            180                 185                 190

Val Glu Tyr Ala Lys Tyr Gly Ser Leu Arg Gly Phe Leu Arg Glu Ser
        195                 200                 205

Arg Lys Val Gly Pro Gly Tyr Leu Gly Ser Gly Gly Ser Arg Asn Ser
    210                 215                 220

Ser Ser Leu Asp His Pro Asp Glu Arg Ala Leu Thr Met Gly Asp Leu
225                 230                 235                 240

Ile Ser Phe Ala Trp Gln Ile Ser Gln Gly Met Gln Tyr Leu Ala Glu
                245                 250                 255

Met Lys Leu Val His Arg Asp Leu Ala Ala Arg Asn Ile Leu Val Ala
            260                 265                 270

Glu Gly Arg Lys Met Lys Ile Ser Asp Phe Gly Leu Ser Arg Asp Val
        275                 280                 285

Tyr Glu Glu Asp Ser Tyr Val Lys Arg Ser Gln Gly Arg Ile Pro Val
    290                 295                 300

Lys Trp Met Ala Ile Glu Ser Leu Phe Asp His Ile Tyr Thr Thr Gln
305                 310                 315                 320

Ser Asp Val Trp Ser Phe Gly Val Leu Leu Trp Glu Ile Val Thr Leu
                325                 330                 335

Gly Gly Asn Pro Tyr Pro Gly Ile Pro Pro Glu Arg Leu Phe Asn Leu
            340                 345                 350

Leu Lys Thr Gly His Arg Met Glu Arg Pro Asp Asn Cys Ser Glu Glu
        355                 360                 365

Met Tyr Arg Leu Met Leu Gln Cys Trp Lys Gln Glu Pro Asp Lys Arg
    370                 375                 380

Pro Val Phe Ala Asp Ile Ser Lys Asp Leu Glu Lys Met Met Val Lys
385                 390                 395                 400

Arg Arg Asp Tyr Leu Asp Leu Ala Ala Ser Thr Pro Ser Asp Ser Leu
                405                 410                 415

Ile Tyr Asp Asp Gly Leu Ser Glu Glu Glu Thr Pro Leu Val Asp Cys
            420                 425                 430

Asn Asn Ala Pro Leu Pro Arg Ala Leu Pro Ser Thr Trp Ile Glu Asn
        435                 440                 445

Lys Leu Tyr Gly Met Ser Asp Pro Asn Trp Pro Gly Glu Ser Pro Val
    450                 455                 460

Pro Leu Thr Arg Ala Asp Gly Thr Asn Thr Gly Phe Pro Arg Tyr Pro
465                 470                 475                 480

Asn Asp Ser Val Tyr Ala Asn Trp Met Leu Ser Pro Ser Ala Ala Lys
                485                 490                 495

Leu Met Asp Thr Phe Asp Ser
            500
```

```
<210> SEQ ID NO 28
<211> LENGTH: 461
<212> TYPE: PRT
<213> ORGANISM: Homo sapiens
<220> FEATURE:
<221> NAME/KEY: misc_feature
<223> OTHER INFORMATION: CCDC6-RET variant c (BAM36436.1)

<400> SEQUENCE: 28

Met Ala Asp Ser Ala Ser Glu Ser Asp Thr Asp Gly Ala Gly Gly Asn
1               5                   10                  15

Ser Ser Ser Ser Ala Ala Met Gln Ser Ser Cys Ser Ser Thr Ser Gly
                20                  25                  30

Gly Gly Gly Gly Gly Gly Gly Gly Gly Gly Gly Lys Ser Gly Gly
            35                  40                  45

Ile Val Ile Ser Pro Phe Arg Leu Glu Glu Leu Thr Asn Arg Leu Ala
        50                  55                  60

Ser Leu Gln Gln Glu Asn Lys Val Leu Lys Ile Glu Leu Glu Thr Tyr
65                  70                  75                  80

Lys Leu Lys Cys Lys Ala Leu Gln Glu Glu Asn Arg Asp Leu Arg Lys
                85                  90                  95

Ala Ser Val Thr Ile Glu Asp Pro Lys Trp Glu Phe Pro Arg Lys Asn
            100                 105                 110

Leu Val Leu Gly Lys Thr Leu Gly Glu Gly Glu Phe Gly Lys Val Val
        115                 120                 125

Lys Ala Thr Ala Phe His Leu Lys Gly Arg Ala Gly Tyr Thr Thr Val
130                 135                 140

Ala Val Lys Met Leu Lys Glu Asn Ala Ser Pro Ser Glu Leu Arg Asp
145                 150                 155                 160

Leu Leu Ser Glu Phe Asn Val Leu Lys Gln Val Asn His Pro His Val
                165                 170                 175

Ile Lys Leu Tyr Gly Ala Cys Ser Gln Asp Gly Pro Leu Leu Leu Ile
            180                 185                 190

Val Glu Tyr Ala Lys Tyr Gly Ser Leu Arg Gly Phe Leu Arg Glu Ser
        195                 200                 205

Arg Lys Val Gly Pro Gly Tyr Leu Gly Ser Gly Gly Ser Arg Asn Ser
210                 215                 220

Ser Ser Leu Asp His Pro Asp Glu Arg Ala Leu Thr Met Gly Asp Leu
225                 230                 235                 240

Ile Ser Phe Ala Trp Gln Ile Ser Gln Gly Met Gln Tyr Leu Ala Glu
                245                 250                 255

Met Lys Leu Val His Arg Asp Leu Ala Ala Arg Asn Ile Leu Val Ala
            260                 265                 270

Glu Gly Arg Lys Met Lys Ile Ser Asp Phe Gly Leu Ser Arg Asp Val
        275                 280                 285

Tyr Glu Glu Asp Ser Tyr Val Lys Arg Ser Gln Gly Arg Ile Pro Val
290                 295                 300

Lys Trp Met Ala Ile Glu Ser Leu Phe Asp His Ile Tyr Thr Thr Gln
305                 310                 315                 320

Ser Asp Val Trp Ser Phe Gly Val Leu Leu Trp Glu Ile Val Thr Leu
                325                 330                 335

Gly Gly Asn Pro Tyr Pro Gly Ile Pro Pro Glu Arg Leu Phe Asn Leu
            340                 345                 350

Leu Lys Thr Gly His Arg Met Glu Arg Pro Asp Asn Cys Ser Glu Glu
        355                 360                 365
```

```
Met Tyr Arg Leu Met Leu Gln Cys Trp Lys Gln Glu Pro Asp Lys Arg
    370                 375                 380

Pro Val Phe Ala Asp Ile Ser Lys Asp Leu Glu Lys Met Met Val Lys
385                 390                 395                 400

Arg Arg Asp Tyr Leu Asp Leu Ala Ala Ser Thr Pro Ser Asp Ser Leu
                405                 410                 415

Ile Tyr Asp Asp Gly Leu Ser Glu Glu Glu Thr Pro Leu Val Asp Cys
            420                 425                 430

Asn Asn Ala Pro Leu Pro Arg Ala Leu Pro Ser Thr Trp Ile Glu Asn
                435                 440                 445

Lys Leu Tyr Gly Arg Ile Ser His Ala Phe Thr Arg Phe
    450                 455                 460
```

<210> SEQ ID NO 29
<211> LENGTH: 5905
<212> TYPE: DNA
<213> ORGANISM: Homo sapiens
<220> FEATURE:
<221> NAME/KEY: misc_feature
<223> OTHER INFORMATION: KIF5B (NM_004521.2)

<400> SEQUENCE: 29

| | | | | | |
|---|---|---|---|---|---|
| ctcctcccgc | accgccctgt | cgcccaacgg | cggcctcagg | agtgatcggg | cagcagtcgg | 60 |
| ccggccagcg | gacggcagag | cgggcggacg | ggtaggcccg | gcctgctctt | cgcgaggagg | 120 |
| aagaaggtgg | ccactctccc | ggtccccaga | acctccccag | cccccgcagt | ccgcccagac | 180 |
| cgtaaagggg | gacgctgagg | agccgcggac | gctctccccg | gtgccgccgc | cgctgccgcc | 240 |
| gccatggctg | ccatgatgga | tcggaagtga | gcattagggt | taacggctgc | cggcgccggc | 300 |
| tcttcaagtc | ccggctcccc | ggccgcctcc | acccggggaa | gcgcagcgcg | gcgcagctga | 360 |
| ctgctgcctc | tcacggccct | cgcgaccaca | agccctcagg | tccggcgcgt | tccctgcaag | 420 |
| actgagcggc | ggggagtggc | tcccggccgc | cggccccggc | tgcgagaaag | atggcggacc | 480 |
| tggccgagtg | caacatcaaa | gtgatgtgtc | gcttcagacc | tctcaacgag | tctgaagtga | 540 |
| accgcggcga | caagtacatc | gccaagtttc | agggagaaga | cacggtcgtg | atcgcgtcca | 600 |
| agccttatgc | atttgatcgg | gtgttccagt | caagcacatc | tcaagagcaa | gtgtataatg | 660 |
| actgtgcaaa | gaagattgtt | aaagatgtac | ttgaaggata | taatgaaaca | atatttgcat | 720 |
| atggacaaac | atcctctggg | aagacacaca | caatggaggg | taaacttcat | gatccagaag | 780 |
| gcatgggaat | tattccaaga | atagtgcaag | atatttttaa | ttatatttac | tccatggatg | 840 |
| aaaatttgga | atttcatatt | aaggtttcat | attttgaaat | atatttggat | aagataaggg | 900 |
| acctgttaga | tgtttcaaag | accaaccttt | cagttcatga | agacaaaaac | cgagttcct | 960 |
| atgtaaaggg | gtgcacagag | cgttttgtat | gtagtccaga | tgaagttatg | gataccatag | 1020 |
| atgaaggaaa | atccaacaga | catgtagcag | ttacaaatat | gaatgaacat | agctctagga | 1080 |
| gtcacagtat | atttcttatt | aatgtcaaac | aagagaacac | acaaacggaa | caaaagctga | 1140 |
| gtggaaaact | ttatctggtt | gatttagctg | gtagtgaaaa | ggttagtaaa | actggagctg | 1200 |
| aaggtgctgt | gctggatgaa | gctaaaaaca | tcaacaagtc | actttctgct | cttggaaatg | 1260 |
| ttatttctgc | tttggctgag | ggtagtacat | atgttccata | tcgagatagt | aaaatgacaa | 1320 |
| gaatccttca | agattcatta | ggtggcaact | gtagaaccac | tattgtaatt | tgctgctctc | 1380 |
| catcatcata | caatgagtct | gaaacaaaat | ctacactctt | atttggccaa | agggccaaaa | 1440 |
| caattaagaa | cacagtttgt | gtcaatgtgg | agttaactgc | agaacagtgg | aaaaagaagt | 1500 |

-continued

```
atgaaaaaga aaagaaaaa aataagatcc tgcggaacac tattcagtgg cttgaaaatg    1560
agctcaacag atggcgtaat ggggagacgg tgcctattga tgaacagttt gacaaagaga    1620
aagccaactt ggaagctttc acagtggata agatattac tcttaccaat gataaaccag    1680
caaccgcaat tggagttata ggaaatttta ctgatgctga agaagaaag tgtgaagaag    1740 aaattgctaa attatacaaa cagcttgatg acaaggatga agaaattaac cagcaaagtc    1800
aactggtaga gaaactgaag acgcaaatgt tggatcagga ggagcttttg gcatctacca    1860
gaagggatca agacaatatg caagctgagc tgaatcgcct tcaagcagaa aatgatgcct    1920
ctaaagaaga agtgaaagaa gttttacagg ccctagaaga acttgctgtc aattatgatc    1980
agaagtctca ggaagttgaa gacaaaacta aggaatatga attgcttagt gatgaattga    2040
atcagaaatc ggcaaccttta gcgagtatag atgctgagct tcagaaactt aaggaaatga    2100
ccaaccacca gaaaaaacga gcagctgaga tgatggcatc tttactaaaa gaccttgcag    2160
aaataggaat tgctgtggga aataatgatg taaagcagcc tgaggaact ggcatgatag    2220 atgaagagtt cactgttgca agactctaca ttagcaaaat gaagtcagaa gtaaaaacca    2280
tggtgaaacg ttgcaagcag ttagaaagca cacaaactga gagcaacaaa aaatggaag    2340 aaaatgaaaa ggagttagca gcatgtcagc ttcgtatctc tcaacatgaa gccaaaatca    2400
agtcattgac tgaataccttt caaaatgtgg aacaaaagaa aagacagttg gaggaatctg    2460
tcgatgccct cagtgaagaa ctagtccagc ttcgagcaca agaaaagtc catgaaatgg    2520 aaaaggagca cttaaataag gttcagactg caaatgaagt taagcaagct gttgaacagc    2580
agatccagag cctagagaa actcatcaaa acagatcag tagtttgaga gatgaagtag    2640
aagcaaaagc aaaacttatt actgatcttc aagaccaaaa ccagaaaatg atgttagagc    2700
aggaacgtct aagagtagaa catgagaagt tgaaagccac agatcaggaa aagagcagaa    2760
aactacatga acttacggtt atgcaagata gacgagaaca agcaagacaa gacttgaagg    2820
gtttggaaga gacagtggca aaagaacttc agactttaca caacctgcgc aaactctttg    2880
ttcaggacct ggctacaaga gttaaaaaga gtgctgagat tgattctgat gacaccggag    2940
gcagcgctgc tcagaagcaa aaaatctcct ttcttgaaaa taatcttgaa cagctcacta    3000
aagtgcacaa acagttggta cgtgataatg cagatctccg ctgtgaactt cctaagttgg    3060
aaaagcgact tcgagctaca gctgagagag tgaaagcttt ggaatcagca ctgaaagaag    3120
ctaaagaaaa tgcatctcgt gatcgcaaac gctatcagca agaagtagat cgcataaagg    3180
aagcagtcag gtcaaagaat atggccagaa gaggcattc tgcacagatt gctaaaccta    3240
ttcgtcccgg gcaacatcca gcagcttctc caactcaccc aagtgcaatt cgtggaggag    3300
gtgcatttgt tcagaacagc cagccagtgg cagtgcgagg tggaggaggc aaacaagtgt    3360
aatcgtttat acatacccac aggtgttaaa aagtaatcga agtacgaaga ggacatggta    3420
tcaagcagtc attcaatgac tataacctct actcccttgg gattgtagaa ttataacttt    3480 taaaaaaat gtataaatta tacctggcct gtacagctgt ttcctaccta ctcttcttgt    3540
aaactctgct gcttcccaac acaactagag tgcaattttg gcatcttagg agggaaaaag    3600
gacagtttac aactgtggcc ctatttatta cacagtttgt ctatcgtgtc ttaaatttag    3660
tctttactgt gccaagctaa ctgtacctta taggactgta cttttttgtat ttttttgtgta    3720 tgtttatttt ttaatctcag tttaaattac ctagctgcta ctgcttcttg tttttctttt    3780
cctattaaaa cgtcttcctt tttttttcttt aagagaaaat ggaacattta ggttaaatgt    3840
ctttaaattt taccacttaa caacactaca tgcccataaa atatatccag tcagtactgt    3900
```

```
attttaaaat cccttgaaat gatgatatca gggttaaaat tacttgtatt gtttctgaag    3960
tttgctcctg aaaactactg tttgagcact gaaacgttac aaatgcctaa taggcatttg    4020
agactgagca aggctacttg ttatctcatg aaatgcctgt tgccgagtta ttttgaatag    4080
aaatatttta aagtatcaaa agcagatctt agtttaaggg agtttggaaa aggaattata    4140
tttctctttt tcctgattct gtactcaaca agtcttgatg gaattaaaat actctgcttt    4200
attctggtga gcctgctagc taatataagt attggacagg taataatttg tcatctttaa    4260
tattagtaaa atgaattaag atattatagg attaaacata attttatacg gttagtactt    4320
tattggccga cctaaatttta tagcgtgtgg aaattgagaa aaatgaagaa acaggacaga   4380
tatatgatga attaaaaata tatataggtc aattttggtc tgaaatccct gaggtgtttt    4440
taacctgcta cactaatttg tacactaatt tatttcttta gtctagaaat agtaaattgt    4500
ttgcaagtca ctaataatca ttagataaat tattttcttg gccatagccg ataattttgt    4560
aatcagtact aagtgtatac gtattttgc cacttttttcc tcagatgatt aaagtaagtc     4620
aacagcttat tttaggaaac tgtaaaagta atagggaaag agatttcact atttgcttca    4680
tcagtggtag gggggcggtg actgcaactg tgttagcaga aattcacaga gaatggggat    4740
ttaaggttag cagagaaact tggaaagttc tgtgttagga tcttgctggc agaattaact    4800
ttttgcaaaa gttttataca cagatatttg tattaaattt ggagccatag tcagaagact    4860
cagatcataa ttggcttatt tttctatttc cgtaactatt gtaatttcca cttttgtaat    4920
aattttgatt taaatataaa atttatttat ttattttttt aatagtcaaa atctttgct    4980 gttgtagtct gcaacctcta aaatgattgt gttgcttttta ggattgatca aagaaacac    5040 tccaaaaatt gagatgaaat gttggtgcag ccagttataa gtaatatagt taacaagcaa    5100
aaaaagtgct gccacctttt atgatgattt tctaaatgga gaaacatttg gctgcatcca    5160
catagacctt tatgttttgt tttcagttga aaacttgcct cctttggcaa cattcgtaaa    5220
tgaagcagaa ttttttttttc tcttttttcc aaatatgtta gttttgttct tgtaagatgt    5280
atcatgggta ttggtgctgt gtaatgaaca acgaatttta attagcatgt ggttcagaat    5340
atacaatgtt aggttttttaa aaagtatctt gatggttctt ttctattat aatttcagac    5400 tttcataaag tgtaccaaga atttcataaa tttgttttca gtgaactgct ttttgctatg    5460
gtaggtcatt aaacacagca cttactctta aaaatgaaaa tttctgatca tctaggatat    5520
tgacacattt caatttgcag tgtctttttg actggatata ttaacgttcc tctgaatggc    5580
attgatagat ggttcagaag agaaactcaa tgaaataaag agaatattta ttcatggcga    5640
ttaattaaat tatttgccta acttaagaaa actactgtgc gtaactctca gtttgtgctt    5700
aactccattt gacatgaggt gacagaagag agtctgagtc tacctgtgga atatgttggt    5760
ttattttcag tgcttgaaga tacattcaca aatacttggt ttgggaagac accgtttaat    5820
tttaagttaa cttgcatgtt gtaaatgcgt tttatgttta aataaagagg aaattttttt    5880
gaaatgtaaa aaaaaaaaaa aaaaa                                          5905
```

<210> SEQ ID NO 30
<211> LENGTH: 963
<212> TYPE: PRT
<213> ORGANISM: Homo sapiens
<220> FEATURE:
<221> NAME/KEY: misc_feature
<223> OTHER INFORMATION: kinesin-1 heavy chain (NP_004512.1)

<400> SEQUENCE: 30

-continued

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Tyr Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415
```

```
Glu Arg Arg Lys Cys Glu Glu Glu Ile Ala Lys Leu Tyr Lys Gln Leu
                420                 425                 430

Asp Asp Lys Asp Glu Glu Ile Asn Gln Gln Ser Gln Leu Val Glu Lys
                435                 440                 445

Leu Lys Thr Gln Met Leu Asp Gln Glu Glu Leu Leu Ala Ser Thr Arg
                450                 455                 460

Arg Asp Gln Asp Asn Met Gln Ala Glu Leu Asn Arg Leu Gln Ala Glu
465                 470                 475                 480

Asn Asp Ala Ser Lys Glu Val Lys Val Leu Gln Ala Leu Glu
                    485                 490                 495

Glu Leu Ala Val Asn Tyr Asp Gln Lys Ser Gln Glu Val Glu Asp Lys
                500                 505                 510

Thr Lys Glu Tyr Glu Leu Leu Ser Asp Glu Leu Asn Gln Lys Ser Ala
                515                 520                 525

Thr Leu Ala Ser Ile Asp Ala Glu Leu Gln Lys Leu Lys Glu Met Thr
                530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                    565                 570                 575

Pro Glu Gly Thr Gly Met Ile Asp Glu Glu Phe Thr Val Ala Arg Leu
                580                 585                 590

Tyr Ile Ser Lys Met Lys Ser Glu Val Lys Thr Met Val Lys Arg Cys
                595                 600                 605

Lys Gln Leu Glu Ser Thr Gln Thr Glu Ser Asn Lys Lys Met Glu Glu
                610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                    645                 650                 655

Lys Arg Gln Leu Glu Glu Ser Val Asp Ala Leu Ser Glu Glu Leu Val
                660                 665                 670

Gln Leu Arg Ala Gln Glu Lys Val His Glu Met Glu Lys Glu His Leu
                675                 680                 685

Asn Lys Val Gln Thr Ala Asn Glu Val Lys Gln Ala Val Glu Gln Gln
                690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                    725                 730                 735

Asn Gln Lys Met Met Leu Glu Gln Glu Arg Leu Arg Val Glu His Glu
                740                 745                 750

Lys Leu Lys Ala Thr Asp Gln Glu Lys Ser Arg Lys Leu His Glu Leu
                755                 760                 765

Thr Val Met Gln Asp Arg Arg Glu Gln Ala Arg Gln Asp Leu Lys Gly
                770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
                    805                 810                 815

Ile Asp Ser Asp Asp Thr Gly Gly Ser Ala Ala Gln Lys Gln Lys Ile
                820                 825                 830

Ser Phe Leu Glu Asn Asn Leu Glu Gln Leu Thr Lys Val His Lys Gln
```

```
                    835                 840                 845
Leu Val Arg Asp Asn Ala Asp Leu Arg Cys Glu Leu Pro Lys Leu Glu
                850                 855                 860

Lys Arg Leu Arg Ala Thr Ala Glu Arg Val Lys Ala Leu Glu Ser Ala
865                 870                 875                 880

Leu Lys Glu Ala Lys Glu Asn Ala Ser Arg Asp Arg Lys Arg Tyr Gln
                885                 890                 895

Gln Glu Val Asp Arg Ile Lys Glu Ala Val Arg Ser Lys Asn Met Ala
                900                 905                 910

Arg Arg Gly His Ser Ala Gln Ile Ala Lys Pro Ile Arg Pro Gly Gln
                915                 920                 925

His Pro Ala Ala Ser Pro Thr His Pro Ser Ala Ile Arg Gly Gly Gly
                930                 935                 940

Ala Phe Val Gln Asn Ser Gln Pro Val Ala Val Arg Gly Gly Gly Gly
945                 950                 955                 960

Lys Gln Val

<210> SEQ ID NO 31
<211> LENGTH: 5842
<212> TYPE: DNA
<213> ORGANISM: Homo sapiens
<220> FEATURE:
<221> NAME/KEY: misc_feature
<223> OTHER INFORMATION: CCDC6 (NM_005436.4)

<400> SEQUENCE: 31
agtgcaatac tgcccaagcc cgggcggggt ctctgttctc tggcagagga ggtcccttgg      60
cagcgggaag cgccctctct ttctctcgcc gccgctccga gtctgcgccc tggtgccagg     120
cgctcagctc ggcgctcccc tgtgctcgcc cggcgcccac tcattcgcag cccggccttc     180
gtcgccgccg cctccctgct gctcctcctc cttccccag cccgccgcgg ccatggcgga      240
cagcgccagc gagagcgaca cggacggggc ggggggcaac agcagcagct cggccgccat     300
gcagtcgtcc tgctcgtcga cctcgggcgg cggcggtggc ggcggggag cggcggcgg      360 tgggaagtcg gggggcattg tcatctcgcc gttccgcctg gaggagctca ccaaccgcct     420
ggcctcgctg cagcaagaga caaggtgct gaagatagag ctggagacct acaaactgaa     480
gtgcaaggca ctgcaggagg agaaccgcga cctgcgcaaa gccagcgtga ccatccaagc     540
cagggctgag caggaagaag aattcattag taacacttta ttcaagaaaa ttcaggcttt     600
gcagaaggag aaagaaaccc ttgctgtaaa ttatgagaaa gaagaagaat tcctcactaa     660
tgagctctcc agaaaattga tgcagttgca gcatgagaaa gccgaactag aacagcatct     720
tgaacaagag caggaatttc aggtcaacaa actgatgaag aaaattaaaa aactggagaa     780
tgacaccatt tctaagcaac ttacattaga acagttgaga cgggagaaga ttgaccttga     840
aaatacattg gaacaagaac aagaagcact agttaatcgc ctctggaaaa ggatggataa     900
gcttgaagct gaaaagcgaa tcctgcagga aaaattagac cagcccgtct ctgctccacc     960
atcgcctaga gatatctcca tggagattga ttctccagaa aatatgatgc gtcacatcag    1020
gtttttaaag aatgaagtgg aacggctgaa gaagcaactg agagctgctc agttacagca    1080
ttcagagaaa atggcacagt atctggagga ggaacgtcac atgagagaag gaacttgag    1140 gctccagagg aagctgcaga gggagatgga gaagagaa gccctctgtc gacagctctc    1200
cgagagtgag tccagcttag aaatggacga cgaaaggtat tttaatgaga tgtctgcaca    1260
aggattaaga cctcgcactg tgtccagccc gatcccttac acaccttctc cgagttcaag    1320
```

```
caggcctata tcacctggtc tatcatatgc aagtcacacg gttggtttca cgccaccaac    1380
ttcactgact agagctggaa tgtcttatta caattccccg ggtcttcacg tgcagcacat    1440
gggaacatcc catggtatca caaggccttc accacggaga agcaacagtc ctgacaaatt    1500
caaacggccc acgccgcctc catctcccaa cacacagacc ccagtccagc cacctccgcc    1560
tccacctccg ccacccatgc agcccacggt ccctcagca gccacctcgc agcctactcc    1620
ttcgcaacat tcggcgcacc cctcctccca gccttaatgc atgagcttag tctgaatttc    1680
aagttgggac tcatccaatg gagccgtcta ctcaacgcca aaggcttcct tctctggcat    1740
atttggatat gacttatttg cactgaggtt atctaggctt cactatccat tgtgttgtaa    1800
atgtttgtca gaaatgcagc cagtgttgtg ggtctacaac actaaccaga cgactttttc    1860
catcagtgtt ttacttgaat cttcatgtac gtccattccc tggctggaac cttcgctgtt    1920
tggtatttgg tatttcagca gcagtgtgca attttgctt ggcccagagc ttcattctcc    1980
tggcttttag gtttgtaaaa gaaaagggga tatcttttt atatttttt ccatgaatct    2040 gcagaaaatt actgagctgt tgttaccctc ctctcattat aatagtgttt accaaacata    2100 ccataattc agcactacaa ttcagaccct tgaaaatctg gctttcagtg tagaacagaa    2160
agttagatga atcagtgccc aagacatatt ttctgtttaa cagaactttc tacagataca    2220
ttttttacag gttattttca ttgtgttatt gacatccatg tctctcgtaa acagatggc    2280 ccaaagtaat gaatcatgtg gctgtacctt ctccacataa atgggatgga taattatcgt    2340
atattaagat gtgattctct tttttatcct taatgttaat ctacttaacc tggccccctc    2400
taacatgagt cgataaatgt tgtcctactc accggtggtt tcaatggcta attagaatgt    2460
gttatttgat ttctgctgca gaaggcagtg tgattgtaac aaaaacaatg cggcttcccc    2520
ctttcgtact tcatttgtgt tctcttaaaa tagagtttga acaaatattt taaaggtgca    2580
aaataccatt agaaaatact atttgaaatg gacattatcg cattatcttg gcataatggc    2640
cagaaaatat tgtattgctt ggcagaaaag aaaataaggt ctaaaggaaa gtagcacatt    2700
agcattgatg gctgttcatt tcacccagta taagcaagtg cagtgtacaa agaagtatat    2760
tctgaataca ttatttccat tcatttagca caaataaatc atttggtttc actttgcagt    2820
ggaacactga gtcactcttt tcttaacacg tgcaacatct taattttgt ttttcagcag    2880 ttgctgtttt gtactttggt agtaaagtga tttttaccac ctgtgtttgc atattttat     2940 atgctgtgga tgaaaataac ttactagaga atgtatattt tatgacaaga atgtgtatct    3000
gttggatata atcagagaac tgaaaagtaa tttatcagta attttaaga gtccatgttt    3060 tgtgacaacc atctctaata gccaactctt tattaaacac actcctaaaa ataaggaacc    3120
atgacattgt agatatttaa tattgtacag tatagaaacc tccattttg ccttcgaatg    3180 catatttaag agttaacaga atgaaaaaaa aaagtcttgt tggataatag tgtttgacta    3240
gcgttttaag aacttgagag taaaagcaac aataagattt tttcacctct tcctgcttcc    3300
acccccaaac tgagaacatc actcaattgt ttggaagaaa ctgtaggtct atataaattt    3360
tatttataat gtatgtgtaa tatacataat cataatacag ttctcagatg cagggaagaa    3420
gtttggcatt taatcattga ggctttaggt ttttgatgtg atcagactgg gccatgtcaa    3480
acccggaatt ttcaccaaca gttcactcac cctcctggta cattgccatt ccaaggaatt    3540
ctgagagtag gcaaacaaat tttgccttca tggtacagtt ctcagttttt cttataggag    3600
aaatatggta tatgtttata agaatctttt atgagattat agatttcaat gctgtggata    3660
```

-continued

```
gtgtcttgca cccaaacaag aaagtccata atggaatgat cttccctcag cttcctatcg   3720
atttagttac ctcttgaaag cacaaaaatt aaaacattgc catatgttga atttttaaaa   3780
agcacttgga gtgagcgaac atttcctgat aaatgccttt tagagatagg ttcttgatat   3840
tcagacatct gcagaaatgt tctggttccc aaagtcattt cacttcgaaa taaaacacag   3900
ctccttcaaa cagcactttt tccacataaa tctagttgcc tctccctgtg acattcaga    3960
actgatagaa caaacactac tcttttgaat ttgatggttc gtgtccttta aagtgtttga   4020
ggacctatgc agagcctgta acacttgggt agtacctgct aggacaattt cttggcaatt   4080
gtcttactac tagggatcag taagatttag attctgagcc cataatggca acagccccct   4140
cacctatggg aagctgactt ccctcagtcg ggcacttctc atggggggctg aacatggttc   4200
ctgccattct gttacccact ctcccaggtg agccctggat tggctcccag aaggcctttg   4260
taaaatcagt agccgtcctg caggcaggtg ggagcaacag gggcttcagt agcttcattt   4320
tcctgtcttg cagacagaga cccttggcta ccactgtgct gctaatagga taagtactct   4380
gttgccagat taccatgcct tttatacaaa accaaattaa cttacctaat acctgacacc   4440
tctttgggct ctgaactgct ttctctcatc aagcatgcta gcactctaga cagaattcta   4500
gaaatttggc agatagtgga agcctttaat tgaacttact ccttcgttga ctgaaaggag   4560
ttttaaattc tgagctcctg agatactgac tagcaaccat ggaatgaatg tgtgaccaga   4620
aagtggcttt gacaccaagt gctactgtcc ctttgtaatt ggcttctaac agaattcaac   4680
cagaaataat tgataatgtg aattttttgtt aattgttcac ttgtaggaaa atagaacatg   4740
tatcacccctt tgttaggtag acatgaactt ttcctgcaca aagccttgct tttagagaat   4800
gcccaataag gcaagaaaaa gcatagtaac ttgtgctttg agagctcaat atttgtatct   4860
tatcagtaca gaagaaatat ttctgtgtaa cttgatcttc tgtctagtac ttgtcttata   4920
ggtaaccaac actgaaaact ttgtagtgat gactaccaaa gaaatacata gtaaaacaac   4980
cttttatttc caaattgtta aagagccagc cattgatgct gctacatgag ttccatgctc   5040
aagagccatt gtaagagatt aagggtttc taggttttg gtgatttttt gtttgttttt    5100
ttctttgttt tttagggttt ttttttcttc tttaattttt tgattaaaac atacacacag   5160
ctgttagcat aaagtcgtgg ggggcatttt ctggaatgct cagcagttct gattaactgc   5220
caagcccagg ttgcctctca tgaggcaact gaaaaaatcc tgtgtcttga tagcatgggt   5280
gctgtgtgtg tgcatgtgtg tgtctgcatt catgccttaa ctcgggttac tgcacaactt   5340
tagttcttga cttagtctgc accgtcatct agattgtatt gtacatctcg gtctgaactt   5400
catcctggca aaaacaaagt tgcaggcaca acagtttaag aatgcattcc tccagaagag   5460
tatctggtca ggttgacccc tgagccttct ttggacttga tttggaactt agcctggaaa   5520
gcgaaagtgg actgtccaac agaaagatgt caacaaggaa aagaggagag ccaagcgcta   5580
gcatgccttt tgcctctgca tatctgtgca cactgtatgt tgttcatgat agcttgtcta   5640
caacttgact aggttggagt tctggtaata gtggcaatct tgacattctt ggtcagagtt   5700
tagagagatg taagactttc aattaatgtc ttatttactc ctttatgttg attagtcttt   5760
gatacatgtg ctgaatcaga aacctaaata aagataattt tttaaaatgt acctcttgag   5820
ccttaaaaaa aaaaaaaaaa aa                                            5842
```

<210> SEQ ID NO 32
<211> LENGTH: 474
<212> TYPE: PRT
<213> ORGANISM: Homo sapiens
<220> FEATURE:
<221> NAME/KEY: misc_feature
<223> OTHER INFORMATION: CCDC6 (NP_005427.2)

<400> SEQUENCE: 32

```
Met Ala Asp Ser Ala Ser Glu Ser Asp Thr Asp Gly Ala Gly Gly Asn
1               5                   10                  15

Ser Ser Ser Ser Ala Ala Met Gln Ser Ser Cys Ser Ser Thr Ser Gly
            20                  25                  30

Gly Gly Gly Gly Gly Gly Gly Gly Gly Gly Lys Ser Gly Gly
        35                  40                  45

Ile Val Ile Ser Pro Phe Arg Leu Glu Glu Leu Thr Asn Arg Leu Ala
50                  55                  60

Ser Leu Gln Gln Glu Asn Lys Val Leu Lys Ile Glu Leu Glu Thr Tyr
65                  70                  75                  80

Lys Leu Lys Cys Lys Ala Leu Gln Glu Glu Asn Arg Asp Leu Arg Lys
                85                  90                  95

Ala Ser Val Thr Ile Gln Ala Arg Ala Glu Gln Glu Glu Glu Phe Ile
                100                 105                 110

Ser Asn Thr Leu Phe Lys Lys Ile Gln Ala Leu Gln Lys Glu Lys Glu
            115                 120                 125

Thr Leu Ala Val Asn Tyr Glu Lys Glu Glu Phe Leu Thr Asn Glu
            130                 135                 140

Leu Ser Arg Lys Leu Met Gln Leu Gln His Glu Lys Ala Glu Leu Glu
145                 150                 155                 160

Gln His Leu Glu Gln Glu Gln Glu Phe Gln Val Asn Lys Leu Met Lys
                165                 170                 175

Lys Ile Lys Lys Leu Glu Asn Asp Thr Ile Ser Lys Gln Leu Thr Leu
                180                 185                 190

Glu Gln Leu Arg Arg Glu Lys Ile Asp Leu Glu Asn Thr Leu Glu Gln
            195                 200                 205

Glu Gln Glu Ala Leu Val Asn Arg Leu Trp Lys Arg Met Asp Lys Leu
210                 215                 220

Glu Ala Glu Lys Arg Ile Leu Gln Glu Lys Leu Asp Gln Pro Val Ser
225                 230                 235                 240

Ala Pro Pro Ser Pro Arg Asp Ile Ser Met Glu Ile Asp Ser Pro Glu
                245                 250                 255

Asn Met Met Arg His Ile Arg Phe Leu Lys Asn Glu Val Glu Arg Leu
                260                 265                 270

Lys Lys Gln Leu Arg Ala Ala Gln Leu Gln His Ser Glu Lys Met Ala
            275                 280                 285

Gln Tyr Leu Glu Glu Glu Arg His Met Arg Glu Glu Asn Leu Arg Leu
        290                 295                 300

Gln Arg Lys Leu Gln Arg Glu Met Glu Arg Arg Glu Ala Leu Cys Arg
305                 310                 315                 320

Gln Leu Ser Glu Ser Glu Ser Ser Leu Glu Met Asp Asp Glu Arg Tyr
                325                 330                 335

Phe Asn Glu Met Ser Ala Gln Gly Leu Arg Pro Arg Thr Val Ser Ser
                340                 345                 350

Pro Ile Pro Tyr Thr Pro Ser Pro Ser Ser Arg Pro Ile Ser Pro
            355                 360                 365

Gly Leu Ser Tyr Ala Ser His Thr Val Gly Phe Thr Pro Pro Thr Ser
        370                 375                 380

Leu Thr Arg Ala Gly Met Ser Tyr Tyr Asn Ser Pro Gly Leu His Val
```

```
                385                 390                 395                 400
        Gln His Met Gly Thr Ser His Gly Ile Thr Arg Pro Ser Pro Arg Arg
                            405                 410                 415

Ser Asn Ser Pro Asp Lys Phe Lys Arg Pro Thr Pro Pro Ser Pro
                        420                 425                 430

Asn Thr Gln Thr Pro Val Gln Pro Pro Pro Pro Pro Pro Pro
                    435                 440                 445

Met Gln Pro Thr Val Pro Ser Ala Ala Thr Ser Gln Pro Thr Pro Ser
                450                 455                 460

Gln His Ser Ala His Pro Ser Ser Gln Pro
        465                 470

<210> SEQ ID NO 33
<211> LENGTH: 3748
<212> TYPE: DNA
<213> ORGANISM: Homo sapiens
<220> FEATURE:
<221> NAME/KEY: misc_feature
<223> OTHER INFORMATION: NCOA4 variant 1 (NM_001145260.1)

<400> SEQUENCE: 33
agagggcagt caagggcttc tggctgaccc gagcggagat ctcgcgagac tgtcagacgt      60
atggcgagag gtgtgggagg aagattgtgt tgtcgcgaga actctgcctt gggccgtag     120 gttagtgtgg ggccgtgtct cagtccaccc aaggtctcct cggatcgcct ggagaggcac    180
tcggacctgt tatgtctgga cacattgctt caacatagaa cgcacatgaa caatgtggag    240
gtctaggctg gaatggggc ccagttgacc acttttgctc tagctggagc agtgaggaga     300
atgaatacct tccaagacca gagtggcagc tccagtaata gagaacccct tttgaggtgt    360
agtgatgcac ggagggactt ggagcttgct attggtggag ttctccgggc tgaacagcaa    420
attaaagata acttgcgaga ggtcaaagct cagattcaca gttgcataag ccgtcacctg    480
gaatgtctta aagccgtgaa gtatggctg tatgaacagg tggaccttat ttatcagctt     540
aaagaggaga cacttcaaca gcaggctcag cagctctact cgttattggg ccagttcaat    600
tgtcttactc atcaactgga gtgtacccaa aacaaagatc tagccaatca agtctctgtg    660
tgcctggaga gactgggcag tttgacccct aagcctgaag attcaactgt cctgctcttt    720
gaagctgaca caattactct gcgccagacc atcaccacat ttgggtctct caaaaccatt    780
caaattcctg agcacttgat ggctcatgct agttcagcaa atattgggcc cttcctggag    840
aagagaggct gtatctccat gccagagcag aagtcagcat ccggtattgt agctgtccct    900
ttcagcgaat ggctccttgg aagcaaacct gccagtggtt atcaagctcc ttacataccc    960
agcaccgacc cccaggactg gcttacccaa aagcagacct tggagaacag tcagacttct   1020
tccagagcct gcaatttctt caataatgtc gggggaaacc taagggcgtt agaaaactgg   1080
ctcctcaaga gtgaaaaatc aagttatcaa aagtgtaaca gccattccac tactagttct   1140
ttctccattg aaatgaaaaa ggttggagat caagagcttc ctgatcaaga tgagatggac   1200
ctatcagatt ggctagtgac tccccaggaa tcccataagc tgcggaagcc tgagaatggc   1260
agtcgtgaaa ccagtgagaa gtttaagctc ttattccagt cctataatgt gaatgattgg   1320
cttgtcaaga ctgactcctg taccaactgt cagggaaacc agcccaaagg tgtggagatt   1380
gaaaacctgg gcaatctgaa gtgcctgaat gaccacttgg aggccaagaa accattgtcc   1440 accccccagca tggttacaga ggattggctt gtccagaacc atcaggaccc atgtaaggta   1500
gaggaggtgt gcagagccaa tgagccctgc acaagctttg cagagtgtgt gtgtgatgag   1560
```

```
aattgtgaga aggaggctct gtataagtgg cttctgaaga aagaaggaaa ggataaaaat    1620
gggatgcctg tggaacccaa acctgagcct gagaagcata aagattccct gaatatgtgg    1680
ctctgtccta gaaaagaagt aatagaacaa actaaagcac caaaggcaat gactccttct    1740
agaattgcta attccttcca agtcataaag aacagcccct tgtcggagtg gcttatcagg    1800
cccccataca agaaggaag tcccaaggaa gtgcctggta ctgaagacag agctggcaaa    1860
cagaagttta aaagccccat gaatacttcc tggtgttcct ttaacacagc tgactgggtc    1920
ctgccaggaa agaagatggg caacctcagc cagttatctt ctggagaaga caagtggctg    1980
cttcgaaaga aggcccagga agtattactt aattcacctc tacaggagga acataacttc    2040
cccccagacc attatggcct ccctgcagtt tgtgatctct ttgcctgtat gcagcttaaa    2100
gttgataaag agaagtggtt atatcgaact cctctacagg catacttcaa aatgaacttt    2160
caagatgtaa ccgttgggaa ttttcagatc ccatgtggat tctagtagtt tatataccta    2220
cctcgaagat gtgaaggaat ggacaagagt tgagcagcct ttctgctgat tatcacacat    2280
catgagctga gtgactgcag cttgccaaat ctttgtgttt ctgggtctga ccaattagct    2340
tagttcttct cctgcctaat tttgaactag taaagcaaag tgagtcatca gattatgagt    2400
tactgtttaa aagaaaaatg ctgtttattc atgctgaggt gattcagttc cctccttctt    2460
acagaagtat tttaattcac cccacactag aaatgcagca tctttgtgga cgtctttttc    2520
acaagcctcc aaggctcctt agattgggtc gttactaaaa gtacattaaa acactcttgt    2580
ttatcgaagt atattgatgt attctaaagc tagtaaactt ccctaacgtt taattgccct    2640
acagatgctt ctcttgctgt gggttttctt ttgttagtgg tctgaaataa ttattttcct    2700
gttctattaa tacatagtgt attttgcaca aaaaaattaa cctggtcaat agtgattacc    2760
aaaatatata ttaataatct tggcaatttt tgacattaat tatgaaacat tttagcccac    2820
gttagttcta cattattctt cacttaaact cagctactgc aaattttgtc tttctgtaaa    2880
tgttattaaa atatccagtg agctctttag aaggactcag tattatttca agactatttt    2940
tgaggtaatt ctagcctttt aaaatattct acagacctac ggggcttaaa agaaccccag    3000
taccgactaa gcaaataggc aaaagacatg ttggaaatgt agtatagtac ttgaaacagt    3060
cactatcata gggataattg gtgcatcctg tgtaaatgga agctgagctt gacacctggt    3120
gcttttaagt agggataaag tcatcctctc actgcaagca cagcatacct gtacctccaa    3180
aagtgacgtt ttagtgaaca ggccgttttc aacacttgtg ccttggggtg ttcattgaag    3240
ctttgtgaaa actactgatg ttttctcagt ctccttaaag ttacgtccat gctttaaaat    3300
gtctgtgtag gagagaagtg gggtttataa tgttttctct aagatatctt gctgctttc    3360 cagactttga aactattaag cttcttaact gcctcttacc ggaaatactt ctggggaaac    3420
ttcatggtcc caaaatgtca ttgccataca gcttcactag agttctttga accacagctg    3480
aaaagagctt tgtattattt tttaattccc tccccagata tcatttagga gtattatata    3540
aaggtggtgg gcaaaaacaa tgtaaggagc ctttccagtt atcttgagtt gcagctctgt    3600
agtttcttga ggccaaacac actgtatttt acaagtcaaa atataattta cattaatcac    3660
tatgttaatg agtatgtaaa acattctttt gcattgatga attttgtatc tgcttccatt    3720
aaaagcataa cagccataaa aaaaaaa                                        3748
```

<210> SEQ ID NO 34
<211> LENGTH: 3659
<212> TYPE: DNA

| | |
|---|---|
| <213> ORGANISM: Homo sapiens | |
| <220> FEATURE: | |
| <221> NAME/KEY: misc_feature | |
| <223> OTHER INFORMATION: NCOA4 variant 2 (NM_001145261.1) | |

<400> SEQUENCE: 34

```
agagggcagt caagggcttc tggctgaccc gagcggagat ctcgcgagac tgtcagacgt      60
atggcgagag gtgtgggagg aagattgtgt tgtcgcgaga actctgcctt gggccgtag      120 gttagtgtgg ggccgtgtct cagtccaccc aaggtctcct cggatcgcct ggagaggcac     180
tcggacctgt tatgtctgga cacattgctt caacatagaa cgcacatgaa caatgtggag     240
gtctaggctg aatggggc ccagttgacc acttttgctc tagctggagc agtgaggaga       300
atgaatacct tccaagacca gagtggcagc tccagtaata gagaacccct tttgaggtgt     360
agtgatgcac ggagggactt ggagcttgct attggtggag ttctccgggc tgaacagcaa     420
attaaagata acttgcgaga ggtcaaagct cagattcaca gttgcataag ccgtcacctg     480
gaatgtctta aagccgtga ggtatggctg tatgaacagg tggaccttat ttatcagctt      540
aaagaggaga cacttcaaca gcaggctcag cagctctact cgttattggg ccagttcaat     600
tgtcttactc atcaactgga gtgtacccaa acaaagatc tagccaatca agtctctgtg      660
tgcctggaga gactgggcag tttgacccctt aagcctgaag attcaactgt cctgctcttt     720
gaagctgaca caattactct cgccagacc atcaccacat ttgggtctct caaaaccatt      780
caaattcctg agcacttgat ggctcatgct agttcagcaa atattgggcc cttcctggag     840
aagagaggct gtatctccat gccagagcag aagtcagcat ccggtattgt agctgtccct    900
ttcagcgaat ggctccttgg aagcaaacct gccagtggtt atcaagctcc ttacataccc     960
agcaccgacc cccaggactg gcttacccaa aagcagacct tggagaacag tcagacttct    1020
tccagagcct gcaatttctt caataatgtc gggggaaacc taagggcttt agaaaactgg    1080
ctcctcaaga gtgaaaaatc aagttatcaa aagtgtaaca gccattccac tactagttct    1140
ttctccattg aaatggaaaa ggttggagat caagagcttc ctgatcaaga tgagatggac    1200
ctatcagatt ggctagtgac tccccaggaa tcccataagc tgcggaagcc tgagaatggc    1260
agtcgtgaaa ccagtgagaa gtttaagctc ttattccagt cctataatgt gaatgattgg    1320
cttgtcaaga ctgactcctg taccaactgt cagggaaacc agcccaaagg tgtggagatt    1380
gaaaacctgg gcaatctgaa gtgcctgaat gaccacttgg aggccaagaa accattgtcc    1440 accccagca tggttacaga ggattggctt gtccagaacc atcaggaccc atgtaaggta     1500
gaggaggtgt gcagagccaa tgagccctgc acaagctttg cagagtgtgt gtgtgatgag    1560
aattgtgaga aggaggctct gtataagtgg cttctgaaga agaaggaaa ggataaaaat    1620 gggatgcctg tggaacccaa acctgagcct gagaagcata aagattccct gaatatgtgg    1680
ctctgtccta gaaagaagt aatagaacaa actaaagcac caaggcaat gactccttct     1740 agaattgcta ttccttcca agtcataaag aacagcccct gtcggagtg gcttatcagg     1800 cccccataca aagaaggaag tcccaaggaa gtgcctggta ctgaagacag agctggcaaa    1860
cagaagttta aagcccccat gaatacttcc tggtgttcct ttaacacagc tgactgggtc    1920
ctgccaggaa agaagatggg caacctcagc cagttatctt ctgagaaga caagtggctg    1980 cttcgaaaga aggcccagga agtattactt aattcacctc tacaggagga acataacttc    2040 ccccccagacc attatggcct ccctgcagtt tgtgatctct ttgcctgtat gcagcttaaa    2100
gttgataaag agaagtggtt atatcgaact cctctacaga tgtgaaggaa tggacaagag    2160
```

-continued

```
ttgagcagcc tttctgctga ttatcacaca tcatgagctg agtgactgca gcttgccaaa   2220
tctttgtgtt tctgggtctg accaattagc ttagttcttc tcctgcctaa ttttgaacta   2280
gtaaagcaaa gtgagtcatc agattatgag ttactgttta aagaaaaat gctgtttatt    2340 catgctgagg tgattcagtt ccctccttct tacagaagta ttttaattca ccccacacta   2400
gaaatgcagc atctttgtgg acgtcttttt cacaagcctc caaggctcct tagattgggt   2460
cgttactaaa agtacattaa aacactcttg tttatcgaag tatattgatg tattctaaag   2520
ctagtaaact tccctaacgt ttaattgccc tacagatgct tctcttgctg tgggttttct   2580
tttgttagtg gtctgaaata attattttcc tgttctatta atacatagtg tattttgcac   2640
aaaaaaatta acctggtcaa tagtgattac caaaatatat attaataatc ttggcaattt   2700
ttgacattaa ttatgaaaca ttttagccca cgttagttct acattattct tcacttaaac   2760
tcagctactg caaattttgt ctttctgtaa atgttattaa aatatccagt gagctcttta   2820
gaaggactca gtattatttc aagactattt ttgaggtaat tctagccttt taaaatattc   2880
tacagaccta cggggcttaa aagaaccccca gtaccgacta agcaaatagg caaaagacat   2940
gttggaaatg tagtatagta cttgaaacag tcactatcat agggataatt ggtgcatcct   3000
gtgtaaatgg aagctgagct tgacacctgg tgcttttaag tagggataaa gtcatcctct   3060
cactgcaagc acagcatacc tgtacctcca aaagtgacgt tttagtgaac aggccgtttt   3120
caacacttgt gccttgggt gttcattgaa gctttgtgaa aactactgat gttttctcag    3180
tctccttaaa gttacgtcca tgctttaaaa tgtctgtgta ggagagaagt ggggtttata   3240
atgttttctc taagatatct ttgctgcttt ccagactttg aaactattaa gcttcttaac   3300
tgcctcttac cggaaatact tctggggaaa cttcatggtc ccaaaatgtc attgccatac   3360
agcttcacta gagttctttg aaccacagct gaaaagagct ttgtattatt ttttaattcc   3420
ctccccagat atcatttagg agtattatat aaaggtggtg ggcaaaaaca atgtaaggag   3480
cctttccagt tatcttgagt tgcagctctg tagtttcttg aggccaaaca cactgtatt    3540 tacaagtcaa aatataattt acattaatca ctatgttaat gagtatgtaa aacattcttt   3600
tgcattgatg aattttgtat ctgcttccat taaaagcata acagccataa aaaaaaaa    3659
```

<210> SEQ ID NO 35
<211> LENGTH: 3588
<212> TYPE: DNA
<213> ORGANISM: Homo sapiens
<220> FEATURE:
<221> NAME/KEY: misc_feature
<223> OTHER INFORMATION: NCOA4 variant 3 (NM_001145262.1)

<400> SEQUENCE: 35

```
attgattcaa ttttacactg tgccaggcat tgtggcattc cacacaaatg gtgagaagct     60
aaaagtgaga aatttggcac aggtgaagaa ggctgggtaa cacatttgaa agactgctaa   120
acaggtcttg catgactggc ctaagtgcaa agtgaagcag cccatcacgc tccagctctc   180
caaatcggag ccggcatttc acccatgtga tacaggagca gtgaggagaa tgaatacctt   240
ccaagaccag agtggcagct ccagtaatag agaacccctt tgaggtgta gtgatgcacg    300 gagggacttg gagcttgcta ttggtggagt tctccgggct gaacagcaaa ttaaagataa   360
cttgcgagag gtcaaagctc agattcacag ttgcataagc cgtcacctgg aatgtcttag   420
aagccgtgag gtatggctgt atgaacaggt ggaccttatt tatcagctta agaggagac    480 acttcaacag caggctcagc agctctactc gttattgggc cagttcaatt gtcttactca   540
```

```
tcaactggag tgtacccaaa acaaagatct agccaatcaa gtctctgtgt gcctggagag    600
actgggcagt ttgacccctta agcctgaaga ttcaactgtc ctgctctttg aagctgacac    660
aattactctg cgccagacca tcaccacatt tgggtctctc aaaaccattc aaattcctga    720
gcacttgatg gctcatgcta gttcagcaaa tattgggccc ttcctggaga agagaggctg    780
tatctccatg ccagagcaga agtcagcatc cggtattgta gctgtccctt tcagcgaatg    840
gctccttgga agcaaacctg ccagtggtta tcaagctcct tacatacccca gcaccgaccc    900 ccaggactgg cttacccaaa agcagacctt ggagaacagt cagacttctt ccagagcctg    960
caatttcttc aataatgtcg ggggaaacct aaagggctta gaaaactggc tcctcaagag   1020
tgaaaaatca agttatcaaa agtgtaacag ccattccact actagttctt tctccattga   1080
aatggaaaag gttggagatc aagagcttcc tgatcaagat gagatggacc tatcagattg   1140
gctagtgact ccccaggaat cccataagct gcggaagcct gagaatggca gtcgtgaaac   1200
cagtgagaag tttaagctct tattccagtc ctataatgtg aatgattggc ttgtcaagac   1260
tgactcctgt accaactgtc agggaaacca gcccaaaggt gtggagattg aaaacctggg   1320
caatctgaag tgcctgaatg accacttgga ggccaagaaa ccattgtcca ccccagcat    1380 ggttacagag gattggcttg tccagaacca tcaggaccca tgtaaggtag aggaggtgtg   1440
cagagccaat gagccctgca caagctttgc agagtgtgtg tgtgatgaga attgtgagaa   1500
ggaggctctg tataagtggc ttctgaagaa agaaggaaag gataaaaatg ggatgcctgt   1560
ggaacccaaa cctgagcctg agaagcataa agattccctg aatatgtggc tctgtcctag   1620
aaaagaagta atagaacaaa ctaaagcacc aaaggcaatg actccttcta gaattgctga   1680
ttccttccaa gtcataaaga cagccccctt gtcggagtgg cttatcaggc ccccatacaa   1740
agaaggaagt cccaaggaag tgcctggtac tgaagacaga gctggcaaac agaagtttaa   1800
aagccccatg aatacttcct ggtgttcctt taacacagct gactgggtcc tgccaggaaa   1860
gaagatgggc aacctcagcc agttatcttc tggagaagac aagtggctgc ttcgaaagaa   1920
ggcccaggaa gtattactta attcacctct acaggaggaa cataacttcc ccccagacca   1980
ttatggcctc cctgcagttt gtgatctctt tgcctgtatg cagcttaaag ttgataaaga   2040
gaagtggtta tatcgaactc ctctacagat gtgaaggaat ggacaagagt tgagcagcct   2100
ttctgctgat tatcacacat catgagctga gtgactgcag cttgccaaat ctttgtgttt   2160
ctgggtctga ccaattagct tagttcttct cctgcctaat tttgaactag taaagcaaag   2220
tgagtcatca gattatgagt tactgtttaa aagaaaaatg ctgtttattc atgctgaggt   2280
gattcagttc cctccttctt acagaagtat tttaattcac cccacactag aaatgcagca   2340
tctttgtgga cgtctttttc acaagcctcc aaggctcctt agattgggtc gttactaaaa   2400
gtacattaaa acactcttgt ttatcgaagt atattgatgt attctaaagc tagtaaactt   2460
ccctaacgtt taattgccct acagatgctt ctcttgctgt gggttttctt ttgttagtgg   2520
tctgaaataa ttatttttcct gttctattaa tacatagtgt attttgcaca aaaaaattaa   2580
cctggtcaat agtgattacc aaaatatata ttaataatct tggcaatttt tgacattaat   2640
tatgaaacat tttagcccac gttagttcta cattattctt cacttaaact cagctactgc   2700
aaattttgtc tttctgtaaa tgttattaaa atatccagtg agctctttag aaggactcag   2760
tattatttca agactatttt tgaggtaatt ctagcctttt aaaatattct acagacctac   2820
ggggcttaaa agaaccccag taccgactaa gcaaataggc aaaagacatg ttggaaatgt   2880
agtatagtac ttgaaacagt cactatcata gggataattg gtgcatcctg tgtaaatgga   2940
```

```
agctgagctt gacacctggt gcttttaagt agggataaag tcatcctctc actgcaagca    3000
cagcatacct gtacctccaa aagtgacgtt ttagtgaaca ggccgttttc aacacttgtg    3060
ccttggggtg ttcattgaag ctttgtgaaa actactgatg tttttctcagt ctccttaaag   3120 ttacgtccat gctttaaaat gtctgtgtag gagagaagtg gggtttataa tgttttctct    3180
aagatatctt tgctgctttc cagactttga aactattaag cttcttaact gcctcttacc    3240
ggaaatactt ctggggaaac ttcatggtcc caaaatgtca ttgccataca gcttcactag    3300
agttctttga accacagctg aaaagagctt tgtattattt tttaattccc tccccagata    3360
tcatttagga gtattatata aaggtggtgg gcaaaaacaa tgtaaggagc ctttccagtt    3420
atcttgagtt gcagctctgt agtttcttga ggccaaacac actgtatttt acaagtcaaa    3480
atataattta cattaatcac tatgttaatg agtatgtaaa acattctttt gcattgatga    3540
attttgtatc tgcttccatt aaaagcataa cagccataaa aaaaaaaa                 3588
```

<210> SEQ ID NO 36
<211> LENGTH: 3562
<212> TYPE: DNA
<213> ORGANISM: Homo sapiens
<220> FEATURE:
<221> NAME/KEY: misc_feature
<223> OTHER INFORMATION: NCOA4 variant 4 (NM_001145263.1)

<400> SEQUENCE: 36

```
agagggcagt caagggcttc tggctgaccc gagcggagat ctcgcgagac tgtcagacgt      60
atggcgagag gtgtgggagg aagattgtgt tgtcgcgaga actctgcctt tgggccgtag     120
gttagtgtgg ggccgtgtct cagtccaccc aaggtctcct cggatcgcct ggagaggcac    180
tcggacctgg agcagtgagg agaatgaata ccttccaaga ccagagtggc agctccagta    240
atagagaacc ccttttgagg tgtagtgatg cacggaggga cttggagctt gctattggtg    300
gagttctccg ggctgaacag caaattaaag ataacttgcg agaggtcaaa gctcagattc    360
acagttgcat aagccgtcac ctggaatgtc ttagaagccg tgaggtatgg ctgtatgaac    420
aggtggacct tatttatcag cttaaagagg agacacttca acagcaggct cagcagctct    480
actcgttatt gggccagttc aattgtctta ctcatcaact ggagtgtacc caaaacaaag    540
atctagccaa tcaagtctct gtgtgcctgg agagactggg cagtttgacc cttaagcctg    600
aagattcaac tgtcctgctc tttgaagctg acacaattac tctgcgccag accatcacca    660
catttgggtc tctcaaaacc attcaaattc ctgagcactt gatggctcat gctagttcag    720
caaatattgg gcccttcctg gagaagagag gctgtatctc catgccagag cagaagtcag    780
catccggtat tgtagctgtc cctttcagcg aatggctcct tggaagcaaa cctgccagtg    840
gttatcaagc tccttacata cccagcaccg accccccagga ctggcttacc caaaagcaga    900
ccttggagaa cagtcagact tcttccgag cctgcaattt cttcaataat gtcgggggaa    960
acctaaaggg cttagaaaac tggctcctca agagtgaaaa atcaagttat caaaagtgta   1020
acagccattc cactactagt tcttttctcca ttgaaatgga aaaggttgga gatcaagagc  1080
ttcctgatca agatgagatg gacctatcag attggctagt gactcccag gaatcccata   1140 agctgcggaa gcctgagaat ggcagtcgtg aaaccagtga gaagtttaag ctcttattcc  1200
agtcctataa tgtgaatgat tggcttgtca agactgactc ctgtaccaac tgtcagggaa   1260
accagcccaa aggtgtggag attgaaaacc tgggcaatct gaagtgcctg aatgaccact   1320
tggaggccaa gaaaccattg tccaccccca gcatggttac agaggattgg cttgtccaga   1380
```

```
accatcagga cccatgtaag gtagaggagg tgtgcagagc caatgagccc tgcacaagct    1440
ttgcagagtg tgtgtgtgat gagaattgtg agaaggaggc tctgtataag tggcttctga    1500
agaaagaagg aaaggataaa aatgggatgc ctgtggaacc caaacctgag cctgagaagc    1560
ataaagattc cctgaatatg tggctctgtc ctagaaaaga agtaatagaa caaactaaag    1620
caccaaaggc aatgactcct tctagaattg ctgattcctt ccaagtcata agaacagcc     1680 ccttgtcgga gtggcttatc aggcccccat acaaagaagg aagtcccaag gaagtgcctg    1740
gtactgaaga cagagctggc aaacagaagt ttaaaagccc catgaatact tcctggtgtt    1800
cctttaacac agctgactgg gtcctgccag gaaagaagat gggcaacctc agccagttat    1860
cttctggaga agacaagtgg ctgcttcgaa agaaggccca ggaagtatta cttaattcac    1920
ctctacagga ggaacataac ttccccccag accattatgg cctccctgca gtttgtgatc    1980
tctttgcctg tatgcagctt aaagttgata agagaagtg gttatatcga actcctctac     2040
agatgtgaag gaatggacaa gagttgagca gcctttctgc tgattatcac acatcatgag    2100
ctgagtgact gcagcttgcc aaatctttgt gtttctgggt ctgaccaatt agcttagttc    2160
ttctcctgcc taattttgaa ctagtaaagc aaagtgagtc atcagattat gagttactgt    2220
ttaaaagaaa aatgctgttt attcatgctg aggtgattca gttccctcct tcttacagaa    2280 gtatttaat tcaccccaca ctagaaatgc agcatcttg tggacgtctt tttcacaagc       2340
ctccaaggct ccttagattg ggtcgttact aaaagtacat taaaacactc ttgtttatcg    2400
aagtatattg atgtattcta aagctagtaa acttccctaa cgtttaattg ccctacagat    2460
gcttctcttg ctgtgggttt tcttttgtta gtggtctgaa ataattattt tcctgttcta    2520
ttaatacata gtgtattttg cacaaaaaaa ttaacctggt caatagtgat taccaaaata    2580
tatattaata atcttggcaa ttttttgacat taattatgaa acattttagc ccacgttagt    2640
tctacattat tcttcactta aactcagcta ctgcaaattt tgtctttctg taaatgttat    2700
taaaatatcc agtgagctct ttagaaggac tcagtattat ttcaagacta tttttgaggt    2760
aattctagcc ttttaaaata ttctacagac ctacggggct taaaagaacc ccagtaccga    2820
ctaagcaaat aggcaaaaga catgttggaa atgtagtata gtacttgaaa cagtcactat    2880
catagggata attggtgcat cctgtgtaaa tggaagctga gcttgacacc tggtgctttt    2940
aagtagggat aaagtcatcc tctcactgca agcacagcat acctgtacct ccaaaagtga    3000
cgttttagtg aacaggccgt tttcaacact tgtgccttgg ggtgttcatt gaagctttgt    3060
gaaaactact gatgttttct cagtctcctt aaagttacgt ccatgcttta aaatgtctgt    3120
gtaggagaga agtggggttt ataatgtttt ctctaagata tctttgctgc tttccagact    3180
ttgaaactat taagcttctt aactgcctct taccggaaat acttctgggg aaacttcatg    3240
gtcccaaaat gtcattgcca tacagcttca ctagagttct ttgaaccaca gctgaaaaga    3300
gctttgtatt attttttaat tccctcccca gatatcattt aggagtatta tataaaggtg    3360
gtgggcaaaa acaatgtaag gagcctttcc agttatcttg agttgcagct ctgtagtttc    3420
ttgaggccaa acacactgta ttttacaagt caaaatataa tttacattaa tcactatgtt    3480
aatgagtatg taaaacattc ttttgcattg atgaattttg tatctgcttc cattaaaagc    3540
ataacagcca taaaaaaaaa aa                                               3562
```

<210> SEQ ID NO 37
<211> LENGTH: 3502
<212> TYPE: DNA

<213> ORGANISM: Homo sapiens
<220> FEATURE:
<221> NAME/KEY: misc_feature
<223> OTHER INFORMATION: NCOA4 variant 5 (NM_005437.3)

<400> SEQUENCE: 37

| | | | | | |
|---|---|---|---|---|---|
| gaactggagt | tgccgtgtga | cgcgtgggcg | ggacgaggcc | cgggctcggg | gacctttcgc | 60 |
| actcgggtca | ggggtaaagc | agcctgtcgc | ttgccgggca | gctggtgagt | cggtgacctg | 120 |
| gcctgtgagg | agcagtgagg | agaatgaata | ccttccaaga | ccagagtggc | agctccagta | 180 |
| atagagaacc | ccttttgagg | tgtagtgatg | cacggaggga | cttggagctt | gctattggtg | 240 |
| gagttctccg | ggctgaacag | caaattaaag | ataacttgcg | agaggtcaaa | gctcagattc | 300 |
| acagttgcat | aagccgtcac | ctggaatgtc | ttagaagccg | tgaggtatgg | ctgtatgaac | 360 |
| aggtggacct | tatttatcag | cttaaagagg | agacacttca | acagcaggct | cagcagctct | 420 |
| actcgttatt | gggccagttc | aattgtctta | ctcatcaact | ggagtgtacc | caaaacaaag | 480 |
| atctagccaa | tcaagtctct | gtgtgcctgg | agagactggg | cagtttgacc | cttaagcctg | 540 |
| aagattcaac | tgtcctgctc | tttgaagctg | acacaattac | tctgcgccag | accatcacca | 600 |
| catttgggtc | tctcaaaacc | attcaaattc | ctgagcactt | gatggctcat | gctagttcag | 660 |
| caaatattgg | gcccttcctg | gagaagagag | gctgtatctc | catgccagag | cagaagtcag | 720 |
| catccggtat | tgtagctgtc | cctttcagcg | aatggctcct | tggaagcaaa | cctgccagtg | 780 |
| gttatcaagc | tccttacata | cccagcaccg | accccagga | ctggcttacc | caaaagcaga | 840 |
| ccttggagaa | cagtcagact | tcttccgagc | ctgcaattt | cttcaataat | gtcgggggaa | 900 |
| acctaaaggg | cttagaaaac | tggctcctca | agagtgaaaa | atcaagttat | caaaagtgta | 960 |
| acagccattc | cactactagt | tcttttctcca | ttgaaatgga | aaaggttgga | gatcaagagc | 1020 |
| ttcctgatca | agatgagatg | gacctatcag | attggctagt | gactccccag | gaatcccata | 1080 |
| agctgcggaa | gcctgagaat | ggcagtcgtg | aaaccagtga | aagtttaag | ctcttattcc | 1140 |
| agtcctataa | tgtgaatgat | tggcttgtca | agactgactc | ctgtaccaac | tgtcagggaa | 1200 |
| accagcccaa | aggtgtggag | attgaaaacc | tgggcaatct | gaagtgcctg | aatgaccact | 1260 |
| tggaggccaa | gaaaccattg | tccaccccca | gcatggttac | agaggattgg | cttgtccaga | 1320 |
| accatcagga | cccatgtaag | gtagaggagg | tgtgcagagc | caatgagccc | tgcacaagct | 1380 |
| ttgcagagtg | tgtgtgtgat | gagaattgtg | agaaggaggc | tctgtataag | tggcttctga | 1440 |
| agaaagaagg | aaaggataaa | aatgggatgc | ctgtggaacc | caaacctgag | cctgagaagc | 1500 |
| ataaagattc | cctgaatatg | tggctctgtc | ctagaaaaga | agtaatagaa | caaactaaag | 1560 |
| caccaaaggc | aatgactcct | tctagaattg | ctgattcctt | ccaagtcata | agaacagcc | 1620 |
| ccttgtcgga | gtggcttatc | aggccccat | acaaagaagg | aagtcccaag | gaagtgcctg | 1680 |
| gtactgaaga | cagagctggc | aaacagaagt | ttaaaagccc | catgaatact | tcctggtgtt | 1740 |
| cctttaacac | agctgactgg | gtcctgccag | gaaagaagat | gggcaacctc | agccagttat | 1800 |
| cttctggaga | agacaagtgg | ctgcttcgaa | agaaggccca | ggaagtatta | cttaattcac | 1860 |
| ctctacagga | ggaacataac | ttcccccccag | accattatgg | cctccctgca | gtttgtgatc | 1920 |
| tctttgcctg | tatgcagctt | aaagttgata | agagaagtg | gttatatcga | actcctctac | 1980 |
| agatgtgaag | gaatggacaa | gagttgagca | gcctttctgc | tgattatcac | acatcatgag | 2040 |
| ctgagtgact | gcagcttgcc | aaatctttgt | gtttctgggt | ctgaccaatt | agcttagttc | 2100 |
| ttctcctgcc | taattttgaa | ctagtaaagc | aaagtgagtc | atcagattat | gagttactgt | 2160 |

```
                                                              -continued
ttaaaagaaa  aatgctgttt  attcatgctg  aggtgattca  gttccctcct  tcttacagaa   2220
gtattttaat  tcaccccaca  ctagaaatgc  agcatctttg  tggacgtctt  tttcacaagc   2280
ctccaaggct  ccttagattg  ggtcgttact  aaaagtacat  aaaacactc   ttgtttatcg   2340 aagtatattg  atgtattcta  aagctagtaa  acttccctaa  cgtttaattg  ccctacagat   2400
gcttctcttg  ctgtgggttt  tcttttgtta  gtggtctgaa  ataattattt  tcctgttcta   2460
ttaatacata  gtgtattttg  cacaaaaaaa  ttaacctggt  caatagtgat  taccaaaata   2520
tatattaata  atcttggcaa  ttttttgacat taattatgaa  acattttagc  ccacgttagt   2580
tctacattat  tcttcactta  aactcagcta  ctgcaaattt  tgtctttctg  taaatgttat   2640
taaaatatcc  agtgagctct  ttagaaggac  tcagtattat  ttcaagacta  tttttgaggt   2700
aattctagcc  ttttaaaata  ttctacagac  ctacggggct  taaaagaacc  ccagtaccga   2760
ctaagcaaat  aggcaaaaga  catgttggaa  atgtagtata  gtacttgaaa  cagtcactat   2820
catagggata  attggtgcat  cctgtgtaaa  tggaagctga  gcttgacacc  tggtgctttt   2880
aagtagggat  aaagtcatcc  tctcactgca  agcacagcat  acctgtacct  ccaaaagtga   2940
cgttttagtg  aacaggccgt  tttcaacact  tgtgccttgg  ggtgttcatt  gaagctttgt   3000
gaaaactact  gatgttttct  cagtctcctt  aaagttacgt  ccatgcttta  aaatgtctgt   3060
gtaggagaga  agtggggttt  ataatgtttt  ctctaagata  tctttgctgc  tttccagact   3120
ttgaaactat  taagcttctt  aactgcctct  taccggaaat  acttctgggg  aaacttcatg   3180
gtcccaaaat  gtcattgcca  tacagcttca  ctagagttct  ttgaaccaca  gctgaaaaga   3240
gctttgtatt  atttttttaat tccctcccca  gatatcattt  aggagtatta  tataaaggtg   3300
gtgggcaaaa  acaatgtaag  gagcctttcc  agttatcttg  agttgcagct  ctgtagtttc   3360
ttgaggccaa  acacactgta  ttttacaagt  caaaatataa  tttacattaa  tcactatgtt   3420
aatgagtatg  taaaacattc  ttttgcattg  atgaattttg  tatctgcttc  cattaaaagc   3480
ataacagcca  taaaaaaaaa  aa                                              3502
```

<210> SEQ ID NO 38
<211> LENGTH: 650
<212> TYPE: PRT
<213> ORGANISM: Homo sapiens
<220> FEATURE:
<221> NAME/KEY: misc_feature
<223> OTHER INFORMATION: NCOA4 isoform 1 (NP_001138732.1)

<400> SEQUENCE: 38

```
Met Gly Ala Gln Leu Thr Thr Phe Ala Leu Ala Gly Ala Val Arg Arg
1               5                   10                  15

Met Asn Thr Phe Gln Asp Gln Ser Gly Ser Ser Ser Asn Arg Glu Pro
            20                  25                  30

Leu Leu Arg Cys Ser Asp Ala Arg Arg Asp Leu Glu Leu Ala Ile Gly
        35                  40                  45

Gly Val Leu Arg Ala Glu Gln Gln Ile Lys Asp Asn Leu Arg Glu Val
    50                  55                  60

Lys Ala Gln Ile His Ser Cys Ile Ser Arg His Leu Glu Cys Leu Arg
65                  70                  75                  80

Ser Arg Glu Val Trp Leu Tyr Glu Gln Val Asp Leu Ile Tyr Gln Leu
                85                  90                  95

Lys Glu Glu Thr Leu Gln Gln Gln Ala Gln Gln Leu Tyr Ser Leu Leu
            100                 105                 110

Gly Gln Phe Asn Cys Leu Thr His Gln Leu Glu Cys Thr Gln Asn Lys
```

```
            115                 120                 125
Asp Leu Ala Asn Gln Val Ser Val Cys Leu Glu Arg Leu Gly Ser Leu
        130                 135                 140
Thr Leu Lys Pro Glu Asp Ser Thr Val Leu Leu Phe Glu Ala Asp Thr
145                 150                 155                 160
Ile Thr Leu Arg Gln Thr Ile Thr Thr Phe Gly Ser Leu Lys Thr Ile
                165                 170                 175
Gln Ile Pro Glu His Leu Met Ala His Ala Ser Ser Ala Asn Ile Gly
            180                 185                 190
Pro Phe Leu Glu Lys Arg Gly Cys Ile Ser Met Pro Glu Gln Lys Ser
        195                 200                 205
Ala Ser Gly Ile Val Ala Val Pro Phe Ser Glu Trp Leu Leu Gly Ser
    210                 215                 220
Lys Pro Ala Ser Gly Tyr Gln Ala Pro Tyr Ile Pro Ser Thr Asp Pro
225                 230                 235                 240
Gln Asp Trp Leu Thr Gln Lys Gln Thr Leu Glu Asn Ser Gln Thr Ser
                245                 250                 255
Ser Arg Ala Cys Asn Phe Phe Asn Asn Val Gly Gly Asn Leu Lys Gly
            260                 265                 270
Leu Glu Asn Trp Leu Leu Lys Ser Glu Lys Ser Ser Tyr Gln Lys Cys
        275                 280                 285
Asn Ser His Ser Thr Thr Ser Ser Phe Ser Ile Glu Met Glu Lys Val
    290                 295                 300
Gly Asp Gln Glu Leu Pro Asp Gln Asp Glu Met Asp Leu Ser Asp Trp
305                 310                 315                 320
Leu Val Thr Pro Gln Glu Ser His Lys Leu Arg Lys Pro Glu Asn Gly
                325                 330                 335
Ser Arg Glu Thr Ser Glu Lys Phe Lys Leu Leu Phe Gln Ser Tyr Asn
            340                 345                 350
Val Asn Asp Trp Leu Val Lys Thr Asp Ser Cys Thr Asn Cys Gln Gly
        355                 360                 365
Asn Gln Pro Lys Gly Val Glu Ile Glu Asn Leu Gly Asn Leu Lys Cys
    370                 375                 380
Leu Asn Asp His Leu Glu Ala Lys Lys Pro Leu Ser Thr Pro Ser Met
385                 390                 395                 400
Val Thr Glu Asp Trp Leu Val Gln Asn His Gln Asp Pro Cys Lys Val
                405                 410                 415
Glu Glu Val Cys Arg Ala Asn Glu Pro Cys Thr Ser Phe Ala Glu Cys
            420                 425                 430
Val Cys Asp Glu Asn Cys Glu Lys Glu Ala Leu Tyr Lys Trp Leu Leu
        435                 440                 445
Lys Lys Glu Gly Lys Asp Lys Asn Gly Met Pro Val Glu Pro Lys Pro
    450                 455                 460
Glu Pro Glu Lys His Lys Asp Ser Leu Asn Met Trp Leu Cys Pro Arg
465                 470                 475                 480
Lys Glu Val Ile Glu Gln Thr Lys Ala Pro Lys Ala Met Thr Pro Ser
                485                 490                 495
Arg Ile Ala Asp Ser Phe Gln Val Ile Lys Asn Ser Pro Leu Ser Glu
            500                 505                 510
Trp Leu Ile Arg Pro Pro Tyr Lys Glu Gly Ser Pro Lys Glu Val Pro
        515                 520                 525
Gly Thr Glu Asp Arg Ala Gly Lys Gln Lys Phe Lys Ser Pro Met Asn
    530                 535                 540
```

Thr Ser Trp Cys Ser Phe Asn Thr Ala Asp Trp Val Leu Pro Gly Lys
545                 550                 555                 560

Lys Met Gly Asn Leu Ser Gln Leu Ser Ser Gly Glu Asp Lys Trp Leu
            565                 570                 575

Leu Arg Lys Lys Ala Gln Glu Val Leu Leu Asn Ser Pro Leu Gln Glu
        580                 585                 590

Glu His Asn Phe Pro Pro Asp His Tyr Gly Leu Pro Ala Val Cys Asp
            595                 600                 605

Leu Phe Ala Cys Met Gln Leu Lys Val Asp Lys Glu Lys Trp Leu Tyr
        610                 615                 620

Arg Thr Pro Leu Gln Ala Tyr Phe Lys Met Asn Phe Gln Asp Val Thr
625                 630                 635                 640

Val Gly Asn Phe Gln Ile Pro Cys Gly Phe
                645                 650

<210> SEQ ID NO 39
<211> LENGTH: 630
<212> TYPE: PRT
<213> ORGANISM: Homo sapiens
<220> FEATURE:
<221> NAME/KEY: misc_feature
<223> OTHER INFORMATION: NCOA4 isoform 2 (NP_001138733.1)

<400> SEQUENCE: 39

Met Gly Ala Gln Leu Thr Thr Phe Ala Leu Ala Gly Ala Val Arg Arg
1               5                   10                  15

Met Asn Thr Phe Gln Asp Gln Ser Gly Ser Ser Ser Asn Arg Glu Pro
            20                  25                  30

Leu Leu Arg Cys Ser Asp Ala Arg Arg Asp Leu Glu Leu Ala Ile Gly
        35                  40                  45

Gly Val Leu Arg Ala Glu Gln Gln Ile Lys Asp Asn Leu Arg Glu Val
    50                  55                  60

Lys Ala Gln Ile His Ser Cys Ile Ser Arg His Leu Glu Cys Leu Arg
65                  70                  75                  80

Ser Arg Glu Val Trp Leu Tyr Glu Gln Val Asp Leu Ile Tyr Gln Leu
                85                  90                  95

Lys Glu Glu Thr Leu Gln Gln Gln Ala Gln Gln Leu Tyr Ser Leu Leu
            100                 105                 110

Gly Gln Phe Asn Cys Leu Thr His Gln Leu Glu Cys Thr Gln Asn Lys
        115                 120                 125

Asp Leu Ala Asn Gln Val Ser Val Cys Leu Glu Arg Leu Gly Ser Leu
    130                 135                 140

Thr Leu Lys Pro Glu Asp Ser Thr Val Leu Leu Phe Glu Ala Asp Thr
145                 150                 155                 160

Ile Thr Leu Arg Gln Thr Ile Thr Thr Phe Gly Ser Leu Lys Thr Ile
                165                 170                 175

Gln Ile Pro Glu His Leu Met Ala His Ala Ser Ser Ala Asn Ile Gly
            180                 185                 190

Pro Phe Leu Glu Lys Arg Gly Cys Ile Ser Met Pro Glu Gln Lys Ser
        195                 200                 205

Ala Ser Gly Ile Val Ala Val Pro Phe Ser Glu Trp Leu Leu Gly Ser
    210                 215                 220

Lys Pro Ala Ser Gly Tyr Gln Ala Pro Tyr Ile Pro Ser Thr Asp Pro
225                 230                 235                 240

Gln Asp Trp Leu Thr Gln Lys Gln Thr Leu Glu Asn Ser Gln Thr Ser

```
                245                 250                 255
Ser Arg Ala Cys Asn Phe Phe Asn Asn Val Gly Gly Asn Leu Lys Gly
            260                 265                 270

Leu Glu Asn Trp Leu Leu Lys Ser Glu Lys Ser Ser Tyr Gln Lys Cys
            275                 280                 285

Asn Ser His Ser Thr Thr Ser Ser Phe Ser Ile Glu Met Glu Lys Val
            290                 295                 300

Gly Asp Gln Glu Leu Pro Asp Gln Asp Glu Met Asp Leu Ser Asp Trp
305                 310                 315                 320

Leu Val Thr Pro Gln Glu Ser His Lys Leu Arg Lys Pro Glu Asn Gly
            325                 330                 335

Ser Arg Glu Thr Ser Glu Lys Phe Lys Leu Leu Phe Gln Ser Tyr Asn
            340                 345                 350

Val Asn Asp Trp Leu Val Lys Thr Asp Ser Cys Thr Asn Cys Gln Gly
            355                 360                 365

Asn Gln Pro Lys Gly Val Glu Ile Glu Asn Leu Gly Asn Leu Lys Cys
            370                 375                 380

Leu Asn Asp His Leu Glu Ala Lys Lys Pro Leu Ser Thr Pro Ser Met
385                 390                 395                 400

Val Thr Glu Asp Trp Leu Val Gln Asn His Gln Asp Pro Cys Lys Val
                405                 410                 415

Glu Glu Val Cys Arg Ala Asn Glu Pro Cys Thr Ser Phe Ala Glu Cys
            420                 425                 430

Val Cys Asp Glu Asn Cys Glu Lys Glu Ala Leu Tyr Lys Trp Leu Leu
            435                 440                 445

Lys Lys Glu Gly Lys Asp Lys Asn Gly Met Pro Val Glu Pro Lys Pro
450                 455                 460

Glu Pro Glu Lys His Lys Asp Ser Leu Asn Met Trp Leu Cys Pro Arg
465                 470                 475                 480

Lys Glu Val Ile Glu Gln Thr Lys Ala Pro Lys Ala Met Thr Pro Ser
                485                 490                 495

Arg Ile Ala Asp Ser Phe Gln Val Ile Lys Asn Ser Pro Leu Ser Glu
            500                 505                 510

Trp Leu Ile Arg Pro Pro Tyr Lys Glu Gly Ser Pro Lys Glu Val Pro
            515                 520                 525

Gly Thr Glu Asp Arg Ala Gly Lys Gln Lys Phe Lys Ser Pro Met Asn
530                 535                 540

Thr Ser Trp Cys Ser Phe Asn Thr Ala Asp Trp Val Leu Pro Gly Lys
545                 550                 555                 560

Lys Met Gly Asn Leu Ser Gln Leu Ser Ser Gly Glu Asp Lys Trp Leu
                565                 570                 575

Leu Arg Lys Lys Ala Gln Glu Val Leu Leu Asn Ser Pro Leu Gln Glu
            580                 585                 590

Glu His Asn Phe Pro Pro Asp His Tyr Gly Leu Pro Ala Val Cys Asp
            595                 600                 605

Leu Phe Ala Cys Met Gln Leu Lys Val Asp Lys Glu Lys Trp Leu Tyr
            610                 615                 620

Arg Thr Pro Leu Gln Met
625                 630

<210> SEQ ID NO 40
<211> LENGTH: 614
<212> TYPE: PRT
<213> ORGANISM: Homo sapiens
```

<220> FEATURE:
<221> NAME/KEY: misc_feature
<223> OTHER INFORMATION: NCOA4 isoform 3 (NP_001138734.1)

<400> SEQUENCE: 40

```
Met Asn Thr Phe Gln Asp Gln Ser Gly Ser Ser Asn Arg Glu Pro
1               5                   10                  15

Leu Leu Arg Cys Ser Asp Ala Arg Arg Asp Leu Glu Leu Ala Ile Gly
            20                  25                  30

Gly Val Leu Arg Ala Glu Gln Ile Lys Asp Asn Leu Arg Glu Val
            35                  40                  45

Lys Ala Gln Ile His Ser Cys Ile Ser Arg His Leu Glu Cys Leu Arg
50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Ala Gln Gln Leu Tyr Ser Leu Leu
                85                  90                  95

Gly Gln Phe Asn Cys Leu Thr His Gln Leu Glu Cys Thr Gln Asn Lys
                100                 105                 110

Asp Leu Ala Asn Gln Val Ser Val Cys Leu Glu Arg Leu Gly Ser Leu
            115                 120                 125

Thr Leu Lys Pro Glu Asp Ser Thr Val Leu Leu Phe Glu Ala Asp Thr
130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
            180                 185                 190

Ala Ser Gly Ile Val Ala Val Pro Phe Ser Glu Trp Leu Leu Gly Ser
            195                 200                 205

Lys Pro Ala Ser Gly Tyr Gln Ala Pro Tyr Ile Pro Ser Thr Asp Pro
210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
            260                 265                 270

Asn Ser His Ser Thr Thr Ser Ser Phe Ser Ile Glu Met Glu Lys Val
            275                 280                 285

Gly Asp Gln Glu Leu Pro Asp Gln Asp Glu Met Asp Leu Ser Asp Trp
290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
            355                 360                 365

Leu Asn Asp His Leu Glu Ala Lys Lys Pro Leu Ser Thr Pro Ser Met
370                 375                 380

Val Thr Glu Asp Trp Leu Val Gln Asn His Gln Asp Pro Cys Lys Val
```

```
385                 390                 395                 400
Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
                420                 425                 430

Lys Lys Glu Gly Lys Asp Lys Asn Gly Met Pro Val Glu Pro Lys Pro
                435                 440                 445

Glu Pro Glu Lys His Lys Asp Ser Leu Asn Met Trp Leu Cys Pro Arg
        450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
                500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
        530                 535                 540

Lys Met Gly Asn Leu Ser Gln Leu Ser Ser Gly Glu Asp Lys Trp Leu
545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
                580                 585                 590

Leu Phe Ala Cys Met Gln Leu Lys Val Asp Lys Glu Lys Trp Leu Tyr
                595                 600                 605

Arg Thr Pro Leu Gln Met
        610

<210> SEQ ID NO 41
<211> LENGTH: 614
<212> TYPE: PRT
<213> ORGANISM: Homo sapiens
<220> FEATURE:
<221> NAME/KEY: misc_feature
<223> OTHER INFORMATION: NCOA4 isoform 3 (NP_001138735.1)

<400> SEQUENCE: 41

Met Asn Thr Phe Gln Asp Gln Ser Gly Ser Ser Ser Asn Arg Glu Pro
1               5                   10                  15

Leu Leu Arg Cys Ser Asp Ala Arg Arg Asp Leu Glu Leu Ala Ile Gly
                20                  25                  30

Gly Val Leu Arg Ala Glu Gln Gln Ile Lys Asp Asn Leu Arg Glu Val
                35                  40                  45

Lys Ala Gln Ile His Ser Cys Ile Ser Arg His Leu Glu Cys Leu Arg
        50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Gln Ala Gln Gln Leu Tyr Ser Leu Leu
                85                  90                  95

Gly Gln Phe Asn Cys Leu Thr His Gln Leu Glu Cys Thr Gln Asn Lys
                100                 105                 110

Asp Leu Ala Asn Gln Val Ser Val Cys Leu Glu Arg Leu Gly Ser Leu
        115                 120                 125
```

```
Thr Leu Lys Pro Glu Asp Ser Thr Val Leu Leu Phe Glu Ala Asp Thr
130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
            180                 185                 190

Ala Ser Gly Ile Val Ala Val Pro Phe Ser Glu Trp Leu Leu Gly Ser
        195                 200                 205

Lys Pro Ala Ser Gly Tyr Gln Ala Pro Tyr Ile Pro Ser Thr Asp Pro
210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
            260                 265                 270

Asn Ser His Ser Thr Thr Ser Ser Phe Ser Ile Glu Met Glu Lys Val
        275                 280                 285

Gly Asp Gln Glu Leu Pro Asp Gln Asp Glu Met Asp Leu Ser Asp Trp
290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
        355                 360                 365

Leu Asn Asp His Leu Glu Ala Lys Lys Pro Leu Ser Thr Pro Ser Met
370                 375                 380

Val Thr Glu Asp Trp Leu Val Gln Asn His Gln Asp Pro Cys Lys Val
385                 390                 395                 400

Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
            420                 425                 430

Lys Lys Glu Gly Lys Asp Lys Asn Gly Met Pro Val Glu Pro Lys Pro
        435                 440                 445

Glu Pro Glu Lys His Lys Asp Ser Leu Asn Met Trp Leu Cys Pro Arg
450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
            500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
530                 535                 540

Lys Met Gly Asn Leu Ser Gln Leu Ser Ser Gly Glu Asp Lys Trp Leu
```

```
                545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
                580                 585                 590

Leu Phe Ala Cys Met Gln Leu Lys Val Asp Lys Glu Lys Trp Leu Tyr
                595                 600                 605

Arg Thr Pro Leu Gln Met
                610

<210> SEQ ID NO 42
<211> LENGTH: 614
<212> TYPE: PRT
<213> ORGANISM: Homo sapiens
<220> FEATURE:
<221> NAME/KEY: misc_feature
<223> OTHER INFORMATION: NCOA4 isoform 3 (NP_005428.1)

<400> SEQUENCE: 42

Met Asn Thr Phe Gln Asp Gln Ser Gly Ser Ser Asn Arg Glu Pro
1               5                   10                  15

Leu Leu Arg Cys Ser Asp Ala Arg Arg Asp Leu Glu Leu Ala Ile Gly
                20                  25                  30

Gly Val Leu Arg Ala Glu Gln Gln Ile Lys Asp Asn Leu Arg Glu Val
            35                  40                  45

Lys Ala Gln Ile His Ser Cys Ile Ser Arg His Leu Glu Cys Leu Arg
        50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Gln Ala Gln Gln Leu Tyr Ser Leu Leu
                85                  90                  95

Gly Gln Phe Asn Cys Leu Thr His Gln Leu Glu Cys Thr Gln Asn Lys
                100                 105                 110

Asp Leu Ala Asn Gln Val Ser Val Cys Leu Glu Arg Leu Gly Ser Leu
            115                 120                 125

Thr Leu Lys Pro Glu Asp Ser Thr Val Leu Leu Phe Glu Ala Asp Thr
        130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
                180                 185                 190

Ala Ser Gly Ile Val Ala Val Pro Phe Ser Glu Trp Leu Leu Gly Ser
            195                 200                 205

Lys Pro Ala Ser Gly Tyr Gln Ala Pro Tyr Ile Pro Ser Thr Asp Pro
        210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
                260                 265                 270

Asn Ser His Ser Thr Thr Ser Ser Phe Ser Ile Glu Met Glu Lys Val
            275                 280                 285
```

```
Gly Asp Gln Glu Leu Pro Asp Gln Asp Glu Met Asp Leu Ser Asp Trp
    290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
        355                 360                 365

Leu Asn Asp His Leu Glu Ala Lys Lys Pro Leu Ser Thr Pro Ser Met
    370                 375                 380

Val Thr Glu Asp Trp Leu Val Gln Asn His Gln Asp Pro Cys Lys Val
385                 390                 395                 400

Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
            420                 425                 430

Lys Lys Glu Gly Lys Asp Lys Asn Gly Met Pro Val Glu Pro Lys Pro
        435                 440                 445

Glu Pro Glu Lys His Lys Asp Ser Leu Asn Met Trp Leu Cys Pro Arg
    450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
            500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
    530                 535                 540

Lys Met Gly Asn Leu Ser Gln Leu Ser Ser Gly Glu Asp Lys Trp Leu
545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
            580                 585                 590

Leu Phe Ala Cys Met Gln Leu Lys Val Asp Lys Glu Lys Trp Leu Tyr
        595                 600                 605

Arg Thr Pro Leu Gln Met
    610

<210> SEQ ID NO 43
<211> LENGTH: 8339
<212> TYPE: DNA
<213> ORGANISM: Homo sapiens
<220> FEATURE:
<221> NAME/KEY: misc_feature
<223> OTHER INFORMATION: TRIM33 transcript variant a (NM_015906.3)

<400> SEQUENCE: 43
ctgcggctgg ggctgggggc ggcggcggcg gcgacgcggg cggcgggcgg cgcggggcgg      60
tccggcgggt tcaaagagga aaacatggcg gaaaacaaag gcggcggcga ggctgagagc     120
ggcggcgggg gcagcggcag cgcgccggta actgccgggg ccgccgggcc cgccgcgcag     180
```

-continued

```
gaggcggagc cgcctctcac cgcggtgctg gtggaggagg aggaggagga aggcggcagg    240
gccggcgctg agggcggcgc ggccgggccc gacgacgggg gggtggccgc ggcctcctcg    300
ggctcggccc aggctgcttc atctcctgcg gcctcagtgg gcactggagt tgccgggggc    360
gcagtatcga cgccggctcc agctccagcc tcggctcccg ctccgggtcc ctcggcaggg    420
ccgcctcctg gaccgccagc ctcgctcctg gacacctgcg ccgtgtgtca gcagagcttg    480
cagagccggc gtgaggcgga gcccaagctg ctgcccgtc ttcactcctt ctgcctgcgc     540
tgcctgcccg agccggagcg ccagctcagc gtgcccatcc cggggggcag caacggcgac    600
atccagcaag ttggtgtaat acggtgccca gtatgccgcc aagaatgcag acagatagac    660
cttgtggata attattttgt gaaagacaca tctgaagctc ctagcagttc tgatgaaaaa    720
tcagaacagg tatgtactag ttgtgaagac aatgcaagtg cagttggctt ttgtgtagaa    780
tgtggagagt ggctatgtaa gacatgtatc gaagcacatc aaagagtaaa atttactaaa    840
gatcacttga tcaggaagaa agaagatgtc tcagagtctg ttggagcatc tggtcaacgc    900
cctgttttct gccctgtaca caaacaagaa cagttgaaac ttttctgtga acatgtgat     960 agattgacat gtagagactg tcagctattg aacacaaag aacataggta tcagtttttg     1020
gaagaagctt ttcaaaatca gaagggtgca attgagaatc tactggcgaa acttcttgag    1080
aagaagaatt atgttcattt tgcagctact caggtgcaga ataggataaa agaagtaaat    1140
gagactaaca aacgagtaga acaggaaatt aaagtggcca ttttcaccct tatcaatgaa    1200
attaataaga aaggaaaatc tctcttacaa cagctagaga atgttacaaa ggaaagacag    1260
atgaagttac tacagcagca gaatgacatc acaggccttt cccggcaggt gaagcatgtt    1320
atgaacttca caaattgggc aattgcaagt ggcagcagca cagcactact atacagcaag    1380
cgactgatta cttttccagtt gcgtcatatt ttgaaagcac ggtgtgatcc tgtccctgct    1440
gctaatggag caatacgttt ccattgtgat cccaccttct gggcaaagaa tgtagtcaat    1500
ttaggtaatc tagtaataga gagtaaacca gctcctggtt atactcctaa tgttgtagtt    1560
gggcaagttc ctccagggac aaaccacatt agtaaaaccc ctggacagat taacttagca    1620
cagcttcgac tccagcacat gcaacaacaa gtatatgcac agaaacatca gcagttgcaa    1680
cagatgagga tgcagcaacc accagcacct gtaccaacta caacaacaac aacacaacag    1740
catcctagac aagcagcccc tcagatgtta caacaacagc ctcctcgatt gatcagtgtg    1800
caaacaatgc aaagaggcaa catgaactgt ggagcttttc aagcccatca gatgagactg    1860
gctcagaatc tgccagaat accagggata cccaggcaca gcggccctca atattccatg     1920
atgcagccac acctccaaag acaacactca aacccagggc atgctggacc ctttcccgta    1980
gtatcggtac acaacaccac aatcaaccca acgagcccta ctacagcaac tatggcaaat    2040
gcaaaccgag gtcccaccag cccatctgtt acagcaatag agctaatccc ctcagttacc    2100
aatccagaaa accttccatc gctgccagat attccaccca tacagttgga agatgctggc    2160
tcaagtagtt tagataatct actaagtaga tacatctcag gcagtcacct accccacag     2220 cctacaagca ccatgaatcc ttctccaggt ccctctgccc tttctccggg atcatcaggt    2280
ttatccaatt ctcacacacc tgtgagaccc ccaagtactt ctagtactgg cagtcgaggc    2340
agctgtgggt catcaggaag aactgctgag aagacaagtc ttagtttcaa atctgatcag    2400
gtgaaggtca agcaagaacc tgggactgaa gatgaaatat gtagcttttc aggaggtgta    2460
aaacaagaaa aaacagagga tggcaggagg agtgcttgca tgttgagcag tcctgagagt    2520
```

```
agcttgacac cacctctctc aaccaacctg catctagaaa gtgaattgga tgcattggca   2580
agcctggaaa accatgtgaa aattgaacct gcagatatga atgaaagctg caaacagtca   2640
gggctcagca gccttgttaa tggaaagtcc ccaattcgaa gcctcatgca caggtcggca   2700
aggattggag gagatggcaa caataaagat gatgacccaa atgaagactg gtgtgctgtc   2760
tgccaaaacg gaggagatct cttgtgctgc gaaaaatgtc caaggtcttt tcatctaact   2820
tgtcatgttc caacactact tagctttcca agtggggact ggatatgcac attttgtaga   2880
gatattggaa agccagaagt tgaatatgat tgtgataatt tgcaacatag taagaagggg   2940
aaaactgcgc aggggttaag ccccgtggac caaggaaaat gtgaacgtct tctgctttac   3000
ctctattgcc atgaattaag tattgaattc caggagcctg ttcctgcttc gataccaaac   3060
tactataaaa ttataaagaa accaatggat ttatccaccg tgaaaaagaa gcttcagaaa   3120
aaacattccc aacactacca aatcccggat gactttgtgg ccgatgtccg tttgatcttc   3180
aagaactgtg aaaggtttaa tgaaatgatg aaagttgttc aagtttatgc agacacacaa   3240
gagattaatt tgaaggctga ttcagaagta gctcaggcag ggaaagcagt tgcattgtac   3300
tttgaagata aactcacaga gatctactca gacaggacct tcgcaccttt gccagagttt   3360
gagcaggaag aggatgatgg tgaggtaact gaggactctg atgaagactt tatacagccc   3420
cgcagaaaac gcctaaagtc agatgagaga ccagtacata taaagtaaaa tgacatggat   3480
ttaaatcaat tgtttaaaaa aaaaaaacg aaaaaaaaaa aaaaaacaca aaaaacccag   3540
aaaactttta agtgttgctg gaatatcctg cctacagtgg gcacctcctt gaagaagctg   3600
atagcttta cacagtatta gattgaaata atggacagaa acacattctt gtcaagaaag   3660
ggggagagaa gtctgtttgc aagtttcaaa gcaaaaagca aaagtgaaat gatttgagga   3720
tttctgttct aatggagatg attctctgat tgttagaaat ggcaaatatt gatgattgtg   3780
tgctattgat tggtgcagga tacttggtat acgagtaaat acttgagact cgtgtcactt   3840
gataaatttt cttttggac taggtcgcac agttattaaa caactttta accctccccc   3900
ttcacacaca tacatatcag gttgttttct agttaaaaac ccaagtagct cagattctac   3960
tttaatgtca gtgcagattt gcattgaatc atgccattat gttttttctc attttatgc    4020
tgttgggtct tagttttaa attgatataa agaactcagc aatggtttta ttttctactc    4080
atacttaggg tttaggaaac actaccacta gttatcattt aatcaacttc aatggtctac    4140
tgaaacaaaa atggtaactt ttcattagtg gattatttag agttatagta gttgtttcca    4200
gaaaacactt cctcacaatt gtacttccca atcaaatcat gtgatcatac agttattccc    4260
atgaaaggca gaatgtttgt ttcaaaatta atctagtttt ctgtacattt aaatttgaga    4320
aggtgacaac tggctctttt ccagtcttcc ttcatgtcag ttttctgata gaccactatt    4380
ggcaaacagt atctgtcaac taccaaatgt gtaaaatttt ctgtatttca ctttgtctta    4440
tttgtaaata gtgaactaaa acttttggca gatcagcaac atttgctgag cctgtttttt    4500
aagctaatgt gtattcttac taatgttcct atcaagaatg gatttgtaat atatgctgtc    4560
tatttctaat gttcacattc atattttgag gttctatctt attttaatag agaacagact    4620
tctcaaaaaa tcttcagaag cagcttatta ttgaaatatc gaaatattga aataaacccg    4680
gtggggttag attactcatc tgtccaccaa gtgggacatt tgcatggact gggggcttaa    4740
aggacttaga agagacctgt aagtaaatcc tgaaaatgag ccaatcccca cttgaatggt    4800
tactggagta aacccacctt taccaccca attacagcac ccgaggccga taaaccaact    4860
tggctctggt tcatttttct tttcttcatt tgtgatgctc agattcaaaa tgtgtgttct    4920
```

```
acactgttac aggcttctct tttgtttgat taaagatttt agtcctactt ttgtatggac    4980
acattagaat attcagagac caaaatagaa gaatttgctg ttagatattt ttcagaagtc    5040
agcagatttg tggcaaatca tttatttgcc tttttaaaaa ttcatttaag cagttcagag    5100
agtagactac tcagaaaatt atttcacgta attgtctaag aggtcaatat ttttaatgc    5160 atattgaatc aaataaagtg ctctaaagaa attattatac aaattccttt gggttgtttt    5220
tcttttctta acaaggggtg ggggtaaaca ggaatatgat tcaggctttc tggttgtgta    5280
tttaaagagt attgatttta ttattactat tgatttactt tattcctggc ttccttttca    5340
cttttctttc aattttttaaa aaataattta agccgttgaa aatataccaa actgttgaaa    5400 catttactc aaattttaaa ttcctaaaaa tgttttttaa taagagggag aaaattattt    5460
aaaaatactt atgcctatgc caatttccct ctttttttcac aaaatccatg atttcagttt    5520
gtaagtagac atatatctaa gggcacattt ttggaaagtg aggaatagca gcagtataac    5580
ttcattttgt caggcctttg agttctaata ttttgtattg ctcttcaaat ggatcctttt    5640
aaaaaaattg tagataatga gtcataaata gattctgcca actgaggga gaaacatttt    5700 aagtaaatat ttttcagtat ttggggcctt aaaaaaataat tgtgtttcct taaaattaca    5760
tgttagatag agtttttagg ttttttttggt tttaagattg gttaaagcaa tttaaaagcc    5820
acttttttgt caacatttaa tagcctccac ttctgttaag ataatgtata ctgctgagga    5880
attactatta atagctatca acataccacc attaaattaa ggtattcact ttagatttt    5940 tattaaagct tttttcttgc acactgatcg tgtgtttct aagctgatt tttcagctct    6000 aatataccta tggttaaaaa gtataaaaac ttaaattgat atttagatat atgttttcct    6060
attagtttat gttttaaaaa gacaaaattg tatctgtcag tccctgaagg cagtttgttt    6120
ttatactctc tcacatttgt atttgttttt taaatggcag tatttttagaa gatttggaga    6180 aaagtccaca taataatgtt ttcttaaaag cttttaaagt ttttgctgta cttcaattta    6240
cttcttccat cagaaaacta agaacaaagt gttgctcagt ctgttccgct gacctaaatt    6300
tgtgttttca gcacttggct cagccaattc actgagtgaa ggaattgctt tatgaggcaa    6360
agcatgtgaa agttctaaag tatggttaga ttgtaggtcg tgctctatat ggaaacatca    6420
aaccattact acagagaaat gataaggcat tggatccact attgaaatta ttatttttgg    6480
atcaacaagt tggtactttc tgacttctgt atcttaacat aagggaattt taggtaatgc    6540
taagtcagtt gtctcatttt ttgtgataag ttttggaatt tttagttaat tgaaataaat    6600 aatgcttta aatagaagta aaggttttat aagtgtgcaa attgtagatt tatcaattac    6660
ctcagcaggt atcctgccat gtaattatta gtgattagtg ttaataagat aatagattca    6720
ggtcttccaa ctatgccctt ggattgtggc ctactgtatg ttattaaatg gtctcttact    6780
atccaaaatg ggagtagatg ctgtggcccc gtctcccttg gcttttacgt cccatatcca    6840 ccccattca tgtacaacat gtgaaatata aaaatctcat ttcttgtcaa atcagcact    6900 gcttatttgc atactcagca tcggatcagt gagtagtttt ataaaaaatc cacgcaccca    6960
actcccttag ttaaaacaga ttcttaattc ataccatgaa ttcttaatttt ctgtaccatc    7020 tatgttaatg atctgctgaa ggtgactcaa gattttcaag gtgtaataca gtttgatcat    7080
gtaccggacc tggatattta atttttttttc cctcacagtt aatctcctcc ttgataaagc    7140
aataacactg ctttgagtct gttgcctaat agcatgtcag aatcctctcc tggatggtga    7200
ttttatagga aagtttgtat gcatatcacc cagtctatct tttaaaaatt aagaaattta    7260
```

| | |
|---|---|
| aatgtatgct ggaagtaatg acactatatt gtggcatttt attttaaaaa ttggggaaag | 7320 |
| ttgcatattt ttttaaaagt aagtgtttga gtaaaaaaat tgaaggtact tttttaagga | 7380 |
| aaaaaattta tatgccacag tttacataga catttcagat tcaacacgta ctcttgaata | 7440 |
| taatggtttc ttttacttgg tcaaaatgca tgtatagcat ttctttcatc ttagttcctt | 7500 |
| gtgtttgcct atgtggtcct ttatatattt tttattgtat cgaagaaaca aaactatctt | 7560 |
| caaaaataag ttaatttgga tatatttgtc atatcaaact acaaagtgta caaagttaag | 7620 |
| tttagcccctt ttctagaaag tgatctttaa aattaaaaat gctcctcttt taaattcacc | 7680 |
| aaatttatgt gtgggaaggc accaaaatga ttttgtaagt gccactgcaa tattcccttt | 7740 |
| caagtgtggc ctaaatttca atcttaagga tggaatgcat gtctgctcct tgttctgaaa | 7800 |
| aatgtaggca tctactacat tttaaaacac agtgaaacat atacataagc ctataaaaaa | 7860 |
| agatttgtgc aatttgaaag cctgttaatt ttttatgtag atacctac acacgaaagg | 7920 |
| gttaaattca cagccttact agttccttgc ttccagtatt tcaattggtc tcctcccctc | 7980 |
| attattatta ttactactag tactattatt tttgcacata gttaactgcc cttcaatatg | 8040 |
| attcttaaaa agtgctgttt ctgtggtatc gtattctcta aataatcata tttaattttt | 8100 |
| taaaacaagg ttgcagtttc taattgtttc gttcctgtgt ttttgctggt gtgtaataaa | 8160 |
| agcaagtttt ttcttttcat ggttatttaa tacattagct gcctgtaaat aattcttgtt | 8220 |
| ataatgctct ggaatgtgtt gtagaagttg tattagatta gttttaaacc cttgtttgaa | 8280 |
| agccacattg ttttggttat ttctattaaa ttagaaaatt gaaaagtttt tcaaatgaa | 8339 |

<210> SEQ ID NO 44
<211> LENGTH: 8288
<212> TYPE: DNA
<213> ORGANISM: Homo sapiens
<220> FEATURE:
<221> NAME/KEY: misc_feature
<223> OTHER INFORMATION: TRIM33 transcript variant b (NM_033020.2)

<400> SEQUENCE: 44

| | |
|---|---|
| ctgcggctgg ggctgggggc ggcggcggcg gcgacgcggg cggcgggcgg cgcggggcgg | 60 |
| tccggcgggt tcaaagagga aaacatggcg gaaaacaaag gcggcggcga ggctgagagc | 120 |
| ggcggcgggg gcagcggcag cgcgccggta actgccgggg ccgccgggcc cgccgcgcag | 180 |
| gaggcggagc cgcctctcac cgcggtgctg gtggaggagg aggaggagga aggcggcagg | 240 |
| gccggcgctg agggcggcgc ggccgggccc gacgacgggg gggtggccgc ggcctcctcg | 300 |
| ggctcggccc aggctgcttc atctcctgcg gcctcagtgg gcactggagt tgccgggggc | 360 |
| gcagtatcga cgccggctcc agctccagcc tcggctcccg ctccgggtcc ctcggcaggg | 420 |
| ccgcctcctg gaccgccagc ctcgctcctg gacacctgcg ccgtgtgtca gcagagcttg | 480 |
| cagagccggc gtgaggcgga gcccaagctg ctgccctgtc ttcactcctt ctgcctgcgc | 540 |
| tgcctgcccg agccggagcg ccagctcagc gtgcccatcc cggggggcag caacggcgac | 600 |
| atccagcaag ttggtgtaat acggtgccca gtatgccgcc aagaatgcag acagatagac | 660 |
| cttgtggata attatttgt gaaagacaca tctgaagctc ctagcagttc tgatgaaaaa | 720 |
| tcagaacagg tatgtactag ttgtgaagac aatgcaagtg cagttggctt ttgtgtagaa | 780 |
| tgtggagagt ggctatgtaa gacatgtatc gaagcacatc aaagagtaaa atttactaaa | 840 |
| gatcacttga tcaggaagaa agaagatgtc tcagagtctg ttggagcatc tggtcaacgc | 900 |
| cctgtttttct gccctgtaca caaacaagaa cagttgaaac tttctgtga aacatgtgat | 960 |

```
agattgacat gtagagactg tcagctattg aacacaaag aacataggta tcagtttttg    1020
gaagaagctt ttcaaaatca gaagggtgca attgagaatc tactggcgaa acttcttgag    1080
aagaagaatt atgttcattt tgcagctact caggtgcaga ataggataaa agaagtaaat    1140
gagactaaca aacgagtaga acaggaaatt aaagtggcca ttttcaccct tatcaatgaa    1200
attaataaga aggaaaatc tctcttacaa cagctagaga atgttacaaa ggaaagacag    1260
atgaagttac tacagcagca gaatgacatc acaggccttt cccggcaggt gaagcatgtt    1320
atgaacttca caaattgggc aattgcaagt ggcagcagca cagcactact atacagcaag    1380
cgactgatta cttccagtt gcgtcatatt ttgaaagcac ggtgtgatcc tgtccctgct    1440
gctaatggag caatacgttt ccattgtgat cccaccttct gggcaaagaa tgtagtcaat    1500
ttaggtaatc tagtaataga gagtaaacca gctcctggtt atactcctaa tgttgtagtt    1560
gggcaagttc ctccagggac aaaccacatt agtaaaaccc ctggacagat taacttagca    1620
cagcttcgac tccagcacat gcaacaacaa gtatatgcac agaaacatca gcagttgcaa    1680
cagatgagga tgcagcaacc accagcacct gtaccaacta caacaacaac aacacaacag    1740
catcctagac aagcagccccc tcagatgtta caacaacagc ctcctcgatt gatcagtgtg    1800
caaacaatgc aaagaggcaa catgaactgt ggagcttttc aagcccatca gatgagactg    1860
gctcagaatg ctgccagaat accagggata cccaggcaca gcggccctca atattccatg    1920
atgcagccac acctccaaag acaacactca aacccagggc atgctggacc ctttcccgta    1980
gtatcggtac acaacaccac aatcaaccca acgagcccta ctacagcaac tatggcaaat    2040
gcaaaccgag gtcccaccag cccatctgtt acagcaatag agctaatccc ctcagttacc    2100
aatccagaaa accttccatc gctgccagat attccaccca tacagttgga agatgctggc    2160
tcaagtagtt tagataatct actaagtaga tacatctcag gcagtcacct accccccacag    2220 cctacaagca ccatgaatcc ttctccaggt ccctctgccc tttctccggg atcatcaggt    2280
ttatccaatt ctcacacacc tgtgagaccc ccaagtactt ctagtactgg cagtcgaggc    2340
agctgtgggt catcaggaag aactgctgag aagacaagtc ttagtttcaa atctgatcag    2400
gtgaaggtca agcaagaacc tgggactgaa atgaaatat gtagcttttc aggaggtgta    2460
aaacaagaaa aaacagagga tggcaggagg agtgcttgca tgttgagcag tcctgagagt    2520
agcttgacac cacctctctc aaccaacctg catctagaaa gtgaattgga tgcattggca    2580
agcctggaaa accatgtgaa aattgaacct gcagatatga atgaaagctg caaacagtca    2640
gggctcagca gccttgttaa tggaaagtcc ccaattcgaa gcctcatgca caggtcggca    2700
aggattggag gagatggcaa caataaagat gatgacccaa atgaagactg gtgtgctgtc    2760
tgccaaaacg gaggagatct cttgtgctgc gaaaaatgtc caaaggtctt tcatctaact    2820
tgtcatgttc caacactact tagctttcca agtgggact ggatatgcac atttttgtaga    2880 gatattggaa agccagaagt tgaatatgat tgtgataatt tgcaacatag taagaagggg    2940
aaaactgcgc aggggttaag ccccgtggac caaaggaaat gtgaacgtct tctgctttac    3000
ctctattgcc atgaattaag tattgaattc caggagcctg ttcctgcttc gataccaaac    3060
tactataaaa ttataaagaa accaatggat ttatccaccg tgaaaaagaa gcttcagaaa    3120
aaacattccc aacactacca aatcccggat gactttgtgg ccgatgtccg tttgatcttc    3180
aagaactgtg aaaggtttaa tgaagctgat tcagaagtag ctcaggcagg gaaagcagtt    3240
gcattgtact ttgaagataa actcacagag atctactcag acaggacctt cgcaccttttg    3300 ccagagtttg agcaggaaga ggatgatggt gaggtaactg aggactctga tgaagacttt    3360
```

```
atacagcccc gcagaaaacg cctaaagtca gatgagagac cagtacatat aaagtaaaat    3420
gacatggatt taaatcaatt gtttaaaaaa aaaaaaacga aaaaaaaaaa aaaaacacaa    3480
aaaacccaga aaacttttaa gtgttgctgg aatatcctgc ctacagtggg cacctccttg    3540
aagaagctga tagcttttac acagtattag attgaaataa tggacagaaa cacattcttg    3600
tcaagaaagg gggagagaag tctgtttgca agtttcaaag caaaaagcaa aagtgaaatg    3660
atttgaggat ttctgttcta atggagatga ttctctgatt gttagaaatg gcaaatattg    3720
atgattgtgt gctattgatt ggtgcaggat acttggtata cgagtaaata cttgagactc    3780
gtgtcacttg ataaattttc ttttttggact aggtcgcaca gttattaaaa caacttttaa    3840
ccctccccct tcacacacat acatatcagg ttgttttcta gttaaaaacc caagtagctc    3900
agattctact ttaatgtcag tgcagatttg cattgaatca tgccattatg ttttttctca    3960
tttttatgct gttgggtctt agtttttaaa ttgatataaa gaactcagca atggttttat    4020
tttctactca tacttagggt ttaggaaaca ctaccactag ttatcattta atcaacttca    4080
atggtctact gaaacaaaaa tggtaacttt tcattagtgg attatttaga gttatagtag    4140
ttgtttccag aaaacacttc ctcacaattg tacttcccaa tcaaatcatg tgatcataca    4200
gttattccca tgaaaggcag aatgtttgtt tcaaaattaa tctagttttc tgtacattta    4260
aatttgagaa ggtgacaact ggctcttttc cagtcttcct tcatgtcagt tttctgatag    4320
accactattg gcaaacagta tctgtcaact accaaatgtg taaaattttc tgtatttcac    4380
tttgtcttat ttgtaaatag tgaactaaaa cttttggcag atcagcaaca tttgctgagc    4440
ctgtttttta agctaatgtg tattcttact aatgttccta tcaagaatgg atttgtaata    4500
tatgctgtct atttctaatg ttcacattca tattttgagg ttctatctta ttttaataga    4560
gaacagactt ctcaaaaaat cttcagaagc agcttattat tgaaatatcg aaatattgaa    4620
ataaacccgg tgggggttaga ttactcatct gtccaccaag tgggacattt gcatggactg    4680
ggggcttaaa ggacttagaa gagacctgta agtaaatcct gaaaatgagc caatccccac    4740
ttgaatggtt actggagtaa acccacccttt accaccccaa ttacagcacc cgaggccgat    4800
aaaccaactt ggctctggtt cattttctct ttcttcattt gtgatgctca gattcaaaat    4860
gtgtgttcta cactgttaca ggcttctctt ttgtttgatt aaagatttta gtcctacttt    4920
tgtatggaca cattagaata ttcagagacc aaaatagaag aatttgctgt tagatatttt    4980
tcagaagtca gcagatttgt ggcaaatcat ttatttgcct ttttaaaaat tcatttaagc    5040
agttcagaga gtagactact cagaaaatta tttcacgtaa ttgtctaaga ggtcaatatt    5100
ttttaatgca tattgaatca aataaagtgc tctaaagaaa ttattataca aattcctttg    5160
ggttgttttt ctttttcttaa caaggggtgg gggtaaacag gaatatgatt caggcttttct    5220 ggttgtgtat ttaaagagta ttgattttat tattactatt gatttacttt attcctggct    5280
tccttttcac ttttctttca attttttaaaa ataatttaa gccgttgaaa atataccaaa    5340
ctgttgaaac attttactca aattttaaat tcctaaaaat gttttttaat aagagggaga    5400
aaattattta aaaatactta tgcctatgcc aatttccctc tttttttcaca aaatccatga    5460 tttcagtttg taagtagaca tatatctaag ggcacatttt tggaaagtga ggaatagcag    5520
cagtataact tcatttttgtc aggcctttga gttctaatat tttgtattgc tcttcaaatg    5580 gatccttttta aaaaaattgt agataatgag tcataaaatag attctgccaa ctgaggggag    5640
aaacatttta agtaaatatt tttcagtatt tggggcctta aaaaataatt gtgtttcctt    5700
```

```
aaaattacat gttagataga gttttaggt ttttttggtt ttaagattgg ttaaagcaat    5760
ttaaaagcca ctttttgtc aacatttaat agcctccact tctgttaaga taatgtatac    5820
tgctgaggaa ttactattaa tagctatcaa cataccacca ttaaattaag gtattcactt    5880 tagattttt attaaagctt ttttcttgca cactgatcgt tgtgtttcta agctgatttt    5940
ttcagctcta atatacctat ggttaaaaag tataaaaact taaattgata tttagatata    6000
tgttttccta ttagtttatg ttttaaaaag acaaaattgt atctgtcagt ccctgaaggc    6060
agtttgtttt tatactctct cacatttgta tttgtttttt aaatggcagt attttagaag    6120
atttggagaa aagtccacat aataatgttt tcttaaaagc ttttaaagtt tttgctgtac    6180
ttcaatttac ttcttccatc agaaaactaa gaacaaagtg ttgctcagtc tgttccgctg    6240
acctaaattt gtgttttcag cacttggctc agccaattca ctgagtgaag gaattgcttt    6300
atgaggcaaa gcatgtgaaa gttctaaagt atggttagat tgtaggtcgt gctctatatg    6360
gaaacatcaa accattacta cagagaaatg ataaggcatt ggatccacta ttgaaattat    6420 tattttttgga tcaacaagtt ggtacttct gacttctgta tcttaacata agggaatttt    6480
aggtaatgct aagtcagttg tctcatttt tgtgataagt tttggaattt ttagttaatt    6540
gaaataaata atgcttttaa atagaagtaa aaggtttata agtgtgcaaa ttgtagattt    6600
atcaattacc tcagcaggta tcctgccatg taattattag tgattagtgt taataagata    6660
atagattcag gtcttccaac tatgcccttg gattgtggcc tactgtatgt tattaaatgg    6720
tctcttacta tccaaaatgg gagtagatgc tgtggccccg tctcccttgg cttttacgtc    6780
ccatatccac ccccattcat gtacaacatg tgaaatataa aaatctcatt tcttgtcaaa    6840
atcagcactg cttatttgca tactcagcat cggatcagtg agtagtttta taaaaaatcc    6900
acgcacccaa ctcccttagt taaaacagat tcttaattca taccatgaat tcttaatttc    6960
tgtaccatct atgttaatga tctgctgaag gtgactcaag attttcaagg tgtaatacag    7020
tttgatcatg taccggacct ggatatttaa ttttttttcc ctcacagtta atctcctcct    7080
tgataaagca ataacactgc tttgagtctg ttgcctaata gcatgtcaga atcctctcct    7140
ggatggtgat tttataggaa agtttgtatg catatcaccc agtctatctt ttaaaaatta    7200
agaaatttaa atgtatgctg gaagtaatga cactatattg tggcattta ttttaaaaat    7260 tggggaaagt tgcatatttt tttaaaagta agtgtttgag taaaaaaatt gaaggtactt    7320
ttttaaggaa aaaaatttat atgccacagt ttacatagac atttcagatt caacacgtac    7380
tcttgaatat aatggtttct tttacttggt caaaatgcat gtatagcatt tctttcatct    7440
tagttccttg tgtttgccta tgtggtcctt tatatatttt ttattgtatc gaagaaacaa    7500
aactatcttc aaaaataagt taatttggat atatttgtca tatcaaacta caaagtgtac    7560
aaagttaagt ttagcccttt tctagaaagt gatctttaaa attaaaaatg ctcctctttt    7620
aaattcacca aatttatgtg tgggaaggca ccaaaatgat tttgtaagtg ccactgcaat    7680
attccctttc aagtgtggcc taaatttcaa tcttaaggat ggaatgcatg tctgctcctt    7740
gttctgaaaa atgtaggcat ctactacatt ttaaaacaca gtgaaacata tacataagcc    7800
tataaaaaaa gatttgtgca atttgaaagc ctgttaattt tttatgtaga catacctaca    7860
cacgaaaggg ttaaattcac agccttacta gttccttgct tccagtattt caattggtct    7920
cctcccctca ttattattat tactactagt actattattt ttgcacatag ttaactgccc    7980
ttcaatatga ttcttaaaaa gtgctgtttc tgtggtatcg tattctctaa ataatcatat    8040
ttaatttttt aaaacaaggt tgcagtttct aattgtttcg ttcctgtgtt tttgctggtg    8100
```

```
tgtaataaaa gcaagttttt tcttttcatg gttatttaat acattagctg cctgtaaata    8160
attcttgtta taatgctctg gaatgtgttg tagaagttgt attagattag ttttaaaccc    8220
ttgtttgaaa gccacattgt tttggttatt tctattaaat tagaaaattg aaaaagtttt    8280
caaatgaa                                                             8288

<210> SEQ ID NO 45
<211> LENGTH: 1127
<212> TYPE: PRT
<213> ORGANISM: Homo sapiens
<220> FEATURE:
<221> NAME/KEY: misc_feature
<223> OTHER INFORMATION: TRIM33 isoform alpha (NP_056990.3)

<400> SEQUENCE: 45
```

Met Ala Glu Asn Lys Gly Gly Gly Glu Ala Glu Ser Gly Gly Gly Gly
1               5                   10                  15

Ser Gly Ser Ala Pro Val Thr Ala Gly Ala Ala Gly Pro Ala Ala Gln
            20                  25                  30

Glu Ala Glu Pro Pro Leu Thr Ala Val Leu Val Glu Glu Glu Glu Glu
        35                  40                  45

Glu Gly Gly Arg Ala Gly Ala Glu Gly Gly Ala Ala Gly Pro Asp Asp
    50                  55                  60

Gly Gly Val Ala Ala Ala Ser Ser Gly Ser Ala Gln Ala Ala Ser Ser
65                  70                  75                  80

Pro Ala Ala Ser Val Gly Thr Gly Val Ala Gly Gly Ala Val Ser Thr
                85                  90                  95

Pro Ala Pro Ala Pro Ala Ser Ala Pro Ala Pro Gly Pro Ser Ala Gly
            100                 105                 110

Pro Pro Pro Gly Pro Pro Ala Ser Leu Leu Asp Thr Cys Ala Val Cys
        115                 120                 125

Gln Gln Ser Leu Gln Ser Arg Arg Glu Ala Glu Pro Lys Leu Leu Pro
    130                 135                 140

Cys Leu His Ser Phe Cys Leu Arg Cys Leu Pro Glu Pro Glu Arg Gln
145                 150                 155                 160

Leu Ser Val Pro Ile Pro Gly Gly Ser Asn Gly Asp Ile Gln Gln Val
                165                 170                 175

Gly Val Ile Arg Cys Pro Val Cys Arg Gln Glu Cys Arg Gln Ile Asp
            180                 185                 190

Leu Val Asp Asn Tyr Phe Val Lys Asp Thr Ser Glu Ala Pro Ser Ser
        195                 200                 205

Ser Asp Glu Lys Ser Glu Gln Val Cys Thr Ser Cys Glu Asp Asn Ala
    210                 215                 220

Ser Ala Val Gly Phe Cys Val Glu Cys Gly Glu Trp Leu Cys Lys Thr
225                 230                 235                 240

Cys Ile Glu Ala His Gln Arg Val Lys Phe Thr Lys Asp His Leu Ile
                245                 250                 255

Arg Lys Lys Glu Asp Val Ser Glu Ser Val Gly Ala Ser Gly Gln Arg
            260                 265                 270

Pro Val Phe Cys Pro Val His Lys Gln Glu Gln Leu Lys Leu Phe Cys
        275                 280                 285

Glu Thr Cys Asp Arg Leu Thr Cys Arg Asp Cys Gln Leu Leu Glu His
    290                 295                 300

Lys Glu His Arg Tyr Gln Phe Leu Glu Glu Ala Phe Gln Asn Gln Lys
305                 310                 315                 320

-continued

```
Gly Ala Ile Glu Asn Leu Leu Ala Lys Leu Leu Glu Lys Lys Asn Tyr
                325                 330                 335

Val His Phe Ala Ala Thr Gln Val Gln Asn Arg Ile Lys Glu Val Asn
                340                 345                 350

Glu Thr Asn Lys Arg Val Glu Gln Glu Ile Lys Val Ala Ile Phe Thr
                355                 360                 365

Leu Ile Asn Glu Ile Asn Lys Lys Gly Lys Ser Leu Leu Gln Gln Leu
            370                 375                 380

Glu Asn Val Thr Lys Glu Arg Gln Met Lys Leu Leu Gln Gln Gln Asn
385                 390                 395                 400

Asp Ile Thr Gly Leu Ser Arg Gln Val Lys His Val Met Asn Phe Thr
                405                 410                 415

Asn Trp Ala Ile Ala Ser Gly Ser Ser Thr Ala Leu Leu Tyr Ser Lys
                420                 425                 430

Arg Leu Ile Thr Phe Gln Leu Arg His Ile Leu Lys Ala Arg Cys Asp
            435                 440                 445

Pro Val Pro Ala Ala Asn Gly Ala Ile Arg Phe His Cys Asp Pro Thr
            450                 455                 460

Phe Trp Ala Lys Asn Val Val Asn Leu Gly Asn Leu Val Ile Glu Ser
465                 470                 475                 480

Lys Pro Ala Pro Gly Tyr Thr Pro Asn Val Val Gly Gln Val Pro
                485                 490                 495

Pro Gly Thr Asn His Ile Ser Lys Thr Pro Gly Gln Ile Asn Leu Ala
                500                 505                 510

Gln Leu Arg Leu Gln His Met Gln Gln Val Tyr Ala Gln Lys His
            515                 520                 525

Gln Gln Leu Gln Gln Met Arg Met Gln Gln Pro Pro Ala Pro Val Pro
            530                 535                 540

Thr Thr Thr Thr Thr Thr Gln Gln His Pro Arg Gln Ala Ala Pro Gln
545                 550                 555                 560

Met Leu Gln Gln Gln Pro Pro Arg Leu Ile Ser Val Gln Thr Met Gln
                565                 570                 575

Arg Gly Asn Met Asn Cys Gly Ala Phe Gln Ala His Gln Met Arg Leu
                580                 585                 590

Ala Gln Asn Ala Ala Arg Ile Pro Gly Ile Pro Arg His Ser Gly Pro
            595                 600                 605

Gln Tyr Ser Met Met Gln Pro His Leu Gln Arg Gln His Ser Asn Pro
            610                 615                 620

Gly His Ala Gly Pro Phe Pro Val Val Ser Val His Asn Thr Thr Ile
625                 630                 635                 640

Asn Pro Thr Ser Pro Thr Thr Ala Thr Met Ala Asn Ala Asn Arg Gly
                645                 650                 655

Pro Thr Ser Pro Ser Val Thr Ala Ile Glu Leu Ile Pro Ser Val Thr
                660                 665                 670

Asn Pro Glu Asn Leu Pro Ser Leu Pro Asp Ile Pro Pro Ile Gln Leu
            675                 680                 685

Glu Asp Ala Gly Ser Ser Leu Asp Asn Leu Leu Ser Arg Tyr Ile
            690                 695                 700

Ser Gly Ser His Leu Pro Pro Gln Pro Thr Ser Thr Met Asn Pro Ser
705                 710                 715                 720

Pro Gly Pro Ser Ala Leu Ser Pro Gly Ser Gly Leu Ser Asn Ser
                725                 730                 735
```

```
His Thr Pro Val Arg Pro Pro Ser Thr Ser Thr Gly Ser Arg Gly
                740                 745                 750

Ser Cys Gly Ser Ser Gly Arg Thr Ala Glu Lys Thr Ser Leu Ser Phe
        755                 760                 765

Lys Ser Asp Gln Val Lys Val Lys Gln Glu Pro Gly Thr Glu Asp Glu
        770                 775                 780

Ile Cys Ser Phe Ser Gly Gly Val Lys Gln Glu Lys Thr Glu Asp Gly
785                 790                 795                 800

Arg Arg Ser Ala Cys Met Leu Ser Ser Pro Glu Ser Ser Leu Thr Pro
            805                 810                 815

Pro Leu Ser Thr Asn Leu His Leu Glu Ser Glu Leu Asp Ala Leu Ala
                820                 825                 830

Ser Leu Glu Asn His Val Lys Ile Glu Pro Ala Asp Met Asn Glu Ser
                835                 840                 845

Cys Lys Gln Ser Gly Leu Ser Ser Leu Val Asn Gly Lys Ser Pro Ile
        850                 855                 860

Arg Ser Leu Met His Arg Ser Ala Arg Ile Gly Gly Asp Gly Asn Asn
865                 870                 875                 880

Lys Asp Asp Asp Pro Asn Glu Asp Trp Cys Ala Val Cys Gln Asn Gly
                    885                 890                 895

Gly Asp Leu Leu Cys Cys Glu Lys Cys Pro Lys Val Phe His Leu Thr
            900                 905                 910

Cys His Val Pro Thr Leu Leu Ser Phe Pro Ser Gly Asp Trp Ile Cys
            915                 920                 925

Thr Phe Cys Arg Asp Ile Gly Lys Pro Glu Val Glu Tyr Asp Cys Asp
930                 935                 940

Asn Leu Gln His Ser Lys Lys Gly Lys Thr Ala Gln Gly Leu Ser Pro
945                 950                 955                 960

Val Asp Gln Arg Lys Cys Glu Arg Leu Leu Leu Tyr Leu Tyr Cys His
                965                 970                 975

Glu Leu Ser Ile Glu Phe Gln Glu Pro Val Pro Ala Ser Ile Pro Asn
            980                 985                 990

Tyr Tyr Lys Ile Ile Lys Lys Pro Met Asp Leu Ser Thr Val Lys Lys
        995                 1000                1005

Lys Leu Gln Lys Lys His Ser Gln His Tyr Gln Ile Pro Asp Asp
    1010                1015                1020

Phe Val Ala Asp Val Arg Leu Ile Phe Lys Asn Cys Glu Arg Phe
    1025                1030                1035

Asn Glu Met Met Lys Val Val Gln Val Tyr Ala Asp Thr Gln Glu
    1040                1045                1050

Ile Asn Leu Lys Ala Asp Ser Glu Val Ala Gln Ala Gly Lys Ala
    1055                1060                1065

Val Ala Leu Tyr Phe Glu Asp Lys Leu Thr Glu Ile Tyr Ser Asp
    1070                1075                1080

Arg Thr Phe Ala Pro Leu Pro Glu Phe Glu Gln Glu Glu Asp Asp
    1085                1090                1095

Gly Glu Val Thr Glu Asp Ser Asp Glu Asp Phe Ile Gln Pro Arg
    1100                1105                1110

Arg Lys Arg Leu Lys Ser Asp Glu Arg Pro Val His Ile Lys
    1115                1120                1125

<210> SEQ ID NO 46
<211> LENGTH: 1110
<212> TYPE: PRT
```

<213> ORGANISM: Homo sapiens
<220> FEATURE:
<221> NAME/KEY: misc_feature
<223> OTHER INFORMATION: TRIM33 isoform beta (NP_148980.2)

<400> SEQUENCE: 46

```
Met Ala Glu Asn Lys Gly Gly Gly Glu Ala Ser Gly Gly Gly Gly
1               5                   10                  15

Ser Gly Ser Ala Pro Val Thr Ala Gly Ala Ala Gly Pro Ala Ala Gln
            20                  25                  30

Glu Ala Glu Pro Pro Leu Thr Ala Val Leu Val Glu Glu Glu Glu
            35                  40                  45

Glu Gly Gly Arg Ala Gly Ala Glu Gly Gly Ala Ala Gly Pro Asp Asp
    50                  55                  60

Gly Gly Val Ala Ala Ala Ser Ser Gly Ser Ala Gln Ala Ala Ser Ser
65                  70                  75                  80

Pro Ala Ala Ser Val Gly Thr Gly Val Ala Gly Gly Ala Val Ser Thr
                85                  90                  95

Pro Ala Pro Ala Pro Ala Ser Ala Pro Ala Pro Gly Pro Ser Ala Gly
                100                 105                 110

Pro Pro Pro Gly Pro Pro Ala Ser Leu Leu Asp Thr Cys Ala Val Cys
                115                 120                 125

Gln Gln Ser Leu Gln Ser Arg Arg Glu Ala Glu Pro Lys Leu Leu Pro
            130                 135                 140

Cys Leu His Ser Phe Cys Leu Arg Cys Leu Pro Glu Pro Glu Arg Gln
145                 150                 155                 160

Leu Ser Val Pro Ile Pro Gly Gly Ser Asn Gly Asp Ile Gln Gln Val
                165                 170                 175

Gly Val Ile Arg Cys Pro Val Cys Arg Gln Glu Cys Arg Gln Ile Asp
                180                 185                 190

Leu Val Asp Asn Tyr Phe Val Lys Asp Thr Ser Glu Ala Pro Ser Ser
                195                 200                 205

Ser Asp Glu Lys Ser Glu Gln Val Cys Thr Ser Cys Glu Asp Asn Ala
    210                 215                 220

Ser Ala Val Gly Phe Cys Val Glu Cys Gly Glu Trp Leu Cys Lys Thr
225                 230                 235                 240

Cys Ile Glu Ala His Gln Arg Val Lys Phe Thr Lys Asp His Leu Ile
                245                 250                 255

Arg Lys Lys Glu Asp Val Ser Glu Ser Val Gly Ala Ser Gly Gln Arg
                260                 265                 270

Pro Val Phe Cys Pro Val His Lys Gln Glu Gln Leu Lys Leu Phe Cys
            275                 280                 285

Glu Thr Cys Asp Arg Leu Thr Cys Arg Asp Cys Gln Leu Leu Glu His
    290                 295                 300

Lys Glu His Arg Tyr Gln Phe Leu Glu Glu Ala Phe Gln Asn Gln Lys
305                 310                 315                 320

Gly Ala Ile Glu Asn Leu Leu Ala Lys Leu Leu Glu Lys Lys Asn Tyr
                325                 330                 335

Val His Phe Ala Ala Thr Gln Val Gln Asn Arg Ile Lys Glu Val Asn
                340                 345                 350

Glu Thr Asn Lys Arg Val Glu Gln Glu Ile Lys Val Ala Ile Phe Thr
            355                 360                 365

Leu Ile Asn Glu Ile Asn Lys Lys Gly Lys Ser Leu Leu Gln Gln Leu
    370                 375                 380
```

```
Glu Asn Val Thr Lys Glu Arg Gln Met Lys Leu Gln Gln Gln Asn
385                 390                 395                 400

Asp Ile Thr Gly Leu Ser Arg Gln Val Lys His Val Met Asn Phe Thr
            405                 410                 415

Asn Trp Ala Ile Ala Ser Gly Ser Thr Ala Leu Leu Tyr Ser Lys
        420                 425                 430

Arg Leu Ile Thr Phe Gln Leu Arg His Ile Leu Lys Ala Arg Cys Asp
            435                 440                 445

Pro Val Pro Ala Ala Asn Gly Ala Ile Arg Phe His Cys Asp Pro Thr
    450                 455                 460

Phe Trp Ala Lys Asn Val Val Asn Leu Gly Asn Leu Val Ile Glu Ser
465                 470                 475                 480

Lys Pro Ala Pro Gly Tyr Thr Pro Asn Val Val Gly Gln Val Pro
            485                 490                 495

Pro Gly Thr Asn His Ile Ser Lys Thr Pro Gly Gln Ile Asn Leu Ala
            500                 505                 510

Gln Leu Arg Leu Gln His Met Gln Gln Val Tyr Ala Gln Lys His
    515                 520                 525

Gln Gln Leu Gln Gln Met Arg Met Gln Gln Pro Pro Ala Pro Val Pro
    530                 535                 540

Thr Thr Thr Thr Thr Thr Gln Gln His Pro Arg Gln Ala Ala Pro Gln
545                 550                 555                 560

Met Leu Gln Gln Gln Pro Pro Arg Leu Ile Ser Val Gln Thr Met Gln
                565                 570                 575

Arg Gly Asn Met Asn Cys Gly Ala Phe Gln Ala His Gln Met Arg Leu
            580                 585                 590

Ala Gln Asn Ala Ala Arg Ile Pro Gly Ile Pro Arg His Ser Gly Pro
            595                 600                 605

Gln Tyr Ser Met Met Gln Pro His Leu Gln Arg Gln His Ser Asn Pro
    610                 615                 620

Gly His Ala Gly Pro Phe Pro Val Val Ser Val His Asn Thr Thr Ile
625                 630                 635                 640

Asn Pro Thr Ser Pro Thr Thr Ala Thr Met Ala Asn Ala Asn Arg Gly
            645                 650                 655

Pro Thr Ser Pro Ser Val Thr Ala Ile Glu Leu Ile Pro Ser Val Thr
            660                 665                 670

Asn Pro Glu Asn Leu Pro Ser Leu Pro Asp Ile Pro Pro Ile Gln Leu
            675                 680                 685

Glu Asp Ala Gly Ser Ser Leu Asp Asn Leu Leu Ser Arg Tyr Ile
    690                 695                 700

Ser Gly Ser His Leu Pro Pro Gln Pro Thr Ser Thr Met Asn Pro Ser
705                 710                 715                 720

Pro Gly Pro Ser Ala Leu Ser Pro Gly Ser Ser Gly Leu Ser Asn Ser
            725                 730                 735

His Thr Pro Val Arg Pro Pro Ser Thr Ser Ser Thr Gly Ser Arg Gly
            740                 745                 750

Ser Cys Gly Ser Ser Gly Arg Thr Ala Glu Lys Thr Ser Leu Ser Phe
    755                 760                 765

Lys Ser Asp Gln Val Lys Val Lys Gln Glu Pro Gly Thr Glu Asp Glu
    770                 775                 780

Ile Cys Ser Phe Ser Gly Gly Val Lys Gln Glu Lys Thr Glu Asp Gly
785                 790                 795                 800

Arg Arg Ser Ala Cys Met Leu Ser Ser Pro Glu Ser Ser Leu Thr Pro
```

-continued

```
                805                 810                 815
Pro Leu Ser Thr Asn Leu His Leu Glu Ser Glu Leu Asp Ala Leu Ala
            820                 825                 830

Ser Leu Glu Asn His Val Lys Ile Glu Pro Ala Asp Met Asn Glu Ser
            835                 840                 845

Cys Lys Gln Ser Gly Leu Ser Ser Leu Val Asn Gly Lys Ser Pro Ile
            850                 855                 860

Arg Ser Leu Met His Arg Ser Ala Arg Ile Gly Gly Asp Gly Asn Asn
865                 870                 875                 880

Lys Asp Asp Pro Asn Glu Asp Trp Cys Ala Val Cys Gln Asn Gly
                885                 890                 895

Gly Asp Leu Leu Cys Cys Glu Lys Cys Pro Lys Val Phe His Leu Thr
            900                 905                 910

Cys His Val Pro Thr Leu Leu Ser Phe Pro Ser Gly Asp Trp Ile Cys
            915                 920                 925

Thr Phe Cys Arg Asp Ile Gly Lys Pro Glu Val Glu Tyr Asp Cys Asp
930                 935                 940

Asn Leu Gln His Ser Lys Lys Gly Lys Thr Ala Gln Gly Leu Ser Pro
945                 950                 955                 960

Val Asp Gln Arg Lys Cys Glu Arg Leu Leu Leu Tyr Leu Tyr Cys His
                965                 970                 975

Glu Leu Ser Ile Glu Phe Gln Gly Pro Val Pro Ala Ser Ile Pro Asn
            980                 985                 990

Tyr Tyr Lys Ile Ile Lys Lys Pro Met Asp Leu Ser Thr Val Lys Lys
            995                 1000                1005

Lys Leu Gln Lys Lys His Ser Gln His Tyr Gln Ile Pro Asp Asp
    1010                1015                1020

Phe Val Ala Asp Val Arg Leu Ile Phe Lys Asn Cys Glu Arg Phe
    1025                1030                1035

Asn Glu Ala Asp Ser Glu Val Ala Gln Ala Gly Lys Ala Val Ala
    1040                1045                1050

Leu Tyr Phe Glu Asp Lys Leu Thr Glu Ile Tyr Ser Asp Arg Thr
    1055                1060                1065

Phe Ala Pro Leu Pro Glu Phe Glu Gln Glu Glu Asp Asp Gly Glu
    1070                1075                1080

Val Thr Glu Asp Ser Asp Glu Asp Phe Ile Gln Pro Arg Arg Lys
    1085                1090                1095

Arg Leu Lys Ser Asp Glu Arg Pro Val His Ile Lys
    1100                1105                1110
```

RET INHIBITOR

CROSS-REFERENCE TO RELATED APPLICATIONS

This application is a National Stage application of PCT/JP2013/075621, filed Sep. 24, 2013, which claims priority from Japanese application JP 2012-211040, filed Sep. 25, 2012.

TECHNICAL FIELD

The present invention relates to a RET inhibitor, an inhibitor of RET tyrosine kinase, a prophylactic or therapeutic agent for diseases including cancers with a mutation in RET and their metastasis, a method for identifying a target patient, and the like, each of which comprises a tetracyclic compound or a salt thereof or a solvate thereof.

BACKGROUND ART

Rearranged during transfection (RET) is a member of the receptor tyrosine kinases belonging to the cadherin superfamily (Surgery, 2007, vol. 141, p. 96-99). RET tyrosine kinase has a transmembrane region in the middle and has a tyrosine kinase region at the carboxyl-terminal side and an extracellular region at the amino-terminal side. It is known that there are three types of proteins due to differences in carboxyl-terminal splicing (TRENDS in Genetics, 2006, vol. 22, p. 627-636: Reference a). RET forms a dimer via a ligand/GFR complex to thereby phosphorylate and activate its own tyrosine (Reference a).

There are reports showing that RET will be involved in oncogenesis upon alterations (point mutation, chromosomal translocation, chromosomal inversion, gene amplification) in RET gene. For example, in thyroid medullary cancer, it is reported that a point mutation in RET gene results in the expression of RET tyrosine kinase with oncogenic ability (Reference a). Moreover, in thyroid papillary cancer, it is reported that RET gene is fused with another gene (e.g., coiled-coil domain containing 6 (CCDC6) gene or nuclear receptor coactivator 4 (NCOA4) gene) by chromosomal inversion or chromosomal translocation to cause the expression of fused tyrosine kinase RET/PTC with oncogenic ability (European Journal of Endocrinology, 2006, vol. 155, p. 645-653). Further, in non-small cell lung cancer, it is reported that RET is fused with kinesin family protein 5B (KIF5B) gene, which is one of the molecules constituting motor protein complexes involved in intracellular microtubule transport, or with CCDC6 gene to cause non-small cell lung cancer by the constitutive tyrosine kinase activity of fused tyrosine kinase KIF5B-RET or CCDC6-RET with oncogenic ability (Nature Medicine. 2012, 18, p. 378-381, WO2012/014795). Moreover, it is reported that the fused tyrosine kinase NCOA4-RET or TRIM33-RET in which RET gene is fused with NCOA4 gene or TRIM33 (tripartite motif-containing 33) gene is present in non-small cell lung cancer patients (J Clin Oncol, 30 (35), Dec. 10, 2012, p. 4352-9; and Cancer Discov 2013 June, 3 (6). June 2013, p. 630-5).

In view of the foregoing, compounds having an inhibitory effect against RET tyrosine kinase are very useful for cancer prevention and treatment.

As inhibitory substances of RET tyrosine kinase, multi-kinase inhibitors such as sorafenib, sunitinib, XL184, vandetanib and ponatinib are reported to have a cell growth inhibitory effect against cell lines expressing KIF5B-RET (Non-patent Document 1: J Clin Oncol 30, 2012, suppl; Abstract no: 7510). Moreover, it is reported that two patients who have RET fusion gene-positive non-small cell lung cancer exhibited partial response to the multi-kinase inhibitor cabozantinib (Non-Patent Document 2: Cancer Discov, 3 (6). June 2013, p. 630-5).

On the other hand, a tetracyclic compound having the following general formula is reported as an inhibitor of anaplastic lymphoma kinase (ALK), a receptor tyrosine kinase belonging to the insulin receptor family (Patent Document 1: WO2010/143664, Patent Document 2: WO2012/023597, Patent Document 3: Japanese Patent Laid-Open No. 2012-126711). This compound is useful as a therapeutic and/or prophylactic agent for tumors with a mutation in ALK gene.

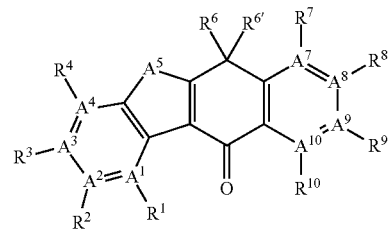

(see the above patent gazette for details of substituents, etc.)

Moreover, it is reported that the following compound with a high concentration (1,000 nM) inhibits many kinases including RET in the Ambit Kinase Screening test (Non-Patent Document 3: Cancer Cell, 19 (5), p. 679-690, 2011, Supplemental Information):

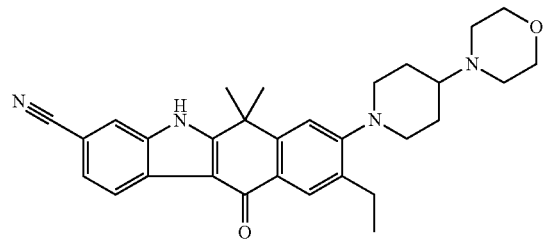 [SMILES: CCc1cc2c(cc1N1CCC(N3CCOCC3)CC1)C(C)(C)c1[nH]c3cc(C#N)ccc3c1C2=O]

However, there is no report showing that the tetracyclic compound found in Patent Document 1 and Non-patent Document 3 is useful as a therapeutic or prophylactic agent for cancers with a mutation in RET.

Moreover, it is reported that the ALK inhibitor crizotinib has no cell growth inhibitory activity against KIF51B-RET-expressing cells (Non-Patent Document 4: Nature Medicine. 2012, 18, p. 378-381).

DOCUMENT LIST

Patent Document

[Patent Document 1] WO2010/143664
[Patent Document 2] WO2012/023597
[Patent Document 3] JP2012-126711A

Non-Patent Document

[Non-Patent Document 1] J Clin Oncol 30, 2012, suppl; Abstract no: 7510

[Non-Patent Document 2] Cancer Discov, 3 (6), June 2013, p. 630-5
[Non-Patent Document 3] Cancer Cell, 19 (5), p. 679-690, 2011, Supplemental Information
[Non-Patent Document 4] Nature Medicine. 2012, 18, p. 378-381

SUMMARY OF THE INVENTION

Problem to be Solved by the Invention

Cancers caused by a mutation in ALK gene and cancers caused by a mutation in RET gene differ in their mechanism of cancer development, the three-dimensional protein structure of their respective kinases, etc., and hence a specific therapeutic and/or prophylactic method is required for each cancer. In lung cancer, it is reported that a group of patients with a mutation in ALK gene does not overlap with a group of patients with a mutation in RET (Nat Med, 2012 Feb. 12, 18 (3), 375-7). These patient groups are clearly distinguished from each other for treatment, and the patients in each group require a specific treatment and/or prevention method.

On the other hand, a compound which inhibits multiple kinases at the same time is known to show a lower therapeutic effect in some cases, because its effective therapeutic range is narrow. Thus, a drug which selectively inhibits a small number of kinases can be regarded as having desired properties in terms of therapeutic effect, and hence there is a demand for such a drug.

Means to Solve the Problem

As a result of extensive and intensive efforts made to solve the above problem, the inventors of the present invention have found, ahead of others, that a tetracyclic compound represented by the following formula (I) or a salt thereof or a solvate thereof has not only inhibitory activity against ALK but also potent inhibitory activity against RET, selectively inhibits RET, is useful for treatment and prevention of diseases including cancers with a mutation in RET and their metastasis, and also has high therapeutic efficacy on these diseases. This finding led to the completion of the present invention.

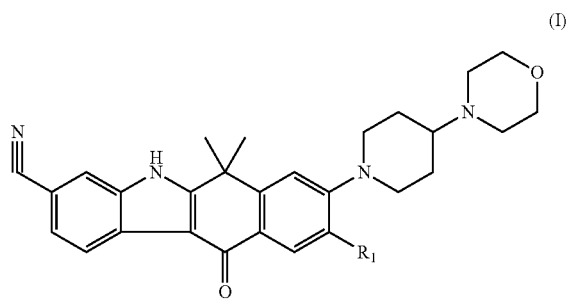

wherein $R_1$ is a $C_{1-6}$ alkyl group.

Namely, according to one aspect of the present invention, the present invention is directed to a therapeutic or prophylactic agent for cancers with a mutation in RET and their metastasis, which comprises a tetracyclic compound shown blow or a salt thereof, etc. According to another aspect, the present invention provides a method for identifying a cancer or a target patient responsive to treatment with the above compound or the like.

More specifically, the present invention is as follows.

[1] A therapeutic and/or prophylactic agent for a tumor with a mutation in RET or for metastasis of the tumor, which comprises a compound represented by formula (I), a salt thereof or a solvate thereof as an active ingredient:

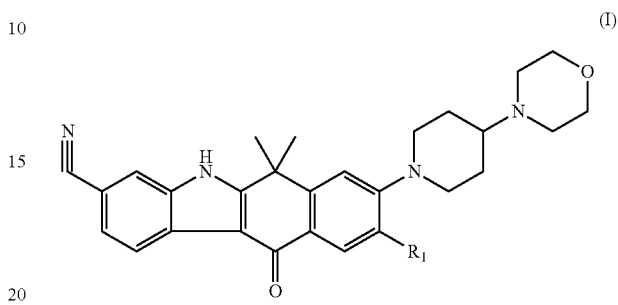

wherein $R_1$ is a $C_{1-6}$ alkyl group.

[2] The therapeutic and/or prophylactic agent according to [1] above, wherein the tumor is selected from the group consisting of acute myelogenous leukemia, chronic myelogenous leukemia, acute lymphocytic leukemia, chronic lymphocytic leukemia, Hodgkin's lymphoma, non-Hodgkin's lymphoma, brain tumor, neuroblastoma, glioma, thyroid cancer, myelodysplastic syndrome, head and neck cancer, esophageal cancer, gastric cancer, colorectal cancer, breast cancer, ovarian cancer, lung cancer, pancreatic cancer, liver cancer, gallbladder cancer, skin cancer, malignant melanoma, kidney cancer, renal pelvic and ureteral cancer, bladder cancer, uterine cancer, testicular cancer, prostate cancer, and tumors metastasized from these tumors.

[3] The therapeutic and/or prophylactic agent according to [1] or [2] above, wherein the tumor is thyroid cancer or lung cancer.

[4] The therapeutic and/or prophylactic agent according to any one of [1] to [3] above, wherein the tumor is thyroid medullary cancer or non-small cell lung cancer.

[4-1] The therapeutic and/or prophylactic agent according to [1] to [4] above, wherein the tumor is a tumor confirmed to show activated RET tyrosine kinase in the tumor tissue.

[4-2] The therapeutic and/or prophylactic agent according to [1] to [4] above, wherein the tumor is a tumor with a mutation which induces activation of RET tyrosine kinase.

[4-2-1] The therapeutic and/or prophylactic agent according to any one of [1] to [4-2] above, wherein the tumor is a tumor with (a) a mutation in the cysteine-rich domain of RET tyrosine kinase, (b) a mutation in the tyrosine kinase domain of RET tyrosine kinase, or (c) a fusion gene of RET and/or a fusion protein of RET.

[4-2-2] The therapeutic and/or prophylactic agent according to any one of [1] to [4-2] above, wherein the tumor is a tumor with a fusion gene of RET and/or a fusion protein of RET.

[4-2-3] The therapeutic and/or prophylactic agent according to any one of [1] to [4-2] and [4-2-2] above, wherein the tumor is a tumor with KIF5B-RET, CCDC6-RET, NCOA4-RET or TRIM33-RET.

[4-3] The therapeutic and/or prophylactic agent according to [1] to [4-2] above, wherein the tumor is a tumor with (a) a mutation in the cysteine-rich domain of RET tyrosine kinase, (b) a mutation in the tyrosine kinase domain of RET tyrosine kinase, or (c) a fusion gene between RET gene and another gene and/or a fusion protein between RET protein and another protein.

[5] The therapeutic and/or prophylactic agent according to any one of [1] to [4-2] above, wherein the tumor is a tumor with a fusion gene between RET gene and another gene and/or a fusion protein between RET protein and another protein.

[5-1] The therapeutic and/or prophylactic agent according to [5] above, wherein the another gene and protein are the gene and protein of KIF5B, CCDC6 or NCOA4 or TRIM33.

[5-2] The therapeutic and/or prophylactic agent according to [5] or [5-1] above, wherein the fusion gene and protein comprises the tyrosine kinase domain of RET gene or protein and the coiled-coil domain of another gene or protein.

[5-2-1] The therapeutic and/or prophylactic agent according to any one of [5] to [5-2] above, wherein a polypeptide constituting the RET protein and a polynucleotide constituting the RET gene are any of the following polypeptides and any of polynucleotides encoding the polypeptides:
(a) a polypeptide consisting of the amino acid sequence shown in SEQ ID NO: 3 or 4;
(b) a polypeptide consisting of an amino acid sequence with substitution, deletion or insertion of one or more amino acids in the polypeptide shown in SEQ ID NO: 3 or 4; and
(c) a polypeptide consisting of an amino acid sequence with 80% or higher identity to the amino acid sequence shown in SEQ ID NO: 3 or 4.

[5-2-2] The therapeutic and/or prophylactic agent according to [5-1] or [5-2-1] above, wherein a polypeptide constituting each of the KIF5B, CCDC6, NCOA4 and TRIM33 proteins and a polynucleotide constituting each of the KIF5B, CCDC6. NCOA4 and TRIM33 genes are any of the following polypeptides and any of polynucleotides encoding the polypeptides:
(1) the polypeptide constituting the KIF5B protein is
(a) a polypeptide consisting of the amino acid sequence shown in SEQ ID NO: 30,
(b) a polypeptide consisting of an amino acid sequence with substitution, deletion or insertion of one or more amino acids in the amino acid sequence shown in SEQ ID NO: 30, or
(c) a polypeptide consisting of an amino acid sequence with 80% or higher identity to the amino acid sequence shown in SEQ ID NO: 30;
(2) the polypeptide constituting the CCDC6 protein is
(a) a polypeptide consisting of the amino acid sequence shown in SEQ ID NO: 31,
(b) a polypeptide consisting of an amino acid sequence with substitution, deletion or insertion of one or more amino acids in the amino acid sequence shown in SEQ ID NO: 31, or
(c) a polypeptide consisting of an amino acid sequence with 80% or higher identity to the amino acid sequence shown in SEQ ID NO: 31;
(3) the polypeptide constituting the NCOA4 protein is
(a) a polypeptide consisting of an amino acid sequence selected from the group consisting of SEQ ID NOs: 38 to 42,
(b) a polypeptide consisting of an amino acid sequence with substitution, deletion or insertion of one or more amino acids in an amino acid sequence selected from the group consisting of SEQ ID NOs: 38 to 42, or
(c) a polypeptide consisting of an amino acid sequence with 80% or higher identity to an amino acid sequence selected from the group consisting of SEQ ID NOs: 38 to 42; and
(4) the polypeptide constituting the TRIM33 protein is
(a) a polypeptide consisting of the amino acid sequence shown in SEQ ID NO: 45 or 46,
(b) a polypeptide consisting of an amino acid sequence with substitution, deletion or insertion of one or more amino acids in the amino acid sequence shown in SEQ ID NO: 45 or 46, or
(c) a polypeptide consisting of amino acid sequence with 80% or higher identity to the amino acid sequence shown in SEQ ID NO: 45 or 46.

[5-2-3] The therapeutic and/or prophylactic agent according to [4-2-2], [5] or [5-2] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;
(c) a polypeptide comprising an amino acid sequence with 80% or higher identity to an amino acid sequence selected from the group consisting of SEQ ID NOs: 15 to 24;
(d) a polypeptide consisting of the amino acid sequence shown in SEQ ID NO: 27 or 28;
(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and
(f) a polypeptide comprising an amino acid sequence with 80% or higher identity to the amino acid sequence shown in SEQ ID NO: 27 or 28.

[5-2-4] The therapeutic and/or prophylactic agent according to [4-2-2], [5] or [5-2] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;
(c) a polypeptide which comprises an amino acid sequence with 90% or higher identity to an amino acid sequence selected from the group consisting of SEQ ID NOs: 15 to 24 and which has tyrosine kinase activity;
(d) a polypeptide consisting of the amino acid sequence shown in SEQ ID NO: 27 or 28;
(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SEQ ID NO: 27 or 28 and which has tyrosine kinase activity; and
(f) a polypeptide which comprises an amino acid sequence with 90% or higher identity to the amino acid sequence shown in SEQ ID NO: 27 or 28 and which has tyrosine kinase activity.

[5-3] The therapeutic and/or prophylactic agent according to [5-2] above, wherein the fusion gene is any of (a) to (d) shown below:

(a) a fusion gene which comprises a polynucleotide having a nucleotide sequence selected from the group consisting of SEQ ID NOs: 5 to 14;

(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;

(c) a fusion gene which comprises a polynucleotide encoding a polypeptide having an amino acid sequence selected from the group consisting of SEQ ID NOs: 15 to 24; or (d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[6] The therapeutic and/or prophylactic agent according to any one of [1] to [4-2] above, wherein the tumor is a tumor with a point mutation in RET gene and/or protein.

[6-1] The therapeutic and/or prophylactic agent according to [6] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.

[6-1-1] The therapeutic and/or prophylactic agent according to [6] or [6-1] above, wherein the point mutation is a mutation in the nucleotide 2091G, 2261 G, 2494G, 2562A or 2861T of a polynucleotide having the nucleotide sequence shown in SEQ ID NO: 1.

[6-2] The therapeutic and/or prophylactic agent according to [6] or [6-1] above, wherein the point mutation is a mutation in the nucleotide 2091 G, 2494G, 2600G or 2943T of a polynucleotide having the nucleotide sequence shown in SEQ ID NO: 1.

[6-3] The therapeutic and/or prophylactic agent according to [6] or [6-1] above, wherein the point mutation is 2091G>T, 2261G>A, 2494G>C, 2562A>T, 2600G>A, 2600G>C, 2861T>G or 2943T>C in a polynucleotide having the nucleotide sequence shown in SEQ ID NO: 1.

[6-3-1] The therapeutic and/or prophylactic agent according to [6], [6-1] or [6-3] above, wherein the point mutation is 2091G>T, 2261G>A, 2494G>C, 2562A>T or 2861T>G in a polynucleotide having the nucleotide sequence shown in SEQ ID NO: 1.

[6-4] The therapeutic and/or prophylactic agent according to [6], [6-1], [6-2] or [6-3] above, wherein the point mutation is 2091G>T, 2494G>C, 2600G>A or 2943T>C in a polynucleotide having the nucleotide sequence shown in SEQ ID NO: 1.

[6-5] The therapeutic and/or prophylactic agent according to [6] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.

[6-5-1] The therapeutic and/or prophylactic agent according to [6] or [6-5] above, wherein the point mutation is a mutation in the amino acid C609, C611, C618, C620, C630, C634, G691, E768, Y791, 5891 or A883 of a polypeptide having the amino acid sequence shown in SEQ ID NO: 3.

[6-6] The therapeutic and/or prophylactic agent according to [6] or [6-5] above, wherein the point mutation is a mutation in the amino acid C609, C611, C618, C620, C630, C634, E768, V804, S891, A883 or M918 of a polypeptide having the amino acid sequence shown in SEQ ID NO: 3.

[6-7] The therapeutic and/or prophylactic agent according to [6] or [6-5] above, wherein the point mutation is C634W, C634Y, G691S, E768D, Y791F, V804M, V804L. S891A or M918T in a polypeptide having the amino acid sequence shown in SEQ ID NO: 3.

[6-7-1] The therapeutic and/or prophylactic agent according to [6], [6-5] or [6-7] above, wherein the point mutation is C634W, C634Y, G691S, E768D, Y791F or S891A in a polypeptide having the amino acid sequence shown in SEQ ID NO: 3.

[6-8] The therapeutic and/or prophylactic agent according to [6] or [6-6] above, wherein the point mutation is C634W, C634Y, E768D, V804M or M918T in a polypeptide having the amino acid sequence shown in SEQ ID NO: 3.

[7] A therapeutic and/or prophylactic agent for a tumor used for a patient with a mutation in RET or for metastasis of the tumor, which comprises a compound represented by formula (I), a salt thereof or a solvate thereof as an active ingredient.

[8] The therapeutic and/or prophylactic agent according to [7] above, wherein the tumor is thyroid cancer or lung cancer.

[8-1] The therapeutic and/or prophylactic agent according to [7] or [8] above, wherein the patient is a patient confirmed to show activated RET tyrosine kinase in the tumor tissue.

[8-2] The therapeutic and/or prophylactic agent according to [7] or [8] above, wherein the patient is a patient with a mutation which induces activation of RET tyrosine kinase.

[8-2-1] The therapeutic and/or prophylactic agent according to any one of [7] to [8-2] above, wherein the patient is a patient with (a) a mutation in the cysteine-rich domain of RET tyrosine kinase, (b) a mutation in the tyrosine kinase domain of RET tyrosine kinase, or (c) a fusion gene of RET and/or a fusion protein of RET.

[8-2-2] The therapeutic and/or prophylactic agent according to any one of [7] to [8-2-1] above, wherein the patient is a patient with a fusion gene of RET and/or a fusion protein of RET.

[8-2-3] The therapeutic and/or prophylactic agent according to any one of [7] to [8-2] and [8-2-2] above, wherein the patient is a patient with KIF5B-RET, CCDC6-RET, NCOA4-RET or TRIM33-RET.

[8-3] The therapeutic and/or prophylactic agent according to any one of [7] to [8-2] above, wherein the patient is a patient with (a) a mutation in the cysteine-rich domain of RET tyrosine kinase, (b) a mutation in the tyrosine kinase domain of RET tyrosine kinase, or (c) a fusion gene between RET gene and another gene and/or a fusion protein between RET protein and another protein.

[9] The therapeutic and/or prophylactic agent according to [7] or [8] above, wherein the patient is a patient with a fusion gene between RET gene and another gene and/or a fusion protein between RET protein and another protein.

[9-1] The therapeutic and/or prophylactic agent according to [8-3] or [9] above, wherein the another gene and protein are KIF5B, CCDC6, NCOA4 or TRIM33.

[9-2] The therapeutic and/or prophylactic agent according to [9] or [9-1] above, wherein the fusion gene and fusion protein comprises the tyrosine kinase domain of RET gene or protein and the coiled-coil domain of another gene or protein.

[9-2-1] The therapeutic and/or prophylactic agent according to any one of [9] to [9-2] above, wherein a polypeptide constituting the RET protein and a polynucleotide constituting the RET gene are any of the following polypeptides and any of polynucleotides encoding the polypeptides:

(a) a polypeptide consisting of the amino acid sequence shown in SEQ ID NO: 3 or 4;
(b) a polypeptide consisting of an amino acid sequence with substitution, deletion or insertion of one or more amino acids in the polypeptide shown in SEQ ID NO: 3 or 4: and
(c) a polypeptide consisting of an amino acid sequence with 80% or higher identity to the amino acid sequence shown in SEQ ID NO: 3 or 4.

[9-2-2] The therapeutic and/or prophylactic agent according to [9-1] above, wherein a polypeptide constituting each of the KIF5B, CCDC6, NCOA4 and TRIM33 proteins and a polynucleotide constituting each of the KIF5B, CCDC6, NCOA4 and TRIM33 genes are any of the following polypeptides and any of polynucleotides encoding the polypeptides:

(1) the polypeptide constituting the KIF5B protein is
(a) a polypeptide consisting of the amino acid sequence shown in SEQ ID NO: 30,
(b) a polypeptide consisting of an amino acid sequence with substitution, deletion or insertion of one or more amino acids in the amino acid sequence shown in SEQ ID NO: 30, or
(c) a polypeptide consisting of an amino acid sequence with 80% or higher identity to the amino acid sequence shown in SEQ ID NO: 30;

(2) the polypeptide constituting the CCDC6 protein is
(a) a polypeptide consisting of the amino acid sequence shown in SEQ ID NO: 31,
(b) a polypeptide consisting of an amino acid sequence with substitution, deletion or insertion of one or more amino acids in the amino acid sequence shown in SEQ ID NO: 31, or
(c) a polypeptide consisting of an amino acid sequence with 80% or higher identity to the amino acid sequence shown in SEQ ID NO: 31;

(3) the polypeptide constituting the NCOA4 protein is
(a) a polypeptide consisting of an amino acid sequence selected from the group consisting of SEQ ID NOs: 38 to 42,
(b) a polypeptide consisting of an amino acid sequence with substitution, deletion or insertion of one or more amino acids in an amino acid sequence selected from the group consisting of SEQ ID NOs: 38 to 42, or
(c) a polypeptide consisting of an amino acid sequence with 80% or higher identity to an amino acid sequence selected from the group consisting of SEQ ID NOs: 38 to 42; and (4) the polypeptide constituting the TRIM33 protein is
(a) a polypeptide consisting of the amino acid sequence shown in SEQ ID NO: 45 or 46,
(b) a polypeptide consisting of an amino acid sequence with substitution, deletion or insertion of one or more amino acids in the amino acid sequence shown in SEQ ID NO: 45 or 46, or
(c) a polypeptide consisting of an amino acid sequence with 80% or higher identity to the amino acid sequence shown in SEQ ID NO: 45 or 46.

[9-2-3] The therapeutic and/or prophylactic agent according to [8-2-2] or [9] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24; (c) a polypeptide comprising an amino acid sequence with 80% or higher identity to an amino acid sequence selected from the group consisting of SEQ ID NOs: 15 to 24;
(d) a polypeptide consisting of the amino acid sequence shown in SEQ ID NO: 27 or 28:
(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and
(f) a polypeptide comprising an amino acid sequence with 80% or higher identity to the amino acid sequence shown in SEQ ID NO: 27 or 28.

[9-2-4] The therapeutic and/or prophylactic agent according to [8-2-2] or [9] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;
(c) a polypeptide which comprises an amino acid sequence with 90% or higher identity to an amino acid sequence selected from the group consisting of SEQ ID NOs: 15 to 24 and which has tyrosine kinase activity;
(d) a polypeptide consisting of the amino acid sequence shown in SEQ ID NO: 27 or 28;
(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SEQ ID NO: 27 or 28 and which has tyrosine kinase activity; and
(f) a polypeptide which comprises an amino acid sequence with 90% or higher identity to the amino acid sequence shown in SEQ ID NO: 27 or 28 and which has tyrosine kinase activity.

[9-3] The therapeutic and/or prophylactic agent according to [9] or [9-2] above, wherein the fusion gene is any of (a) to (d) shown below:
(a) a fusion gene which comprises a polynucleotide having a nucleotide sequence selected from the group consisting of SEQ ID NOs: 5 to 14;
(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;
(c) a fusion gene which comprises a polynucleotide encoding a polypeptide having an amino acid sequence selected from the group consisting of SEQ ID NOs: 15 to 24; or
(d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[10] The therapeutic and/or prophylactic agent according to [7] or [8] above, wherein the patient is a patient with a point mutation in RET gene and/or protein.

[10-1] The therapeutic and/or prophylactic agent according to [10] above, wherein the point mutation in RET is a point mutation in the cysteine-rich domain or in the tyrosine kinase domain of RET tyrosine kinase.

[10-2] The therapeutic and/or prophylactic agent according to [10] or [10-1] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.

[10-2-1] The therapeutic and/or prophylactic agent according to any one of [10] to [10-2] above, wherein the point mutation is a mutation in the nucleotide 2091 G, 2261G, 2494G, 2562A or 2861 T of a polynucleotide having the nucleotide sequence shown in SEQ ID NO: 1.

[10-3] The therapeutic and/or prophylactic agent according to any one of [10] to [10-2], wherein the point mutation in RET is a mutation in the nucleotide 2091G, 2494G, 2600G or 2943T of a polynucleotide having the nucleotide sequence shown in SEQ ID NO: 1.

[10-4] The therapeutic and/or prophylactic agent according to any one of [10] to [10-2] above, wherein the point mutation is 2091G>T, 2261G>A, 2494G>C, 2562A>T, 2600G>A, 2600G>C, 2861T>G or 2943T>C in a polynucleotide having the nucleotide sequence shown in SEQ ID NO: 1.

[10-4-1] The therapeutic and/or prophylactic agent according to any one of [10] to [10-2] and [10-4] above, wherein the point mutation is 2091G>T, 2261G>A, 2494G>C, 2562A>T or 2861T>G in a polynucleotide having the nucleotide sequence shown in SEQ ID NO: 1.

[10-5] The therapeutic and/or prophylactic agent according to any one of [10] to [10-2], [10-4] above, wherein the point mutation in RET is 2091G>T, 2494G>C, 2600G>A or 2943T>C in a polynucleotide having the nucleotide sequence shown in SEQ ID NO: 1.

[10-6] The therapeutic and/or prophylactic agent according to [10] or [10-1] above, wherein the point mutation is a mutation in the amino acid C609, C611, C618, C620, C630, C634, G691, E768, Y791, V804, S891. A883 or M918 of a polypeptide having the amino acid sequence shown in SEQ ID NO: 3.

[10-6-1] The therapeutic and/or prophylactic agent according to [10], [10-1] or [10-6] above, wherein the point mutation is a mutation in the amino acid C609, C611, C618, C620, C630, C634, G691, E768, Y791, S891 or A883 of a polypeptide having the amino acid sequence shown in SEQ ID NO: 3.

[10-7] The therapeutic and/or prophylactic agent according to [10], [10-1] or [10-6] above, wherein the point mutation in RET is a mutation in the amino acid C609, C611, C618, C620, C630, C634, E768, V804, S891, A883 or M918 of a polypeptide having the amino acid sequence shown in SEQ ID NO: 3.

[10-8] The therapeutic and/or prophylactic agent according to [10], [10-1] or [10-6] above, wherein the point mutation is C634W, C634Y, G691S. E768D, Y791F, V804M, V804L, S891A or M918T in a polypeptide having the amino acid sequence shown in SEQ ID NO: 3.

[10-8-1] The therapeutic and/or prophylactic agent according to [10], [10-1], [10-6] or [10-8] above, wherein the point mutation is C634W, C634Y, G691S, E768D, Y791F or S891A in a polypeptide having the amino acid sequence shown in SEQ ID NO: 3.

[10-9] The therapeutic and/or prophylactic agent according to any one of [10], [10-1] or [10-6] to [10-8] above, wherein the point mutation in RET is C634Y, E768D, V804M or M918T in a polypeptide having the amino acid sequence shown in SEQ ID NO: 3.

[10-10] The therapeutic and/or prophylactic agent according to any one of [10] to [10-9] above, wherein the patient is a patient detected for the presence of a mutation in RET by Sanger sequencing or FISH method.

[11] The therapeutic and/or prophylactic agent according to any one of [1] to [10-10] above, wherein $R^1$ is ethyl.

[11-1] The therapeutic and/or prophylactic agent according to any one of [1] to [11] above, wherein the compound is a hydrochloride.

[11-2] The therapeutic and/or prophylactic agent according to any one of [1] to [11-S] above, wherein the therapeutic and/or prophylactic agent selectively inhibits RET.

[12] A RET inhibitor, which comprises a compound of formula (I), a salt thereof or a solvate thereof as an active ingredient.

[12-1] Use of a compound of formula (I), a salt thereof or a solvate thereof for inhibition of RET.

[12-2] A method for preventing and/or treating a tumor with a mutation in RET and metastasis of the tumor, which comprises administering a patient with an effective therapeutic amount of a compound represented by formula (I), a salt thereof or a solvate thereof.

[12-3] Use of a compound represented by formula (I), a salt thereof or a solvate thereof for prevention and/or treatment of a tumor with a mutation in RET and metastasis of the tumor.

[12-3-1] The use according to [12-3] above, wherein the mutation in RET is (a) a mutation in the cysteine-rich domain of RET tyrosine kinase, (b) a mutation in the tyrosine kinase domain of RET tyrosine kinase, or (c) the formation of a fusion gene of RET and/or a fusion protein of RET.

[12-3-2] The use according to [12-3] or [12-3-1] above, wherein the mutation in RET results in the formation of a fusion gene of RET and/or a fusion protein of RET.

[12-3-3] The use according to any one of [12] to [12-2-2] above, wherein the mutation in RET results in the formation of KIF5B-RET, CCDC6-RET, NCOA4-RET or TRIM33-RET.

[12-3-4] The use according to any one of [12-3] to [12-3-3] above, wherein the compound of formula (I), the salt thereof or the solvate thereof selectively inhibits RET.

[12-3-5] The use according to any one of [12-3] to [12-3-4] above, wherein $R_1$ is ethyl.

[12-3-6] The use according to any one of [12-3] to [112-3-5] above, wherein the compound is a hydrochloride.

[12-3-7] The use according to any one of [12-3] to [12-3-6] above, wherein the tumor is thyroid cancer or lung cancer.

[13] A method for identifying a subject to be administered with a compound represented by formula (I), a salt thereof or a solvate thereof, which comprises the step of detecting a mutation in RET in a tissue from the subject.

[13-1] The method according to [13] above, wherein the tissue is a tissue confirmed to show activated RET tyrosine kinase.

[13-2] The method according to [13] above, wherein the tissue has a mutation which induces activation of RET tyrosine kinase.

[13-2-1] The method according to any one of [13] to [13-2] above, wherein the mutation in RET is (a) a mutation in the cysteine-rich domain of RET tyrosine kinase, (b) a mutation in the tyrosine kinase domain of RET tyrosine kinase, or (c) the formation of a fusion gene of RET and/or a fusion protein of RET.

[13-2-2] The method according to any one of [13] to [13-2-1] above, wherein the mutation in RET results in the formation of a fusion gene of RET and/or a fusion protein of RET.

[13-2-3] The method according to any one of [13] to [13-2-2] above, wherein the mutation in RET results in the formation of KIF5B-RET, CCDC6-RET, NCOA4-RET or TRIM33-RET.

[13-3] The method according to any one of [13] to [13-2] above, wherein the tissue has (a) a mutation in the cysteine-rich domain of RET tyrosine kinase, (b) a mutation in the tyrosine kinase domain of RET tyrosine kinase, or (c) a fusion gene between RET gene and another gene and/or a fusion protein between RET protein and another protein.

[13-4] The method according to any one of [13] to [13-3] above, wherein the mutation in RET results in the formation of a fusion gene between RET gene and another gene and/or a fusion protein between RET protein and another protein.

[13-5] The method according to [13-4] above, wherein another gene and protein are KIF5B, CCDC6, NCOA4 or TRIM33.

[13-6] The method according to [13-5] above, wherein the fusion gene and fusion protein comprise the tyrosine kinase domain of RET gene or protein and the coiled-coil domain of another gene or protein.

[13-6-1] The method according to any one of [13-4] to [13-6] above, wherein a polypeptide constituting the RET protein and a polynucleotide constituting the RET gene are any of the following polypeptides and any of polynucleotides encoding the polypeptides:
(a) a polypeptide consisting of the amino acid sequence shown in SEQ ID NO: 3 or 4;
(b) a polypeptide consisting of an amino acid sequence with substitution, deletion or insertion of one or more amino acids in the polypeptide shown in SEQ ID NO: 3 or 4; and
(c) a polypeptide consisting of an amino acid sequence with 80% or higher identity to the amino acid sequence shown in SEQ ID NO: 3 or 4.

[13-6-2] The method according to [13-5] above, wherein a polypeptide constituting each of the KIF5B, CCDC6, NCOA4 and TRIM33 proteins and a polynucleotide constituting each of the KIF5B, CCDC6, NCOA4 and TRIM33 genes are any of the following polypeptides and any of polynucleotides encoding the polypeptides:
(1) the polypeptide constituting the KIF5B protein is
(a) a polypeptide consisting of the amino acid sequence shown in SEQ ID NO: 30,
(b) a polypeptide consisting of an amino acid sequence with substitution, deletion or insertion of one or more amino acids in the amino acid sequence shown in SEQ ID NO: 30, or
(c) a polypeptide consisting of an amino acid sequence with 80% or higher identity to the amino acid sequence shown in SEQ ID NO: 30;
(2) the polypeptide constituting the CCDC6 protein is
(a) a polypeptide consisting of the amino acid sequence shown in SEQ ID NO: 31,
(b) a polypeptide consisting of an amino acid sequence with substitution, deletion or insertion of one or more amino acids in the amino acid sequence shown in SEQ ID NO: 31, or
(c) a polypeptide consisting of an amino acid sequence with 80% or higher identity to the amino acid sequence shown in SEQ ID NO: 31;
(3) the polypeptide constituting the NCOA4 protein is
(a) a polypeptide consisting of an amino acid sequence selected from the group consisting of SEQ ID NOs: 38 to 42,
(b) a polypeptide consisting of an amino acid sequence with substitution, deletion or insertion of one or more amino acids in an amino acid sequence selected from the group consisting of SEQ ID NOs: 38 to 42, or
(c) a polypeptide consisting of an amino acid sequence with 80% or higher identity to an amino acid sequence selected from the group consisting of SEQ ID NOs: 38 to 42; and
(4) the polypeptide constituting the TRIM33 protein is
(a) a polypeptide consisting of the amino acid sequence shown in SEQ ID NO: 45 or 46,
(b) a polypeptide consisting of an amino acid sequence with substitution, deletion or insertion of one or more amino acids in the amino acid sequence shown in SEQ ID NO: 45 or 46, or
(c) a polypeptide consisting of an amino acid sequence with 80% or higher identity to the amino acid sequence shown in SEQ ID NO: 45 or 46.

[13-6-3] The method according to [13-2-1], [13-2-2], [13-3] or [13-4] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;
(c) a polypeptide comprising an amino acid sequence with 80% or higher identity to an amino acid sequence selected from the group consisting of SEQ ID NOs: 15 to 24;
(d) a polypeptide consisting of the amino acid sequence shown in SEQ ID NO: 27 or 28;
(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and
(f) a polypeptide comprising an amino acid sequence with 80% or higher identity to the amino acid sequence shown in SEQ ID NO: 27 or 28.

[13-6-4] The method according to [13-2-1], [13-2-2], [13-3], [13-4] or [13-6-3] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;
(c) a polypeptide which comprises an amino acid sequence with 90% or higher identity to an amino acid sequence selected from the group consisting of SEQ ID NOs: 15 to 24 and which has tyrosine kinase activity;
(d) a polypeptide consisting of the amino acid sequence shown in SEQ ID NO: 27 or 28;

(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SEQ ID NO: 27 or 28 and which has tyrosine kinase activity; and (f) a polypeptide which comprises an amino acid sequence with 90% or higher identity to the amino acid sequence shown in SEQ ID NO: 27 or 28 and which has tyrosine kinase activity.

[13-7] The method according to [13-6] above, wherein the fusion gene is any of (a) to (d) shown below:

(a) a fusion gene which comprises a polynucleotide having a nucleotide sequence selected from the group consisting of SEQ ID NOs: 5 to 14;

(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;

(c) a fusion gene which comprises a polynucleotide encoding a polypeptide having an amino acid sequence selected from the group consisting of SEQ ID NOs: 15 to 24; or (d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[13-8] The method according to [13] to [13-2] above, wherein the tissue has a point mutation in RET.

[13-9] The method according to [13-8] above, wherein the tissue has a point mutation in the cysteine-rich domain or in the tyrosine kinase domain of RET tyrosine kinase.

[13-10] The method according to [13-8] or [13-9] above, wherein the point mutation is a mutation in the nucleotide 2091G, 2261G, 2494G, 2562A, 2600G, 2861T or 29431T of a polynucleotide having the nucleotide sequence shown in SEQ ID NO: 1.

[13-10-1] The method according to any one of [13-8] to [13-10] above, wherein the point mutation is a mutation in the nucleotide 2091G, 2261G, 2494G, 2562A or 2861T of a polynucleotide having the nucleotide sequence shown in SEQ ID NO: 1.

[13-11] The method according to any one of [13-8] to [13-10] above, wherein the point mutation is a mutation in the nucleotide 2091 G, 2494G, 2600G or 2943T of a polynucleotide having the nucleotide sequence shown in SEQ ID NO: 1.

[13-12] The method according to any one of [13-8] to [13-10] above, wherein the point mutation is 2091G>T, 2261G>A, 2494G>C, 2562A>T, 2600G>A, 2600G>C, 2861 T>G or 2943T>C in a polynucleotide having the nucleotide sequence shown in SEQ ID NO: 1.

[13-12-1] The method according to any one of [13-8] to [13-10] and [13-12] above, wherein the point mutation is 2091G>T, 2261G>A, 2494G>C, 2562A>T or 2861T>G in a polynucleotide having the nucleotide sequence shown in SEQ ID NO: 1.

[13-13] The method according to any one of [13-8] to [13-12] above, wherein the point mutation is 2091G>T, 2494G>C, 2600G>A or 2943T>C in a polynucleotide having the nucleotide sequence shown in SEQ ID NO: 1.

[13-14] The method according to [13-8] or [13-9] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.

[13-14-1] The method according to [13-8], [13-9] or [13-14] above, wherein the point mutation is a mutation in the amino acid C609, C611, C618, C620, C630, C634, G691, E768, Y791, 5891 or A883 of a polypeptide having the amino acid sequence shown in SEQ ID NO: 3.

[13-15] The method according to [13-8], [13-9] or [13-14] above, wherein the point mutation is a mutation in the amino acid C609, C611, C618, C620, C630, C634, E768, V804, S891, A883 or M918 of a polypeptide having the amino acid sequence shown in SEQ ID NO: 3.

[13-16] The method according to [13-8], [13-9] or [13-14] above, wherein the point mutation is C634W, C634Y, G691S, E768D, Y791F, V804M, V804L, S891A or M918T in a polypeptide having the amino acid sequence shown in SEQ ID NO: 3.

[13-16-1] The method according to [13-8], [13-9] or [13-14] above, wherein the point mutation is C634W, C634Y, G691S, E768D, Y791F or S891A in a polypeptide having the amino acid sequence shown in SEQ ID NO: 3.

[13-17] The method according to any one of [13-8] to [13-16] above, wherein the point mutation in RET is C634Y, E768D, V804M or M918T in a polypeptide having the amino acid sequence shown in SEQ ID NO: 3.

[13-18] The method according to any one of [13] to [13-17] above, wherein the method identifies a subject to be administered with a compound represented by formula (I), a salt thereof or a solvate thereof for treatment and/or prevention of a tumor with a mutation in RET or metastasis of the tumor.

[13-19] The method according to any one of [13] to [13-18] above, wherein the tumor is thyroid cancer or lung cancer.

[13-20] The method according to any one of [13] to [13-19] above, wherein the compound represented by formula (I), the salt thereof or the solvate thereof selectively inhibits RET.

[13-21] The method according to any one of [13] to [13-20] above, wherein $R^1$ is ethyl.

[13-22] The method according to any one of [13] to [13-21] above, wherein the compound of formula (I), the salt thereof or the solvate thereof is hydrochloride of the compound of formula (I).

[14] A prophylactic and/or therapeutic method for a tumor with a mutation in RET and for metastasis of the tumor, which comprises identifying a patient with a mutation in RET and administering the patient with an effective therapeutic amount of a compound represented by formula (I), a salt thereof or a solvate thereof.

[15] A method for identifying or preliminarily identifying a patient sensitive to a compound represented by formula (I), a salt thereof or a solvate thereof, which comprises the steps of:

detecting the presence of a mutation in RET in a sample obtained from the patient; and determining or preliminarily determining that the patient has sensitivity to the compound, the salt thereof or the solvate thereof, on the basis of the presence of a mutation in RET in the sample.

[15-1] The method according to [15] above, further comprising the step of detecting activation of RET tyrosine kinase.

[15-2] The method according to [15] above, wherein the mutation in RET is a mutation which induces activation of RET tyrosine kinase.

[15-2-1] The method according to any one of [15] to [15-2] above, wherein the mutation in RET is (a) a mutation in the cysteine-rich domain of RET tyrosine kinase, (b) a mutation in the tyrosine kinase domain of RET tyrosine kinase, or (c) the formation of a fusion gene of RET and/or a fusion protein of RET.
[15-2-2] The method according to any one of [15] to [15-2-1] above, wherein the mutation in RET results in the formation of a fusion gene of RET and/or a fusion protein of RET.
[15-2-3] The method according to any one of [15] to [15-2-2] above, wherein the mutation in RET results in the formation of KIF5B-RET, CCDC6-RETI, NCOA4-RET or TRIM33-RET.
[15-3] The method according to any one of [15] to [15-2] above, wherein the mutation in RET is (a) a mutation in the cysteine-rich domain of RET tyrosine kinase, (b) a mutation in the tyrosine kinase domain of RET tyrosine kinase, or (c) the formation of a fusion gene between RET gene and another gene and/or a fusion protein between RET protein and another protein.
[15-4] The method according to any one of [15] to [15-3] above, wherein the mutation in RET results in the formation of a fusion gene between RET gene and another gene and/or a fusion protein between RET protein and another protein.
[15-5] The method according to [15-4] above, wherein the other gene and protein are KIF5B, CCDC6, NCOA4 or TRIM33.
[15-6] The method according to [15-4] or [15-5] above, wherein the fusion gene between RET gene and another gene and the fusion protein between RET protein and another protein comprise the tyrosine kinase domain of RET gene or protein and the coiled-coil domain of another gene or protein.
[15-6-1] The method according to any one of [15-4] to [15-6] above, wherein a polypeptide constituting the RET protein and a polynucleotide constituting the RET gene are any of the following polypeptides and any of polynucleotides encoding the polypeptides:
(a) a polypeptide consisting of the amino acid sequence shown in SEQ ID NO: 3 or 4;
(b) a polypeptide consisting of an amino acid sequence with substitution, deletion or insertion of one or more amino acids in the polypeptide shown in SEQ ID NO: 3 or 4; and
(c) a polypeptide consisting of an amino acid sequence with 80% or higher identity to the amino acid sequence shown in SEQ ID NO: 3 or 4.
[15-6-2] The method according to [15-5] above, wherein a polypeptide constituting each of the KIF5B, CCDC6, NCOA4 and TRIM33 proteins and a polynucleotide constituting each of the KIF5B, CCDC6, NCOA4 and TRIM33 genes are any of the following polypeptides and any of polynucleotides encoding the polypeptides:
(1) the polypeptide constituting the KIF5B protein is
(a) a polypeptide consisting of the amino acid sequence shown in SEQ ID NO: 30,
(b) a polypeptide consisting of an amino acid sequence with substitution, deletion or insertion of one or more amino acids in the amino acid sequence shown in SEQ ID NO: 30, or
(c) a polypeptide consisting of an amino acid sequence with 80% or higher identity to the amino acid sequence shown in SEQ ID NO: 30;
(2) the polypeptide constituting the CCDC6 protein is
(a) a polypeptide consisting of the amino acid sequence shown in SEQ ID NO: 31,
(b) a polypeptide consisting of an amino acid sequence with substitution, deletion or insertion of one or more amino acids in the amino acid sequence shown in SEQ ID NO: 31, or
(c) a polypeptide consisting of an amino acid sequence with 80% or higher identity to the amino acid sequence shown in SEQ ID NO: 31;
(3) the polypeptide constituting the NCOA4 protein is
(a) a polypeptide consisting of an amino acid sequence selected from the group consisting of SEQ ID NOs: 38 to 42,
(b) a polypeptide consisting of an amino acid sequence with substitution, deletion or insertion of one or more amino acids in an amino acid sequence selected from the group consisting of SEQ ID NOs: 38 to 42, or
(c) a polypeptide consisting of an amino acid sequence with 80% or higher identity to an amino acid sequence selected from the group consisting of SEQ ID NOs: 38 to 42; and
(4) the polypeptide constituting the TRIM33 protein is
(a) a polypeptide consisting of the amino acid sequence shown in SEQ ID NO: 45 or 46,
(b) a polypeptide consisting of an amino acid sequence with substitution, deletion or insertion of one or more amino acids in the amino acid sequence shown in SEQ ID NO: 45 or 46, or
(c) a polypeptide consisting of an amino acid sequence with 80% or higher identity to the amino acid sequence shown in SEQ ID NO: 45 or 46.
[15-6-3] The method according to [15-2-1], [15-2-2], [15-3] or [15-4] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;
(c) a polypeptide comprising an amino acid sequence with 80% or higher identity to an amino acid sequence selected from the group consisting of SEQ ID NOs: 15 to 24;
(d) a polypeptide consisting of the amino acid sequence shown in SEQ ID NO: 27 or 28;
(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and
(f) a polypeptide comprising an amino acid sequence with 80% or higher identity to the amino acid sequence shown in SEQ ID NO: 27 or 28.
[15-6-4] The method according to [15-2-1], [15-2-2], [15-3] or [15-4] above, wherein a polypeptide constituting the fusion protein and a polynucleotide constituting the fusion gene are any of the following polypeptides (a) to (f) and any of polynucleotides encoding the polypeptides:
(a) a polypeptide consisting of an amino acid sequence selected from the group consisting of SEQ ID NOs: 15 to 24;
(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;

(c) a polypeptide which comprises an amino acid sequence with 90% or higher identity to an amino acid sequence selected from the group consisting of SEQ ID NOs: 15 to 24 and which has tyrosine kinase activity;
(d) a polypeptide consisting of the amino acid sequence shown in SEQ ID NO: 27 or 28;
(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SEQ ID NO: 27 or 28 and which has tyrosine kinase activity; and
(f) a polypeptide which comprises an amino acid sequence with 90% or higher identity to the amino acid sequence shown in SEQ ID NO: 27 or 28 and which has tyrosine kinase activity.

[15-6-5] The method according to [15-3] or [15-4] above, wherein the fusion gene is any of (a) to (d) shown below:
(a) a fusion gene which comprises a polynucleotide having a nucleotide sequence selected from the group consisting of SEQ ID NOs: 5 to 14;
(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;
(c) a fusion gene which comprises a polynucleotide encoding a polypeptide having an amino acid sequence selected from the group consisting of SEQ ID NOs: 15 to 24; or
(d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[15-7] The method according to any one of [15] to [15-2] above, wherein the mutation in RET is a point mutation.
[15-8] The method according to [15-7] above, wherein the point mutation is a point mutation in the cysteine-rich domain or in the tyrosine kinase domain of RET tyrosine kinase.
[15-9] The method according to [15-7] or [15-8] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.
[15-9-1] The method according to any one of [15-7] to [15-9] above, wherein the point mutation is a mutation in the nucleotide 2091G. 2261G, 2494G, 2562A or 286 IT of a polynucleotide having the nucleotide sequence shown in SEQ ID NO: 1.
[15-10] The method according to any one of [15-7] or [15-9] above, wherein the point mutation is a mutation in the nucleotide 2091G, 2494G, 2600G or 2943T of a polynucleotide having the nucleotide sequence shown in SEQ ID NO: 1.
[15-11] The method according to any one of [15-7] to [15-9] above, wherein the point mutation is 2091G>T, 2261 G>A, 2494G>C, 2562A>T, 2600G>A, 2600G>C, 2861T>G or 2943T>C in a polynucleotide having the nucleotide sequence shown in SEQ ID NO: 1.
[15-11-1] The method according to any one of [15-7] to [15-9-1] and [15-1] above, wherein the point mutation is 2091G>T, 2261G>A, 2494G>C, 2562A>T or 2861T>G in a polynucleotide having the nucleotide sequence shown in SEQ ID NO: 1.
[15-12] The method according to any one of [15-7] to [15-11] above, wherein the point mutation is 2091G>T, 2494G>C, 2600G>A or 2493T>C in a polynucleotide having the nucleotide sequence shown in SEQ ID NO: 1.
[15-13] The method according to [15-7] or [15-8] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.
[15-13-1] The method according to [15-7], [15-8] or [15-13] above, wherein the point mutation is a mutation in the amino acid C609, C611, C618, C620, C630, C634, G691, E768, Y791, S891 or A883 of a polypeptide having the amino acid sequence shown in SEQ ID NO: 3.
[15-14] The method according to [15-7], [15-8] or [15-13] above, wherein the point mutation is a mutation in the amino acid C609, C611, C618, C620, C630, C634, E768, V804, S891, A883 or M918 of a polypeptide having the amino acid sequence shown in SEQ ID NO: 3.
[15-15] The method according to [15-7], [15-8] or [15-13] above, wherein the point mutation is C634W, C634Y, G691S, E768D, Y791F, V804M, V804L, S891A or M918T in a polypeptide having the amino acid sequence shown in SEQ ID NO: 3.
[15-15-1] The method according to [15-7], [15-8], [15-13] or [15-15] above, wherein the point mutation is C634W, C634Y, G691S, E768D, Y791F or S891A in a polypeptide having the amino acid sequence shown in SEQ ID NO: 3.
[15-16] The method according to any one of [15-7] to [15-15], wherein the point mutation is C634W, C634Y, E768D, V804M or M918T in a polypeptide having the amino acid sequence shown in SEQ ID NO: 3.
[15-17] The method according to any one of [15] to [15-16] above, wherein the patient is a patient with thyroid cancer or lung cancer.
[15-18] The method according to any one of [15] to [15-17] above, wherein the patient is a patient with thyroid medullary cancer or non-small cell lung cancer.
[15-19] The method according to any one of [15] to [15-18] above, wherein the compound of formula (I), the salt thereof or the solvate thereof selectively inhibits RET.
[15-20] The method according to any one of [15] to [15-18] above, wherein $R^1$ is ethyl.
[15-21] The method according to any one of [15] to [15-19] above, wherein the compound is a hydrochloride.
[16] A method for predicting the sensitivity of a patient to a compound of formula (I), a salt thereof or a solvate thereof, which comprises the steps of;
(1) confirming the presence or absence of a mutation in RET in a sample obtained from the patient; and
(2) determining or preliminarily determining that the patient has sensitivity to the compound of formula (I), the salt thereof or the solvate thereof, provided that the mutation in RET is present.

Effects of the Invention

The therapeutic and/or prophylactic agent of the present invention has a potent inhibitory effect against RET, particularly against RET tyrosine kinase, and is useful as a prophylactic or therapeutic agent (particularly therapeutic agent) for proliferative diseases. Moreover, the active ingredient in the present invention is useful as a prophylactic or therapeutic agent (particularly therapeutic agent) for diseases including various types of cancers, such as leukemia (e.g., acute myelogenous leukemia, chronic myelogenous leukemia, acute lymphocytic leukemia, chronic lymphocytic leukemia), malignant lymphoma (e.g., Hodgkin's lymphoma, non-Hodgkin's lymphoma), brain tumor, neuroblastoma, glioma, thyroid cancer, myelodysplastic syndrome, head and neck cancer, esophageal cancer, gastric cancer, colorectal cancer, breast cancer, ovarian cancer, lung cancer, pancreatic cancer, liver cancer, gallbladder cancer, skin cancer, malignant melanoma, kidney cancer, renal pelvic and ureteral cancer, bladder cancer, uterine cancer, testicular cancer and prostate cancer. The active ingredient in the present invention is further useful as a prophylactic or therapeutic agent (particularly therapeutic agent) for infiltration and metastasis of solid cancers.

The present invention achieves the identification of a cancer or a patient with a mutation in RET and achieves the effective treatment, etc. of such a patient using the compound represented by formula (I) or the like.

BRIEF DESCRIPTION OF THE DRAWING

FIG. 1 shows the antitumor activity of compound 1 using xenograft mouse models having CCDC6-RET fusion gene (Example 6).

MODE FOR CARRYING OUT THE INVENTION

An explanation will be given below of the therapeutic or prophylactic agent of the present invention and preparation procedures thereof.

Definitions

In the context of the present invention, the term "$C_{1-6}$ alkyl group" refers to a monovalent group derived from a linear or branched aliphatic hydrocarbon containing 1 to 6 carbon atoms by removing any one of the hydrogen atoms. More specifically, examples include a methyl group, an ethyl group, an isopropyl group, a butyl group, a n-butyl group, an isobutyl group, a sec-butyl group, a t-butyl group, a pentyl group, an isopentyl group, a 2,3-dimethylpropyl group, a hexyl group, a 2,3-dimethylhexyl group, a 1,1-dimethylpentyl group, a heptyl group and an octyl group. Preferred is a $C_{1-6}$ alkyl group, more preferred is a $C_{1-5}$ alkyl group, even more preferred is a $C_{1-4}$ alkyl group, and still even more preferred is a $C_{1-3}$ alkyl group.

In the context of the present invention, the expression "with a mutation in RET", "a mutation in RET" or "a mutation of RET" is intended to mean that a mutation occurs in RET gene and/or RET protein. In the context of the present invention, the expression "with a mutation in RET", "a mutation in RET" includes a point mutation, a deletion mutation or an insertion mutation in RET gene and/or RET protein, translocation- or inversion-mediated fusion between RET gene and another gene, as well as fusion protein formation between RET protein and another protein. The expression "with a mutation in RET", "a mutation in RET" or "a mutation of RET" further includes amplification of RET gene and/or amplification of RET protein, caused by an increased number of DNA regions on the genome compared to the normal state upon cleavage and rejoining of RET gene, impairment in the repair functions for RET gene, etc.

In the context of the present invention, the term "RET gene" is intended to mean a gene encoding RET (rearranged during transfection) tyrosine kinase. The RET gene of the present invention is intended to mean RET gene of any origin. Specifically, examples include, but are not limited to, a gene having a polynucleotide consisting of the nucleotide sequence shown in SEQ ID NO: 1 or 2, and a polynucleotide encoding a polypeptide consisting of the amino acid sequence shown in SEQ ID NO: 3 or 4.

In the context of the present invention, the term "RET protein" is intended to mean a protein consisting of an amino acid sequence constituting RET tyrosine kinase. The RET protein of the present invention is intended to mean RET protein of any origin. Specifically, examples include, but are not limited to, a protein having a polypeptide consisting of the amino acid sequence shown in SEQ ID NO: 3 or 4. It is known that there are three types of proteins RET9, RET43 and RET51 for RET tyrosine kinase due to differences in carboxyl-terminal splicing (TRENDS in Genetics. 2006, vol. 22, p. 627-636), and polypeptides consisting of amino acids constituting these three types of proteins also fall within "RET protein."

In the present invention, the polypeptide constituting the RET protein and the polynucleotide constituting the RET gene include the following polypeptides and genes encoding the polypeptides:

a polypeptide consisting of an amino acid sequence with substitution, deletion or insertion of one or more (preferably 1 to 10, particularly preferably 1 to 5) amino acids in the polypeptide shown in SEQ ID NO: 3 or 4: and a polypeptide consisting of an amino acid sequence with 80% or higher (preferably 85% or higher, more preferably 90% or higher, further preferably 95% or higher) identity to the amino acid sequence shown in SEQ ID NO: 3 or 4.

In the context of the present invention, the expression "polynucleotide encoding a polypeptide" encompasses every polynucleotide capable of encoding a specific polypeptide and encompasses any of genomic DNA and cDNA. The polynucleotide includes even a degenerate polynucleotide composed of any codon encoding the same amino acid.

In the present invention, the identity of an amino acid sequence can be calculated by: properly aligning at least two sequences to be compared with each other; determining identical amino acid residues between the sequences; determining the number of matching sites; and subsequently dividing the number of the matching sites by the total number of residues in the sequence region to be compared and multiplying the obtained numeric value by 100. For example, the identity of a specific amino acid sequence to the amino acid sequence shown in SEQ ID NO: 3 can be calculated by: determining the number of matching sites between two sequences, i.e., the amino acid sequence shown in SEQ ID NO: 3 and the specific amino acid sequence, by the above method; and subsequently dividing the number of the matching sites by the total number of residues in the amino acid sequence shown in SEQ ID) NO: 3 and multiplying the obtained numeric value by 100.

Alternatively, the identity of an amino acid sequence may be determined by the Karlin-Altschul BLAST algorithm (Proc. Natl. Acad. Sci. USA (1993) 90: 5873-7). On the basis of this algorithm, a program called BLASTN or BLASTX has been developed (Altschul et al., J. Mol. Biol. (1990) 215: 403-10). Each nucleotide sequence can be analyzed by BLASTN on the basis of BLAST using parameters set to, for example, score=100 and wordlength=12. Also, each amino acid sequence can be analyzed by BLASTX on the basis of BLAST using parameters set to, for example, score=50 and wordlength=3. In the case of using BLAST and Gapped BLAST programs, the default parameters of each program are used. Specific approaches of these analysis methods are known in the art (see information provided by the website of BLAST (Basic Local Alignment Search Tool), NCBI (National Center for Biotechnology Information)).

In the context of the present invention, the term "hybridizing" is intended to mean hybridizing to a target DNA or polynucleotide under stringent conditions. The stringent conditions can be determined on the basis of the melting temperature (Tm) of a nucleic acid to form a complex according to a routine method. Specifically, the stringent conditions involve "5×SSPE, 5×Denhardt's solution, 0.5% SDS, 50% formamide, 200 μg/ml salmon sperm DNA, 42° C. overnight" as conditions for hybridization and "0.5×SSC, 0.1% SDS, 42° C." as conditions for washing. More stringent conditions involve "5×SSPE, 5×Denhardt's solution, 0.5% SDS, 50% formamide, 200 μg/ml salmon sperm DNA, 42° C. overnight" as conditions for hybridization and "0.2× SSC, 0.1% SDS, 65° C." as conditions for washing.

The expression "with a mutation in RET", "a mutation in RET" or "a mutation of RET" further includes a state where a mutation which induces activation of RET tyrosine kinase or a mutation which activates RET tyrosine kinase and induces oncogenesis (e.g., thyroid cancer, lung cancer) has occurred in RET gene and/or RET protein. The activation of RET tyrosine kinase can be confirmed by detecting phosphorylated RET in a tumor tissue by immunostaining or the like using an anti-phosphorylated RET antibody.

In the context of the present invention, the expression "activation of RET tyrosine kinase" or "state where RET tyrosine kinase has been activated" is intended to mean that an amino acid residue (e.g., a tyrosine residue) contained in RET tyrosine kinase has been phosphorylated, and includes the amount of phosphorylated RET tyrosine kinase protein is increased in a subject (e.g., a sample taken from a subject) (e.g., when compared to a normal subject). In addition, the expression "activation of RET tyrosine kinase" or "state where RET tyrosine kinase has been activated" includes a state where phosphorylated RET tyrosine kinase induces phosphorylation of a protein serving as a target of RET tyrosine kinase (hereinafter referred to as a target protein). The expression "activation of RET tyrosine kinase" or "state where RET tyrosine kinase has been activated" include not only the amount of phosphorylated RET tyrosine kinase protein, but also the amount of the above target protein in a phosphorylated form is increased.

In the context of the present invention, the expression "having tyrosine kinase activity" is intended to mean having activity as an enzyme that phosphorylates an amino acid residue, for example, a tyrosine residue, contained in tyrosine kinase. The tyrosine kinase activity of a polypeptide constituting the RET protein can be confirmed by, for example, the above method. In addition, the expression "having tyrosine kinase activity" includes having activity as an enzyme that phosphorylates an amino acid residue of a targeted protein.

Mutations reported to induce activation of RET tyrosine kinase include (1) a mutation in the cysteine-rich domain of RET, (2) a mutation in the tyrosine kinase domain of RET, and (3) formation of a fusion gene between RET gene and another gene or a fusion protein between RET protein and another protein (TRENDS in Genetics, 2006, vol. 22, p. 627-636). The human RET gene is located on chromosome 10 (10q1.2) and composed of 21 exons. The "cysteine-rich domain of RET" refers to a region rich in cysteine found in RET tyrosine kinase, and a polynucleotide encoding this domain is located at exons 10 and 11. The "tyrosine kinase domain of RET" refers to a region having tyrosine kinase activity found in RET tyrosine kinase, and a polynucleotide encoding this domain is located at exons 12 to 18 (TRENDS in Genetics, 2006, vol. 22, p. 627-636).

Specific examples of the above mutations (1) to (3) include those listed below. In the context of the present invention, the expression "with a mutation in RET" or "a mutation in RET" includes a state where any of these mutations (1) to (3) has occurred in RET gene and/or RET protein.
(1) Mutation in the Cysteine-Rich Domain
  A mutation in C609, C611, C618, C620, C630, C634 or elsewhere in the amino acid sequence shown in SEQ ID NO: 3 (e.g., C634W, C634Y)
(2) Mutation in the Tyrosine Kinase Domain
  A mutation in E768, V804, S891, A883, M918 or elsewhere in the amino acid sequence shown in SEQ ID NO: 3 (e.g., E768D. V804M, V804L, M918T)
(3) Formation of a Fusion Gene Between RET Gene and Another Gene or a Fusion Protein Between RET Protein and Another Protein
  Formation of KIF5B-RET fusion gene and/or fusion protein comprising the coiled-coil domain of KIF5B and the tyrosine kinase domain of RET
  Formation of CCDC6-RET fusion gene and/or fusion protein comprising the coiled-coil domain of CCDC6 and the tyrosine kinase domain of RET
  Formation of NCOA4-RET fusion gene and/or fusion protein comprising the coiled-coil domain of NCOA4 and the tyrosine kinase domain of RET
  Formation of TRIM33-RET fusion gene and/or fusion protein comprising the coiled-coil domain of TRIM33 and the tyrosine kinase domain of RET In the context of the present invention, the expression "gene of KIF5B" or "KIF5B gene" is intended to mean a gene encoding KIF5B (Kinesin family protein 5B), and the expression "protein of KIF5B" or "KIF5B protein" is intended to mean a protein consisting of an amino acid sequence constituting KIF5B. These terms are intended to mean a gene or a protein of KIF5B of any origin. Examples of a polynucleotide constituting the KIF5B gene and a polypeptide constituting the KIF5B protein specifically include, but are not limited to, a polynucleotide consisting of the nucleotide sequence shown in SEQ ID NO: 29 and a polypeptide consisting of the amino acid sequence shown in SEQ ID NO: 30. The polypeptide constituting the KIF5B protein and the polynucleotide constituting the KIF5B gene further include the following polypeptides and polynucleotides encoding the polypeptides:
  a polypeptide consisting of an amino acid sequence with substitution, deletion or insertion of one or more (preferably 1 to 10, particularly preferably 1 to 5) amino acids in the amino acid sequence shown in SEQ ID NO: 30; and
  a polypeptide consisting of an amino acid sequence with 80% or higher (preferably 85% or higher, more preferably 90% or higher, further preferably 95% or higher) identity to the amino acid sequence shown in SEQ ID NO: 30.

The human KIF5B gene is located in chromosome 10 and composed of 26 exons. Candidates for the nucleotide sequence of KIF5B-RET fusion gene include, but are not limited to, those shown in SEQ ID NO: 5, SEQ ID NO: 6, SEQ ID NO: 7, SEQ ID NO: 8, SEQ ID NO: 9, SEQ ID NO: 10, SEQ ID NO: 11. SEQ ID NO: 12, SEQ ID NO: 13 and SEQ ID NO: 14. Candidates for the amino acid sequence of KIF5B-RET fusion protein include, but are not limited to, those shown in SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 and SEQ ID NO: 24. Such KIF5B-RET fusion gene and fusion protein are reported to comprise the coiled-coil domain of KIF5B and the kinase domain of RET (Nature Medicine. 2012, 18, p. 378-381, Nature Medicine. 2012, 18, p. 382-384). In the present invention, the polypeptide constituting the KIF5B-RET fusion protein and the polynucleotide constituting the KIF5B-RET fusion gene additionally include the following polypeptides and polynucleotides encoding the polypeptides:

(i) a polypeptide comprising an amino acid sequence selected from the group consisting of SEQ ID NOs: 15 to 24, or a polypeptide comprising an amino acid sequence with substitution, deletion or insertion of one or more (preferably 1 to 10, particularly preferably 1 to 5) amino acids in an amino acid sequence selected from the group consisting of SEQ ID NOs: 15 to 24;

(ii) a polypeptide comprising an amino acid sequence with 80% or higher (preferably 85% or higher, more preferably 90% or higher, further preferably 95% or higher) identity to an amino acid sequence selected from the group consisting of SEQ ID NOs: 15 to 24; and (iii) a polypeptide which is the polypeptide (i) or (ii) and which has tyrosine kinase activity.

In the context of the present invention, the expression "gene of CCDC6" or "CCDC6 gene" is intended to mean a gene encoding CCDC6 (coiled-coil domain containing 6), and the expression "protein of CCDC6" or "CCDC6 protein" is intended to mean a protein consisting of an amino acid sequence constituting CCDC6. These terms are intended to mean a gene or a protein of CCDC6 of any origin. Examples of a polynucleotide constituting the CCDC6 gene and a polypeptide constituting the CCDC6 protein specifically include, but are not limited to, a polynucleotide consisting of the nucleotide sequence shown in SEQ ID NO: 31 and a polypeptide consisting of the amino acid sequence shown in SEQ ID NO: 32. The polypeptide constituting the CCDC6 protein and the polynucleotide constituting the CCDC6 gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in the amino acid sequence shown in SEQ ID NO: 31; and a polypeptide consisting of an amino acid sequence with 80% or higher (preferably 85% or higher, more preferably 90% or higher, further preferably 95% or higher) identity to the amino acid sequence shown in SEQ ID NO: 31.

Human CCDC6 is located in chromosome 10 and composed of 9 exons.

Examples of the nucleotide sequence of CCDC6-RET fusion gene include, but are not limited to, those shown in SEQ ID NOs: 25 and 26. Examples of the amino acid sequence of the CCDC6-RET fusion protein include, but are not limited to, those shown in SEQ ID NOs: 27 and 28. Such CCDC6-RET fusion gene and fusion protein are reported to comprise the coiled-coil domain of CCDC6 and the tyrosine kinase domain of RET (Nat Med. 2012 Feb. 12; 18 (3): 378-81).

Examples of the polypeptide constituting the CCDC6-RET fusion protein and the polynucleotide constituting the CCDC6-RET fusion gene additionally include the following polypeptides and polynucleotides encoding the polypeptides:

(i) a polypeptide comprising the amino acid sequence shown in SEQ ID NO: 27 or 28, or a polypeptide comprising an amino acid sequence with substitution, deletion or insertion of one or more (preferably 1 to 10, particularly preferably 1 to 5) amino acids in the amino acid sequence shown in SEQ ID NO: 27 or 28;

(ii) a polypeptide comprising an amino acid sequence with 80% or higher (preferably 85% or higher, more preferably 90% or higher, further preferably 95% or higher) identity to the amino acid sequence shown in SEQ ID NO: 27 or 28; and (iii) a polypeptide which is the polypeptide (i) or (ii) and which has tyrosine kinase activity.

In the context of the present invention, the expression "gene of NCOA4" or "NCOA4 gene" is intended to mean a gene encoding NCOA4 (nuclear receptor coactivator 4), and the expression "protein of NCOA4" or "NCOA4 protein" is intended to mean a protein consisting of an amino acid sequence constituting NCOA4. These terms are intended to mean a gene or a protein of NCOA4 of any origin. Examples of a polynucleotide constituting the NCOA4 gene and a polypeptide constituting the NCOA4 protein specifically include, but are not limited to, a polynucleotide consisting of a nucleotide sequence selected from the group consisting of SEQ ID NOs: 33 to 37 and a polypeptide consisting of an amino acid sequence selected from the group consisting of SEQ ID NOs: 38 to 42. The polypeptide constituting the NCOA4 protein and the polynucleotide constituting the NCOA4 gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in an amino acid sequence selected from the group consisting of SEQ ID NOs: 38 to 42; and a polypeptide consisting of an amino acid sequence with 80% or higher (preferably 85% or higher, more preferably 90% or higher, further preferably 95% or higher) identity to an amino acid sequence selected from the group consisting of SEQ ID NOs: 38 to 42.

Human NCOA4 is located in chromosome 10. A gene in which NCOA4 exon 6 is fused with RET exon 12 is reported as a NCOA4-RET fusion gene. This fusion gene and its fusion protein are reported to comprise the coiled-coil domain of NCOA4 and the tyrosine kinase domain of RET (J Clin Oncol, 30 (35), Dec. 10, 2012, p. 4352-9).

In the context of the present invention, the expression "gene of TRIM33" or "TRIM33 gene" is intended to mean a gene encoding TRIM33 (tripartite motif-containing 33), and the expression "protein of TRIM33" or "TRIM33 protein" is intended to mean a protein consisting of an amino acid sequence constituting TRIM33. These terms are intended to mean a gene or a protein of TRIM33 of any origin. Examples of a polynucleotide constituting the TRIM33 gene and a polypeptide constituting the TRIM33 protein specifically include, but are not limited to, a polynucleotide consisting of the nucleotide sequence shown in SEQ ID NO: 43 or 44 and a polypeptide consisting of the amino acid sequence shown in SEQ ID NO: 45 or 46. The polypeptide constituting the TRIM33 protein and the polynucleotide constituting the TRIM33 gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in the amino acid sequence shown in SEQ ID NO: 45 or 46; and a polypeptide consisting of an amino acid sequence with 80% or higher (preferably 85% or higher, more preferably 90% or higher, further preferably 95% or higher) identity to the amino acid sequence shown in SEQ ID NO: 45 or 46.

Human TRIM33 is located in chromosome 1. A gene in which TRIM33 exon 14 is fused with RET exon 12 is reported as a TRIM33-RET fusion gene. This fusion gene and its fusion protein are reported to comprise the coiled-coil domain of TRIM33 and the tyrosine kinase domain of RET (Cancer Discov, 3 (6), June 2013, p. 630-5).

The coiled-coil domain is a domain involved in protein dimerization. KIF5B-RET, CCDC6-RET, NCOA4-RET and TRIM33-RET are therefore considered to form dimers through their coiled-coil domains. These proteins are considered to cause the abnormal activation of RET tyrosine kinase via the dimerization between their coiled-coil domains to induce oncogenesis (Nature Medicine. 2012, 18, p. 378-381: Nature Medicine. 2012, 18, p. 382-384; J Clin Oncol, 30 (35), Dec. 10, 2012, p. 4352-9; and Cancer Discov 2013 June, 3 (6), June 2013, p. 630-5).

Examples of a mutation in RET protein in thyroid cancer (e.g., thyroid medullary cancer) include C634W, C634Y, E768D, V804M, V804L and M918T mutations in the amino acid sequence shown in SEQ ID NO: 3 (the amino acid sequence of RET). The expressions "C634W," "C634Y," "E768D," "V804M," "V804L" and "M918T" each represent an amino acid mutation, expressed with a numeral representing a specific position which is sandwiched between single-letter symbols of amino acids before and after the mutation. For example, "C634W" denotes a Cys to Trp substitution in the 634th amino acid from the N-terminus of a specific amino acid sequence. Namely, the numeral represents the amino acid position counted from the N-terminus of a specific amino acid sequence, while the single-letter symbols of amino acids appearing before and after the numeral represent amino acids before and after the substitution, respectively.

Mutations in RET gene corresponding to the above mutations include 2091G>T, 2494G>C, 2600G>A, 2600G>C and 2943T>C mutations in the nucleotide sequence shown in SEQ ID NO: 1 (the nucleotide sequence of RET). The expressions "2091 G>T," "2494G>C," "2600G>A," "2600G>C" and "2943T>C" each represent a nucleotide mutation, expressed with a numeral representing a specific position followed by bases before and after the mutation. For example, "2091G>T" denotes a G to T substitution in the 2091 st nucleotide from the 5' end of a specific base sequence. Namely, the numeral represents the base position counted from the 5' end of a specific base sequence, while the base appearing after the numeral and before the symbol ">" represents a base before the substitution and the base appearing after the symbol ">" represents a base after the substitution.

Examples of a mutation in RET in lung cancer (e.g., non-small cell lung cancer) include the formation of KIF5B-RET fusion gene and/or protein, CCDC6-RET fusion gene and/or protein, NCOA4-RET fusion gene and/or protein, TRIM33-RET fusion gene and/or protein, etc. More specifically, examples include, but are not limited to, those listed below.

Formation of KIF5B-RET fusion gene and/or fusion protein comprising the coiled-coil domain of KIF5B and the tyrosine kinase domain of RET Formation of CCDC6-RET fusion gene and/or fusion protein comprising the coiled-coil domain of CCDC6 and the tyrosine kinase domain of RET Formation of NCOA4-RET fusion gene and/or fusion protein comprising the coiled-coil domain of NCOA4 and the tyrosine kinase domain of RET Formation of TRIM33-RET fusion gene and/or fusion protein comprising the coiled-coil domain of TRIM33 and the tyrosine kinase domain of RET In the context of the present invention, the expression "fusion gene of RET," "fusion gene between RET gene and another gene" refers to a gene in which all or a part of RET gene is fused with all or a part of another gene (e.g., KIF5B gene, CCIXD6 gene, NCOA4 gene).

In the context of the present invention, the term "KIF5B-RET fusion gene" refers to a gene in which all or a part of RET gene is fused with all or a part of KIF5B gene. The term "CCDC6-RET fusion gene" refers to a gene in which all or a part of RET gene is fused with all or a part of CCDC6 gene. The term "NCOA4-RET fusion gene" refers to a gene in which all or a part of RET gene is fused with all or a part of NCOA4 gene. The term "TRIM33-RET fusion gene" refers to a gene in which all or a part of RET gene is fused with all or a part of TRIM33 gene.

In the context of the present invention, the expression "fusion protein of RET," "fusion protein between RET protein and another protein" refers to a protein in which all or a part of RET protein is fused with all or a part of another protein (e.g., KIF5B protein, CCDC6 protein, NCOA4 protein, TRIM33 protein).

In the context of the present invention, the term "KIF5B-RET fusion protein" refers to a protein in which all or a part of RET protein is fused with all or a part of KIF5B protein. The term "CCDC6-RET fusion protein" refers to a protein in which all or a part of RET protein is fused with all or a part of CCDC6 protein. The term "NCOA4-RET fusion protein" refers to a protein in which all or a part of RET protein is fused with all or a part of NCOA4 protein. The term "TRIM33-RET fusion protein" refers to a protein in which all or a part of RET protein is fused with all or a part of TRIM33 protein.

In the context of the present invention, the term "KIF5B-RET" is intended to mean KIF5B-RET fusion gene and/or KIF5B-RET fusion protein. The term "CCDC6-RET" is intended to mean CCDC6-RET fusion gene and/or CCDC6-RET fusion protein. The term "NCOA4-RET" is intended to mean NCOA4-RET fusion gene and/or NCOA4-RET fusion protein. The term "TRIM33-RET" is intended to mean TRIM33-RET fusion gene and/or TRIM33-RET fusion protein.

The expression "tumor with a mutation in RET" is intended to mean a tumor with a mutation in RET gene and/or protein in tumor cells.

The term "therapeutic agent" is intended to mean a pharmaceutical agent for directly or indirectly ameliorating a target disease or for preventing exacerbations of the target disease. More specifically, it is intended to mean a pharmaceutical agent for use in growth inhibition or size reduction of tumor tissues, inhibition of metastasis, reduction of tumor markers, amelioration of systemic symptoms or extension of survival period in a patient, etc.

The term "prophylactic agent" is intended to mean a pharmaceutical agent for use in pre-treatment of a patient at risk of suffering from a target disease such that the target disease is not developed.

The expression "metastasis of the tumor" is intended to mean metastasis of the primary tumor to other tissues. A therapeutic agent for "metastasis of the tumor" is intended to mean a pharmaceutical agent for inhibiting or suppressing metastasis of the tumor, or a pharmaceutical agent for growth inhibition or size reduction of tumor recurring as a result of metastasis. A prophylactic agent for "metastasis of the tumor" is intended to mean a pharmaceutical agent for use in pre-treatment such that the tumor does not metastasize or does not recur as a result of metastasis.

The expression "tumors metastasized from tumors" is intended to mean that the tumors listed as primary tumors metastasize to other tissues and develop therein.

The expression "subject to be administered" is intended to mean a subject for which a pharmaceutical agent can be expected to provide a therapeutic effect based on its mechanism of action. More specifically, it is intended to mean a patient with a proliferative disease for which growth inhibition or size reduction of tumor tissues, inhibition of metastasis, reduction of tumor markers, and amelioration of systemic symptoms in the patient can be expected.

The expression "tissue from the subject" is intended to mean a tissue contained in blood, alveoli, a biopsy sample, a sputum sample or the like taken from a subject such as a patient.

The expression "patient with a mutation in RET" is intended to mean that the patient has a mutation in RET gene and/or protein either in tumor or non-tumor tissue taken from a patient.

The term "RET inhibitor" is intended to mean a pharmaceutical agent which inhibits the activity of RET kinase, preferably a pharmaceutical agent which binds to RET kinase and has an inhibitory effect against the activity of RET kinase.

The expression "selectively inhibiting RET" is intended to mean that inhibitory activity against RET tyrosine kinase is high in terms of $IC_{50}$ value when compared with inhibitory activity against many other kinases (e.g., ABL, EGFR, FGFR2, HER2, IGFIR, JAK1, KIT, MET, AKT1, MEK1) except for ALK.

The expression "preliminarily determining" or "preliminarily identifying" is intended to mean providing information about the presence of a mutation in RET in order to determine or identify a sensitive patient.

In the present invention, the salt of the compound represented by formula (I) includes, for example: hydrochloride, hydrobromide, hydroiodide, phosphate, phosphonate and sulfate; sulfonates such as methanesulfonate and p-toluenesulfonate; carboxylate such as acetate, citrate, malate, tartrate, succinate and salicylate; alkali metal salts such as sodium salt and potassium salt; alkaline earth metal salts such as magnesium salt and calcium salt; and ammonium salts such as ammonium salt, alkylammonium salt, dialkylammonium salt, trialkylammonium salt and tetraalkylammonium salt. Preferred examples include hydrochloride and methanesulfonate. Hydrochloride is more preferred.

Such a salt is produced by contacting the compound with an acid or a base available in pharmaceutical production.

In the present invention, the compound represented by formula (I) or the salt thereof may be anhydrous or may form a solvate such as a hydrate. The term "solvation" used herein refers to a phenomenon where solute molecules or ions in a solution strongly attract solvent molecules adjacent thereto to create one molecular population and refers to, for example, hydration if the solvent is water. The solvate may be a hydrate or a non-hydrate. An alcohol (e.g., methanol, ethanol, n-propanol), dimethylformamide, or the like can be used as the non-hydrate.

Also, the compound or the salt thereof used in the present invention can exist in some tautomeric forms, for example, enol and imine forms, keto and enamine forms and mixtures thereof. The tautomers exist as a mixture of tautomeric sets in a solution. One tautomer is usually dominant in a solid form. The expression "one tautomer" in the present invention includes all tautomers of the compound used in the present invention.

The present invention includes all of stereoisomers (e.g., enantiomers, diastereomers (including cis and trans geometric isomers)) of the compound represented by formula (I), racemates of the isomers and other mixtures. The compound used in the present invention may have, for example, one or more asymmetric points in formula (I). The present invention includes racemic mixtures, diastereomeric mixtures and enantiomers of such compounds.

The compound according to the present invention may be obtained in a free form. In such a case, the free from can be converted to a salt that may be formed by the compound or to a hydrate or solvate thereof according to a routine method. Alternatively, the compound according to the present invention may be obtained as a salt, hydrate or solvate of the compound. In such a case, these forms can be converted to a free form of the compound according to a routine method.

Also, a substance used in the present invention includes a prodrug of the compound of formula (I). In this context, the term "prodrug" is intended to mean a derivative of the compound of formula (I) that is converted to the compound of formula (I) or a pharmaceutically acceptable salt thereof through enzymatic or nonenzymatic degradation under physiological conditions after administration. The prodrug may be inactive when administered to a patient, but exists in vivo as the active compound of formula (I) converted therefrom.

The prodrug, for example, converts to a desired drug form when a specific pH is reached or through the action of an enzyme.

Typical Production Method

The compound represented by formula (I) that serves as the active ingredient of the therapeutic or prophylactic agent of the present invention can be produced according to a method described in International Publication No. WO2010/143664, though the method for producing the compound represented by formula (I) is not limited thereto.

Therapeutic and/or Prophylactic Agent of the Present Invention

The term "therapeutic and/or prophylactic agent" used in the present invention refers to a pharmaceutical agent that is used for treatment or prevention or for treatment and prevention and specifically refers to a pharmaceutical agent that is used, for example, for treating or preventing the target disease or for suppressing progression (preventing exacerbations or maintaining the status quo) of the disease state.

The therapeutic and/or prophylactic agent of the present invention can be used as a pharmaceutical composition comprising a selected compound useful for the present invention and additionally a pharmaceutically acceptable carrier.

The term "pharmaceutically acceptable carrier" used herein is intended to mean one or more compatible solid or liquid excipients or encapsulating materials that are suitable for administration to mammals. The term "acceptable" used herein is intended to mean that the compound of interest and other ingredients are miscible in a composition in such a manner that reaction substantially reducing the pharmaceutical effectiveness of the composition does not occur therebetween under ordinary use conditions. As a matter of course, the pharmaceutically acceptable carrier must have sufficiently high purity and sufficiently low toxicity suitable for administration to, preferably an animal, more preferably a mammal, to be treated.

Examples of a material that may be used as the pharmaceutically acceptable carrier include: sugars such as lactose, glucose and sucrose; starches such as corn starch and potato starch; cellulose and its derivatives such as carboxymethyl-cellulose sodium, ethylcellulose and methylcellulose; tragacanth gum powder; malt; gelatin; talc; solid lubricants such as stearic acid and magnesium stearate; calcium sulfate; plant oils such as peanut oil, cottonseed oil, sesame oil, olive oil, corn oil and cacao oil; polyhydric alcohols such as propylene glycol, glycerin, sorbitol, mannitol and polyethylene glycol; alginic acid; emulsifiers such as TWEEN; wetting agents such as lecithin; colorants; flavors; tableting agents; stabilizers; antioxidants; antiseptics; pyrogen-free water; isotonic saline; and phosphate buffer solutions.

Examples of a method for administering the therapeutic and/or prophylactic agent of the present invention include oral, rectal, parenteral (intravenous, intramuscular, subcutaneous), intracisternal, intravaginal, intraperitoneal, intravesical and local (drip, powder, ointment, gel or cream) routes and inhalation (into oral cavity or using nasal sprays). Examples of the dosage form thereof include: solid preparations such as tablets, capsules, granules, powders and pills; liquid preparations such as aqueous and nonaqueous oral solutions and suspensions, and parenteral solutions charged in containers adapted to division into individual doses; and freeze-dried preparations that can be dissolved in use. Alternatively, the dosage form may be adapted to various administration methods encompassing controlled-release formulations as in subcutaneous implantation.

These preparations are produced by a well known method using additives such as excipients, lubricants (coating agents), binders, disintegrants, stabilizers, flavoring agents and diluents.

Examples of the excipients can include starches such as starch, potato starch and corn starch, lactose, crystalline cellulose and calcium hydrogen phosphate.

Examples of the coating agents can include ethylcellulose, hydroxypropylcellulose, hydroxypropylmethylcellulose, shellac, talc, carnauba wax and paraffin.

Examples of the binders can include polyvinylpyrrolidone, Macrogol and the compounds similar to the excipients.

Examples of the disintegrants can include compounds similar to the excipients and chemically modified starches and celluloses such as croscarmellose sodium, carboxymethyl starch sodium and cross-linked polyvinylpyrrolidone.

Examples of the stabilizers can include: p-hydroxybenzoate esters such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid.

Examples of the flavoring agents can include sweeteners, acidulants and flavors usually used.

The liquid preparations can be produced using a solvent such as ethanol, phenol, chlorocresol, purified water or distilled water.

Examples of the surfactants or emulsifiers can include polysorbate 80, polyoxyl 40 stearate, sodium lauryl sulfate and Lauromacrogol.

The amount of the prophylactic and/or therapeutic agent of the present invention used differs depending on symptom, age, body weight, relative health conditions, the presence of other medications, administration methods, etc. In the case of oral agents, a general effective amount, for example, for a patient (warm-blooded animal, particularly a human) is preferably 0.001 to 3000 mg/kg body weight, more preferably 0.01 to 300 mg/kg body weight, per day in terms of the amount of the active ingredient (compound represented by formula (I)), and the daily dose in an adult patient having a normal body weight is in the range of preferably 1 to 800 mg. In the case of parenteral agents, a general effective amount is preferably 0.001 to 1000 mg/kg body weight, more preferably 0.01 to 300 mg/kg body weight, per day. Desirably, this amount is administered at a single dose or several divided doses per day according to symptom.

The prophylactic and/or therapeutic agent of the present invention may be formulated by a method described in International Publication No. WO2012/023597.

The therapeutic and/or prophylactic agent of the present invention may be used in combination with one or more pharmaceutical agents selected from, for example, other chemotherapeutic agents, hormone therapeutic agents, immunotherapeutic agents and molecular target drugs (hereinafter, collectively referred to as concomitant agents). Such an active ingredient may be a low-molecular-weight compound. Alternatively, such an active ingredient may be a low-molecular-weight compound, may be a high-molecular-weight protein, polypeptide or antibody, or may be a vaccine or the like. Moreover, two or more of these active ingredients may be mixed for use at an appropriate ratio.

Examples of the "chemotherapeutic agents" include alkylating agents, platinum preparations, metabolic antagonists, topoisomerase inhibitors, anticancer antibiotics and plant-derived anticancer agents. Examples of the "alkylating agents" include nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, ethoglucid, altretamine, ambamustine, dibrospidium hydrochloride, fotemustine, prednimustine, pumitepa, ribomustin, temozolomide, treosulfan, trofosfamide, zinostatin stimalamer, adozelesin, cystemustine and bizelesin. Examples of the "platinum preparations" include carboplatin, cisplatin, miboplatin, nedaplatin and oxaliplatin. Examples of the "metabolic antagonists" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, galocitabine, emitefur), aminopterin, leucovorin calcium, tabloid, butocin, calcium folinate, calcium levofolinate, cladribine, fludarabine, gemcitabine, hydroxycarbamide, pentostatin, piritrexim, idoxuridine, mitoguazone, tiazofurin and ambamustine. Examples of topoisomerase I inhibitors (e.g., irinotecan, topotecan), topoisomerase II inhibitors (e.g., sobuzoxane) and the "anticancer antibiotics" include anthracycline anticancer agents (doxorubicin hydrochloride, daunorubicin hydrochloride, aclarubicin hydrochloride, pirarubicin hydrochloride, epirubicin hydrochloride, etc.), actinomycin D, actinomycin C, mitomycin C, chromomycin A3, bleomycin hydrochloride, bleomycin sulfate, peplomycin sulfate, neocarzinostatin, mithramycin, sarkomycin, carzinophilin, mitotane, zorubicin hydrochloride, mitoxantrone hydrochloride and idarubicin hydrochloride. Examples of the "plant-derived anticancer agents" include *vinca* alkaloid anticancer agents (vinblastine sulfate, vincristine sulfate, vindesine sulfate, etc.), taxane anticancer agents (paclitaxel, docetaxel, etc.) etoposide, etoposide phosphate, teniposide and vinorelbine.

Examples of the "hormone therapeutic agents" include adrenocortical hormone drugs (e.g., dexamethasone, prednisolone, betamethasone, triamcinolone). Among them, prednisolone is preferred.

Examples of the "immunotherapeutic agents (biological response modifiers: BRMs)" include Picibanil, Krestin, sizofiran, lentinan, ubenimex, interferons, interleukins, macrophage colony-stimulating factors, granulocyte colony-stimulating factors, lymphotoxins, BCG vaccines, *Corynebacterium parvum*, levamisole, polysaccharide K and procodazole.

The "molecular target drugs" include, for example, "pharmaceutical agents that inhibit the action of cell growth factors and their receptors". The "cell growth factors" may be any substance that promotes cell growth, and examples typically include peptides with a molecular weight of 20,000 or lower which are factors that exert action at lower concentrations through binding to their receptors and specifically include (1) EGF (epidermal growth factor) and substances having substantially the same activity thereas [e.g., EGF, heregulin (HER2 ligand)], (2) insulin and substances having substantially the same activity thereas [e.g., insulin, IGF (insulin-like growth factor)-1, IGF-2], (3) FGF (fibroblast growth factor) and substances having substantially the same activity thereas [e.g., acidic FGF, basic FGF, KGF (keratinocyte growth factor), FGF-10], (4) VEGF (vascular endothelial growth factor) and (5) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor)].

The "cell growth factor receptors" may be any receptor having the ability to bind to the above cell growth factors, and specific examples include EGF receptors, heregulin receptors (HER2), insulin receptors, IGF receptors, FGF receptor-1 or FGF receptor-2, HGF receptors (c-met), VEGF receptors and SCF receptors (c-kit). Examples of the "pharmaceutical agents that inhibit the action of cell growth factors" include Herceptin (HER2 antibody), GLEEVEC (c-kit, abl inhibitor) and Tarceva (EGF receptor inhibitor).

The molecular target drugs also include pharmaceutical agents each inhibiting the actions of a plurality of cell growth factors, and pharmaceutical agents that block intracellular signals generated by cell growth factors.

In addition to the above pharmaceutical agents, L-asparaginase, aceglatone, procarbazine hydrochloride, protoporphyrin-cobalt complex salts, mercury-hematoporphyrin sodium, differentiation inducers (e.g., retinoid, vitamin Ds), angiogenesis inhibitors, α-blockers (e.g., tamsulosin hydrochloride), and the like can also be used.

Among those described above, a platinum complex (e.g., carboplatin, cisplatin, oxaliplatin), a metabolic antagonist (e.g., gemcitabine, pemetrexed), a topoisomerase I inhibitor (e.g., irinotecan, topotecan), a plant-derived anticancer agent (taxane drugs (e.g., paclitaxel, docetaxel), vinorelbine), an anticancer antibiotic (e.g., mitomycin C), a hormone therapeutic agent (e.g., prednisolone), an immunotherapeutic agent (e.g., Picibanil, Krestin), a molecular target drug (e.g., anti-VEGF antibodies such as bevacizumab, EGFR inhibitors such as erlotinib, VEGFR inhibitors such as sunitinib), or the like is preferred as a concomitant agent. Cisplatin, gemcitabine, paclitaxel, bevacizumab, or the like is more preferred. Alternatively, the therapeutic and/or prophylactic agent of the present invention may be used in combination with a combination therapy using these pharmaceutical agents. Examples include combined use with a combination therapy of cisplatin, vinblastine and mitomycin C, cisplatin and vinorelbine, cisplatin and paclitaxel, cisplatin and gemcitabine, carboplatin and paclitaxel, pemetrexed and cisplatin, or bevacizumab, cisplatin and pemetrexed.

In the present invention, the timings of administration of the active ingredient of the present invention and the concomitant agent are not limited, and they may be administered simultaneously or at a time interval to a subject to be administered. Alternatively, the active ingredient of the present invention and the concomitant agent may be administered as a single preparation comprising them to a subject to be administered. For example, they may be administered by a multidrug therapy which involves drip-injecting a plurality of drugs in combination over 3 to 6 months or by a method which involves taking oral agents over approximately 2 years.

Also, a preoperative adjuvant therapy such as "chemotherapy" may be performed before execution of surgery in order to inhibit already spread tumor (cancer) cells to prevent recurrence as a result of metastasis or for the purpose of reducing the extent of surgery.

A postoperative adjuvant therapy such as "chemotherapy" may be further performed in order to inhibit the growth of tumor (cancer) cells that have not been removed by local treatment such as surgery or radiation to prevent recurrence as a result of metastasis.

The anticancer agent that may be used in combination with the active ingredient of the present invention may act on not only cancer cells but also normal cells, resulting in the occurrence of adverse reactions. Typical adverse reactions include nausea caused by gastrointestinal mucosal damage, vomiting, anorexia, stomatitis, diarrhea or constipation, taste abnormality, decrease in leukocyte, erythrocyte or platelet level or alopecia caused by bone marrow damage, immune compromise, etc. The active ingredient of the present invention and the concomitant agent may be used in combination with an adverse reaction-reducing agent in order to prevent these adverse reactions. Examples include antiemetics effectively suppressing nausea (e.g., granisetron hydrochloride) and drugs promoting recovery from bone marrow damage (e.g., erythropoietin, G-CSF, GM-CSF).

The dose of the concomitant agent can be appropriately selected with reference to a dose clinically used. The mixing ratio between the active ingredient of the present invention and the concomitant agent can be appropriately selected according to the subject to be administered, administration routes, the target disease, symptom, combination of the pharmaceutical agents, etc. For example, when the subject to be administered is a human, 0.01 to 100 parts by weight of the concomitant agent may be used with respect to 100 parts by weight of a preparation comprising the active ingredient of the present invention.

Method for Detecting Mutation in RET

The therapeutic and/or prophylactic agent of the invention of the present application is expected to be therapeutically and/or prophylactically effective by administration to a subject confirmed to have a mutation in RET. This suggests that a patient confirmed to have a mutation in RET is sensitive to the therapeutic and/or prophylactic agent of the invention of the present application. In the present invention, the method for detecting a mutation in RET includes a method for detecting a mutation in RET gene and a method for detecting a mutation in RET protein.

The method for detecting a mutation in RET gene comprises the step of detecting the presence of a RET gene-related specific polynucleotide shown below in a sample obtained from the subject and the amplification of the specific polynucleotide.

Specifically, the method comprises the following steps (1) to (3):

(1) A sample (blood, pulmonary alveolus, a biopsied sample, an expectoration sample, etc.) is taken from the subject;

(2) Genomic DNA or a transcript thereof (e.g., mRNA, cDNA, protein) is extracted from the sample. The genomic DNA can be extracted by a method known in the art. This extraction can be conveniently performed using a commercially available DNA extraction kit.

(3) The presence of a specific polynucleotide in the extracted genomic DNA or transcript thereof (e.g., mRNA, cDNA, protein) and the presence or absence of amplification of the specific polynucleotide are detected.

The presence of the specific polynucleotide can be detected using gene analysis methods known in the art (e.g., methods such as PCR, reverse transcription PCR, Sanger sequencing, in situ hybridization and microarray method) singly or in combination.

In the event of detecting the presence of the specific polynucleotide sequence by using mRNA, the detection can be performed by gene amplification reaction such as reverse transcription PCR using primers designed to be capable of specifically amplifying the polynucleotide sequence to be detected. The primer design can be performed using primer design software (e.g., Primer Express; PE Biosystems) or the like.

In addition, the PCR products which are obtained by PCR and reverse transcription PCR are analyzed by agarose gel electrophoresis, and the successful obtainment of an amplification fragment with a size of interest can be confirmed by ethidium bromide staining or the like. The successful obtainment of an amplification fragment with a size of interest shows that the specific polynucleotide is present in the sample obtained from the subject.

A point mutation, deletion mutation or insertion mutation in RET gene can be detected by detecting the presence of the specific polynucleotide using, for example, a combined method of the above reverse transcription PCR and Sanger sequencing, or a single-nucleotide extension reaction method known in the art.

A fusion gene between RET gene and another gene can be detected by a method for detecting the presence of the specific polynucleotide using a combined method of the above reverse transcription PCR and Sanger sequencing or using an in situ hybridization technique. The detection using the in situ hybridization technique can be performed by, for example, fluorescent in situ hybridization (FISH), chromogenic in situ hybridization (CISH) or silver in situ hybridization (SISH) known in the art.

A probe which can be used in hybridization is a nucleic acid molecule of at least 32 consecutive nucleotides (16 upstream nucleotides and 16 downstream nucleotides flanking the fusion point) that hybridizes under stringent conditions (preferably under more stringent conditions) to the specific polynucleotide or its complementary strand, but not limited to. A probe comprising the sequence of a specific portion in a polynucleotide having a nucleotide sequence selected from the group consisting of SEQ ID NOs: 5 to 14, 25 and 26, or its complementary strand can also be used.

The stringent conditions can be determined on the basis of the melting temperature (Tm) of a nucleic acid to form a complex according to a routine method. Specifically, the stringent conditions involve "5×SSPE. 5×Denhardt's solution, 0.5% SDS, 50% formamide, 200 µg/ml salmon sperm DNA, 42° C. overnight" as conditions for hybridization and "0.5×SSC, 0.1% SDS, 42° C." as conditions for washing. More stringent conditions involve "5×SSPE, 5×Denhardt's solution, 0.5% SDS, 50% formamide, 200 µg/ml salmon sperm DNA, 42° C. overnight" as conditions for hybridization and "0.2×SSC, 0.1% SDS, 65° C." as conditions for washing.

Detection of the amplification of RET gene can be conducted by detecting the amplification of the specific polynucleotide by the above in situ hybridization technique or by comparative genomic hybridization (CGH) using genomic DNA.

The specific polynucleotide to be detected refers to a polynucleotide having a base varied due to a point mutation, deletion mutation or insertion mutation in polynucleotide constituting RET gene, a polynucleotide constituting the fusion gene between RET gene and another gene (e.g., KIF5B gene, CCDC6 gene, NCOA4 gene, TRIM33 gene), or amplified polynucleotide constituting RET gene. Examples of such a polynucleotide include, but are not limited to, the polynucleotides shown below and polynucleotides hybridizing under stringent conditions to polynucleotides consisting of sequences complementary to these polynucleotides (particularly polynucleotides encoding polypeptides having tyrosine kinase activity).

(1) Polynucleotide Constituting Fusion Gene Between RET Gene and KIF5B Gene:

Polynucleotide comprising the nucleotide sequence shown in SEQ ID NO: 5

Polynucleotide comprising the nucleotide sequence shown in SEQ ID NO: 6

Polynucleotide comprising the nucleotide sequence shown in SEQ ID NO: 7

Polynucleotide comprising the nucleotide sequence shown in SEQ ID NO: 8

Polynucleotide comprising the nucleotide sequence shown in SEQ ID NO: 9

Polynucleotide comprising the nucleotide sequence shown in SEQ ID NO: 10

Polynucleotide comprising the nucleotide sequence shown in SEQ ID NO: 11

Polynucleotide comprising the nucleotide sequence shown in SEQ ID NO: 12

Polynucleotide comprising the nucleotide sequence shown in SEQ ID NO: 13

Polynucleotide comprising the nucleotide sequence shown in SEQ ID NO: 14

(2) Polynucleotide Constituting Fusion Gene Between RET Gene and CCDC6 Gene:

Polynucleotide comprising the nucleotide sequence shown in SEQ ID NO: 25

Polynucleotide comprising the nucleotide sequence shown in SEQ ID NO: 26

(3) Polynucleotide Constituting RET Gene:

Polynucleotide comprising the nucleotide sequence shown in SEQ ID NO: 1

Polynucleotide comprising the nucleotide sequence shown in SEQ ID NO: 2

(4) Polynucleotide Having a Base Varied Due to a Point Mutation, Deletion Mutation or Insertion Mutation in Polynucleotide Constituting RET Gene:

Polynucleotide comprising a nucleotide sequence with a mutation in the nucleotide 2091 G, 2261G, 2494G, 2562A, 2600G, 2861 T or 2943T (e.g., 2091G>T, 2261G>A, 2494G>C, 2562A>T, 2600G>A, 2600G>C, 2861T>G or 2943T>C mutation) of a polynucleotide having the nucleotide sequence shown in SEQ ID NO: 1

Polynucleotide comprising a polynucleotide encoding a polypeptide with a mutation in the amino acid C609, C611, C618, C620, C630, C634, E768, V804, S891, A883 or M918 (e.g., C634W, C634Y, E768D, V804M. V804L or M918T mutation) of a polypeptide having the amino acid sequence shown in SEQ ID NO: 3

The method for detecting a mutation in RET further includes a method for detecting a mutation in RET protein in addition to the above method.

The method for detecting a mutation in RET comprises the step of detecting the presence of a specific polypeptide (hereinafter, referred to as a polypeptide to be detected) in a sample obtained from the subject. The step of detecting a polypeptide to be detected involves preparing a lysate from a sample obtained from the subject (e.g., cancer tissues or cells obtained from the subject).

In the event that a polypeptide to be detected is fusion protein between RET protein and another protein, the presence of polypeptide to be detected can be detected by for example, immunoassay or enzyme activity assay using an antibody against KIF5B, CCDC6, NCOA4 or TRIM33 and an anti-RET antibody in combination. Preferably, an approach such as enzyme immunoassay, two-antibody sandwich ELISA, fluorescent immunoassay, radioimmunoassay or Western blotting using a monoclonal or polyclonal antibody specific for the polypeptide to be detected can be used. In addition to above mentioned method, detection of a mutation (including a point mutation, a deletion mutation and an insertion mutation) in RET protein can be conducted by detecting the presence of a polypeptide to be detected using Western blotting, mass spectrometry, or the like.

Examples of the polypeptide to be detected include, but are not limited to, the polypeptides shown below and polypeptides with deletion, substitution and/or insertion of one or more amino acids (e.g., 1 to 10, 1 to 5, or 1 to 3 amino acids) in these polypeptides (particularly polypeptides having tyrosine kinase activity).

(1) Polypeptide Constituting Fusion Protein Between RET Protein and KIF5B Protein:

Polypeptide comprising the amino acid sequence shown in SEQ ID NO: 15
Polypeptide comprising the amino acid sequence shown in SEQ ID NO: 16
Polypeptide comprising the amino acid sequence shown in SEQ ID NO: 17
Polypeptide comprising the amino acid sequence shown in SEQ ID NO: 18
Polypeptide comprising the amino acid sequence shown in SEQ ID NO: 19
Polypeptide comprising the amino acid sequence shown in SEQ ID NO: 20
Polypeptide comprising the amino acid sequence shown in SEQ ID NO: 21
Polypeptide comprising the amino acid sequence shown in SEQ ID NO: 22
Polypeptide comprising the amino acid sequence shown in SEQ ID NO: 23
Polypeptide comprising the amino acid sequence shown in SEQ ID NO: 24

(2) Polypeptide Constituting Fusion Protein Between RET Protein and CCDC6 Protein:

Polypeptide comprising the amino acid sequence shown in SEQ ID NO: 27
Polypeptide comprising the amino acid sequence shown in SEQ ID NO: 28

(3) Polypeptide Constituting RET Protein

Polypeptide comprising the amino acid sequence shown in SEQ ID NO: 3
Polypeptide comprising the amino acid sequence shown in SEQ ID NO: 4

(4) Polypeptide Having a Point Mutation in a Polypeptide Constituting RET Protein Polypeptide encoded by a polynucleotide comprising a nucleotide sequence with a mutation in the nucleotide 2091G, 2261G, 2494G, 2562A, 26000, 2861T or 2943T (e.g., 2091G>T, 2261G>A, 2494G>C, 2562A>T, 2600G>A, 2600G>C, 2861T>G or 2943T>C mutation) of a polynucleotide having the nucleotide sequence shown in SEQ ID NO: 1

Polypeptide with a mutation in the amino acid C609. C611. C618, C620, C630, C634, G691, E768, Y791, V804, S891, A883 or M918 (e.g., C634W, C634Y, G691 S, E768D, Y791F, V804M, V804L, S891A or M918T mutation) of a polypeptide having the amino acid sequence shown in SEQ ID NO: 3

In addition, the presence of the fusion gene between RET gene and KIF5B gene or other fusion genes can be detected by methods described in International Publication No. WO2012/014795, Nature Medicine, 2012, 18, p. 378-381, J Clin Oncol, 30 (35), Dec. 10, 2012, p. 4352-9, Cancer Discov 2013 June, 3 (6), June 2013, p. 630-5, etc.

In addition to the above method, the activation of RET tyrosine kinase may be detected. The activation of RET tyrosine kinase can be confirmed by detecting phosphorylated RET in a tumor tissue by immunostaining or the like using an anti-phosphorylated RET antibody.

EXAMPLES

Hereinafter, the present invention will be described more specifically with reference to Examples. However, the present invention is not intended to be limited to these Examples.

Compound 1 (9-ethyl-6,6-dimethyl-8-(4-morpholin-4-yl-piperidin-1-yl)-11-oxo-6,1-dihydro-5H-benzo[b]carbazole-3-carbonitrile, or 9-ethyl-6,6-dimethyl-8-[4-(morpholin-4-yl)piperidin-1-yl]-11-oxo-6,11-dihydro-5H-benzo[b]carbazole-3-carbonitrile) represented by formula II (compound described in Example 366 of WO2010/143664) was subjected to pharmacological tests described in Examples 1 to 6.

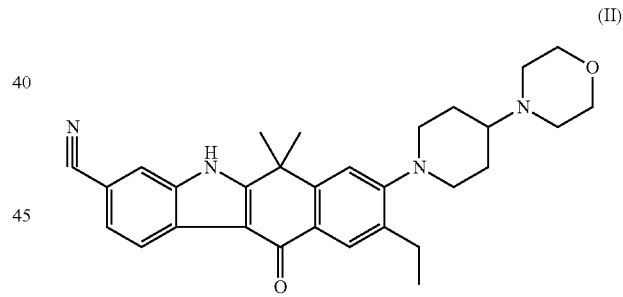

(II)

Example 1

Evaluation of RET Kinase Inhibitory Activity and Binding Affinity

The RET kinase inhibitory activity of compound 1 was evaluated with inhibitory activity against the phosphorylation reaction of a biotinylated peptide (EGPWLEEEEE-AYGWMDF) as an index using RET kinase containing a N-terminally GST-tagged RET kinase domain (Carna Biosciences). The phosphorylated biotinylated peptide was detected by the TR-FRET (time-resolved fluorescence resonance energy transfer) method using an europium labeled anti-phosphorylation antibody. 50% inhibition concentration ($IC_{50}$ value) was calculated by the logistic regression method. As a result, compound 1 exhibited RET kinase inhibitory activity with an $IC_{50}$ value of 4.8 nM.

The dissociation constant (Kd value) of compound 1 for RET kinase was also measured by KINOMEst$_{SCAN}$™ (DiscoveRx). As a result, compound 1 exhibited binding affinity to RET with Kd value of 7.6 nM.

Example 2

Establishment of KIF5B-RET-Expressing Cells and Evaluation of Cell Growth Inhibitory Activity Against these Cells An expression plasmid CS-GS 104J-M67 (GeneCopoeia) containing KIF5B-RET variant 1 (gene in which a region from the N-terminus of KIF5B CDS to exon 15 was fused with a region from exon 12 of RET CDS to the C-terminus) (SEQ ID NO: 5) was transfected into mouse lymphocytes Ba/F3 (RIKEN Cell Bank) by electroporation. After transfection, the cells were cultured overnight in an RPMI-1640 medium (Sigma-Aldrich) containing 10% FBS (Bovogen Biologicals) and 1 ng/mL recombinant mouse IL-3 (R&D systems). Then, the culture supernatant was replaced with an RPMI-1640 medium containing 10% FBS. The cells were seeded into a 96-well plate by the limiting dilution method. Approximately 2 weeks later, the expression of phosphorylated RET in cells grown in the absence of IL-3 was detected by Western blotting. This was used as an index to establish a cell line Ba/F3 KIF5B-RET stably expressing KIF5B-RET.

The Ba/F3 KIF5BR-RET cells were seeded into a 96-well plate at a concentration of 2,500 cells/well in an RPMI-1640 medium containing 10% FBS. A hydrochloride salt of compound 1 was diluted to 1 nM to 10 µM (final concentrations) with dimethyl sulfoxide and added to the 96-well plate. Dimethyl sulfoxide was added as a negative control. After culture at 37° C. for 2 days in the presence of 5% $CO_2$, a cell counting reagent CellTiter-Glo® Luminescent Cell Viability Assay (Promega Corporation) was added thereto and stirred, followed by the measurement of luminescence intensity using a luminescence measurement apparatus Envision (PerkinElmer). The measurement value in a well supplemented with only a medium was defined as a cell viability of 0%, while the measurement value in a well supplemented with dimethyl sulfoxide was defined as a cell viability of 100%. The cell viability of the Ba/F3 KIF5B-RET cells was calculated at each concentration of compound 1. The $IC_{50}$ value was determined from the obtained values by the logistic regression method. As a result, compound 1 inhibited cell growth of Ba/F3 KIF5B-RET cells with $IC_{50}$ value of 86 nM.

These results demonstrated that compound 1 can inhibit the kinase activity of RET and can inhibit the growth of a cell line expressing KIF5B-RET.

Example 3

Evaluation of Cell Growth Inhibitory Activity Against Thyroid Medullary Cancer Cell Line TT Cell growth inhibitory activity was evaluated using a thyroid medullary cancer cell line TT (American Type Culture Collection) with a RET kinase active mutation (C634W).

The TT cells were seeded into a 96-well plate at a concentration of 5,000 cells/well in F-12K Nutrient Mixture (Life Technologies Corporation) containing 10% FBS and cultured overnight at 37° C. in the presence of 5% $CO_2$. Then, a hydrochloride salt of compound 1 was diluted to 1 nM to 10 µM (final concentrations) with dimethyl sulfoxide and added to the 96-well plate. Dimethyl sulfoxide was added as a negative control. After culture at 37° C. for 5 days in the presence of 5% $CO_2$, a cell counting reagent CellTiter-Glo® Luminescent Cell Viability Assay was added thereto and stirred, followed by the measurement of luminescence intensity using a luminescence measurement apparatus Envision. The measurement value in a well supplemented with only a medium was defined as a cell viability of 0%, while the measurement value in a well supplemented with dimethyl sulfoxide was defined as a survival rate of 100%. The cell viability of the TT cells was calculated at each concentration of compound 1. The $IC_{50}$ value was determined from the obtained values by the logistic regression method. As a result, compound 1 inhibited cell growth of TT cells with $IC_{50}$ value of 190 nM.

Example 4

REF Kinase Mutant Inhibitory Activity

The RET kinase mutant inhibitory activity of compound 1 was evaluated with inhibitory activity against the phosphorylation reaction of a biotinylated peptide (EGPWLEEEEAYGWMDF) as an index using a RET kinase mutant containing a N-terminally GST-tagged RET kinase domain (Carna Biosciences, Millipore). The phosphorylated biotinylated peptide was detected by the TR-FRET method using an europium labeled anti-phosphorylation antibody. The $IC_{50}$ value was calculated by the logistic regression method. The test results are shown in Table 1. Compound 1 exhibited inhibitory activity against each mutant of RET kinase with a mutation (V804L, V804M) in a gatekeeper residue.

TABLE 1

| RET mutant | $IC_{50}$ (nM) |
|---|---|
| RET G691S | 9.5 |
| RET Y791F | 14 |
| RET V804L | 32 |
| RET V804M | 53 |
| RET S891A | 8.3 |
| RET M918T | 5.7 |

Example 5

Evaluation of Cell Growth Inhibitory Activity Against Non-Small Cell Lung Cancer Cell Line LC-2/ad Cell growth inhibitory activity was evaluated using a non-small cell lung cancer cell line LC-2/ad (RIKEN, J Thorac Oncol. 2012 December, 7 (12), 1872-6) harboring CCDC6-RET fusion gene.

The LC-2/ad cells were seeded into a 96-well plate at a concentration of 2,000 cells/well in a medium of a 1:1 mixture of RPMI-1640 and Ham containing 15% FBS and 25 mM HEPES and cultured overnight at 37° C. in the presence of 5% $CO_2$. Then, a hydrochloride salt of compound 1 was diluted to 1 nM to 1 µM (final concentrations) with dimethyl sulfoxide and added to the 96-well plate. Dimethyl sulfoxide was added as a negative control. After culture at 37° C. for 5 days in the presence of 5% $CO_2$, a cell counting reagent CellTiter-Glo® Luminescent Cell Viability Assay was added thereto and stirred, followed by the measurement of luminescence intensity using a luminescence measurement apparatus Envision. The measurement value in a well supplemented with only a medium was defined as a cell viability of 0%, while the measurement value in a well supplemented with dimethyl sulfoxide was defined as a cell viability of 100%. The cell viability of the LC-2/ad cells was calculated at each concentration of compound 1. The $IC_{50}$ value was determined from the obtained values by the logistic regression method. As a result, compound 1 inhibited cell growth of LC-2/ad cells with $IC_{50}$ value of 190 nM.

Example 6

Evaluation of Antitumor Activity in Xenograft Mouse Model Harboring CCDC6-RET Fusion Gene The in vivo antitumor activity of compound 1 was evaluated in non-small cell lung cancer cell line LC-2/ad-implanted mouse models. LC-2/ad was subcutaneously implanted to SCID mice and randomized after tumor size reached 200 to 350 mm. The administration of the compound was started on the day of randamization. The vehicles used for dissolving the compound were 0.02 N HCl, 10% dimethyl sulfoxide. 10% Cremophor EL, 15% PEG400 and 15% HPCD (2-hydroxypropyl-β-cyclodextrin) (indicated by final concentration). Compound 1 was orally administered once a day to each mouse at a dose of 20 mg/kg or 60 mg/kg for 14 days. As a result, a dose-dependent tumor growth inhibitory effect and tumor regression were confirmed for all tumors. During this test, a significant body weight loss of a mouse was not observed at any dose. The results about the antitumor activity are shown in FIG. 1.

The invention claimed is:

1. A method for treating a non-small cell lung cancer tumor with a mutation in RET, which comprises administering to a patient in need thereof 9-ethyl-6,6-dimethyl-8-(4-morpholin-4-yl-piperidin-1-yl)-11-oxo-6,11-dihydro-5H-benzo[b]carbazole-3-carbonitrile or a pharmaceutically acceptable salt thereof in a daily dosage amount of 20 mg/kg to 60 mg/kg,
    wherein the tumor is a tumor with a) a fusion gene between i) an RET gene and ii) another gene, which is KIF5B or CCDC6, and/or b) a fusion protein of an RET protein and another protein, which is KIF5B or CCDC6, wherein the patient does not have an ALK gene mutation and the tumor is not a tumor caused by an ALK gene mutation.

2. A method of treating a non-small cell lung cancer tumor in a patient with a mutation in RET, which comprises administering to the patient 9-ethyl-6,6-dimethyl-8-(4-morpholin-4-yl-piperidin-1-yl)-11-oxo-6,11-dihydro-5H-benzo[b]carbazole-3-carbonitrile or a pharmaceutically acceptable salt thereof in a daily dosage amount of 20 mg/kg to 60 mg/kg,
    wherein the patient is a patient with a) a fusion gene between i) an RET gene and ii) another gene, which is KIF5B or CCDC6, and/or b) a fusion protein of an RET protein and another protein, which is KIF5B or CCDC6, wherein the patient does not have an ALK gene mutation and the tumor is not a tumor caused by an ALK gene mutation.

3. The method according to claim 1, wherein the compound is a hydrochloride of 9-ethyl-6,6-dimethyl-8-(4-morpholin-4-yl-piperidin-1-yl)-11-oxo-6,11-dihydro-5H-benzo[b]carbazole-3-carbonitrile.

4. The method of claim 1, wherein the tumor is a tumor with CCDC6-RET fusion gene and/or CCDC6-RET fusion protein.

5. The method of claim 2, wherein the patient is a patient with CCDC6-RET fusion gene and/or CCDC6-RET fusion protein.

6. The method according to claim 2, wherein the compound is a hydrochloride of 9-ethyl-6,6-dimethyl-8-(4-morpholin-4-yl-piperidin-1-yl)-11-oxo-6,11-dihydro-5H-benzo[b]carbazole-3-carbonitrile.

7. The method of claim 1, wherein the daily dosage amount of 9-ethyl-6,6-dimethyl-8-(4-morpholin-4-yl-piperidin-1-yl)-11-oxo-6,11-dihydro-5H-benzo[b]carbazole-3-carbonitrile or a pharmaceutically acceptable salt is about 20 mg/kg.

8. The method of claim 2, wherein the daily dosage amount of 9-ethyl-6,6-dimethyl-8-(4-morpholin-4-yl-piperidin-1-yl)-11-oxo-6,11-dihydro-5H-benzo[b]carbazole-3-carbonitrile or a pharmaceutically acceptable salt is about 20 mg/kg.

9. The method of claim 1, wherein the tumor is a tumor with KIF5B-RET fusion gene and/or KIF5B-RET fusion protein.

10. The method of claim 2, wherein the patient is a patient with KIF5B-RET fusion gene and/or KIF5B-RET fusion protein.

* * * * *